US012636385B2

(12) United States Patent
Sohn

(10) Patent No.: US 12,636,385 B2
(45) Date of Patent: May 26, 2026

(54) SELECTIVE LIGANDS FOR TAU AGGREGATES

(71) Applicant: Sentonix, Inc., Arlington, MA (US)

(72) Inventor: Daniel Dungan Sohn, Stockholm (SE)

(73) Assignee: Sentonix, Inc., Arlington, MA (US)

( * ) Notice: Subject to any disclaimer, the term of this patent is extended or adjusted under 35 U.S.C. 154(b) by 1131 days.

(21) Appl. No.: 17/046,683

(22) PCT Filed: Apr. 10, 2019

(86) PCT No.: PCT/EP2019/059165

§ 371 (c)(1),
(2) Date: Oct. 9, 2020

(87) PCT Pub. No.: WO2019/197502

PCT Pub. Date: Oct. 17, 2019

(65) Prior Publication Data

US 2021/0138092 A1 May 13, 2021

(30) Foreign Application Priority Data

Apr. 11, 2018 (GB) ..................................... 1806004

(51) Int. Cl.

| | |
|---|---|
| ***A61K 51/04*** | (2006.01) |
| ***A61K 31/4545*** | (2006.01) |
| ***A61K 31/506*** | (2006.01) |
| ***A61P 25/28*** | (2006.01) |
| ***C07B 59/00*** | (2006.01) |
| ***C07D 401/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 498/04*** | (2006.01) |

(52) U.S. Cl.

CPC ...... *A61K 51/0459* (2013.01); *A61K 31/4545* (2013.01); *A61K 31/506* (2013.01); *A61K 51/0455* (2013.01); *A61P 25/28* (2018.01); *C07B 59/002* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 498/04* (2013.01); *C07B 2200/05* (2013.01)

(58) Field of Classification Search

CPC .............. A61K 31/506; A61K 31/4545; A61K 51/0459; C07D 409/14

See application file for complete search history.

(56) References Cited

U.S. PATENT DOCUMENTS

| | | | | |
|---|---|---|---|---|
| 8,633,019 B2 * | 1/2014 | Paushkin | ............ | C07D 413/04 514/17.7 |
| 12,304,901 B2 | 5/2025 | Sohn | | |
| 2012/0302755 A1 | 11/2012 | Szardenings et al. | | |
| 2024/0165276 A1 | 5/2024 | Sohn | | |

FOREIGN PATENT DOCUMENTS

| | | |
|---|---|---|
| DE | 3722992 A1 | 1/1989 |
| WO | WO 2006/044503 A2 | 4/2006 |
| WO | WO 2006/080821 A1 | 8/2006 |
| WO | WO-2007086800 A1 | 8/2007 |
| WO | WO 2012/164071 A1 | 12/2012 |
| WO | WO 2014/140592 A1 | 9/2014 |
| WO | WO 2015/110263 A1 | 7/2015 |
| WO | WO-2017009454 A1 | 1/2017 |
| WO | WO-2017153601 A1 | 9/2017 |
| WO | WO-2019025595 A1 | 2/2019 |
| WO | WO-2019049061 A1 | 3/2019 |
| WO | WO 2019/197502 A1 | 10/2019 |

(Continued)

OTHER PUBLICATIONS

Arendt et al., "Tau and tauopathies," *Brain Research Bulletin*, 2016, 126, pp. 238-292.

Åslund et al., "Novel Pentameric Thiophene Derivatives for in Vitro and in Vivo Optical Imaging of a Plethora of Protein Aggregates in Cerebral Amyloidoses," *ACS Chemical Biology*, 2009, vol. 4, No. 8, pp. 673-684.

Bäck et al., "Anionic Oligothiophenes Compete for Binding of X-34 but not PIB to Recombinant Aβ Amyloid Fibrils and Alzheimer's Disease Brain-Derived Aβ," *Chemistry A European Journal*, Dec. 2016, vol. 22, Issue 51, pp. 18335-18338.

(Continued)

*Primary Examiner* — James W Rogers

(74) *Attorney, Agent, or Firm* — Sterne, Kessler, Goldstein & Fox P.L.L.C.

(57) ABSTRACT

The invention provides a compound of formula (I): or a pharmaceutically acceptable salt, ester, amide or carbamate thereof, or a salt of such an ester, amide or carbamate. The invention further provides uses of the compounds of formula (I) and compositions comprising compounds of formula (I), including the use of such compounds for the detection of tau deposits, and the use of such compounds and compositions as diagnostic agents in the diagnosis or monitoring of the progression of a disease or disorder such as Alzheimer's disease, corticobasal degeneration and progressive supranuclear palsy, or for the prevention or treatment of a disease or disorder such as Alzheimer's disease, corticobasal degeneration and progressive supranuclear palsy.

(I)

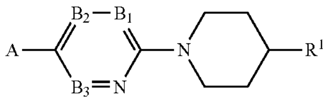

19 Claims, 12 Drawing Sheets

(56) References Cited

FOREIGN PATENT DOCUMENTS

WO WO-2021074351 A1 4/2021
WO WO-2024094816 A1 5/2024

OTHER PUBLICATIONS

Ballatore et al., "Tau-mediated neurodegeneration in Alzheimer's disease and related disorders," *Nature Reviews: Neuroscience*, Sep. 2007, vol. 8, pp. 663-672.
Biernat et al., "The switch of tau protein to an Alzheimer-like state includes the phosphorylation of two serine-proline motifs upstream of the microtubule binding region," The EMBO Journal, Apr. 1992, vol. 11, Issue 4, pp. 1593-1597.
Cesura et al., "Characterization of the binding of [$^3$H]Ro 41-1049 to the active site of human monoamine oxidase-A," *Molecular Pharmacology*, vol. 37, Issue 3, Mar. 1990, pp. 358-366.
Clavaguera et al., "Brain homogenates from human tauopathies induce tau inclusions in mouse brain," *Proceedings of the National Academy of Sciences*, Jun. 2013, vol. 110, No. 23, pp. 9535-9540.
Fodero-Tavoletti et al., "$^{18}$F-THK523: a novel in vivo tau imaging ligand for Alzheimer's disease," *Brain*, 2011, 134, pp. 1089-1100.
Hashimoto et al., "Radiosynthesis, Photoisomerization, Biodistribution, and Metabolite Analysis of 11C-PBB3 as a Clinically Useful PET Probe for Imaging of Tau Pathology," *Journal of Nuclear Medicine*, Sep. 2014, vol. 55, No. 9, pp. 1532-1538.
Hostetler et al., "Preclinical Characterization of 18F-MK-6240, a Promising PET Tracer for In Vivo Quantification of Human Neurofibrillary Tangles," Journal of Nuclear Medicine, Oct. 2016, vol. 57, Issue 10, pp. 1599-1606.
International Search Report and Written Opinion, Patent Cooperation Treaty No. PCT/EP2019/059165, Jul. 10, 2019, ten pages.
Johnson et al., "AZD2184: a radioligand for sensitive detection of β-amyloid deposits," *Journal of Neurochemistry*, Mar. 2009, vol. 108, Issue 5, pp. 1177-1186.
Jureus et al., "Characterization of AZD4694, a novel fluorinated Aβ plaque neuroimaging PET radioligand," *Journal of Neurochemistry*, vol. 114, Issue 3, Aug. 2010, pp. 784-794.
Klingstedt et al., "Distinct Spacing Between Anionic Groups: An Essential Chemical Determinant for Achieving Thiophene-Based Ligands to Distinguish b-Amyloid or Tau Polymorphic Aggregates," *Chemistry—A European Journal*, Jun. 2015, vol. 21, Issue 25, pp. 9072-9082.
Klingstedt et al., "Synthesis of a library of oligothiophenes and their utilization as fluorescent ligands for spectral assignment of protein aggregates," *Organic & Biomolecular Chemistry*, Sep. 2011, vol. 9, Issue 24, pp. 8356-8370.
Klingstedt et al., "The Structural Basis for Optimal Performance of Oligothiophene-Based Fluorescent Amyloid Ligands: Conformational Flexibility is Essential for Spectral Assignment of a Diversity of Protein Aggregates," *Chemistry—A European Journal*, Jul. 2013, vol. 19, Issue 31, pp. 10179-10192.
Klunk et al., "Imaging Brain Amyloid in Alzheimer's Disease with Pittsburgh Compound-B," Annals of Neurology, Mar. 2004, vol. 55, Issue 3, pp. 306-319.
Kudo et al., "2-(2-[2-Dimethylaminothiazol-5-yl]Ethenyl)-6-(2-[Fluoro]Ethoxy) Benzoxazole: A Novel PET Agent for In Vivo Detection of Dense Amyloid Plaques in Alzheimer's Disease Patients," *The Journal of Nuclear Medicine*, Apr. 2007, vol. 48, No. 4, pp. 553-561.
Levine and Walker, "Molecular polymorphism of Aβ in Alzheimer's disease," *Neurobiology of Aging*, Apr. 2010, vol. 31, Issue 4, pp. 542-548.
Li et al., "Tau-based therapies in neurodegeneration: opportunities and challenges," *Nature Reviews Drug Discovery*, Dec. 2017, vol. 16, pp. 863-883.
Lu et al., "Molecular Structure of β-Amyloid Fibrils in Alzheimer's Disease Brain Tissue," *Cell*, vol. 154, Issue 6, Sep. 12, 2013, pp. 1257-1268.
Maarouf et al., "Histopathological and molecular heterogeneity among individuals with dementia associated with Presenilin mutations," *Molecular Neurodegeneration*, 2008, vol. 3, No. 20, 18 pages.
Maruyama et al., "Imaging of Tau Pathology in a Tauopathy Mouse Model and in Alzheimer Patients Compared to Normal Controls," *Neuron*, vol. 79, Issue 6, Sep. 18, 2013, pp. 1094-1108.
Morozova et al., "Conformational Features of Tau Fibrils from Alzheimer's Disease Brain Are Faithfully Propagated by Unmodified Recombinant Protein," *Biochemistry*, 2013, 52(40), pp. 6960-6967.
Mullard, A., "Pharma pumps up anti-tau Alzheimer pipeline despite first Phase III failure," *Nature Reviews: Drug Discovery*, vol. 15, Sep. 2016, pp. 591-592.
Murugan et al., "Cross-interaction of tau PET tracers with monoamine oxidase B: evidence from in silico modelling and in vivo imaging," *European Journal of Nuclear Medicine and Molecular Imaging*, 2019, 46:1369-1382.
Nilsson, "Small organic probes as amyloid specific ligands—Past and recent molecular scaffolds," *FEBS Letters: Protein Folding, Misfolding and Disease*, Aug. 20, 2009, vol. 583, Issue 16, pp. 2593-2599.
Qiang et al., "Structural variation in amyloid-β fibrils from Alzheimer's disease clinical subtypes," *Nature*, Jan. 2017, 541, pp. 217-221.
Ross and Poirier, "Protein aggregation and neurodegenerative disease," *Nature Medicine*, Jul. 2004, 10, pp. S10-S17.
Saint-Aubert et al., "Tau PET imaging: present and future directions," *Molecular Neurodegeneration*, 2017, vol. 12, Article 19, twenty-one pages.
Shirani et al., "A Palette of Fluorescent Thiophene-Based Ligands for the Identification of Protein Aggregates," Chemistry—A European Journal, Oct. 2015, vol. 21, Issue 43, pp. 15133-15137.
Shirani et al., "Synthesis of Thiophene-Based Optical Ligands That Selectively Detect Tau Pathology in Alzheimer's Disease," *Chemistry—A European Journal*, Dec. 2017, vol. 23, Issue 67, pp. 17127-17135.
Small et al., "PET of Brain Amyloid and Tau in Mild Cognitive Impairment," *The New England Journal of Medicine*, Dec. 21, 2006, 355:25, pp. 2652-2663.
Taghavi et al., "N'-Benzylidene-Benzohydrazides as Novel and Selective Tau-PHF Ligands," *Journal of Alzheimer's Disease*, Dec. 12, 2011, vol. 27, No. 4, pp. 835-843.
Tsugeno et al., "Regions of the Molecule Responsible for Substrate Specificity of Monoamine Oxidase A and B: A Chimeric Enzyme Analysis," *The Journal of Biochemistry*, vol. 118, Issue 5, Oct. 1995, pp. 974-980, https://doi.org/10.1093/jb/118.5.974.
Weyler et al., "Purification and properties of mitochondrial monoamine oxidase type A from human placenta," *Journal of Biological Chemistry*, vol. 260, Issue 24, Oct. 25, 1985, pp. 13199-13207.
Xia et al., "[$^{18}$F]T807, a novel tau positron emission tomography imaging agent for Alzheimer's disease," *Alzheimer's & Dementia*, vol. 9, Issue 6, Nov. 2013, pp. 666-676.
XP002791969, STN Database accession No. 387364-96-7, Jan. 28, 2002 (Jan. 28, 2002), Retrieved from the Internet: URL:Chemical Abstracts Service, Columbus, Ohio, US, one page.
XP002791970, STN Database accession No. 34812-99-1, Jan. 20, 2002 (Jan. 20, 2002), Retrieved from the Internet: URL:Chemical Abstracts Service, Columbus, Ohio, US, one page.
XP002791971, STN Database accession No. 887413-71-0, Jun. 12, 2002 (Jun. 12, 2002), Retrieved from the Internet: URL:Chemical Abstracts Service, Columbus, Ohio, US, one page.
Yang et al., "Brain Amyloid Imaging—FDA Approval of Florbetapir F18 Injection," *The New England Journal of Medicine*, Sep. 6, 2012, 367:10, pp. 885-887.
Zhang et al., "A Highly Selective and Specific PET Tracer for Imaging of Tau Pathologies," *Journal of Alzheimer's Disease*, Aug. 22, 2012, vol. 31, No. 3, pp. 601-612.
Enamine Advanced HTS Collection Catalogue, "Compound with CAS Registry No. 930868-12-5," Chemcats Abstract Accession No. 1472294918, accessed in Jun. 2019, 1 page.
Gleave, R.J., et al., "Synthesis and evaluation of 3-amino-6-aryl-pyridazines as selective CB(2) agonists for the treatment of inflammatory pain," Bioorganic & Medicinal Chemistry Letters 20(2):465-468, Elsevier, Netherlands (Jan. 2010).

(56) References Cited

OTHER PUBLICATIONS

International Search Report and Written Opinion for International Application No. PCT/EP2023/080605, European Patent Office, Netherlands, mailed on Feb. 2, 2024, 10 pages.
International Search Report and Written Opinion for International Application No. PCT/EP2020/079139, European Patent Office, Netherlands, mailed on Feb. 1, 2021, 16 pages.
United Kingdom Search for GB Application No. 1806004.6, United Kingdom Intellectual Property Office, United Kingdom, mailed on Dec. 10, 2018, 5 pages.
United Kingdom Search for GB Application No. 1914989.7, United Kingdom Intellectual Property Office, United Kingdom, mailed on Apr. 9, 2020, 2 pages.
Co-pending Application, U.S. Appl. No. 19/096,266, inventor Sohn, Daniel. D., filed Mar. 31, 2025 (Not yet Published).

* cited by examiner

Figure 7:

| Compound | t½ (min) |
|---|---|
| AZD2184 | 6.65 |
| Example Compound 43 | 379 |
| Example Compound 47 | 15.8 |
| Example Compound 43 | 8.21 |

Figure 8:

| Compound | MAO-A Binding<br>% inhibition of control |
|---|---|
| Example Compound 43 | -0.8 |
| Example Compound 48 | -2.2 |
| THK-5117 | 47 |

Figure 9:

| Compound | MAO-A activity<br>% inhibition of control | MAO-B recombinant enzyme activity<br>% inhibition of control |
|---|---|---|
| Example Compound 43 | -2.0 | 21 |
| Example Compound 48 | -0.3 | 7.7 |
| THK-5117 | 5.4 | 22.9 |

SELECTIVE LIGANDS FOR TAU AGGREGATES

CROSS-REFERENCE TO RELATED APPLICATIONS

This application is a National Stage of international PCT Patent Application No. PCT/EP2019/059165 filed on Apr. 10, 2019, which claims the benefit of Great Britain Patent Application Serial No. 1806004.6, filed on Apr. 11, 2018.

FIELD OF THE INVENTION

The present invention relates to compounds of formula (I) and compositions comprising compounds of formula (I). The compounds of the present invention are useful in the diagnosis and treatment of neurodegenerative diseases, and especially tauopathies such as Alzheimer's disease.

INTRODUCTION

Alzheimer's disease is a neurodegenerative disorder causing symptoms that include memory loss, difficulties with thinking, problem-solving, speech and/or language, personality changes, hallucinations, delusions, low mood and anxiety. It is the most common cause of dementia. Alzheimer's is a progressive disease and over time more symptoms develop, and the symptoms become more severe.

Protein deposits are the pathological hallmarks of a wide range of neurodegenerative diseases (C. A. Ross, M. A. Poirier, *Nat. Med.* 2004, 10, 10-17), including Alzheimer's disease and corticobasal degeneration. Small hydrophobic ligands that are selective for protein aggregates having an extensive cross β-pleated sheet conformation and sufficient structural regularity have been developed. The most common ligands are derivatives of Congo Red or thioflavins and a variety of other molecular scaffolds have also been reported (K. P. R. Nilsson, *FEBS Lett.* 2009, 583, 2593-2599). However, most of these ligands can only generally detect disease-associated protein aggregates, and they are not able to detect specific disease-associated protein aggregates consisting of a distinct protein.

The microtubule associated protein tau is one protein deposit shown to cause neurodegeneration. Tau can form intracellular fibrillary deposits in neurons and glial cells, and these tau deposits are linked to a large variety of disorders, collectively referred to as tauopathies. Tauopathies include more than 20 disorders including Alzheimer's disease, progressive supranuclear palsy (PSP), corticobasal degeneration (CBD), and Pick's disease. Although dysfunction of tau has unequivocally been shown to be able to cause neurodegeneration, the precise mechanisms of how tau is involved in neurodegenerative disorders is still poorly understood. According to currently emerging cell biological concepts, tau might play a role in the regulation of neuronal plasticity in a wide array of neuronal networks. In addition, it might be involved in regulating genome stability (Arendt, T., et al, Brain Research Bulletin, 2016, 126, 238-292).

In Alzheimer's disease, the two major proteinaceous deposits are extracellular senile plaques consisting of aggregated amyloid-β (Aβ) peptide and intraneuronal neurofibrillary tangles (NFTs) composed of aggregated tau (C. A. Ross, M. A. Poirier, *Nat. Med.* 2004, 10, 10-17; C. Ballatore, V. M. Y Lee, J. Q. Trojanowski. *Nat Rev Neurosci.* 2007, 8, 663-672). The development of ligands that can specifically target Aβ or tau deposits are essential for clinical diagnostic of Alzheimer's disease, as well as for evaluating the contribution of these respective aggregated species to the complex molecular pathology in Alzheimer's disease brain. Molecular scaffolds enabling visualization of Aβ deposits in humans with Alzheimer's disease by positron emission tomography (PET) imaging have been presented (W. E. Klunk, et al, *Ann. Neurol.* 2004, 55, 306-319; Y. Kudo, et al, *J. Nucl. Med.* 2007, 48, 553-561; and L. Yang, D., et al, *N. Engl. J. Med.* 2012, 367, 885-887). More recently, some molecular scaffolds targeting the other pathological hallmark in Alzheimer's disease, tau deposits, have also been recognized (G. W. Small, et al, *N. Eng. J. Med.* 2006, 355, 2652-2663; Taghavi, et al, *Alzheimers Dis.* 2011, 27, 835-843; M. T. Fodero-Tavoletti, et al, *Brain.* 2011, 134, 1089-1100; W. Zhang, et al, *Alzheimers Dis.* 2012, 31, 601-612; M. Maruyama, et al, *Neuron* 2013, 79, 1094-1108; and C. F. Xia, et al. *Alzheimers Dement.* 2013, 9, 666-676).

Luminescent conjugated oligothiophenes (LCOs) have been utilized for fluorescence imaging of protein aggregates. Compared to conventional ligands, LCOs have been shown to detect a wider range of disease-associated protein aggregates (A. Åslund, et al, ACS Chem. Biol. 2009, 4, 673-684; T. Klingstedt, et al, *Org. Biomol. Chem.* 2011, 9, 8356-8370; H. Shirani, et al, *Chemistry* 2015, 21, 15133-15137). In addition, LCOs having distinct chemical compositions can be utilized for spectral assessment of distinct protein aggregates, such as Aβ or tau deposits in Alzheimer's disease (T. Klingstedt, et al, *Chemistry* 2013, 19, 10179-1019; T. Klingstedt, et al, *Chemistry* 2015, 21, 9072-9082.). Lately, a thiophene based tetrameric ligand, q-FTAA-CN with a striking higher affinity for Aβ deposits than aggregated species composed of tau was identified (M. Back, et al, *Chemistry.* 2016, 22, 18335-18338).

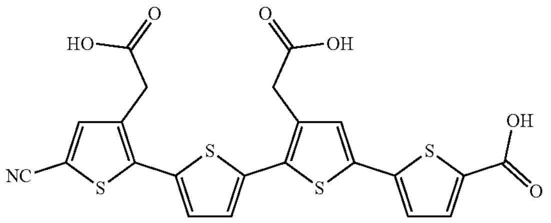

q-FTAA-CN

PBB3 is also known to be a tau specific ligand (M. Maruyama, et al, *Neuron* 2013, 79, 1094-1108).

PBB3

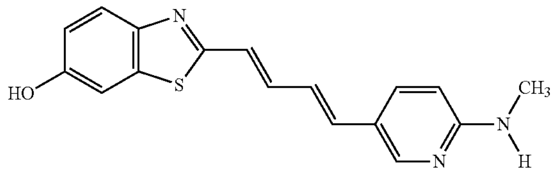

MK6240 is also known to be a tau specific ligand (E. D. Hostetler, et al, *J Nucl Med* 2016, 57, 1599-1606).

MK-6240

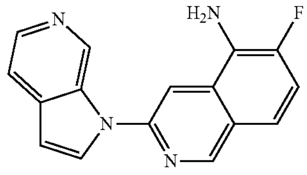

However, different morphotypes of Aβ and tau aggregates have been reported (C. L. Maarouf, 1 et al, *Mol. Neurodegener.* 2008, 3, 20; H. Levine, L. C. Walker, *Neurobiol. Aging* 2010, 31, 542-548; F. Clavaguera, et al, *Proc. Natl. Acad. Sci. USA* 2013, 110, 9535-9540; J. X. Lu, et al, *Cell* 2013, 154, 1257-1268; W. Qiang, et al, *Nature.* 2017, 541, 217-221). The existence of distinct aggregate morphotypes has been suggested to explain the heterogeneous phenotype reported for several neurodegenerative protein aggregation diseases. Hence, a variety of ligands will be necessary to achieve an accurate assessment of the diversity of pathological protein deposits present in neurodegenerative diseases, such as Alzheimer's disease. As such, there is a need to develop further small molecular ligands that target specific disease-associated protein aggregates, and in particular further molecular scaffolds enabling visualization of tau deposits, for example in humans with Alzheimer's disease (and other tauopathies).

Further, the known tau specific ligand PBB3 has been reported to have the significant disadvantage of undergoing photoisomerisation when exposed to fluorescent light (Hashimoto, H., et al, J Nucl Med (2014), Vol. 55, No. 9, pages 1532-1538). Hashimoto et al reported that at 1 min after exposure of a sample of $^{11}$C-PBB3 to fluorescent light, the radiochemical purity of $^{11}$C-PBB3 decreased to 77%, and from 10 to 60 min, the radiochemical purity was approximately 50%. Hashimoto et al also reported that the isomer of $^{11}$C-PBB3 that was formed showed much less specific binding to tau in the brain sections of Alzheimer's disease patients. This property makes PBB3 difficult to synthesize, radiolabel, store, and handle. This limits the practicality of using this tau ligand in in vitro experimentation and in vivo acquisitions (Saint-Aubert, L., et al, Molecular Neurodegeneration (2017), Vol. 12, No. 9*: Tau PET imaging: present and future directions*).

SUMMARY OF INVENTION

The invention provides a compound of formula (I), or a pharmaceutically acceptable salt, ester, amide or carbamate thereof, or a salt of such an ester, amide or carbamate, (I)

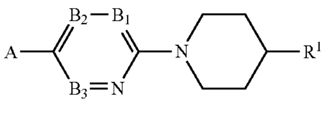

wherein

A is

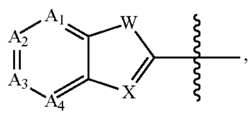

and $A_1$ and $A_4$ are independently selected from the group consisting of N and CH;

$A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

W is selected from the group consisting of O, S and NH;

X is selected from the group consisting of N and CH;

or A is

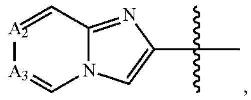

and $A_2$ is selected from the group consisting of N, $CR^2$ and CH and $A_3$ is selected from the group consisting of N and CH, or $A_2$ is selected from the group consisting of N and CH and $A_3$ is selected from the group consisting of N, $CR^2$ and CH;

$B_1$, $B_2$, and $B_3$, are each independently selected from the group consisting of N, CH and $CR^3$, wherein at least one of $B_1$, $B_2$, and $B_3$ is CH or $CR^3$;

$R^1$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; $C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$ alkylS; $C_{1-6}$alkylS═O; $C_{1-6}$alkyl$SO_2$; $NO_2$;

—$N(R^a)_2$; —$C_{1-6}alkylN(R^a)_2$; —$N(R^a)C(O)H$; —$N(R^a)C(O)C_{1-6}alkyl$ optionally substituted with 1, 2 or 3 halogen; $CO_2H$; $C(O)N(R^g)_2$; and —$C_{1-6}alkylC(O)N(R^g)_2$;

when present $R^3$ is selected from the group consisting of halogen; OH; $C_{1-6}$alkyl optionally substituted with 1, 2 or 3 halogen (preferably 1, 2 or 3 fluorine); and —$OC_{1-6}$alkyl optionally substituted with 1, 2 or 3 halogen (preferably 1, 2 or 3 fluorine);

when present $R^a$, $R^b$, $R^c$ and $R^d$ are each independently selected from the group consisting of H and $C_{1-6}$alkyl optionally substituted with 1, 2 or 3 halogen;

when present $R^3$ is selected from the group consisting of H or $C_{1-6}$alkyl optionally substituted with 1, 2 or 3 halogens;

when present $R^f$ is selected from the group consisting of H; halogen; —$CH_2$(halogen), —CH(halogen)$_2$, —C(halogen)$_3$, and OH;

when present each $R^g$ is independently selected from the group consisting of H; $C_{1-6}$alkyl; $C_{1-6}$alkyl substituted with 1, 2 or 3 halogen; $C_{1-6}$alkyl substituted with 1, 2 or 3 OH group; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group; and p is 2, 3, 4, 5, 6, 7 or 8.

For example, the compound of the invention is a compound of formula (I), or a pharmaceutically acceptable salt, ester, amide or carbamate thereof, or a salt of such an ester, amide or carbamate, with the proviso that the compounds is not selected from the group consisting of

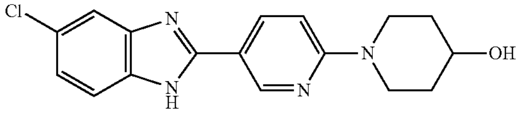

and

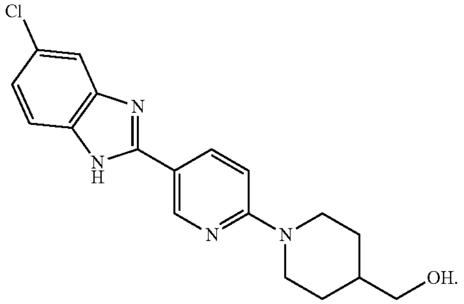

The invention also provides a pharmaceutical or diagnostic composition comprising a compound of formula (I), together with a pharmaceutically suitable carrier.

The invention further provides a compound of formula (I) (or a composition comprising a compound of formula (I)) for use as a diagnostic agent wherein the compound of formula (I) comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

The invention further provides the use of a compound of formula (I) for the detection of tau deposits.

The invention further provides a method of diagnosing a patient or monitoring disease progression in a patient comprising administering a compound of formula (I) (or a composition comprising a compound of formula (I)) to the patient, wherein the compound of formula (I) comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

The invention further provides a compound of formula (I) or a composition comprising a compound of formula (I), for use as a medicament.

BRIEF DESCRIPTION OF THE DRAWINGS

FIG. 7 shows the calculated half-life ($t_{1/2}$) in minutes of Example Compound 43, Example Compound 47 and Example Compound 48, and AZD2184 in rat brain tissue.

FIG. 8 shows the results of the MAO-A binding assay for Example Compound 43, Example Compound 48 and the known known tau specific ligand THK-5117 presented as % inhibition of control.

FIG. 9 shows the MAO enzyme and uptake assay results for Example Compound 43, Example Compound 48 and the known known tau specific ligand THK-5117 presented as % inhibition of control.

DETAILED DESCRIPTION

Figure 1:
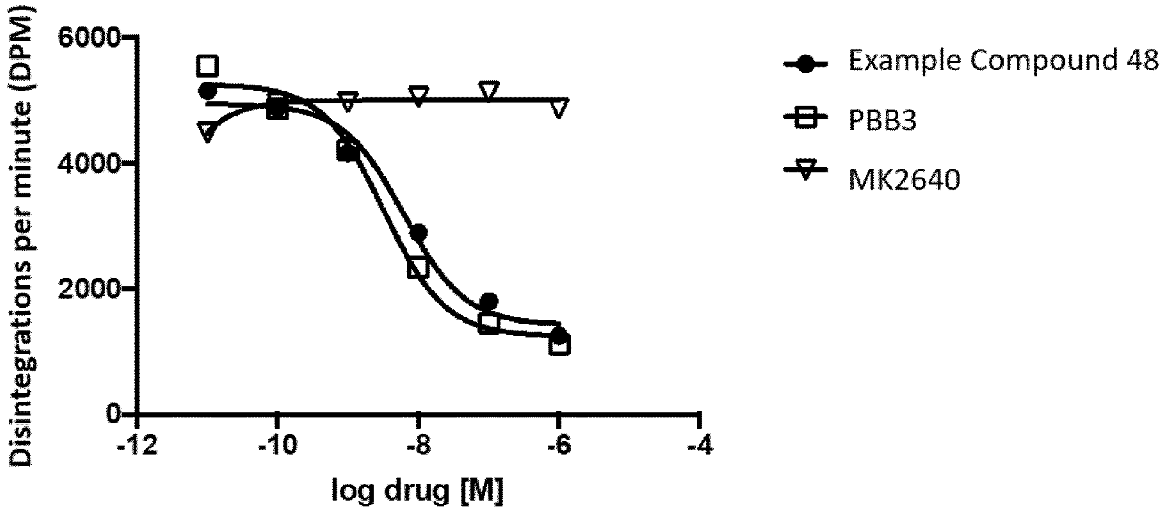
FIG. 1 shows the in vitro competitive binding of Example Compound 48 and the known tau specific ligands PBB3 and MK6240 to 0N4R tau fibrils for in the presence of [$^3$H]-Example Compound 68.

The present inventors have synthesized various compounds of formula (I) and shown that compounds of formula (I) have excellent binding affinity for tau deposits. The preferred compounds of the invention are also selective tau deposit ligands, i.e. as well as having excellent binding affinity for tau deposits, they also selectively bind tau deposits in preference to amyloid beta (Aβ) deposits.

Furthermore, the compounds of the present invention are not light sensitive, as they do not have a photoisomerisable double bonds in their structure. Therefore, they have significant advantages over the known tau selective ligand PBB3 with respect to their synthesis (including radiolabeling), storage, and handling, and can be feasibly used in in vitro experimentation and in vivo acquisitions.

A further advantage of the compounds of the invention is that the compounds bind to the four-repeat (4R) isomer forms of tau. 4R forms of tau are known to be present in various tauopathies, such as Alzheimer's disease, progressive supranuclear palsy and corticobasal degeneration. This makes the compounds of the invention especially useful for the diagnosis and/or the treatment or prophylaxis of conditions associated with 4R forms of tau, such as Alzheimer's disease, progressive supranuclear palsy and corticobasal degeneration.

A further advantage of the compounds of the invention is that they are expected to have low binding affinity for MAO enzymes in the human brain, as shown for Example Compounds 43 and 48 of the present invention in biological example (d), below. As reported in Murugan, N. A., et al, Eur J Nucl Med Mol Imaging. (2019) doi: 10.1007/s00259-019-04305-8, areas of the brain with the highest concentrations of MAO-B overlap with areas of tau pathology in taopathies such as CBD and PSP. Therefore, it is undesirable for a tau deposit ligand to have off-target binding to MAO, as such off-target effects severely limit the use of the tau deposit ligand for in vivo tau imaging. The compounds of the invention are expected to be specific to tau accumulation in the brain, and thus have good specificity and sensitivity when used as tau imaging agent in vivo in all taupathies, including CBD and PSP.

Isotopic forms, for example where a hydrogen atom is replaced with deuterium ($^2H$) or tritium ($^3H$), or a carbon atom is replaced with a $^{13}C$ atom, or a fluorine atom is replaced with a $^{18}F$ atom, are included within the invention. Certain isotopic forms may have beneficial biological properties, for example improved metabolic stability or enhanced therapeutic activity over other isotopic forms. Some specific isotopic forms may be useful for biological imaging purposes, for example carbon-11 ($^{11}C$), nitrogen-13 ($^{13}N$), oxygen-15 ($^{15}O$), fluorine-18 ($^{18}F$) or iodine-120 ($^{120}I$) isotopic variants may be used for positron emission tomography, and tritium ($H^3$) and iodine-125 ($I^{125}$) may be used for in vitro studies.

The present invention provides compounds of formula (I):

(I)

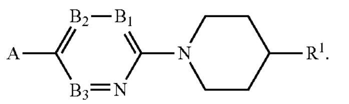

In the compound of formula (I), A may be

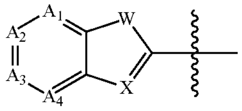

or

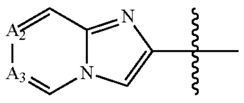

.

In embodiments where A is:

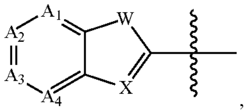

, $A_1$ and $A_4$ are independently selected from the group consisting of N and CH; $A_2$ is selected from the group consisting of N, $CR^2$ and CH, and $A_3$ is selected from the group consisting of N and CH, and wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH.

$A_1$ and $A_4$ may independently selected from the group consisting of N and CH; and $A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

In certain preferred embodiments, $A_1$ and $A_4$ are CH; or $A_1$ is N and $A_4$ is CH.

Preferably $A_1$ and $A_4$ are CH. Even more preferably, $A_1$ and $A_4$ are CH, and $A_2$ is selected from the group consisting of N, $CR^2$ and CH and $A_3$ is selected from the group consisting of N and CH; or $A_2$ is selected from the group consisting of N and CH and $A_3$ is selected from the group consisting of N, $CR^2$ and CH.

Even more preferably, $A_1$ and $A_4$ are CH, $A_2$ is selected from the group consisting of N and CH, and $A_3$ is selected from the group consisting of N, $CR^2$ and CH.

In other preferred embodiments, $A_1$ is N and $A_4$ is CH. Even more preferably, $A_1$ is N, $A_4$ is CH, $A_2$ is selected from the group consisting of N, $CR^2$ and CH, and $A_3$ is selected from the group consisting of N and CH; or $A_1$ is N, $A_4$ is CH, $A_2$ is selected from the group consisting of N and CH, and $A_3$ is selected from the group consisting of N, $CR^2$ and CH. Even more preferably, $A_1$ is N, $A_4$ is CH, $A_2$ is selected from the group consisting of N, $CR^2$ and CH, and $A_3$ is selected from the group consisting of N and CH.

In certain preferred embodiments, $A_2$ is selected from the group consisting of $CR^2$ and CH and $A_3$ is selected from the group consisting of N and CH. In another preferred embodiment, $A_2$ is selected from the group consisting of N and CH (and is preferably CH) and $A_3$ is selected from the group consisting of $CR^2$ and CH.

In certain preferred embodiments, $A_3$ and $A_4$ are independently selected from the group consisting of N and CH. In such embodiments, preferably at least three of $A_1$, $A_2$, $A_3$ and $A_4$ are CH or at least two of $A_1$, $A_2$, $A_3$ and $A_4$ are CH.

In one preferred embodiment, $A_1$ and $A_4$ are independently selected from the group consisting of N and CH, and:

$A_2$ is selected from the group consisting of N, $CR^2$ and CH, and $A_3$ is selected from the group consisting of N and CH, wherein at least three of $A_1$, $A_2$, $A_3$, and $A_4$ are CH, or wherein $A_2$ is $CR^2$ and at least two of $A_1$, $A_3$ and $A_4$ is CH; or $A_2$ is selected from the group consisting of N and CH, and $A_3$ is selected from the group consisting of N, $CR^2$ and CH, wherein at least three of $A_1$, $A_2$, $A_3$, and $A_4$ are CH, or wherein $A_3$ is $CR^2$ and at least two of $A_1$, $A_2$ and $A_4$ is CH.

More preferably, $A_1$ and $A_4$ are CH. For example, $A_1$ and $A_4$ are CH, and:

$A_2$ is selected from the group consisting of N, $CR^2$ and CH, and $A_3$ is selected from the group consisting of N and CH, wherein at least one of $A_2$ and $A_3$ is CH, or wherein $A_2$ is $CR^2$; or $A_2$ is selected from the group consisting of N and CH, and $A_3$ is selected from the group consisting of N, $CR^2$ and CH, wherein at least one of $A_2$ and $A_3$ is CH, or wherein $A_3$ is $CR^2$.

In another preferred embodiment, at least two of $A_1$, $A_2$, $A_3$, and $A_4$ are CH, for example three of $A_1$, $A_2$, $A_3$, and $A_4$ are CH. In one preferred embodiment each of $A_1$, $A_2$, $A_3$, and $A_4$ is CH.

In another preferred embodiment, at least one of $A_1$, $A_2$, $A_3$, and $A_4$ are CH and at least one of $A_1$, $A_2$, $A_3$, and $A_4$ is N, for example one of $A_1$, $A_2$, $A_3$, and $A_4$ is CH and two of $A_1$, $A_2$, $A_3$, and $A_4$ are N.

In another preferred embodiments three of $A_1$, $A_2$, $A_3$, or $A_4$ are CH, and the remaining $A_1$, $A_2$, $A_3$, or $A_4$ group is N or CH; or is N or $CR^2$; or is $CR^2$. For example, each of $A_1$, $A_2$, and $A_4$ are CH, and $A_3$ is N or CH; or $A_3$ is N or $CR^2$; or $A_3$ is $CR^2$. In another embodiment, each of $A_1$, $A_3$, and $A_4$ are CH, and $A_2$ is N or CH; or $A_2$ is N or $CR^2$; or $A_2$ is $CR^2$. In one preferred embodiment each of $A_1$, $A_3$, and $A_4$ are CH, and $A_2$ is $CR^2$ (and even more preferably, $R^2$ is O—$C_{1-6}$alkyl optionally substituted with 1, 2 or 3 halogen or OH groups).

In another preferred embodiment, $A_1$, $A_2$, $A_3$, and $A_4$ are independently selected from the group consisting of N and CH, wherein at least three of $A_1$, $A_2$, $A_3$, and $A_4$ are CH (for example $A_1$, $A_2$, and $A_4$ are CH, and $A_3$ is N or CH).

In an especially preferred embodiment, $A_1$ and $A_4$ are CH, $A_2$ is selected from the group consisting of $CR^2$ and CH, and $A_3$ is selected from the group consisting of N and CH; or $A_1$ and $A_4$ are CH, $A_2$ is selected from the group consisting of N and CH (and is preferably CH), and $A_3$ is selected from the group consisting of $CR^2$ and CH. Even more preferably, $A_1$ and $A_4$ are CH, $A_2$ is selected from the group consisting of $CR^2$ and CH (and preferably is $CR^2$), and $A_3$ is selected from the group consisting of N and CH (and preferably is CH).

In another especially preferred embodiments each of $A_1$ and $A_3$ is N, $A_3$ is CH, and $A_2$ is $CR^2$; or each of $A_2$ and $A_4$ is N, $A_1$ is CH, and $A_3$ is $CR^2$. Even more preferably $A_1$ and $A_3$ is N, $A_3$ is CH, and $A_2$ is $CR^2$ (and preferably $R^2$ is O—$C_{1-6}$alkyl optionally substituted with 1, 2 or 3 halogen or OH groups).

In embodiments where A is:

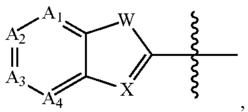
,

W is selected from the group consisting of O, S and NH; and X is selected from the group consisting of N and CH. In some preferred embodiments, W is selected from the group consisting of S or O. In other preferred embodiments, X is N. In certain embodiments W is selected from the group consisting of S or O, and X is selected from the group consisting of N or CH. In one preferred embodiment, W is S and X is N. In another preferred embodiment W is NH and X is CH.

In certain embodiments, W is S and X is CH; W is NH and X is N; or W is O and X is CH. In an especially preferred embodiment, W is S and X is N.

In certain embodiments, W is S and X is N or CH; W is NH and X is CH; or W is O and X is CH or N. More preferably W is S and X is N or CH; or W is NH and X is CH; or W is O and X is CH.

In another especially preferred embodiment, W is NH and X is CH.

In compounds where A is

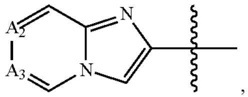
, preferably $A_2$ is selected from the group consisting of $CR^2$ and CH and $A_3$ is selected from the group consisting of N and CH, or $A_2$ is selected from the group consisting of N and CH (and is preferably CH) and $A_3$ is selected from the group consisting of $CR^2$ and CH. In certain preferred embodiments, $A_2$ is $CR^2$ and $A_3$ is selected from the group consisting of N and CH, or $A_2$ is selected from the group consisting of N and CH (and is preferably CH) and $A_3$ is $CR^2$.

In one preferred embodiment, $A_2$ is CH or N and $A_3$ is selected from the group consisting of N and CH, or $A_2$ is selected from the group consisting of N and CH (and is preferably CH) and $A_3$ is selected from the group consisting of CH or N (and is preferably CH).

$B_1$, $B_2$, and $B_3$ are each independently selected from the group consisting of N, CH and $CR^3$, wherein at least one of $B_1$, $B_2$, and $B_3$ is selected from the group consisting of CH and $CR^3$ (for example, two of $B_1$, $B_2$, and $B_3$ are independently selected from the group consisting of N, CH and $CR^3$, and one of $B_1$, $B_2$, and $B_3$ is selected from the group consisting of CH and $CR^3$). Preferably, at least two of $B_1$, $B_2$, and $B_3$ are selected from the group consisting of CH and $CR^3$ (for example, one of $B_1$, $B_2$, and $B_3$ is selected from the group consisting of N, CH and $CR^3$, and two of $B_1$, $B_2$, and $B_3$ are independently selected from the group consisting of CH and $CR^3$). For example, at least one of $B_1$, $B_2$, and $B_3$ is CH, and at least one of $B_1$, $B_2$, and $B_3$ (i.e. at least one of the remaining two of $B_1$, $B_2$, and $B_3$) is selected from the group consisting of $CR^3$ and CH. In certain preferred embodiments, at least two of $B_1$, $B_2$, and $B_3$ are CH.

In certain preferred embodiments, $B_1$ is N. In certain other preferred embodiments, $B_3$ is N.

In certain preferred embodiments, $B_1$, $B_2$, and $B_3$ are each independently selected from the group consisting of N, CH and $CR^3$, wherein at least one of $B_1$, $B_2$, and $B_3$ is CH, and at least one of $B_1$, $B_2$, and $B_3$ (i.e. at least one of the remaining two of $B_1$, $B_2$, and $B_3$) is selected from the group consisting of $CR^3$ and CH. Even more preferably, $B_1$, $B_2$, and $B_3$ are each independently selected from the group consisting of N, CH and $CR^3$, wherein at least two of $B_1$, $B_2$, and $B_3$ are CH.

In certain preferred embodiments, two of $B_1$, $B_2$, and $B_3$ are CH, and the other $B_1$, $B_2$, or $B_3$ group is selected from the group consisting of N and $CR^3$.

In one preferred embodiment $B_1$ and $B_2$ are selected from the group consisting of N and CH, and $B_3$ is selected from the group consisting of N, CH and $CR^3$, wherein at least one of $B_1$, $B_2$, and $B_3$ is CH or $CR^3$, and preferably at least two of $B_1$, $B_2$, and $B_3$ are CH and/or $CR^3$. For example, $B_1$ and $B_2$ are CH and $B_3$ is CH or $CR^3$ (and preferably $B_1$ and $B_2$ are CH and $B_3$ is $CR^3$), or $B_1$ is N, $B_2$ is CH, and $B_3$ is CH or $CR^3$ (and preferably $B_1$ is N, $B_2$ is CH, and $B_3$ is CH).

In another preferred embodiment, $B_2$ and $B_3$, are each independently selected from the group consisting of $CR^3$ and CH, and $B_1$ is selected from the group consisting of N, $CR^3$ and CH (for example, $B_1$ is N or CH). Preferably, $B_2$ and $B_3$ are each CH, and $B_1$ is selected from the group consisting of N, $CR^3$ and CH (for example, $B_1$ is N or CH). Even more preferably, $B_2$ and $B_3$ are each CH, and $B_1$ is N; or $B_1$, $B_2$, or $B_3$ are each CH. In an alternative embodiment, one of $B_2$ and $B_3$ is $CR^3$ and the other is CH, and $B_1$ is selected from the group consisting of N, $CR^3$ and CH (and preferably N and CH, for example $B_1$ is N, or $B_1$ is CH).

In another embodiment, $B_1$ and $B_2$ are each independently selected from the group consisting of $CR^3$ and CH, and $B_3$ is selected from the group consisting of N, $CR^3$ and CH (for example, $B_3$ is N or CH). Preferably, $B_1$ and $B_2$ are each CH, and $B_3$ is selected from the group consisting of N, $CR^3$ and CH (for example, $B_3$ is N or CH). Even more preferably, $B_1$ and $B_2$ are each CH, and $B_3$ is N; or $B_1$, $B_2$, and $B_3$ are each CH. In an alternative embodiment, one of $B_1$ and $B_2$ is $CR^3$ and the other is CH, and $B_3$ is selected from the group consisting of N, $CR^3$ and CH (and preferably N and CH, for example $B_3$ is N, or $B_3$ is CH).

In certain preferred embodiments, $B_1$ or $B_3$ is $CR^3$ (and preferably $B_1$ or $B_3$ is CF).

In embodiments wherein $B_1$, $B_2$, and/or $B_3$ may be $CR^3$ (especially in embodiments wherein $B_1$ or $B_3$ is $CR^3$) it is especially preferred that $R^3$ is F (i.e. preferably $B_1$, $B_2$ and/or $B_3$ are CF (for example $B_1$ is CF, or $B_3$ is CF).

In certain preferred embodiments, $B_2$ is CH.

In one especially preferred embodiment, $B_1$, $B_2$, and $B_3$ are each CH. In another especially preferred embodiment, two of $B_1$, $B_2$, and $B_3$ are CH, and one of $B_1$, $B_2$, and $B_3$ is CF. In another especially preferred embodiment, two of $B_1$, $B_2$, and $B_3$ are CH, and one of $B_1$, $B_2$, and $B_3$ is N.

In another especially preferred embodiment, $B_1$ and $B_2$ are each CH and $B_3$ is CH or $CR^3$ (more preferably $B_3$ is $CR^3$); or $B_2$ and $B_3$ are each CH and $B_1$ is CH or N (more preferably $B_1$ is N). In very especially preferred embodiment, $B_1$ and $B_2$ are each CH and $B_3$ is CH or CF (more preferably $B_3$ is CF); or $B_2$ and $B_3$ are each CH and $B_1$ is CH or N (more preferably $B_1$ is N).

$R^1$ may be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)— $N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$— $R^f$.

$R^1$ may also be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)— $N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$— $R^f$.

More preferably, $R^1$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)— $N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^1$ may also be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen;

—$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

Even more preferably, $R^1$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with with 1, 2 or 3 halogen.

Also preferably, $R^1$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In especially preferred embodiments, $R^1$ is selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen. $R^1$ may also be selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

Even more preferably, $R^1$ is selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F); C(O)—$N(H)_2$; and C(O)—O—$C_{1-3}$alkyl optionally substituted with 1, 2 or 3 halogen (preferably F). $R^1$ may also be selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); and —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F).

In certain very preferred embodiments, $R^1$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and more preferably wherein $R^1$ is selected from the group consisting of $C_{1-3}$alkyl optionally substituted with 1 OH group; C(O)—$N(H)_2$; and C(O)—O—$C_{1-3}$alkyl.

In another preferred embodiment, $R^1$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^1$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^1$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F); C(O)—$N(R^d)_2$; and C(O)—O—$C_{1-6}$alkyl optionally substituted with 1 halogen (preferably F).

In another preferred embodiment, $R^1$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^1$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^1$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F).

In another preferred embodiment, $R^1$ is selected from the group consisting of halogen (preferably F); —OH; —$C_1$alkyl optionally substituted with 1, 2 or 3 (preferably 1) halogen (preferably F) or OH groups; —O—$C_{1-6}$alkyl optionally substituted with 1, 2 or 3 (preferably 1) halogen (preferably F) or OH groups; C(O)—$N(R^d)_2$; and C(O)—O—$C_{1-6}$alkyl optionally substituted with 1, 2 or 3 (preferably 1) halogen (preferably F).

In another preferred embodiment, $R^1$ is selected from the group consisting of halogen (preferably F); —OH; —$C_1$alkyl optionally substituted with 1, 2 or 3 (preferably 1) halogen (preferably F) or OH groups; and —O—$C_{1-6}$alkyl optionally substituted with 1, 2 or 3 (preferably 1) halogen (preferably F) or OH groups.

In a further preferred embodiment, $R^1$ is —$C_{1-3}$alkyl optionally substituted with 1, 2 or 3 (preferably 1) halogen (preferably F) or OH groups, C(O)—N(H)$_2$ or C(O)—O—$C_{1-3}$alkyl.

In a further preferred embodiment, $R^1$ is —$C_{1-3}$alkyl optionally substituted with 1, 2 or 3 (preferably 1) halogen (preferably F).

In a further preferred embodiment, $R^1$ is C(O)—N(H)$_2$.

In a further preferred embodiment, $R^1$ is C(O)—O—$C_{1-3}$alkyl.

When present, each $R^2$ may be independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS; $C_{1-6}$alkylS═O; $C_{1-6}$alkylSO$_2$; NO$_2$; —N($R^a$)$_2$; —$C_{1-6}$alkylN($R^a$)$_2$; —N($R^a$)C(O)H; —N($R^a$)C(O)$C_{1-6}$alkyl optionally substituted with 1, 2 or 3 halogen; CO$_2$H; C(O)N($R^g$)$_2$; —$C_{1-6}$alkylCO$_2$H; and —$C_{1-6}$alkylC(O)N($R^g$)$_2$.

Preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS; $C_{1-6}$alkylS═O; $C_{1-6}$alkylSO$_2$; NO$_2$; —N($R^a$)$_2$; —$C_{1-6}$alkylN($R^a$)$_2$; —N($R^a$)C(O)H; —N($R^a$)C(O)$C_{1-6}$alkyl optionally substituted with 1, 2 or 3 halogen; C(O)N($R^g$)$_2$; and —$C_{1-6}$alkylC(O)N($R^g$)$_2$;

Preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; —N($R^a$)C(O)H; —N($R^a$)C(O)$C_{1-6}$alkyl optionally substituted with 1, 2 or 3 halogen; CO$_2$H; C(O)N($R^g$)$_2$; —$C_{1-6}$alkylCO$_2$H; and —$C_{1-6}$alkylC(O)N($R^g$)$_2$.

More preferably, when present, each $R^2$ is independently selected from the group consisting of halogen; OH; CN; $C_{1-6}$alkyl optionally substituted with 1, 2 or 3 halogen or OH groups; 0-$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; CO$_2$H; C(O)N($R^g$)$_2$; —$C_{1-6}$alkylCO$_2$H; and —$C_{1-6}$alkylC(O)N($R^g$)$_2$. Even more preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; and C(O)N($R^g$)$_2$.

In one preferred embodiment, when present, each $R^2$ is independently selected from the group consisting of halogen; OH; CN; O—$C_{1-6}$alkyl optionally substituted with 1, 2 or 3 halogen or OH groups; C(O)—O—$C_{1-6}$alkyl optionally substituted with 1, 2 or 3 halogen; and C(O)N($R^g$)$_2$. More preferably, when present, each $R^2$ is independently selected from the group consisting of halogen; OH; CN; O—$C_{1-3}$alkyl optionally substituted with 1, 2 or 3 halogen or OH groups; C(O)—O—$C_{1-3}$alkyl optionally substituted with 1, 2 or 3 halogen; and C(O)N($R^g$)$_2$. In such embodiments, when present, preferably $R^a$ is independently selected from the group consisting of H and $C_{1-6}$alkyl optionally substituted with 1 halogen, and more preferably $R^a$ is H; or, when present, $R^g$ is independently selected from the group consisting of H, $C_{1-6}$alkyl, and $C_{1-6}$alkyl substituted with 1 halogen (preferably F).

In an especially preferred embodiment, when present, each $R^2$ is independently selected from the group consisting of OH; O—$C_{1-6}$alkyl optionally substituted with 1, 2 or 3 halogen or OH groups; and C(O)N(H)$_2$. Even more preferably, each $R^2$ is independently selected from the group consisting of OH; O—$C_{1-3}$alkyl optionally substituted with 1 halogen; and C(O)N(H)$_2$. For example, each $R^2$ is independently selected from the group consisting of OH; O—$C_{1-3}$alkyl (preferably O-methyl); and C(O)N(H)$_2$.

In an especially preferred embodiment, when present, each $R^2$ is independently selected from the group consisting of OH and O—$C_{1-6}$alkyl optionally substituted with 1, 2 or 3 halogen (for example fluorine) or OH groups, and more preferably selected from the group consisting of OH and O—$C_{1-3}$alkyl optionally substituted with 1 halogen (for example fluorine) or OH group.

When present $R^3$ may be selected from the group consisting of halogen (e.g. F, Br, Cl, or I); OH; $C_{1-6}$alkyl optionally substituted with 1, 2 or 3 halogen (preferably 1, 2 or 3 fluorine); and —O$C_{1-6}$alkyl optionally substituted with 1, 2 or 3 halogen (preferably 1, 2 or 3 fluorine). Preferably, $R^3$ is selected from the group consisting of halogen (e.g. F, Br, Cl, or I); OH; $C_{1-3}$alkyl optionally substituted with 1, 2 or 3 halogen (preferably 1, 2 or 3 fluorine). More preferably, $R^3$ is selected from the group consisting of halogen (e.g. F, Br, Cl, or I); $C_{1-3}$alkyl optionally substituted with 1, 2 or 3 halogen (preferably 1, 2 or 3 fluorine) (for example $CH_2F$, $CHF_2$ or $CF_3$) and O—$C_{1-3}$alkyl optionally substituted with 1, 2 or 3 halogen (preferably 1, 2 or 3 fluorine) (for example $PCH_2F$, $PCHF_2$ or $PCF_3$). Even more preferably, $R^3$ is selected from the group consisting of halogen and —O$C_{1-6}$alkyl optionally substituted with 1 halogen (for example —$OCH_3$ or —$OCH_2F$). Most preferably, $R^3$ is halogen, and especially F.

When present $R^a$, $R^b$, $R^c$ and $R^d$ may each independently selected from the group consisting of H and $C_{1-6}$alkyl optionally substituted with 1, 2 or 3 halogen. Preferably, $R^a$, $R^b$, $R^c$ and $R^d$ are each independently selected from the group consisting of H and $C_{1-3}$alkyl optionally substituted with 1, 2 or 3 halogen (preferably F). In one embodiment, $R^a$, $R^b$, $R^c$ and $R^d$ may each independently selected from the group consisting of H and $C_{1-3}$alkyl (i.e. unsubstituted $C_{1-3}$alkyl). In another embodiments, $R^a$, $R^b$, $R^c$ and $R^d$ are each independently selected from the group consisting of H and $C_{1-3}$alkyl optionally substituted with 1 halogen (preferably F).

In one preferred embodiment, when present, $R^a$ is preferably H or $C_{1-3}$alkyl, and more preferably $R^a$ is H.

In one preferred embodiment, when present each $R^d$ is independently selected from the group consisting of H and $C_{1-3}$alkyl optionally substituted with 1 halogen (preferably F), and more preferably each $R^d$ is H.

When present $R^e$ is selected from the group consisting of H and $C_{1-6}$alkyl optionally substituted with 1, 2 or 3 halogens. Preferably, $R^e$ is selected from the group consisting of H and $C_{1-3}$alkyl optionally substituted with 1, 2 or 3 halogens. More preferably, $R^e$ is selected from the group consisting of H and $C_{1-3}$alkyl optionally substituted with 1 halogen (preferably F).

When present $R^f$ may be selected from the group consisting of H; halogen; —$CH_2$(halogen), —$CH_2$(halogen)$_2$, —C(halogen)$_3$ and OH. Preferably, $R^f$ is selected from the group consisting of H; halogen and OH. More preferably, $R^f$ is selected from the group consisting of H and halogen (preferably F).

When present, each $R^g$ may be independently selected from the group consisting of H, $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with 1 —$OS(O)_2CH_3$ group; and $C_{1-6}$alkyl substituted with 1 —$S(O)_2OCH_3$ group. Preferably, when present, each $R^g$ may be independently selected from the group consisting of H, $C_{1-6}$alkyl, $C_{1-6}$alkyl substituted with 1 halogen (preferably F); $C_{1-6}$alkyl substituted with 1 OH group; $C_{1-6}$alkyl substituted with 1 —$OC_{1-3}$alkyl group; $C_{1-6}$alkyl substituted with a —$OS(O)_2CH_3$ group; and $C_{1-6}$alkyl substituted with a —$S(O)_2OCH_3$ group. For example, when present, each $R^g$ may be independently selected from the group consisting of H, $C_{1-6}$alkyl, and $C_{1-6}$alkyl substituted with 1 halogen (preferably F); or selected from the group consisting of H, and $C_{1-6}$alkyl.

In one preferred embodiment, when present, one $R^g$ is H, and the second $R^g$ is selected from the group consisting of $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group. In another preferred embodiment, when present, one $R^g$ is $C_{1-6}$alkyl, and the second $R^g$ is selected from the group consisting of H, $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group. For example, when present one $R^g$ is H, and the second $R^g$ is selected from the group consisting of $C_{1-6}$alkyl, $C_{1-6}$alkyl substituted with 1, 2 or 3 halogen (preferably F); and $C_{1-6}$alkyl substituted with 1, 2 or 3 OH groups. Or, for example, when present, both $R^g$ groups (i.e. both groups of an "$(R^g)_2$") are $C_{1-6}$alkyl, or both are $C_{1-6}$alkyl substituted with 1, 2 or 3 halogen (preferably F); or both are $C_{1-6}$alkyl substituted with 1, 2 or 3 OH groups.

p may be 2, 3, 4, 5, 6, 7 or 8. Alternatively, in certain embodiments, p may be 1, 2, 3, 4, 5, 6, 7 or 8. Preferably, p is 3, 4, 5 or 6, and more preferably p is 3, 4 or 5. In certain preferred embodiments, p is 3.

In certain preferred embodiments, the compound of formula (I) has the formula (Ia)

(Ia)

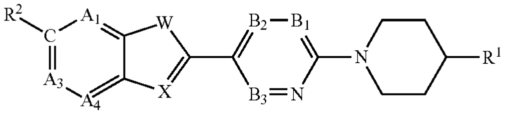

In such embodiments, preferably $A_1$, $A_3$, and $A_4$ are independently selected from the group consisting of N and CH, and at least one of $A_1$, $A_3$, and $A_4$ is CH (and preferably wherein each of $A_1$ and $A_4$ is CH, and $A_3$ is N or CH). In certain preferred embodiments, each of $A_1$, $A_3$, and $A_4$ is CH. In certain preferred embodiments, $A_1$ is N and $A_4$ is CH, and $A_3$ is N or CH; and even more preferably $A_1$ is N and $A_4$ is CH, and $A_3$ is N.

In embodiments wherein the compound of formula (I) is a compound of formula (Ia), especially preferably, W is S and X is N. Also preferably in embodiments wherein the compound of formula (I) is a compound of formula (Ia), W is NH and X is CH.

In embodiments wherein the compound of formula (I) is a compound of formula (Ia), preferably $R^2$ is selected from the group consisting of OH; O—$C_{1-6}$alkyl optionally substituted with 1, 2 or 3 halogen or OH groups; and C(O)N$(R^g)_2$ (for example C(O)N$(H)_2$). More preferably, $R^2$ is selected from the group consisting of OH; O—$C_{1-3}$alkyl optionally substituted with 1 halogen (for example fluorine) or OH group); and C(O)N$(H)_2$. Even more preferably $R^2$ is selected from the group consisting of OH and C(O)N$(H)_2$; or $R^2$ is independently selected from the group consisting of OH and O—$C_{1-3}$alkyl optionally substituted with 1 halogen (for example fluorine) or OH group).

In another preferred embodiment wherein the compound of formula (I) is a compound of formula (Ia), $A_1$, $A_3$, and $A_4$ are each CH. Especially preferably $R^2$ is H or O—$C_{1-6}$alkyl optionally substituted with 1, 2 or 3 halogen or OH groups. Also preferably, W is S and X is N. Also preferably, $B_1$, $B_2$ and $B_3$ are each CH. Also preferably, $R^1$ is selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen, and even more preferably selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group. Also preferably, $R^1$ is selected from the group consisting of —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—N$(R^d)_2$; and C(O)—O—$C_{1-6}$alkyl optionally substituted with 1 halogen (preferably F), and more preferably $R^1$ is selected from the group consisting of —$C_{1-6}$alkyl optionally substituted with 1 halogen (preferably F) or OH group; C(O)—N$(R^d)_2$ (preferably wherein each $R^d$ is H); and C(O)—O—$C_{1-6}$alkyl optionally substituted with 1 halogen (preferably F); and even more preferably wherein $R^1$ is selected from the group consisting of $C_{1-6}$alkyl optionally substituted with 1 OH group; C(O)—N$(H)_2$; and C(O)—O—$C_{1-6}$alkyl.

In another preferred embodiment wherein the compound of formula (I) is a compound of formula (Ia), $A_1$ is N, $A_4$ is CH, and $A_3$ is N or CH; and even more preferably where $A_1$ is N, $A_4$ is CH, and $A_3$ is N. Especially preferably $R^2$ is H or O—$C_{1-6}$alkyl optionally substituted with 1, 2 or 3 halogen or OH groups. Also preferably, W is S and X is N, or W is NH and X is CH, and even more preferably W is NH and X is CH. Also preferably, $B_1$, $B_2$ and $B_3$ are each CH; or $B_1$ and $B_2$ are CH and $B_3$ is $CR^3$ (and more preferably or $B_1$ and $B_2$ are CH and $B_3$ is $CR^3$). Also preferably, $R^1$ is selected from the group consisting of —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—$N(R^d)_2$; and C(O)—O—$C_{1-6}$alkyl optionally substituted with 1 halogen (preferably F), and more preferably $R^1$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and even more preferably wherein $R^1$ is selected from the group consisting of $C_{1-6}$alkyl optionally substituted with 1 OH group; C(O)—$N(H)_2$; and C(O)—O—$C_{1-6}$alkyl.

In certain preferred embodiments, the compound of formula (I) has the formula (Ib)

(Ib)

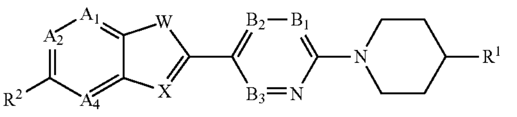

In such embodiments, preferably $A_1$, $A_2$, and $A_4$ are independently selected from the group consisting of N and CH, and at least one of $A_1$, $A_2$, and $A_4$ is CH (and preferably wherein each of $A_1$ and $A_4$ is CH, and $A_2$ is N or CH). In certain preferred embodiments, each of $A_1$, $A_2$, and $A_4$ is CH.

In embodiments wherein the compound of formula (I) is a compound of formula (Ib), especially preferably, W is S and X is N. Also preferably in embodiments wherein the compound of formula (I) is a compound of formula (Ib), W is NH and X is CH.

In embodiments wherein the compound of formula (I) is a compound of formula (Ib), preferably $R^2$ is OH; O—$C_{1-6}$alkyl optionally substituted with 1, 2 or 3 halogen or OH groups; or $C(O)N(R^g)_2$ (for example $C(O)N(H)_2$). More preferably, $R^2$ is selected from the group consisting of OH; O—$C_{1-3}$alkyl optionally substituted with 1 halogen; and $C(O)N(H)_2$. Even more preferably each $R^2$ is independently selected from the group consisting of OH and 0-$C_{1-3}$alkyl (preferably O-methyl). Also very preferably each $R^2$ is independently selected from the group consisting of OH and O—$C_{1-3}$alkyl optionally substituted with 1 halogen (for example fluorine).

In another preferred embodiment wherein the compound of formula (I) is a compound of formula (Ib), and each of $A_1$, $A_2$, and $A_4$ is CH. Especially preferably $R^2$ is selected from the group consisting of OH and O—$C_{1-3}$alkyl optionally substituted with 1 halogen. Also preferably, W is S and X is N or W is NH and X is CH, and even more preferably W is NH and X is CH. Also preferably, $B_1$, $B_2$ and $B_3$ are each CH; or $B_1$ and $B_2$ are CH and $B_3$ is $CR^3$; or $B_1$ is N and $B_2$ and $B_3$ are each CH (and more preferably or $B_1$ and $B_2$ are CH and $B_3$ is $CR^3$ or $B_1$ is N and $B_2$ and $B_3$ are each CH). Also preferably, $R^1$ is selected from the group consisting of —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—$N(R^d)_2$; and C(O)—O—$C_{1-6}$alkyl optionally substituted with 1 halogen (preferably F), and more preferably $R^1$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and even more preferably wherein $R^1$ is selected from the group consisting of $C_{1-6}$alkyl optionally substituted with 1 OH group; C(O)—$N(H)_2$; and C(O)—O—$C_{1-6}$alkyl.

In preferred embodiments of the invention, the compound of the invention is a compound of formula (I) (for example, a compound of formula (Ib)), with the proviso that the compounds is not selected from the group consisting of

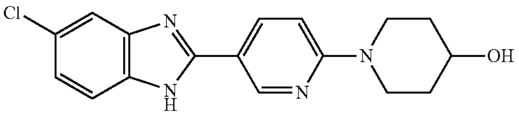

and

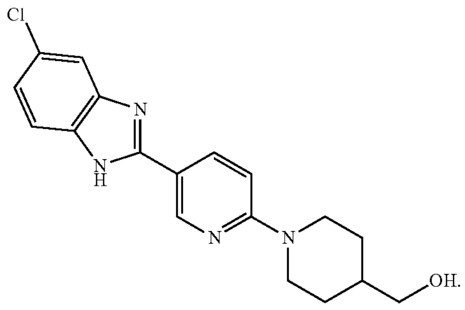

Compounds of formula (I) include, but are not limited to, the compounds specifically mentioned in the Examples herein (including pharmaceutically acceptable esters, amides, carbamates or salts thereof, including salts of such esters, amides or carbamates).

Preferred compounds of the invention are Example Compounds 1 to 77, described in the Examples section below.

In the compounds of the invention, one or more of the atoms may be an isotope. In the compounds of the invention, one or more of the atoms may be a radiolabeled atom (which may also be referred to as a radioisotope), for example one, two or three of the atoms may be a radiolabeled atom. In particular, one or more of the atoms of $R^1$, $R^2$, $R^3$ and/or $R^e$ may be a radiolabeled atom. A radiolabeled atom may be selected from the group consisting of $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^3H$, $^{11}C$, $^{14}C$, $^{13}N$, $^{15}O$, $^{18}F$, $^{19}F$, $^{120}I$, $^{123}I$ and $^{125}I$, more preferably $^3H$, $^{11}C$, $^{13}N$, $^{15}O$, $^{18}F$, $^{120}I$, $I^{123}$, and $^{125}I$, even more preferably $^{11}C$, $^{13}N$, $^{15}O$, and $^{18}F$, and most preferably $^{18}F$ and $^{11}C$.

Depending upon the substituents present in compounds of the formula (I), the compounds may form esters, amides, carbamates and/or salts. Salts of compounds of formula (I) which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of formula (I) and their pharmaceutically acceptable salts, and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids or bases. In particular, suitable salts formed with acids include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, hydroiodic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of formula (I) may have an appropriate group converted to an ester, an amide or a carbamate. Typical ester and amide groups formed from an acid group in the compound of the invention include —$COOR^h$, —$CONR^h_2$, —$SO_2OR^h$, or —$SO_2N(R^h)_2$, while typical ester and amide and carbamate groups formed from an —OH or a basic nitrogen of an aromatic heterocycle in the compound of the formula (I) include —$OC(O)R^h$, —$NC(O)R^h$, —$NCO_2R^h$, —$OSO_2R^h$, and —$NSO_2R^h$, where $R^h$ is selected from the group consisting of $C_{1-8}$alkyl, $C_{2-8}$alkenyl, $C_{2-5}$alkynyl, $C_{3-8}$cycloalkyl and $C_{3-8}$cycloalkyl$C_{1-8}$alkyl, halo$C_{1-8}$alkyl, dihalo$C_{1-8}$alkyl, trihalo$C_{1-8}$alkyl, phenyl and phenyl$C_{1-3}$alkyl; more preferably $R^h$ is selected from the group consisting of $C_{1-6}$alkyl, $C_{2-6}$alkenyl, $C_{2-6}$alkynyl, $C_{3-5}$cycloalkyl and $C_{3-8}$cycloalkyl$C_{1-6}$alkyl.

Those skilled in the art of organic chemistry will appreciate that many organic compounds can form complexes with solvents in which they are reacted or from which they are precipitated or crystallized. These complexes are known as "solvates". For example, a complex with water is known as a hydrate. Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that the compounds of formula (I), as well as esters, amides, carbamates and/or salts thereof may therefore be present in the form of solvates. Solvates of compounds of formula (I) which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of formula (I) and their pharmaceutically acceptable esters, amides, carbamates and/or salts thereof.

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, these are preferably methyl, ethyl, n-propyl, n-butyl groups. Among branched alkyl groups, there may be mentioned isopropyl, tertbutyl, isobutyl, 1-ethylpropyl and 1-ethylbutyl groups.

As used herein, the term "halogen" or "halo" means fluorine (F), chlorine (Cl), bromine (Br), or iodine (I).

Labeled Compounds of the Invention

Compounds of the invention may be labeled. A "label" (which may be a radiolabel or other detectable label, or a tag, marker, detectable marker, tracer, radiotracer or equivalent) is any atom or group suitable for imaging and/or assaying (for example, identifying, imaging, diagnosing, evaluating, detecting and/or quantitating) in vivo or in vitro, and in particular imaging and diagnosing. Suitable labels include, for example, radioisotopes (which may also be referred to as "radiolabeled atoms"), radionuclides, isotopes, positron emitters, gamma emitters, fluorescent groups, luminescent groups, chromogenic groups, biotin (in conjunction with streptavidin complexation) or photoaffinity groups. The type of label chosen will depend on the desired detection method. The position at which the label is integrated or attached to the compounds of the present invention is not particularly limited.

Examples of isotopes (such as radioisotopes, radionuclides, positron emitters and gamma emitters) which may be used to label compounds of the invention, include but are not limited to: $^{2}H$, $^{3}H$, $^{11}C$, $^{13}C$, $^{14}C$, $^{13}N$, $^{15}O$, $^{18}F$, $^{19}F$, $^{75}Br$, $^{76}Br$, $^{77}Br$, $^{120}I$, $^{123}I$, $^{124}I$, $^{125}I$ and $^{131}I$; preferably $^{2}H$, $^{3}H$, $^{11}C$, $^{13}N$, $^{15}O$, $^{18}F$, $I^{120}$, $I^{123}$ and $I^{125}$; more preferably $^{11}C$, $^{13}N$, $^{15}O$, $^{18}F$, $I^{120}$, and $I^{123}$; and even more preferably $^{18}F$.

Isotopic form (which also may be referred to as "isotopic variants") of the compounds of the invention can generally be prepared by conventional procedures such as by the methods described in the Examples section using appropriate isotopic variations of suitable reagents that are commercially available or prepared by known synthetic techniques. Radioisotopes, radionuclides, positron emitters and gamma emitters can be included into the compounds of the present invention by methods which are routine in the field of organic chemistry. For example, they may be introduced by using a correspondingly labeled starting material when the desired compound of the present invention is prepared. Illustrative methods of introducing detectable labels are described, for instance, in US 2012/0302755.

In certain preferred embodiments, compounds of the invention are labeled. In the compounds of the invention, one or more H, one or more C, one or more N, one or more O, one or more F, one or more Br, and/or one or I may be replaced with a $^{3}H$; $^{11}C$, $^{13}C$ or $^{14}C$; $^{13}N$; $^{15}O$; $^{18}F$ or $^{19}F$; $^{75}Br$ or $^{76}Br$; $^{120}I$, $^{123}I$, $^{125}I$ or $^{131}I$, respectively. Preferably one or more C, one or more N, one or more O, one or more F, and/or one or I may be replaced with a $^{11}C$ or $^{14}C$; $^{13}N$; $^{15}O$; $^{18}F$ or $^{19}F$; $^{120}I$, $^{123}I$ or $^{125}I$, respectively; and more preferably $^{11}C$, $^{13}N$, $^{15}O$, $^{18}F$ and $^{120}I$ respectively. $^{11}C$, $^{13}N$, $^{15}O$, $^{18}F$ and $^{120}I$ are radioactive isotopes. They decay mainly by positron emission. Therefore, the inclusion of such atoms in a compound of the invention makes the compound detectable by positron emission tomography. As such, compounds of the invention comprising one or more $^{11}C$, $^{13}N$, $^{15}O$, $^{18}F$ or $^{120}I$ are especially useful as a radioactive tracers, also referred to as a radioactive ligands, for positron emission tomography (PET).

In the compounds of the invention, one or more I may be replaced with an $^{123}I$ radioactive isotope. The inclusion of such an atom in a compound of the invention makes the compound detectable by single-photon emission computed tomography (SPECT). As such compounds of the invention comprising one or more $^{123}I$ are especially useful as a radioactive tracers for SPECT.

In the compounds of the invention, one or more H may be replaced with an $^{3}H$ radioactive isotope. The inclusion of such an atom in a compound of the invention makes the compound detectable by autoradiography or liquid scintillation counting. Compounds of the invention comprising one or more $^{3}H$ are especially useful as a radioactive tracers for in vitro studies.

In the compounds of the invention, one or more I may be replaced with an $^{125}I$ radioactive isotope. The inclusion of such an atom in a compound of the invention makes the compound detectable by autoradiography, gamma-counter crystal detectors, scintigraphy, gamma imaging, and SPECT. Compounds of the invention comprising one or more $^{125}I$ are especially useful as a radioactive tracers for in vitro studies and in vitro SPECT.

In certain preferred embodiments, labeled compounds of the invention may be labeled so that they may be detected in vivo using in vivo magnetic resonance spectroscopy (MRS), magnetic resonance imaging, PET, single-photon SPECT and combinations thereof. For example, a compound of the invention may be labeled with $^{19}F$ or $^{13}C$ for MRS/MRI; may be radiolabeled with $C^{11}$, $N^{13}$, $O^{15}$, $F^{18}$ or $I^{120}$ for PET imaging; or may be radiolabeled with $I^{123}$ or $I^{125}$ for SPECT. Preferably the compounds of the invention comprise one or more radioisotopes selected from $C^{11}$, $N^{13}$, $O^{15}$, $F^{18}$ and $I^{120}$.

The compounds of the invention comprise a number of C atoms. One or more C in a compound of the invention may be replaced with a $^{11}C$. For example, one C is replaced with one $^{11}C$; or two C are replaced with two $^{11}C$; or three C are replaced with three $^{11}C$. Preferably, one C is replaced with one $^{11}C$.

The compounds of the invention comprise one or more N. One or more N in a compound of the invention may be replaced with a $^{13}N$. For example, one N is replaced with a $^{13}N$; or (if present) two N are replaced with two $^{13}N$; or (if present) three N are replaced with three $^{13}N$. Preferably, if one at least one N is present in the compound of the invention, one N is replaced with a $^{13}N$.

For compounds of the invention comprising one or more O, one or more O in the compound may be replaced with an $^{15}O$. For example, (if present) one O is replaced with an $^{15}O$; or (if present) two O are replaced with two $^{15}O$; or (if present) three O are replaced with three $^{15}O$. Preferably, if one at least one O is present in the compound of the invention, one O is replaced with an $^{15}O$.

For compounds of the invention comprising one or more F, one or more F in the compound may be replaced with a $^{18}F$. For example, (if present) one F is replaced with a $^{18}F$; or (if present) two F are replaced with two $^{18}F$; or (if present) three F are replaced with three $^{18}F$. Preferably, if at least one F is present in the compound of the invention, one F is replaced with a $^{18}F$. Preferably one F is replaced with one $^{18}F$.

For compounds of the invention comprising one or more I, one or more I in the compound may be replaced with an $^{120}I$. For example, (if present) one I is replaced with an $^{120}I$; or (if present) two I are replaced with two $^{120}I$; or (if present) three I are replaced with three $^{120}I$. Preferably, if at least one I is present in the compound of the invention, one I is replaced with an $^{120}I$.

Alternatively, or additionally, for compounds of the invention comprising one or more I, one or more I in the compound may alternatively be replaced with an $^{123}I$ or $^{125}I$. For example, (if present) one I is replaced with an $^{123}I$ or $^{125}I$; or (if present) two I are replaced with two $^{123}I$ or two $^{125}I$; or (if present) three I are replaced with three $^{123}I$ or three $^{125}I$. Preferably, if at least one I is present in the compound of the invention, one I is replaced with an $^{123}I$ or $^{125}I$.

The compounds of the invention comprise a number of H atoms. One or more H in a compound of the invention may be replaced with a $^{3}H$. For example, one H is replaced with one $^{3}H$; or two H are replaced with two $^{3}H$; or three H are replaced with three $^{3}H$, or at least three H are replaced with at least three $^{3}H$. Preferably one H is replaced with one $^{3}H$.

Uses of Compounds of the Invention

The present invention provides compounds that are selective tau deposit/aggregate ligands. The terms "tau deposit ligand" and "tau aggregate ligand" as used herein are intended to cover any moiety which binds to a tau deposit (a tau deposit may also be referred to as a tau aggregate). For example, the compounds of the present invention may bind to one or more of: pathologically aggregated tau, hyperphosphorylated tau, neurofibrillary tangles, paired helical filaments, straight filaments, neurotoxic soluble oligomers, polymers and fibrils. The compounds of the present invention are particularly suitable for binding to various types of tau deposits (i.e. tau aggregates). In particular, the compounds of the invention are suitable for binding to tau deposits comprising 4R isomer forms of tau (i.e. tau aggregates comprising 4R isomer forms of tau).

Preferred compounds of the present invention have excellent binding affinity for tau deposits. For example, preferably compounds of the invention have an $IC_{50}$ value for tau deposits in a competitive binding assay that is less than 100 nM, preferably less than 70 nM, preferably less than 60 nM, more preferably less than 55 nM, more preferably less than 50 nM, more preferably less than 40 nM, more preferably less than 30 nM, more preferably less than 25 nM, more preferably less than 20 nM, and even more preferably less than 15 nM, for example less than 13 nM, less than 10 nM, less than 8 nM, less than 6 nM, less than nM, less than 4 nM, less than 3 nM, or less than 2 nM. In one preferred embodiment, compounds of the invention have an $IC_{50}$ value for tau deposits of less than 70 nM in a competitive binding assay. In another preferred embodiment, compounds of the invention have an $IC_{50}$ value for tau deposits of less than 50 nM in a competitive binding assay. In another preferred embodiment, compounds of the invention have an $IC_{50}$ value for tau deposits of less than 30 nM in a competitive binding assay. In another preferred embodiment, compounds of the invention have an $IC_{50}$ value for tau deposits of less than 20 nM in a competitive binding assay. In another preferred embodiment, compounds of the invention have an $IC_{50}$ value for tau deposits of less than 15 nM in a competitive binding assay. In another preferred embodiment, compounds of the invention have an $IC_{50}$ value for tau deposits of less than 10 nM in a competitive binding assay. In another preferred embodiment, compounds of the invention have an $IC_{50}$ value for tau deposits of less than 5 nM in a competitive binding assay. In another preferred embodiment, compounds of the invention have an $IC_{50}$ value for tau deposits of less than 3 nM in a competitive binding assay. It is especially preferred that compounds of the invention have an $IC_{50}$ value for tau deposits of less than 10 nM in a competitive binding assay Preferred compounds of the present invention, as well as having excellent binding affinity for tau deposits (for example binding for tau at a level described above in a competitive binding assay), are selective tau deposit ligands. "Selective", in this context, means any tau deposit ligand that binds to a tau deposit in preference to an Aβ deposit. For example, preferably compounds of the invention have a binding affinity for tau is at least 1.2 times that for Aβ, and more preferably at least 1.5 times, more preferably at least 2 times, more preferably at least 3 times, more preferably at least 5 times, more preferably at least 8 times, more preferably at least 10 times, more preferably at least 12 times, and even more preferably at least 15 times, for example at least 18 times, at least 20 times, at least 22 times, at least 25 times, at least 30 times, at least 40 times, at least 50 times, at least 100 times or at least 150 times. In one preferred embodiment, compounds of the invention have a binding affinity for tau that is at least 2 times that for Aβ. In one preferred embodiment, compounds of the invention have a binding affinity for tau that is at least 3 times that for Aβ. In another preferred embodiment, compounds of the invention have a binding affinity for tau that is at least 5 times that for Aβ. In another preferred embodiment, compounds of the invention have a binding affinity for tau that is at least 10 times that for Aβ. In another preferred embodiment, compounds of the invention have a binding affinity for tau that is at least 15 times that for Aβ. In another preferred embodiment, compounds of the invention have a binding affinity for tau that is at least 20 times that for Aβ. In another preferred embodiment, compounds of the invention have a binding affinity for tau that is at least 30 times that for Aβ. In an especially preferred embodiment, compounds of the invention have a binding affinity for tau that is at least 3 times that for Aβ.

In certain very preferred embodiments, compounds of the invention have a binding affinity for tau that is at least 3 times that for Aβ, and have an $IC_{50}$ value for tau deposits of less than nM in a competitive binding assay (and more preferably less than 20 nM, and most preferably less than 10 nM).

It is also preferred that the compounds of the invention have a C Log P that is less than 7.0, preferably less than 6.5, preferably less than 5.0, more preferably less than 4.5, more preferably less than 4.0, more preferably less than 3.5, and more preferably less than 3.0, for example less than 2.8, less than 2.5, less than 2.3, less than 2.0, or less than 1.8.

The compounds of the present invention find utility in the diagnosis and/or the treatment or prophylaxis of conditions associated with tau deposits. For example, the compounds of the present invention find utility in the diagnosis and/or treatment or prophylaxis of tauopathies, for example: Alzheimer's disease, corticobasal degeneration (CBD), Pick's disease, progressive supranuclear palsy (PSP), Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Straussler-Scheinker syndrome, British dementia, familial Danish dementia, dementia pugiiistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the C.379C>T (p.R127W) mutation in the CYP27A1 gene, TARDBP mutation p.IIe383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Straussler-Scheinker with tau, mutations in LRRK2, SLC9A6-related mental retardation, and white matter tauopathy with globular glial inclusions. The compounds of the present invention are especially useful in the diagnosis and/or treatment (in particular the diagnosis) of Alzheimer's disease, corticobasal degeneration, Pick's disease, Parkinson's disease, chronic traumatic encephalopathy and progressive supranuclear palsy; and even more especially Alzheimer's disease and corticobasal degeneration.

The compound of the invention may be for use as a therapeutic agent (or medicament) in the treatment of a disease or disorder associated with tau deposits (i.e. tauopathies), such as the tauopathies listed above.

The invention also provides a method for the treatment or prophylaxis of a condition associated with a disease or disorder associated with tau deposits (i.e. tauopathies) in a mammal (in particular in a human), which comprises administering to the mammal a therapeutically effective amount of a compound according to the invention, or a composition comprising a compound according to the invention together with a pharmaceutically acceptable carrier. Clinical conditions mediated by tau deposits that may be treated by the method of the invention are tauopathies, for example the tauopathies listed above.

The invention also provides the use of a compound according to the invention, for the manufacture of a medicament for the treatment or prophylaxis of a condition associated with a disease or disorder associated with tau deposits (i.e. tauopathies), for example the tauopathies listed above.

The compound of the invention may also be used as a diagnostic agents (for in vivo and/or in vitro diagnostic use) for the detection of tau deposits, and preferably for the selective detection of tau deposits.

The compounds of the invention may be used for diagnostic purposes because they have the ability to target a particular pathology (tau deposits) and can be detected at the desired site. The compounds of the invention are especially useful because they selectively bind to tau deposits over Aβ deposits. This makes the compounds of the invention especially useful for diagnosis of tauopathies, such as the tauopathies listed above, and in particular Alzheimer's disease and corticobasal degeneration. For example, compounds of the invention are able to detect the presence and the level of tau deposits in a patient with or suspected of having a disease or disorder associated with tau deposits (i.e. tauopathies), such as the tauopathies listed above. The compounds of the invention are also especially useful for diagnosis of tauopathies because the compounds of the invention do not show off-target MAO binding or inhibitory activity. As MAO are present in the brain in areas that overlap with tau pathology in certain tauopathies, such off-target effects are undesirable in tau deposit ligands.

The compounds of the invention can bind tau deposits both in vivo and in vitro. The compound of the invention may be for use as a diagnostic agent (for in vivo and/or in vitro diagnostic use) in the diagnosis of disease or disorder associated with tau deposits (i.e. tauopathies), such as the tauopathies listed above.

When used as a diagnostic agent, the compounds of the invention may optionally be in labeled form, as described above. Thus the present invention also provides the use of a compound of the invention in a labeled form for use as a diagnostic agent for the diagnosis of conditions associated with a disease or disorder associated with tau deposits (i.e. a tauopathy). In such embodiments, preferably the compound of the invention in labeled form comprises one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^{3}H$, $^{11}C$, $^{14}C$, $^{13}N$, $^{15}O$, $^{18}F$, $^{19}F$, $^{120}I$, $^{123}I$ and $^{125}I$, and more preferably $^{3}H$, $^{11}C$, $^{13}N$, $^{15}O$, $^{18}F$, $^{120}I$, $^{123}I$, and $^{125}I$. When used as a diagnostic agent (especially for in vivo use), and the compound is radioactively labeled, for example with $^{11}C$, $^{13}N$, $^{15}O$, $^{18}F$ or $^{120}I$ (preferably $^{18}F$), the compounds of the invention may be detected by positron emission topography. When used as a diagnostic agent (especially for in vivo use), and the compound is radioactively labeled, for example with $^{123}I$ or $^{125}I$, the compounds of the invention may be detected by SPECT. When used as a diagnostic agent (especially for in vitro use), and the compound is radioactively labeled, for example with $^{3}H$ or $^{125}I$, the compounds of the invention may be detected by autoradiography.

As mentioned above, the compounds of the invention may be used for diagnostic purposes because they have the ability to target a particular pathology (tau deposits) and can be detected at the desired site. As such, the compounds of the invention when used as diagnostic agents are especially useful as imaging agents. Imaging agents are compounds that allow the imaging of specific organs, tissues, diseases and physiological functions. Such imaging allows for diagnosing disease, monitoring disease progression, and tracking therapeutic response.

A compound of the invention when used as a diagnostic agent, and in particular as an imaging agent, may be detected via radioscintigraphy, assays, chemilumensence, electrochemiluminescence, near infrared luminescence, fluorescence, spectroscopy, autoradiography, liquid scintillation counting, gamma imaging, magnetic resonance imaging (MRI), magnetic resonance spectroscopy (MRS), scintigraphy, single-photon emission computed tomography (SPECT), computed tomography (CT scan), and/or positron emission tomography (PET).

In embodiments of the invention wherein the compound of the invention is for use as a diagnostic agent, and in particular as an imaging agent, the type of detection instrument available is a major factor in selecting if a label is required, and what label to choose. For example, where imaging requires an isotope to be detected, the type of detection instrument used will guide if a label is needed (i.e. is the isotope naturally occurring or not, and at what abundance is it present in when it occurs naturally), and, if so, what isotope to use. In one aspect, the compound of the invention is labeled, and the form of labeling chosen must have a type of decay detectable by a given type of instrument. Moreover, other considerations such as the half-life of the radioisotopes are taken into account when selecting an isotope label for in vivo imaging.

The compounds of the invention for use as diagnostic agents for in vivo imaging (in particular imaging of tau deposits and/or quantification of tau deposits) are preferably used in conjunction with non-invasive neuroimaging techniques such as in vivo MRS, MRI, PET, SPECT and combinations thereof. A compound of the invention may be labeled with $^{11}C$, $^{13}N$, $^{15}O$, $^{18}F$ or $^{120}I$, for PET imaging; or may be radiolabeled with $^{123}I$ (or $^{125}I$) for SPECT imaging. No labeling may be required for in vivo MRS or MRI, or a compound may be labeled with $^{13}C$ for MRS or MRI.

The present invention also provides a method of diagnosing a patient or monitoring disease progression in a patient comprising administering a compound of the invention to the patient. The method may further comprise detecting the compound of the invention in vivo at the site of interest in a patient (e.g. the brain) using PET or SPECT, or detecting the compound in a sample from the patient. Preferably in such embodiments the compound of the invention comprises one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^{3}H$, $^{11}C$, $^{14}C$, $^{13}N$, $^{15}O$, $^{18}F$, $^{19}F$, $^{120}I$, $^{123}I$ and $^{125}I$, and more preferably $^{11}C$, $^{13}N$, $^{15}O$, $^{18}F$ or $^{120}I$. The present invention also provides method of diagnosing a patient or monitoring disease progression in a patient comprising contacting a compound of the invention with a sample taken from the patient.

The method may further comprise detecting the compound of the invention using radioscintigraphy, assays, chemilumensence, electrochemiluminescence, autoradiography, near infrared luminescence, fluorescence, spectroscopy, liquid scintillation counting, gamma imaging, scintigraphy, magnetic resonance imaging (MRI), magnetic resonance spectroscopy (MRS), single-photon emission computed tomography (SPECT), or computed tomography (CT scan).

In the methods of diagnosing a disease or disorder associated with tau deposits as described herein, the method may comprise:

i) administering to the subject a diagnostically effective amount of a compound of the invention;

ii) allowing the compound of the invention to distribute into the tissue of interest (such as brain or body fluids such as cerebrospinal fluid (CSF)): and iii) imaging the tissue of interest, wherein an increase in binding of the compound of the invention to the tissue of interest compared to a normal or control level of binding indicates that the subject is suffering from or is at risk of developing a disorder associated with tau deposits.

The compounds of the invention can be used for imaging tau deposits in any sample or a specific body part or body area of a patient which suspected to contain tau deposits. The compounds of the invention are particularly suitable for imaging of tau deposits in the brain, as well as in body fluids such as cerebrospinal fluid (CSF).

Diagnosis of a disease or disorder associated with tau deposits in a patient may be achieved by detecting the specific binding of a compound according to the invention to the tau deposits in a sample or in situ, which includes:

(a) bringing the sample or a specific body part or body area suspected to contain the tau deposits (e.g. the brain and/or CSF) into contact with a compound of the invention which binds the tau deposits.

(b) allowing the compound of the invention to bind to the tau deposits to form a compound/tau deposits complex, (c) detecting the formation of the compound/tau deposits complex, (d) optionally correlating the presence or absence of the compound/tau deposits complex with the presence or absence of tau deposits in the sample or specific body part or area, and (e) optionally comparing the amount of the compound/tau deposits complex to a normal or control value, wherein an increase in the amount of the compound/tau deposits complex compared to a normal control value may indicate that the patient is suffering from or is at risk of developing a tau-associated disorder.

After the sample or a specific body part or body area has been brought into contact with the compound of the invention (e.g. the brain and/or CSF), the compound is allowed to bind to the tau deposits. The amount of time required for binding will depend on the type of test (e.g. in vitro or in vivo) and can be determined by a person skilled in the art by routine experiments.

The presence or absence of the compound/tau deposits is then optionally correlated with the presence or absence of tau deposits in the sample or specific body part or area. The amount of the compound/tau deposits complex can be compared to a normal or control value which has been determined in a sample or a specific body part or body area of a healthy subject, wherein an increase in the amount of the compound/tau deposits complex compared to a normal or control value may indicate that the patient is suffering from or is at risk of developing a disease or disorder associated with tau deposits (i.e. a tauopathy). The present invention also relates to a method of determining the amount of tau deposits in a tissue and/or a body fluid. This method comprises the steps of:

(1) providing a sample representative of the tissue and/or body fluid under Investigation (e.g. the brain and/or CSF);

(2) testing the sample for the presence of tau deposits with a compound of the present invention;

(3) determining the amount of compound bound to the tau deposits; and (4) calculating the amount of tau deposits in the tissue and/or body fluid.

The sample can be tested for the presence of tau deposits with a compound of the invention by bringing the sample into contact with a compound of the invention, allowing the compound of the invention to bind to the tau deposits to form a compound/tau deposit complex and detecting the formation of the compound/tau deposit as explained above.

Monitoring minimal residual disorder in a patient suffering from a disorder associated with tau deposits who has been treated with a therapeutic agent useful in the prevention or treatment of a disorder associated with tau deposits (for example a therapeutic agent useful in the prevention or treatment of one or more or the tauopathies listed above) may be achieved by:

carrying out steps (a) to (d) above; and (e) optionally comparing the amount of the compound/tau deposit complex to a normal or control value, wherein an increase in the amount of the complex compared to a normal or control value may indicate that the patient may still suffer from a minimal residual disease.

How steps (a) to (e) can be conducted has already been explained above.

Predicting responsiveness of a patient suffering from a disorder associated with tau deposits and being treated with a therapeutic agent useful in the prevention or treatment of a disorder associated with tau deposits can be achieved by carrying out steps (a) to (d) above; and (e) optionally comparing the amount of the compound/tau deposit complex to a normal or control value.

How steps (a) to (e) can be conducted has already been explained above.

In the method for predicting responsiveness the amount of the compound/tau deposits complex can be optionally compared at various points of time during the treatment, for instance, before and after onset of the treatment or at various points of time after the onset of the treatment. A change, especially a decrease, in the amount of the compound/tau deposits complex may indicate that the patient has a high potential of being responsive to the respective treatment.

A compound according to the present invention can also be incorporated into a test kit for detecting tau deposits. The test kit typically comprises a container holding one or more compounds according to the present Invention and instructions for using the compound for the purpose of binding to tau deposits to form a compound/tau deposit complex and detecting the formation of the compound/tau deposit complex such that presence or absence of the compound/tau deposit complex correlates with the presence or absence of the tau deposits.

Dosing

The amount of compound of the invention which is required to achieve a diagnostic or therapeutic effect will, of course, vary with the particular compound, the route of administration, the subject under treatment, including the type, species, age, weight, sex, and medical condition of the subject and the renal and hepatic function of the subject, and the particular disorder or disease being treated, diagnosed or monitored, as well as its severity. An ordinarily skilled physician, veterinarian or clinician can readily determine and prescribe the effective amount of the drug required to prevent, counter or arrest the progress of the condition or be used to diagnose a condition or the progression of a condition.

Oral dosages of the present invention, when used for as a diagnostic or therapeutic agent, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the compound of the invention for the symptomatic adjustment of the dosage to the patient to be treated. A medicament typically contains from about 0.01 mg to about 500 mg of the compound of the invention, preferably from about 1 mg to about 100 mg of compound of the invention. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. For diagnostic use, preferably the compounds of the present invention may be administered in a single daily dose. Furthermore, preferred compounds for the present invention can be administered in intranasal form via topical use of suitable intranasal vehicles, or via transdermal routes, using those forms of transdermal skin patches well known to those of ordinary skill in the art.

While it is possible for the compound of the invention to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier. Pharmaceutical compositions of the invention may take the form of a pharmaceutical formulation as described below.

Formulations

"Pharmaceutical" as used here does not necessarily mean therapeutic, for example, a pharmaceutical formulation may be used as a diagnostic agent, such as an imaging agent. The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient to be treated or diagnosed.

The formulations may conveniently be presented in unit dosage form and may be prepared by any of the methods well known in the art of pharmacy. All methods include the step of bringing the compound of the invention into association with the carrier which constitutes one or more accessory ingredients. In general the formulations are prepared by uniformly and intimately bringing into association the compound of the invention with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the compound of the invention; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The compound of the invention may also be presented as a bolus, electuary or paste.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for topical administration in the mouth, for example buccally or sublingually, include lozenges comprising the compound of the invention in a flavoured basis such as sucrose and acacia or tragacanth, and pastilles comprising the compound of the invention in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the compound of the invention.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient (i.e. sole therapeutic agent or sole diagnostic agent) in a medicament, it is also possible for the compound to be used in combination with one or more further active ingredient. For example, a compound of the invention may be used as the sole diagnostic agent in a diagnostic composition, or it is also possible for the compound to be used in combination with one or more further diagnostic agents and/or one or more therapeutic agents. Alternatively, a compound of the invention may be used as the sole diagnostic agents and/or therapeutic agent in a medicament, or it is also possible for the compound to be used in combination with one or more further therapeutic agents and/or one or more diagnostic agents.

Thus, the invention also provides a compound according to the invention together with a further diagnostic agent, for simultaneous, sequential or separate administration. Such further diagnostic agents may be further compounds according to the invention, or they may be different diagnostic agents. The further diagnostic agent may be an agent useful in the diagnosis of tauopathies (for example the tauopathies listed above).

In certain preferred embodiments, the further diagnostic agent may be an agent that is selective for Aβ deposits useful in diagnosis of Alzheimer's disease. The further diagnostic agent may be detectable by radioscintigraphy, magnetic resonance imaging (MRI), assays, chemilumensence, near infrared luminescence, fluorescence, autoradiography, liquid scintillation counting, gamma imaging, scintigraphy, magnetic resonance imaging, magnetic resonance spectroscopy, SPECT, computed tomography (CT scan) and/or positron emission tomography (PET). Preferably, the further diagnostic agent is detectable by positron emission tomography. For example, the further agent may be a PET ligand.

For example, the compounds of the invention may be effectively administered in combination with (or may be used in vitro for in vitro diagnosis with) effective amounts of one or more other diagnostic agents such as luminescent conjugated oligothiophenes (e.g. q-FTAA-CN, p-FTAA-CN, h-FTAA-CN), Pittsburgh compound B (PiB), fludeoxyglucose F 18 (FDG), florbetapir, flutemetamol, NAV4694, PBB3, AT-100, 4G8, Congo red, Thioflavin S, Thioflavin T, m-I-stilbene, chrysamine G, BF-277, TZDM, FDDNP, MeO-X-04, IMPY, NIAD-4 $^{3}$H-X-34, luminescent conjugated polythiophenes (e.g. polythiophene acetic acid (PTAA), tPTAA, POWT, tPOWT, POMT, tPOMY) and GTP1 (Genentech Tau Probe 1).

The invention further provides a compound according to the invention together with a further therapeutic agent, for simultaneous, sequential or separate administration. Such further therapeutic agents may be further compounds according to the invention, or they may be different therapeutic agents, for example an agent useful in the prevention or treatment of one or more or the tauopathies listed above. For example, the compounds of the invention may be effectively administered in combination with effective amounts of other agents such as antibodies (for example active immunisation (e.g. ACI-35 (AC Immune/Janssen), and AADvac1 (Axon Neuroscience)), passive immunization (e.g. tau antibodies, such as BMS-986168 (IPN007, Bristol-Myers Squibb Company), C2N-8E12 (C2N/AbbVie), and RG6100 (R07105705, AC Immune/Genentech; aducanumab; solanezumab; gantenerumab; and crenezumab), RG7345 (R06926496, MAb86, F. Hoffmann-La Roche), PHF1, 4E6G7, $6B_2G12$), MK-8719 (Merck & Co.), TPI-287 (Cortice Biosciences), methylene blue (for example TRx 0327 and Rember), dopaminergic treatments (for example levodopa, caridopa, dopamine agonists (e.g. bromocriptine, perfolide, pramipexole, ropinirole)), cholinesterase inhibitors (e.g. tacrine, donepezil, rivastigmine, galantamine), monoamine oxidase inhibitors (e.g. selegiline), antocholinerginc agents (e.g. trihexyphenidyl, benztropine mesylate, biperiden, procyclidine), antihistamine (e.g. diphenhydramine), antipsychotic drugs, analgesic drugs, anti-inflammatories, riluzole, non-steroidal anti-inflammatory drugs, caffein A2A receptor antagonists, CERE-120 (adeno-associated virus serotype 2-neurturin), amantadine, tolcapone, entacapone, ethosuximide, trazodone, and dibenzoylmethane.

The above other diagnostic and therapeutic agents, when employed in combination with the compounds of the present invention, may be used, for example, in those amounts indicated in the Physicians' Desk Reference (PDR) or as otherwise determined by one of ordinary skill in the art.

The compounds of the invention as described above, optionally in labeled form, also find use as a reference compound in methods of identifying ligands for the tau deposits. Thus, the invention provides a method of identifying a ligand for tau deposits which comprises use of a compound of the invention or a compound of the invention in labeled form, as a reference compound. For example, such a method may involve a competitive binding experiment in which binding of a compound of the invention to the tau deposits is reduced by the presence of a further compound which has tau deposits-binding characteristics, for example stronger tau deposits-binding characteristics than the compound of the invention in question.

Experimental

Synthesis of Compounds of the Invention

General Information

All reagents and solvents used were analytical grade and commercially available. Anhydrous reactions were routinely used for reactions. Reactions were typically run under inert atmosphere of nitrogen ($N_2$).

$^{1}$H Spectra were recorded on a Bruker 500 NMR spectrometer. Mass spectra were recorded on a Waters Acquity system (LC) and a single quadruple 3100 mass spectrometer. The mass spectrometer was equipped with an electrospray ion source (ES) operating in a positive or negative mode. The capillary voltage was 3.5 kV and the cone voltage was 30 V. The mass spectrometer was scanned between m/z 100-850 with a scan time of 0.5 s. The column temperature was set to 50° C. with a linear gradient starting at 95% A (A: 10 mM $NH_4HCO_3$) and ending in 100% B (B: MeCN). The column used was an Acquity UPLC™ BEH $C_{18}$ 1.7 µm, 2.1×50 mm run at 0.4 ml/min.

The HPLC used was an Agilent 1100 coupled to an Agilent 1290 Infinity DAD. The column used was an XBridge Cis 3.5 µm, 3.0×50 mm run at 0.8 ml/min. The column temperature was set to 50° C. with a linear gradient starting at 98-2% A over 3.5 min (A: 10 mM $NH_4HCOs$) then holding 98% B (B: MeCN) for 1.5 min.

The semi-prep was a Gilson with a 322 pump. The column used was a Kromasil $C_8$ 7 µm, 20×250 mm.

Microwave heating was performed in a Biotage Initiator 2.0.

Chromatography separations were performed using Silica gel 60 (0.040-0.063 mm) in a filter funnel or by using a Teledyne ISCO CombiFlash Rf with varying sizes (4-120 g) of RediSep Rf Silica columns. TLC plates were Merck Silica gel 60 $F_{254}$.

The term room temperature (rt) means, unless otherwise specified, a temperature between 16 and 25° C. The term reflux means, unless otherwise stated, in reference to an employed solvent using a temperature at or slightly above the boiling point of the named solvent.

General Procedures

General procedure 1 ('GP1'):

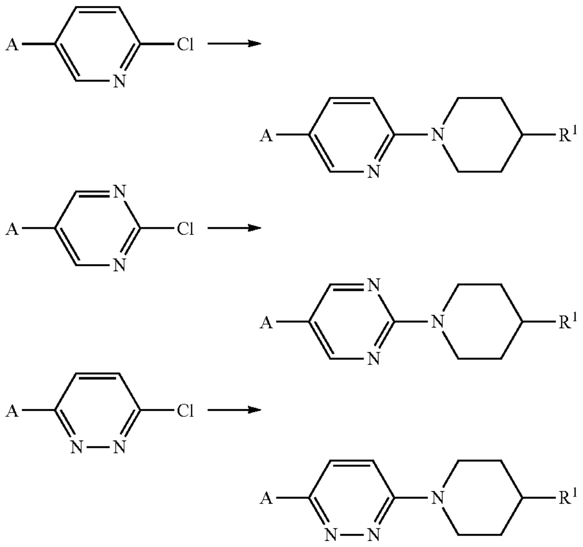

A chloro substituted pyridine/pyrimidine/pyrazine (1 equivalent) and a substituted piperidine (1.5-4 equivalents, for example 3 equivalents) or salt thereof were dissolved or slurried in a suitable solvent (for example NMP, DMF or an alcohol (ethanol or methanol)) and subjected to heat either by an oil bath or using the microwave at a temperature between 120-160° C. for 60 min to overnight (for example 90 min). Where the substituted piperidine is in the form of a HCl salt, an excess of triethylamine (TEA) is added.

The reaction was routinely run in methanol and the product was isolated, upon cooling of the reaction mixture, by cooling the solution and washing with cold methanol. In the cases where the product was impure then chromatography was used to isolate the pure product.

Synthesis of Intermediate Compounds

Intermediate 1: 2-(6-Chloro-3-pyridyl)-1,3-benzothiazole

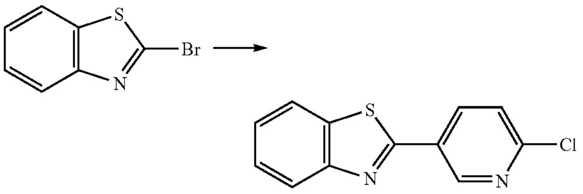

2-Bromo-1,3-benzothiazole (1.24 g, 7.5 mmol) and (6-chloro-3-pyridyl)boronic acid (1.19 g, 1.3 eq) were weighed into a 20 ml microwave vial and dissolved in DMF (14 ml). $N_2$ was bubbled through the mixture for >5 min. Tetrakis (0.40 g, 6 mol %) was then added followed by 2 M potassium carbonate (5.8 ml, 2 eq). $N_2$ was again bubbled through the mixture for 2 min and the vial was capped. The reaction mixture was subjected to the microwave at 70° C. for 16 h.

The reaction mixture was diluted with ethyl acetate and the solid was filtered, and washed with ethyl acetate. The organic phase was washed with water, treated with brine twice, dried over anhydrous $MgSO_4$, and the solvent was removed in vacuo to give the crude product.

The crude product was purified on the ISCO (80 g silica column, applied with DCM, eluted with 5-10% ethyl acetate/hexane over 8 min) to give 2-(6-chloro-3-pyridyl)-1,3-benzothiazole (0.75 g, solid). $^1$H-NMR (DMSO-d6) ∂ 9.12 (s, 1H), 8.51 (dd, 1H), 7.22 (d, 1H), 8.12 (d, 1H), 7.74 (d, 1H), 7.60 (t, 1H), 7.52 (t, 1H).

Intermediate 2: 2-(6-Chloropyridin-3-yl)-1,3-benzoxazole

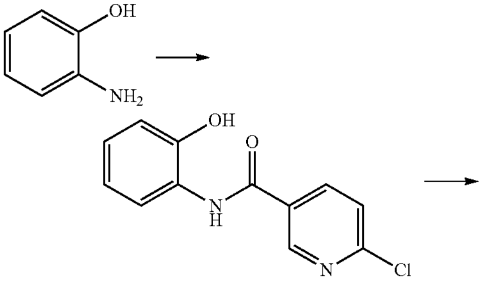

-continued

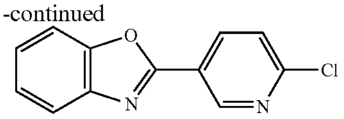

2-Aminophenol (2.0 g, 18.3 mmol) was dissolved in THF (40 ml) with triethylamine (TEA) (5.1 ml, 2 eq). 6-Chloropyridine-3-carbonyl chloride (3.6 g, 1.1 eq) dissolved in THF (20 ml) was added dropwise. The reaction mixture was then stirred for 15 min and then heated to reflux with a heat gun for 5 min.

The reaction mixture was allowed to cool and ether/water was added. The organic phase was separated, treated with brine, dried with $MgSO_4$, filtered, and the solvent was removed in vacuo to give the crude product. Ether was added to the crude product, the solid was titurated, filtered, and washed with ether to give 3.6 g solid crude product.

A portion of the crude product (2.4 g) was dissolved in THF (25 ml) and absolute ethanol (25 ml) added. The mixture was stirred and 2 M NaOH (20 ml) was added dropwise. The reaction mixture was stirred at room temperature (rt) overnight.

Most of the solvent was then removed and the mixture neutralized with 3 M HCl (12-13 ml). The solid was filtered, washed with water, dried (vacuum over $P_2O_5$) to give the pure intermediate 6-chloro-N-(2-hydroxyphenyl)pyridine-3-carboxamide (1.82 g, solid).

Hexachloroethane (4.38 g, 2.5 eq) was dissolved in DCM (70 ml), and triphenylphosphine (5.7 g, 3 eq) was added followed by TEA (8.1 ml, 8 eq). The reaction mixture was allowed to stir for 10 min and then the 6-chloro-N-(2-hydroxyphenyl)pyridine-3-carboxamide (1.8 g, 7.24 mmol) was added portionwise (4 portions). The reaction was monitored by HPLC, and after 10 min was found to be complete.

The reaction mixture was poured on a silica filter-funnel (10 cm, packed with DCM, eluted with DCM then 10% ethyl acetate/hexane (Rf 0.15)) to give 2-(6-chloropyridin-3-yl)-1,3-benzoxazole (1.31 g solid, 78% yield, $^1$H-NMR (DMSO-d6) ∂ 9.16 (d, 1H), 8.55 (dd, 1H), 7-80-7.87 (m, 2H), 7.77 (d, 1H), 7.42-7.51 (m, 2H).

Intermediate 3: 2-Chloro-5-{[1,3]oxazolo[4,5-c]pyridin-2-yl}pyridine

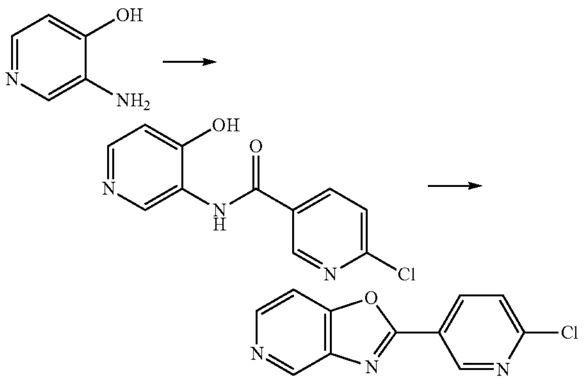

4-Hydroxy-3-aminopyridine (2.0 g, 18.2 mol) was slurried in THF (40 ml), and TEA (5 ml, 2 eq) was added. DMF (20 ml) was then added, followed by dropwise addition of 6-chloronicotinoyl chloride (3.52 g, 1.1 eq), dissolved in THF (20 ml). The reaction mixture was allowed to stir overnight.

The reaction mixture was then poured on ice/water, filtered, washed with water, washed with AcCN/ether 1:3, and then washed with ether to give the intermediate 6-chloro-N-(4-hydroxypyridin-3-yl)pyridine-3-carboxamide as a solid (3.38 g, 74% yield).

Hexachloroethane (1.19 g, 2.5 eq) was dissolved in DCM (20 ml), and triphenylphosphine (1.57 g, 3 eq) was added followed by TEA (2.2 ml, 8 eq). The reaction mixture was allowed to stir for 10 min then 6-chloro-N-(4-hydroxypyridin-3-yl)pyridine-3-carboxamide (0.5 g, 2.0 mol) was added portionwise (3 portions).

After 5 minutes the reaction mixture was poured on a silica filter-funnel (7 cm, packed with DCM) eluted with DCM then 60-65% ethyl acetate/hexane (Rf 0.15-0.20) to give the product, co-eluted with triphenylphosphine oxide (in every fraction).

The fractions were combined, the solvent was removed in vacuo, and 10-20 ml DCM was added. The mixture was cooled with an ice-bath, the solid that formed was filtered, and washed with cold DCM, to give 2-chloro-5-{[1,3]oxazolo[4,5-c]pyridin-2-yl}pyridine (265 mg solid, 53% yield), MS m/z (M+1)231.9, 233.9).

Intermediate 4: 2-(6-Chloropyridin-3-yl)-6-methoxy-1,3-benzothiazole

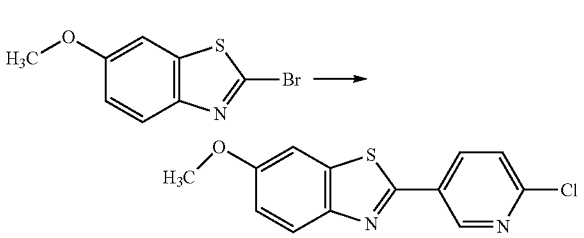

2-Bromo-6-methoxy-1,3-benzothiazole (0.73 g, 3.0 mmol) and (6-chloro-3-pyridyl)boronic acid (0.61 g, 1.3 eq) were weighed into a 20 ml microwave vial and dissolved in DMF (8 ml). $N_2$ was bubbled through the mixture. Tetrakis (0.21 g, 6 mol %) was then added followed by 2 M potassium carbonate (3 ml, 2 eq). $N_2$ was again bubbled through the mixture for 1 min and the vial was capped. The reaction mixture was subjected to the microwave at 75° C. for 4 h.

The reaction mixture was diluted with ethyl acetate, treated with brine, dried over anhydrous $MgSO_4$ and the solvent was removed in vacuo.

The crude product was purified on the ISCO (40 g silica column, applied with DCM, eluted with 10-40% ethyl acetate/hexane over 14 min) to give 2-(6-chloropyridin-3-yl)-6-methoxy-1,3-benzothiazole (240 mg solid, 37% yield). 1H-NMR (DMSO-d6) ∂ 9.04 (dd, 1H), 8.43 (dd, 1H), 7.99 (d, 1H), 7.77 (d, 1H), 7.70 (dd, 1H), 7.17 (dd, 1H), 3.86 (s, 3H).

Intermediate 5: {2-[4-(2-Hydroxyethyl)piperidin-1-yl]pyrimidin-5-yl}boronic acid

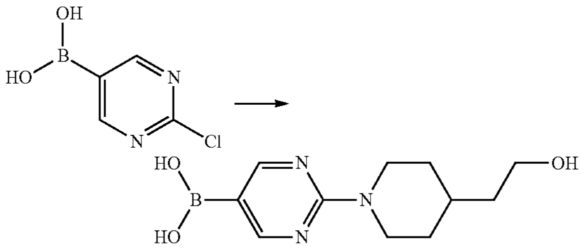

In a sealed vial, 2-chloropyrimidin-5-yl)boronic acid (1 eq) and 2-(piperidin-4-yl)ethan-1-ol (1 eq) were dissolved with triethylamine (TEA) (1.4 eq) in anhydrous methanol or absolute ethanol (2.5 ml/mmol boronic acid). The reaction was run in a preheated oil bath at 80° C. for 45 min. The progression of the reaction was monitored by the formation of the product mass (MS m/z $(M+1)_{252}$, (M−1): 250).

No purification was carried out, and the reaction mixture solution containing the crude {2-[4-(2-hydroxyethyl)piperidin-1-yl]pyrimidin-5-yl}boronic acid was used directly in the Suzuki reactions.

Intermediate 6: 5-(1-Benzofuran-2-yl)-2-chloropyridine

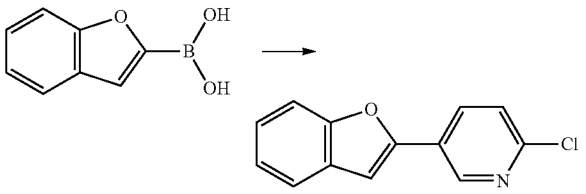

Benzofuran-2-boronic acid (1.0 g, 6.17 mmol) and 5-bromo-2-chloropyridine (1 eq) were weighed in a 20 ml microwave vial and then they were slurried in dioxane (8 ml). $N_2$ was bubbled through the mixture for >5 min. 2 M $Na_2CO_3$ (0.98 g, 1.5 eq), water (3 ml) and tetrakis (355 mg, 0.05 eq) were then added. $N_2$ was bubbled through the mixture for >5 min and the vial was capped. The reaction was run in a preheated oil bath at 80° C. for 30 min.

The reaction mixture was then was cooled, DCM added, the mixture decanted and washed with water, dried with $MgSO_4$, filtered, and then the solvent was was removed in vacuo give the crude product. The crude product that was purified on the ISCO to give 5-(1-benzofuran-2-yl)-2-chloropyridine (90 mg, 6% yield). $^1$H-NMR ($CDCl_3$) ∂ 8.99 (d, 1H), 8.08 (dd, 1H), 7.61 (d, 1H), 7.54 (d, 1 h), 7.41 (d, 1H), 7.34 (t, 1H), 7.27 (t, 1H), 7.12 (s, 1H).

Intermediate 7: 5-(1-Benzofuran-2-yl)-2-chloropyrimidine

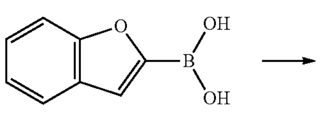

-continued

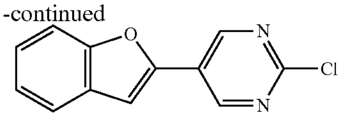

Benzofuran-2-boronic acid (1.0 g, 6.17 mmol) and 5-bromo-2-chloropyrimidine (1.19 g, 1 eq) were weighed in a 20 ml microwave vial and then they were slurried in dioxane (8 ml). $N_2$ was bubbled through the mixture for >5 min. Then 2 M $Na_2CO_3$ (0.98 g, 1.5 eq), water (3 ml) and tetrakis (355 mg, 0.05 eq) were added. $N_2$ was bubbled through for >5 min and the vial was capped. The reaction was run in a preheated oil bath at 90° C. for 18 h.

The reaction mixture was then cooled, DCM was added, then the organic phase was decanted and washed with water, dried with $MgSO_4$, filtered and the solvent was removed in vacuo to give the crude product.

Hexane/DCM was added to the crude product and the solid was filtered off. The filtrate was evaporated and then it was dissolved in about 5 ml DCM/hexane and applied to an 80 g silica column on the ISCO (eluted with 0-10% ethyl acetate/hexane over 5 minutes) to give 5-(1-benzofuran-2-yl)-2-chloropyrimidine (300 mg solid, 21% yield). TLC: 10% ethyl acetate/hexane 0.18. $^1$H-NMR (DMSO-d6) ∂ 7.29 (s, 2H), 7.76 (s, 1H), 7.75 (d, 1H), 7.68 (d, 1H), 7.41 (t, 1H), 7.32 (t, 1H).

Intermediate 8: 3-(1-Benzofuran-2-yl)-6-chloropyridazine

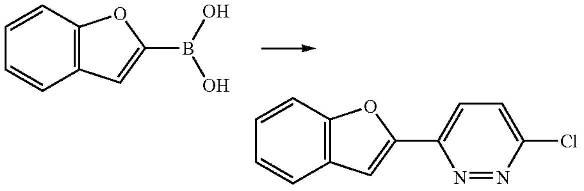

Benzofuran-2-boronic acid (1.0 g, 6.17 mmol) and 3,6-dichloropyridazine (1.19 g, 1 eq) were weighed in a 20 ml microwave vial and then they were slurried in dioxane (8 ml) and $N_2$ was bubbled through for >5 min. 2 M $Na_2CO_3$ (0.98 g, 1.5 eq), water (3 ml) and tetrakis (355 mg, 0.05 eq) were then added. $N_2$ was bubbled through for >5 min and the vial was capped. The reaction was run in a preheated oil bath at 90° C. for 2 h.

The reaction mixture was then cooled, DCM was added, then the organic phase was decanted and washed with water, dried with $MgSO_4$, filtered and the solvent was removed in vacuo to give the crude product.

DCM with some hexane was added to the crude product and the solid was filtered, washed with DCM/hexane 1:1 to give 3-(1-benzofuran-2-yl)-6-chloropyridazine (340 mg solid, 24% yield). TLC 15% ethyl acetate/hexane Rf 0.21. $^1$H-NMR (DMSO-d6) ∂ 8.31 (dd, 1H), 8.06 (dd, 1H), 7.90 (s, 1H), 7.80 (d, 1H), 7.74 (d, 1H), 7.46 (t, 1H), 7.36 (t, 1H).

Intermediate 9: 2-(6-Chloropyridin-3-yl)-1,3-benzothiazol-6-ol

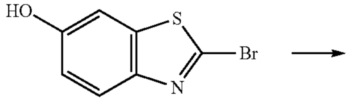

-continued

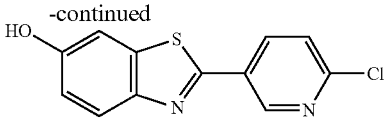

2-Bromo-5-hydroxybenzthiazole (176 mg, 77 μmol) and 2-chloropyridine-5-boronic acid (145 mg, 1.3 eq) were dissolved in DMF (2.2 ml) in a 5 ml microwave vial. $N_2$ was bubbled through the solution for 1 min and then tetrakis (50 mg, 6 mol %) and 2 M potassium carbonate (1.07 ml, 3 eq) were added. $N_2$ was bubbled through the solution again for >1 min. The vial was capped and the reaction was run in a preheated oil bath at 70° C. for 2 h.

The reaction mixture was then diluted with DCM/water, extracted three times with DCM, washed with water, dried with $MgSO_4$, filtered, and the solvent was removed in vacuo to give the crude product.

The crude product was purified on the ISCO (40 g silica, applied DCM, eluted with 10-30% ethyl acetate/hexane over 10 min) to give 2-(6-chloropyridin-3-yl)-1,3-benzothiazol-6-ol (103 mg solid, 51% yield, MS m/z (M−1) 260.9, 262.8).

Intermediate 12-1: [1-(5-Bromo-6-fluoropyridin-2-yl)piperidin-4-yl]methanol

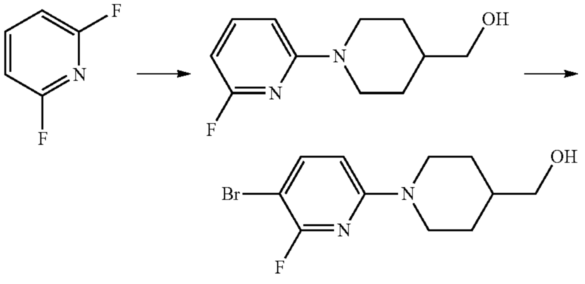

Difluoropyridine (1.6 ml, 17.4 mmol) was dissolved in dioxane (15 ml) and 4-piperidinemethanol (2.0 g, 1 eq) was added followed by Hunig's base (4.5 ml, 1.5 eq). The reaction was heated to reflux for 1 h.

The reaction mixture was diluted with ethyl acetate, washed with water, treated with brine, dried with $MgSO_4$, filtered and the solvent was removed in vacuo to give the crude product.

The crude product was purified on the ISCO (40 g silica, applied with DCM, eluted with 25-40% ethyl acetate/hexane over 5 min) to give 1.94 g oil (53% yield, MS m/z $(M+1)_{211}$).

The oil (1.94 g, 9.2 mmol) was dissolved in acetonitrile (50 ml), cooled with an ice-bath and NBS (1.8 g, 1.1 eq) was added. The reaction was allowed to stir at rt for 1 h. The reaction mixture was poured onto ice and was allowed to stir overnight.

The reaction mixture was diluted with ethyl acetate, washed with water, treated with brine, dried with $MgSO_4$, filtered and the solvent was removed in vacuo to give the crude product.

The crude product was purified on the ISCO (40 g silica, applied with DCM, eluted with 25-50% ethyl acetate/hexane over 10 min) to give [1-(5-bromo-6-fluoropyridin-2-yl)piperidin-4-yl]methanol (1.78 g solid, 67% yield, MS m/z (M+1) 289, 291). TLC: 50% ethyl acetate Rf 0.18.

Intermediate 12-2:2-[1-(5-Bromo-6-fluoropyridin-2-yl)piperidin-4-yl]ethan-1-ol

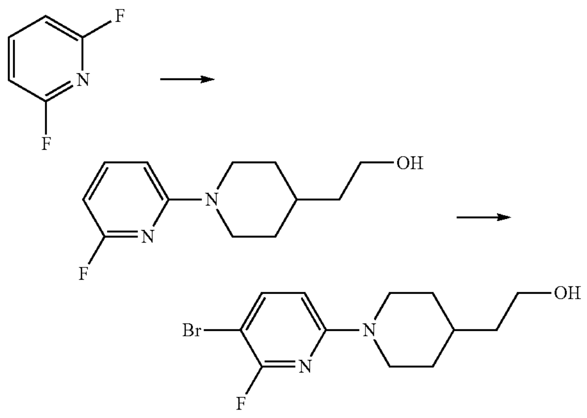

4-Piperidineethanol (0.35 g, 2.7 mmol) was dissolved in dioxane (4 ml) and difluoropyridine (300 μl, 1.2 eq) was added followed by Hunig's base (700 μl, 1.5 eq). The reaction was heated to reflux overnight.

The reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 20-35% ethyl acetate/hexane over 4 min) to give a clear oil (414 mg, 68% yield, M+1 225). TLC: 50% ethyl acetate/hexane Rf 0.25.

The oil (414 mg, 1.85 mmol) was dissolved in acetonitrile (10 ml), cooled with an ice-bath and N-bromosuccinimide (NBS) (345 mg, 1.1 eq) was added. The reaction was allowed to stir at rt for 1 h. The reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 20-25% ethyl acetate/hexane over 8.5 min) to give 2-[1-(5-bromo-6-fluoropyridin-2-yl) piperidin-4-yl]ethan-1-ol (425 mg solid, 76% yield), MS m/z (M+1) 303, 305.

Intermediate 15: {2-[1-(5-Bromopyridin-2-yl)piperidin-4-yl]ethan-1-ol

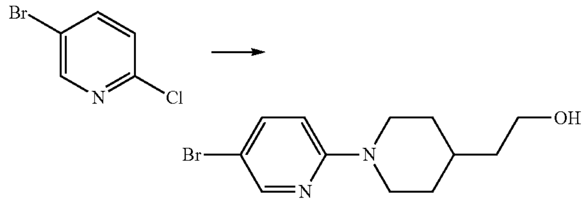

5-Bromo-2-chloropyridine (300 mg, 1.56 mmol) and 4-piperidineethanol (600 mg, 3 eq) mixed with methanol (12 ml) were added to a 20 ml microwave vial, and TEA (435 μl, 2 eq) added. The reaction vial was capped and the reaction was subjected to the microwave for 6 h at 160° C.

The cooled reaction mixture was diluted with ethyl acetate, washed with water, treated with brine, dried with $MgSO_4$, filtered and the solvent was removed in vacuo to give the crude product.

The crude product was purified on the ISCO (24 g silica, applied with DCM, eluted with 20-40% ethyl acetate/hexane over 10 min) to give {2-[1-(5-bromopyridin-2-yl)piperidin-4-yl]ethan-1-ol (286 mg solid, 64% yield, MS m/z (M+1) 285.2, 287.2). TLC: 50% ethyl acetate/hexane Rf 0.23.

Intermediate 16: tert-Butyl 2-{6-[4-(2-hydroxyethyl)piperidin-1-yl]pyridin-3-yl}-5-methoxy-1H-indole-1-carboxylate

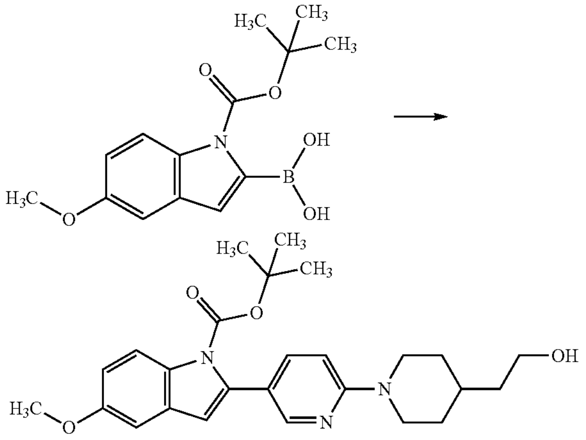

{1-[(tert-Butoxy)carbonyl]-5-methoxy-1H-indol-2-yl}boronic acid (122 mg, 1.2 eq) and {2-[1-(5-bromopyridin-2-yl)piperidin-4-yl]ethan-1-ol (intermediate 15) (100 mg, 0.35 mmol) were dissolved in dioxane (2.1 ml) in a 5 ml microwave vial. The solution was bubbled with $N_2$ for 2.5 min, then $Pd(dppf)Cl_2$ DCM 1:1 complex (14 mg, 5 mol %) was added, followed by 2 M $K_2CO_3$ (0.53 ml, 3 eq). The solution was again bubbled with $N_2$ for 5 min then the vial was capped. The reaction was run in a preheated oil bath at 90° C. overnight.

The reaction mixture was cooled then filtered through silica, washed with ethyl acetate, washed with water, treated with brine, dried with $MgSO_4$, filtered and the solvent was removed in vacuo to give the crude product.

The crude product was purified on the ISCO (12 g silica, applied with DCM, eluted with 30-55% ethyl acetate/hexane over 8 min) to give tert-butyl 2-{6-[4-(2-hydroxyethyl) piperidin-1-yl]pyridin-3-yl}-5-methoxy-1H-indole-1-carboxylate (130 mg film, 82% yield, MS m/z (M+1) 452). TLC: 50% ethyl acetate/hexane Rf 0.15.

Intermediate 17: 6-[(tert-Butyldimethylsilyl)oxy]-2-(6-chloropyridin-3-yl)-1,3-benzothiazole

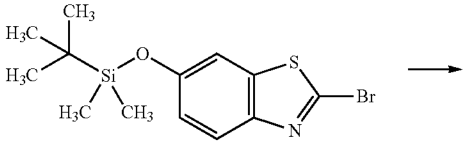

-continued

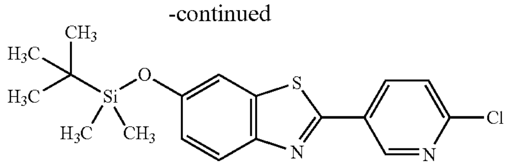

In a 20 ml microwave vial, 2-chloropyridine-5-boronic acid (315 mg, 2.0 mmol) and 2-bromo-6-[(tert-butyldimethylsilyl)oxy]-1,3-benzothiazole (720 mg, 1.05 eq) were dissolved in dioxane (12 ml). The solution was bubbled with $N_2$ for 3 min, then Pd(dppf)$Cl_2$ DCM 1:1 complex (82 mg, 5 mol %) was added, followed by 2 M $K_2CO_3$ (3 ml, 3 eq). The solution was again bubbled with $N_2$ for 5 min then the vial was capped. The reaction was run in a preheated oil bath at 90° C. for 30 min.

To the cooled reaction mixture ethyl acetate was added, the aqueous phase was removed, dried with $MgSO_4$, filtered and the solvent was removed in vacuo to give the crude solid.

The crude product was purified on the ISCO (40 g silica, applied with toluene, eluted with 0-6% ethyl acetate/hexane over 6 min) to give 6-[(tert-butyldimethylsilyl)oxy]-2-(6-chloropyridin-3-yl)-1,3-benzothiazole (0.50 g oil, 66% yield, MS m/z (M+1) 377.2). TLC: 5% ethyl acetate/hexane Rf 0.15.

Intermediate 18: {2-[4-(Hydroxymethyl)piperidin-1-yl]pyrimidin-5-yl}boronic acid

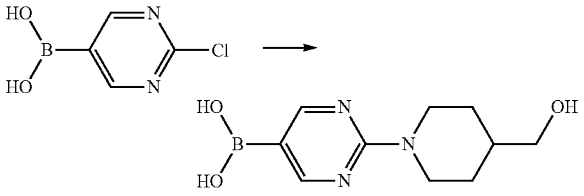

In a 20 ml microwave vial, 2-chloropyrimidine-5-boronic acid (320 mg, 2 mmol) and 4-piperidinemethanol (240 mg, 1.05 eq) were dissolved in absolute ethanol (5 ml) and triethylamine (340 µl, 1.2 eq) added. The reaction was bubbled with $N_2$ for 30 s and the vial was then capped and the reaction was run in a preheated oil bath at 80° C. for 30 min.

The cooled mixture was used as is (in solution without isolation) in the Suzuki reactions (m/z (M+1) 238.3, (M−1) 236.2).

Intermediate 19:2-(6-Chloropyridin-3-yl)-1,3-benzoxazol-6-ol

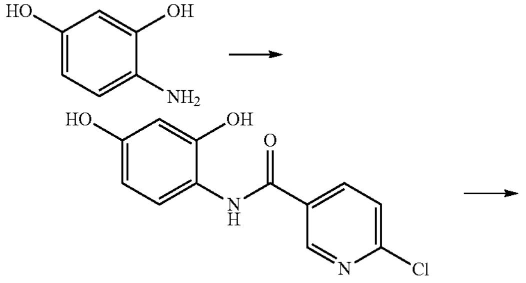

-continued

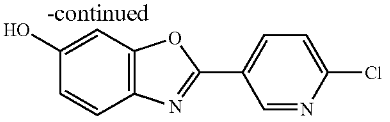

4-Aminoresorcinol HCl (620 mg, 2.8 mmol) was slurried in THF (10 ml) and triethylamine (1.6 ml, 3 eq) was added. To the stirred solution, cooled with an ice-bath, 6-chloronicotinoyl chloride (2.0 g, 3 eq) dissolved in THF (15 ml) was added dropwise. After the addition the mixture was allowed to stir for 3 days at rt.

The reaction was poured out on ice and the solid was filtered. The wet solid was dissolved in THF (25 ml) and ethanol (25 ml) by heating. 2 M NaOH (20 ml) was added dropwise to the still warm solution. After 10 min the organic solvent was removed on the rotory evaporator and the mixture dissolved by adding more water. The solution was neutralized wit 6 M HCl (6 ml) and the solid was filtered to give 6-chloro-N-(2,4-dihydroxyphenyl)pyridine-3-carboxamide (0.71 g, 71% yield, m/z (M−1) 263.1).

The 6-chloro-N-(2,4-dihydroxyphenyl)pyridine-3-carboxamide was cyclized by dissolving hexachloroethane (1.63 g, 2.5 eq) and triphenylphosphine (2.17 g, 3 eq) in DCM (30 ml) and adding triethylamine (3.1 ml, 8 eq). The mixture was allowed to stir for 10 min then 6-chloro-N-(2,4-dihydroxyphenyl)pyridine-3-carboxamide (0.71 g, 2.7 mmol) was added in 2 portions.

After 30 min at rt the reaction was extracted with 2 M NaOH, the aqueous phase was filtered and the solution was acidified with 6 M HCl. After standing overnight, the solid was filtered and dried (vacuum over $P_2O_5$) to give 2-(6-chloropyridin-3-yl)-1,3-benzoxazol-6-ol (61 mg, 9% yield, m/z (M−1) 245.0).

Intermediate 20: Ethyl 1-(5-Bromo-6-fluoropyridin-2-yl)piperidine-4-carboxylate

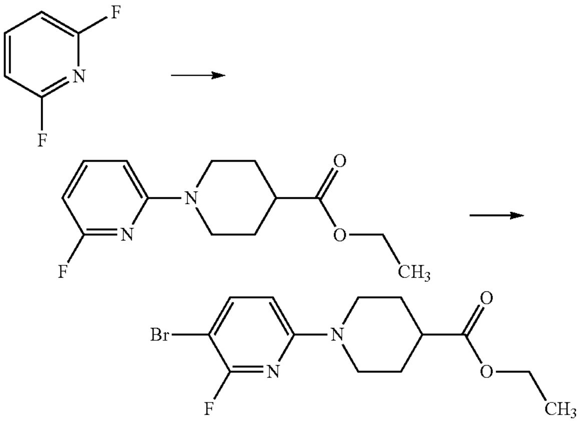

In a 20 ml microwave vial was 2,6-difluoropyridine (1.6 ml, 17.4 mmol) dissolved in pyridine (12 ml) and 4-piperidine ethyl ester (2.68 ml, 1 eq) added. The vial was capped and was subjected to the microwave at 190° C. for 1 h.

The solvent was removed in vacuo, toluene was added and the solvent was again removed. The remains were taken up in ethyl acetate, washed with water, treated with brine, dried with $MgSO_4$, filtered and the solvent was removed in vacuo to give crude ethyl 1-(6-fluoropyridin-2-yl)piperidine-4-carboxylate.

The ethyl 1-(6-fluoropyridin-2-yl)piperidine-4-carboxylate was purified on the ISCO (40 g silica, applied with hexane with a little DCM, eluted with 0-10% ethyl acetate/hexane over 5 min) to give ethyl 1-(6-fluoropyridin-2-yl)piperidine-4-carboxylate (2.78 g oil, 63% yield, m/z (M+1) 253.2). TLC 10% ethyl acetate/hexane Rf 0.29.

Ethyl 1-(6-fluoropyridin-2-yl)piperidine-4-carboxylate (2.78 g, 11.0 mmol) was dissolved in acetonitrile (50 ml), cooled with an ice-bath, and NBS (2.03 g, 1.04 eq) was added. The reaction was stirred for 10 min then the bath was removed and the reaction was allowed to stir at rt for 1 h.

The reaction was poured out on ice and was allowed to stir overnight. The reaction was taken into ethyl acetate, washed with water, treated with brine, dried with $MgSO_4$, filtered and the solvent was removed in vacuo to give crude ethyl 1-(5-bromo-6-fluoropyridin-2-yl)piperidine-4-carboxylate.

The crude ethyl 1-(5-bromo-6-fluoropyridin-2-yl)piperidine-4-carboxylate was purified on the ISCO (40 g silica, applied with hexane with a little DCM, eluted with 0-15% ethyl acetate/hexane over 8 min) to give ethyl 1-(5-bromo-6-fluoropyridin-2-yl)piperidine-4-carboxylate (3.42 g solid, 94% yield, m/z (M+1) 333.1, (M−1) 331.3). TLC 15% ethyl acetate/hexane Rf 0.23.

tert-Butyl 5-(dimethylcarbamoyl)-1H-indole-1-carboxylate (0.83 g, 2.88 mmol) and triisopropylborate (1.0 ml, 1.5 eq) were dissolved in dry THF (4 ml) and cooled to 0° C. LDA (4.3 ml, about 1.5 eq, made by N,N-dimethylamine and butyl lithium) was added over 50 min. The reaction was then allowed to stir at 0° C. for 40 min. More triisopropylborate (1.3 ml, 2 eq) was added to the reaction and LDA (5.7 ml, about 2 eq) was added over 5 min at 0° C. The reaction was allowed to stir for 40 min at 0° C.

The reaction was then quenched (at 0° C.) with 2 M HCl, stirred for 5 min, and then extracted twice with ethyl acetate, treated with brine, dried with $MgSO_4$, filtered, stripped to give {1-[(tert-butoxy)carbonyl]-5-(dimethylcarbamoyl)-1H-indol-2-yl}boronic acid (1.0 g foam, 99% yield, MS m/z (M+1) 333, (M−1) 331).

Intermediate 21: {1-[(tert-Butoxy)carbonyl]-6-(methylcarbamoyl)-1H-indol-2-yl}boronic acid

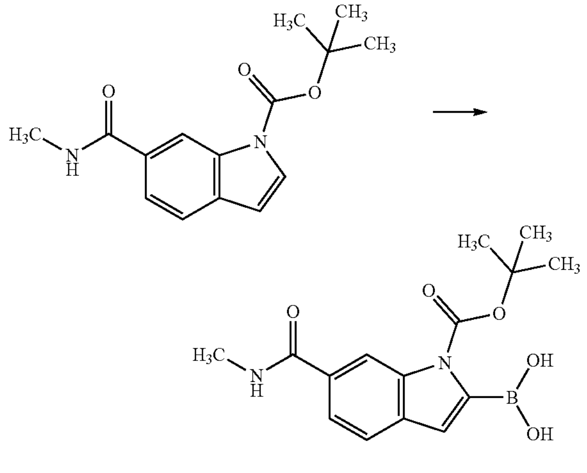

tert-Butyl 6-(methylcarbamoyl)-1H-indole-1-carboxylate (0.83 g, 2.88 mmol) and triisopropylborate (0.82 ml, 1.5 eq) were dissolved in dry THF (6 ml) and cooled to 0° C. 2 M LDA in THF (3.55 ml, 1.5 eq) was added over 50 min, dropwise. The reaction was then allowed to stir at 0° C. for 1 h.

The reaction was then quenched (at 0° C.) with 2 M HCl (until acidic) and the reaction stirred for 5 min. It was then extracted with ethyl acetate, washed with water, treated with brine, dried with $MgSO_4$, filtered and the solvent removed in vacuo to give the crude product. Ether was added, refluxed and the residue was titurated. The solid was filtered, washed with hot ether to give {1-[(tert-butoxy)carbonyl]-6-(methylcarbamoyl)-1H-indol-2-yl}boronic acid (0.51 g solid, 68% yield, m/z (M+1) 319.2, (M−1) 317.2).

Intermediate 22: tert-Butyl 5-[(tert-butyldimethylsilyl)oxy]-2-{6-[4-(ethoxycarbonyl)piperidin-1-yl]-2-fluoropyridin-3-yl}-1H-indole-1-carboxylate

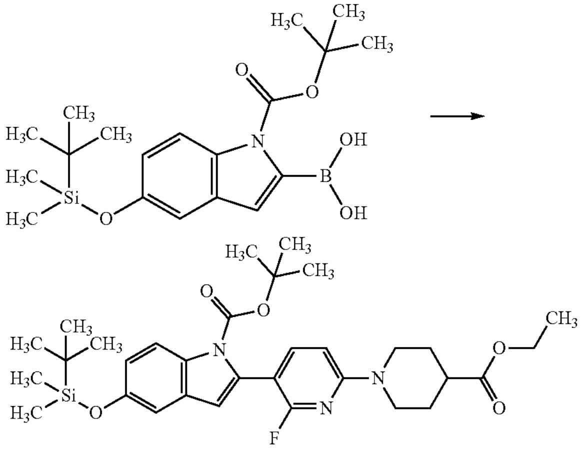

{1-[(Tert-butoxy)carbonyl]-5-[(tert-butyldimethylsilyl)oxy]-1H-indol-2-yl}boronic acid (165 mg, 0.5 mmol) and (ethyl 1-(5-bromo-6-fluoropyridin-2-yl)piperidine-4-carboxylate (intermediate 20, 235 mg, 1.2 eq) were dissolved in dioxane (3 ml) in a 5 ml microwave vial. The solution was bubbled with $N_2$ for 2.5 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then capped. The reaction was run in a preheated oil bath at 90° C. for 1 h.

The cooled reaction mixture was diluted with ethyl acetate, treated with brine, dried with $MgSO_4$, filtered and the solvent was removed in vacuo to give the crude product.

The crude product was purified on the ISCO (12 g silica, applied with hexane, eluted with 5-12% ethyl acetate/hexane over 4 min) to give tert-butyl 5-[(tert-butyldimethylsilyl)oxy]-2-{6-[4-(ethoxycarbonyl)piperidin-1-yl]-2-fluoropyridin-3-yl}-1H-indole-1-carboxylate (271 mg oil, 91% yield, m/z (M+1) 598.4). TLC 20% ethyl acetate/hexane Rf 0.30.

Intermediate 23: 1-(5-Bromo-6-fluoropyridin-2-yl)piperidine-4-carboxamide

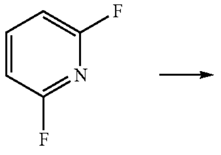

-continued

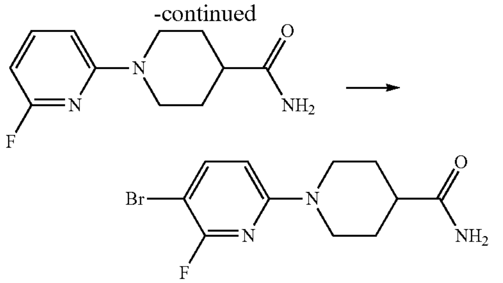

2,6-Difluoropyridine (1.6 ml, 17.4 mmol) was dissolve in pyridine (12 ml) and isonipecotamide (2.23 g, 1 eq) was added. The reaction was subjected to a microwave 190° C. for 1 h.

Ethyl acetate was added to the mixture, the mixture was heated, and then the black solid was filtered off (no product) and the filtrate was evaporated to dryness in vacuo. The remains were taken into ethyl acetate by heating, treated with brine, dried with $MgSO_4$, filtered and the solvent was removed in vacuo to give the crude 1-(6-fluoropyridin-2-yl) piperidine-4-carboxamide product.

The 1-(6-fluoropyridin-2-yl)piperidine-4-carboxamide was purified using silica on a filter funnel (7 cm, run in ethyl acetate eluting with about 2 I). The pure fractions were pooled, the solvent was mostly removed, hexane was added and the solid was filtered, and then washed with hexane to give 1-(6-fluoropyridin-2-yl)piperidine-4-carboxamide (1.18 g solid, 30% yield, m/z (M+1) 224.1, (M−1) 222.2). TLC ethyl acetate Rf 0.12.

1-(6-Fluoropyridin-2-yl)piperidine-4-carboxamide (1.18 g, 5.29 mmol) was dissolved in acetonitrile (50 ml), cooled with an ice-bath and NBS (0.95 g, 1.01 eq) was added. The ice-bath was removed and the heterogeneous mixture was stirred for 1 h.

The reaction mixture was cooled with an ice-bath, the solid was filtered, and washed with cold acetonitrile to give 1-(5-bromo-6-fluoropyridin-2-yl)piperidine-4-carboxamide (1.25 g solid, yield 79%, m/z (M+1) 302.1, 304.2, (M−1) 300.1, 302.1). TLC ethyl acetate Rf 0.11.

Intermediate 24: tert-Butyl 5-[(tert-butyldimethylsilyl)oxy]-2-[6-(4-carbamoylpiperidin-1-yl)-2-fluoropyridin-3-yl]-1H-indole-1-carboxylate

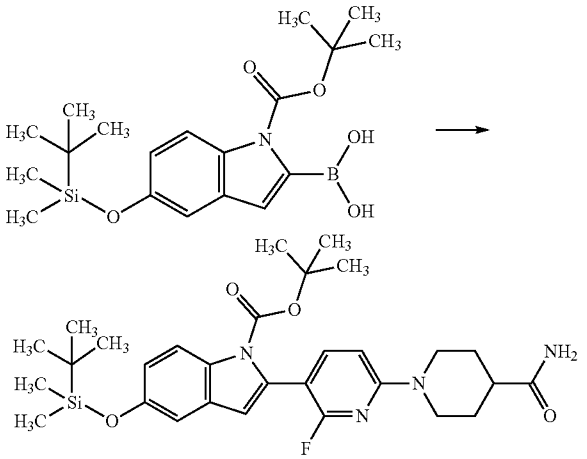

{1-[(tert-Butoxy)carbonyl]-5-[(tert-butyldimethylsilyl)oxy]-1H-indol-2-yl}boronic acid (235 mg, 1.2 eq) and 1-(6-fluoropyridin-2-yl)piperidine-4-carboxamide (intermediate 23, 151 mg, 0.5 mmol) were dissolved in dioxane (3 ml) in a 5 ml microwave vial. The solution was bubbled with $N_2$ for 2.5 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then capped. The reaction was run in a preheated oil bath at 90° C. for 1 h.

The cooled reaction mixture was diluted with ethyl acetate, treated with brine, dried with $MgSO_4$, filtered and the solvent was removed to give the crude product.

The crude product was purified on the ISCO (12 g silica, applied with DCM, eluted with 90-95% ethyl acetate/hexane over 3.5 min) to give tert-butyl 5-[(tert-butyldimethylsilyl)oxy]-2-[6-(4-carbamoylpiperidin-1-yl)-2-fluoropyridin-3-yl]-1H-indole-1-carboxylate (186 mg film, 65% yield, m/z (M+1) 569.5). TLC ethyl acetate Rf 0.18.

Intermediate 25: tert-Butyl 2-[6-(4-carbamoylpiperidin-1-yl)-2-fluoropyridin-3-yl]-5-methoxy-1H-indole-1-carboxylate

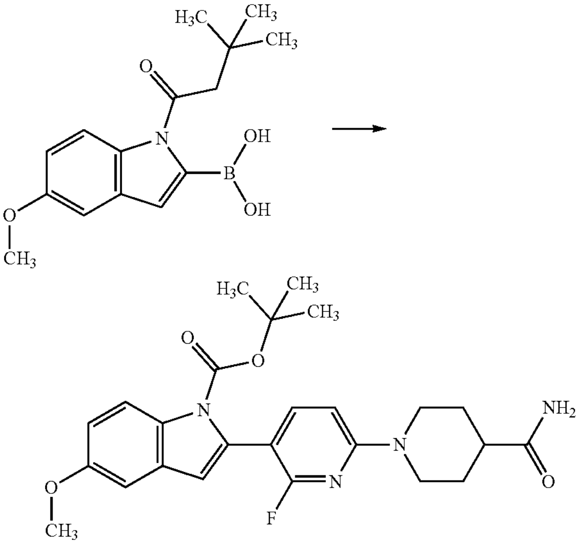

{1-[(tert-Butoxy)carbonyl]-5-methoxy-1H-indol-2-yl}boronic acid (175 mg, 1.2 eq) and 1-(6-fluoropyridin-2-yl)piperidine-4-carboxamide (intermediate 23,151 mg, 0.5 mmol) were dissolved in dioxane (3 ml) in a 5 ml microwave vial. The solution was bubbled with $N_2$ for 2.5 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then capped. The reaction was run in a preheated oil bath at 90° C. for 1 h.

The cooled reaction mixture was diluted with ethyl acetate, treated with brine, dried with $MgSO_4$, filtered and the solvent was removed in vacuo to give the crude product.

The crude product was purified on the ISCO (12 g silica, applied with DCM, eluted with 90-100% ethyl acetate/hexane over 5 min) to give tert-butyl 2-[6-(4-carbamoylpiperidin-1-yl)-2-fluoropyridin-3-yl]-5-methoxy-1H-indole-1-carboxylate (195 mg film, 84% yield, m/z (M+1) 469.4, (M−1) 467.3). TLC ethyl acetate Rf 0.15.

Intermediate 26:5-Bromo-2-[4-(2-fluoroethyl)piperidin-1-yl]pyrimidine

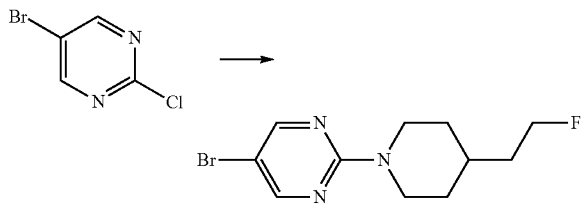

5-Bromo-2-chloropyrimidine (0.75 g, 3.9 mmol) was dissolved in dioxane (5 ml) and 4-piperidinemethylfluoride (1.0 g, 1.7 eq) was added followed by Hunig's base (1.5 ml, 2.3 eq). The reaction was stirred at 100° C. for 15 min.

The reaction mixture was diluted with water/ethyl acetate, washed with water, treated with brine, dried with $MgSO_4$, filtered and the solvent was removed in vacuo to give the crude product.

The crude product was purified on the ISCO (12 g silica, applied with hexane, eluted with 0-10% ethyl acetate/hexane over 8 min) to give 5-bromo-2-[4-(2-fluoroethyl)piperidin-1-yl]pyrimidine (0.86 g solid, 81% yield, m/z (M+1) 276.1, (M−1) 274.1). TLC 50% ethyl acetate/hexane Rf 0.20.

Intermediate 27: tert-Butyl 5-[(tert-butyldimethylsilyl)oxy]-2-{2-[4-(fluoromethyl)piperidin-1-yl]pyrimidin-5-yl}-1H-indole-1-carboxylate

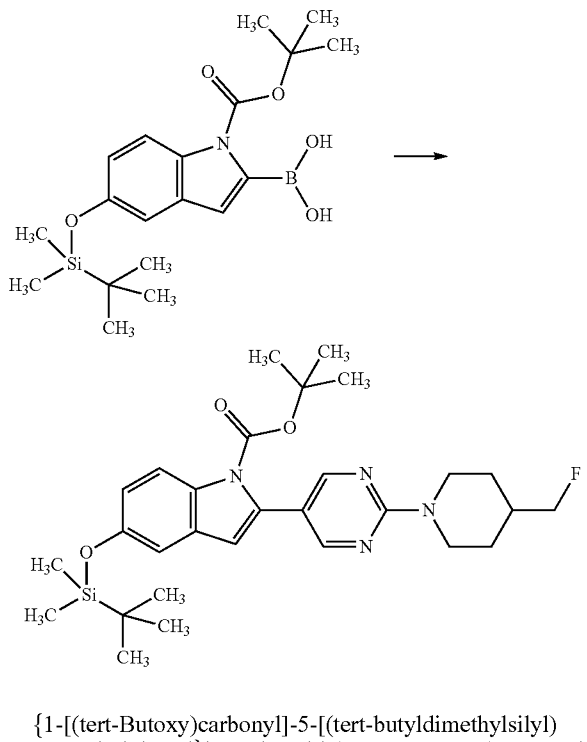

{1-[(tert-Butoxy)carbonyl]-5-[(tert-butyldimethylsilyl)oxy]-1H-indol-2-yl}boronic acid (235 mg, 1.2 eq) mg, and 5-bromo-2-[4-(2-fluoroethyl)piperidin-1-yl]pyrimidine (intermediate 26, 138 mg, 0.5 mmol) were dissolved in dioxane (3 ml) in a 5 ml microwave vial. The solution was bubbled with $N_2$ for 2.5 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then capped. The reaction was run in a preheated oil bath at 90° C. for 1 h.

The cooled reaction mixture was diluted with ethyl acetate, treated with brine, dried with $MgSO_4$, filtered and the solvent was removed in vacuo to give the crude product.

The crude product was purified on the ISCO (24 g silica, applied with hexane DCM 2:1, eluted with 0-10% ethyl acetate/hexane over 8 min) to give tert-butyl 5-[(tert-butyldimethylsilyl)oxy]-2-{2-[4-(fluoromethyl)piperidin-1-yl]pyrimidin-5-yl}-1H-indole-1-carboxylate (216 mg foam, 80% yield, m/z (M+1) 541.5). TLC 20% ethyl acetate/hexane Rf 0.38.

Intermediate 28:1-tert-Butyl 6-methyl 2-{2-[4-(fluoromethyl)piperidin-1-yl]pyrimidin-5-yl}-1H-indole-1,6-dicarboxylate

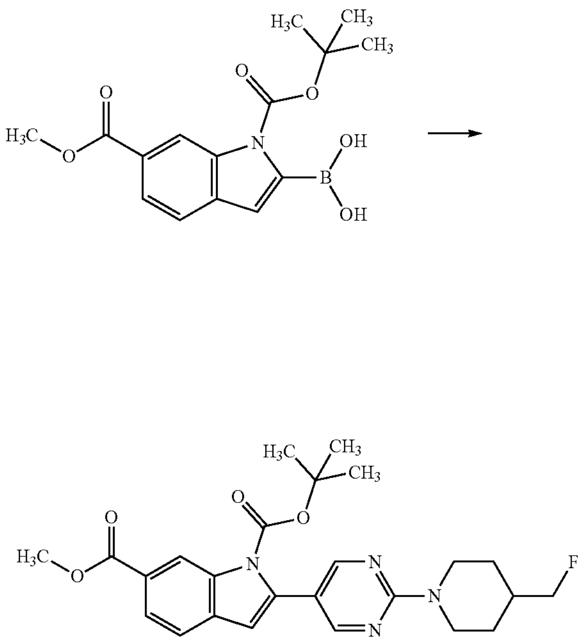

{1-[(tert-Butoxy)carbonyl]-6-(methoxycarbonyl)-1H-indol-2-yl}boronic acid (192 mg, 1.2 eq) and 5-bromo-2-[4-(2-fluoroethyl)piperidin-1-yl]pyrimidine (intermediate 26,138 mg, 0.5 mmol) were dissolved in dioxane (3 ml) in a 5 ml microwave vial. The solution was bubbled with $N_2$ for 2.5 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then capped.

The reaction was run in a preheated oil bath at 90° C. for 1 h. The cooled reaction mixture was diluted with ethyl acetate, treated with brine, dried with $MgSO_4$, filtered and the solvent was removed in vacuo to give the crude product.

The crude product was purified on the ISCO (12 g silica, applied with DCM, eluted with 10-14% ethyl acetate/hexane over 3 min) to give 1-tert-butyl 6-methyl 2-{2-[4-(fluoromethyl)piperidin-1-yl]pyrimidin-5-yl}-1H-indole-1,6-dicarboxylate (170 mg solid, 68% yield, m/z (M+1) 469.4). TLC 20% ethyl acetate/hexane 0.17.

Intermediate 29: 1-(5-Bromopyridin-2-yl)piperidine-4-carboxamide

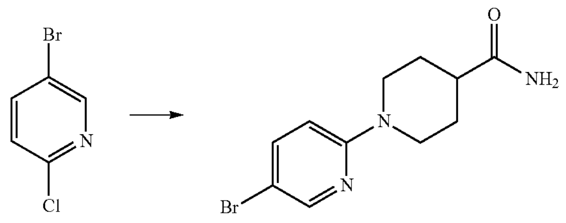 [SMILES: Clc1ccc(Br)cn1 ; NC(=O)C1CCN(c2ccc(Br)cn2)CC1]

5-Bromo-2-chloropyridine (193 mg, 1.0 mmol) and isonipecotamide (770 mg, 6 eq) were dissolved in methanol (14 ml). The reaction was subjected to a microwave 160° C. for 8 h.

The solvent was removed, ethyl acetate added to the remains and the solid was filtered off. The solvent was removed and the crude was purified on a filter funnel (7 cm, eluting with ethyl acetate eluting with about 1l, then 5% methanol/ethyl acetate for the product). The solvent was mostly removed, hexane was added and the solid was filtered, washed with hexane to give 1-(5-bromopyridin-2-yl)piperidine-4-carboxamide (80 mg solid, 28% yield, m/z (M+1) 284.2, 286.2, (M−1) 282.1, 284.1). TLC ethyl acetate Rf 0.12. TLC ethyl acetate with 5% methanol Rf 0.30.

Intermediate 30: tert-Butyl 2-[6-(4-carbamoylpiperidin-1-yl)pyridin-3-yl]-5-methoxy-1H-indole-1-carboxylate

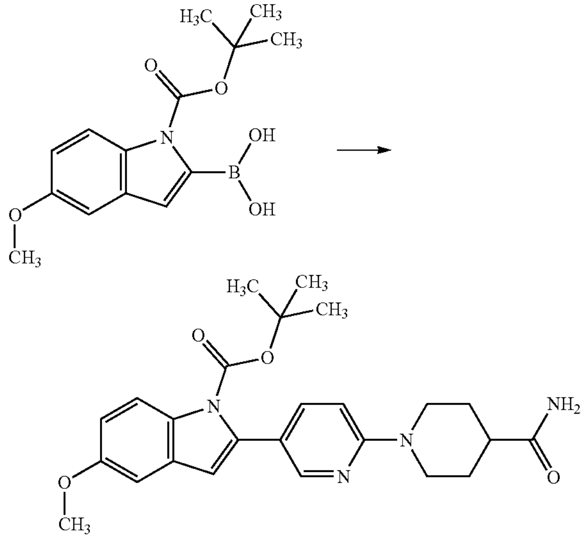

{1-[(tert-Butoxy)carbonyl]-5-methoxy-1H-indol-2-yl}boronic acid (100 mg, 1.2 eq) and 1-(5-bromopyridin-2-yl)piperidine-4-carboxamide (intermediate 29, 80 mg, 0.28 mmol) were dissolved in dioxane (1.7 ml) in a 5 ml microwave vial. The solution was bubbled with $N_2$ for 2 min, then $Pd(dppf)Cl_2$ DCM 1:1 complex (12 mg, 5 mol %) was added followed by 2 M $K_2CO_3$ (425 μl, 3 eq). The solution was again bubbled with $N_2$ for 5 min then capped. The reaction was run in a preheated oil bath at 90° C. for 1 h.

The cooled reaction mixture was diluted with ethyl acetate, treated with brine, dried with $MgSO_4$, filtered and the solvent was removed in vacuo to give the crude product.

The crude product was purified on the ISCO (12 g silica, applied with DCM, eluted with 0-2% methanol/ethyl acetate over 5 min) to give tert-butyl 2-[6-(4-carbamoylpiperidin-1-yl)pyridin-3-yl]-5-methoxy-1H-indole-1-carboxylate (110 mg foam, 92% yield, m/z (M+1) 451.4, (M−1) 449.4). TLC ethyl acetate Rf 0.12. TLC ethyl acetate with 5% methanol Rf 0.30.

Intermediate 31: [1-(5-Bromopyrimidin-2-yl)piperidin-4-yl]methanol

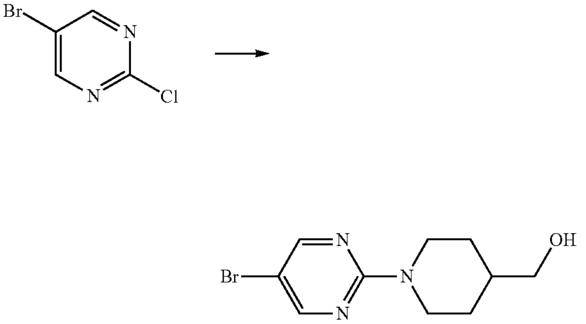

5-bromo-2-chloropyrimidine (772 mg, 4 mmol) and 4-piperidinemethanol (1.38 g, 3 eq) were dissolved in methanol (10 ml) in a 20 ml microwave vial. The reaction was run in a preheated oil bath at 80° C. for 1 h.

The solvent was removed, the remains were dissolved in ethyl acetate, washed with water, treated with brine, dried with $MgSO_4$, filtered and the solvent was removed in vacuo to give the crude product.

The crude product was purified on the ISCO (25 g silica, applied with DCM, eluted with 30-50% ethyl acetate/hexane over 5 min) to give [1-(5-bromopyrimidin-2-yl)piperidin-4-yl]methanol (755 mg solid, 69% yield, m/z (M+1) 272.1, 274.1). TLC 50% ethyl acetate/hexane Rf 0.22.

Intermediate 32: tert-Butyl 5-[(tert-butyldimethylsilyl)oxy]-2-{2-[4-(hydroxymethyl)piperidin-1-yl]pyrimidin-5-yl}-1H-indole-1-carboxylate

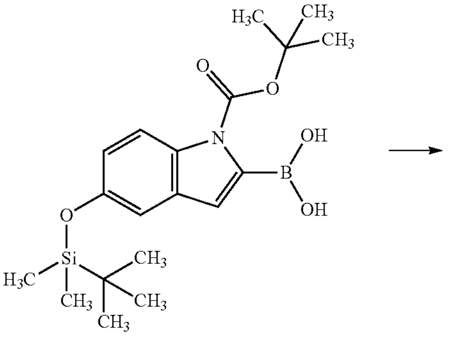

-continued

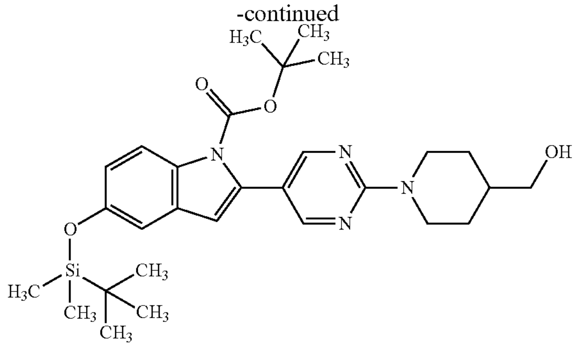

{1-[(tert-Butoxy)carbonyl]-5-[(tert-butyldimethylsilyl)oxy]-1H-indol-2-yl}boronic acid (430 mg, 1.1 eq) and [1-(5-bromopyrimidin-2-yl)piperidin-4-yl]methanol (intermediate 31, 272 mg, 1 mmol) were dissolved in dioxane (6 ml) in a 20 ml microwave vial. The solution was bubbled with $N_2$ for 3 min, then Pd(dppf)$Cl_2$ DCM 1:1 complex (41 mg, 5 mol %) was added followed by 2 M $K_2CO_3$ (1.5 ml, 3 eq). The solution was again bubbled with $N_2$ for 5 min then capped. The reaction was run in a preheated oil bath at 90° C. for 1 h.

The cooled reaction mixture was diluted ethyl acetate, the aqueous phase removed, the solution dried with $MgSO_4$, filtered and the solvent was removed in vacuo to give the crude product.

The crude product was purified on the ISCO (25 g silica, applied with DCM, eluted with 30-45% ethyl acetate/hexane over 6 min) to give tert-butyl 5-[(tert-butyldimethylsilyl)oxy]-2-{2-[4-(hydroxymethyl)piperidin-1-yl]pyrimidin-5-yl}-1H-indole-1-carboxylate (452 mg oil, 84% yield, m/z (M+1) 539.4). TLC 50% ethyl acetate/hexane 0.22.

Intermediate 33: tert-Butyl 2-{2-fluoro-6-[4-(hydroxymethyl)piperidin-1-yl]pyridin-3-yl}-1H-pyrrolo[2,3-b]pyridine-1-carboxylate

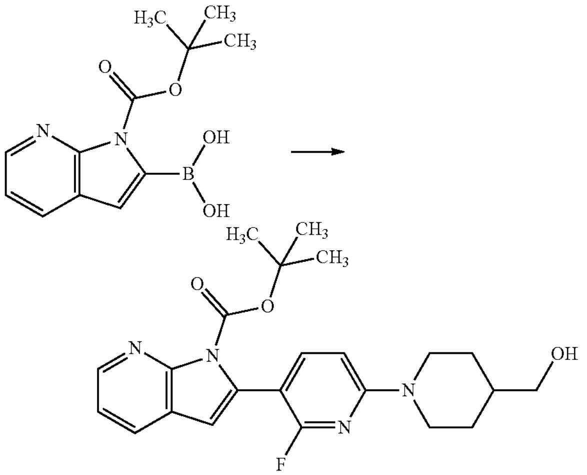

{1-[(tert-Butoxy)carbonyl]-1H-pyrrolo[2,3-b]pyridin-2-yl}boronic acid (253 mg, 1.2 eq) and [1-(5-bromo-6-fluoropyridin-2-yl)piperidin-4-yl]methanol (intermediate 12-1, 233 mg, 0.81 mmol) were dissolved in dioxane (5 ml) in a 20 ml microwave vial. The solution was bubbled with $N_2$ for 3 min, then Pd(dppf)$Cl_2$ DCM 1:1 complex (33 mg, 5 mol %) was added followed by 2 M $K_2CO_3$ (1.2 ml, 3 eq). The solution was again bubbled with $N_2$ for 5 min then capped. The reaction was run in a preheated oil bath at 90° C. for 30 min.

The cooled reaction mixture was diluted with ethyl acetate, treated with brine, dried with $MgSO_4$, filtered and the solvent was removed in vacuo to give the crude product.

The crude product was purified on the ISCO (24 g silica, applied with DCM, eluted with 40-70% ethyl acetate/hexane over 10 min) to give tert-butyl 2-{2-fluoro-6-[4-(hydroxymethyl)piperidin-1-yl]pyridin-3-yl}-1H-pyrrolo[2,3-b]pyridine-1-carboxylate (144 mg oil, yield 42%, HPLC Rf 3.23 min, m/z (M+1) 427.3) TLC ethyl acetate Rf 0.34.

Intermediate 34: {1-[(tert-Butoxy)carbonyl]-5-methoxy-1H-pyrrolo[2,3-b]pyridin-2-yl}boronic acid

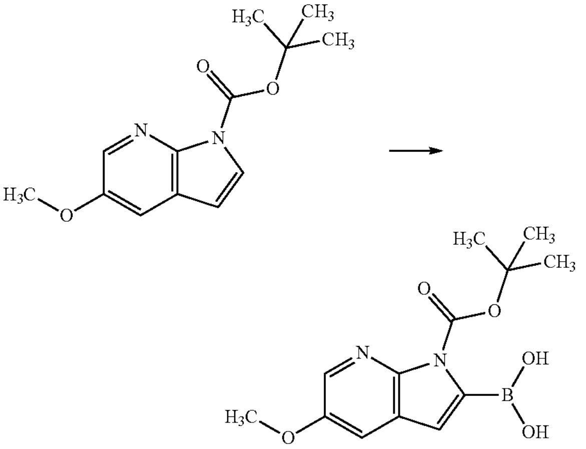

tert-Butyl 5-methoxy-1H-pyrrolo[2,3-b]pyridine-1-carboxylate (0.79 g, 3.18 mmol) and triisopropylborate (1.1 ml, 1.5 eq) were dissolved in dry THF (6 ml) and cooled to 0° C. 2 M LDA (2.7 ml, 1.5 eq) was added over 40 min, dropwise. The reaction was then allowed to stir at 0° C. for 1 h.

The reaction was then quenched (at 0° C.) with a saturated $NH_4Cl$ solution (10 ml) and stirred for 5 min. It was then extracted with ethyl acetate, washed with a saturated $NH_4Cl$ solution, dried with $MgSO_4$, filtered and the solvent removed in vacuo to give crude {1-[(tert-butoxy)carbonyl]-5-methoxy-1H-pyrrolo[2,3-b]pyridin-2-yl}boronic acid used as is in the next reaction (911 mg slightly impure product 91% by HPLC, m/z (M+1) 293.2, 291.1).

Intermediate 35: tert-Butyl 2-{2-fluoro-6-[4-(hydroxymethyl)piperidin-1-yl]pyridin-3-yl}-5-methoxy-1H-pyrrolo[2,3-b]pyridine-1-carboxylate

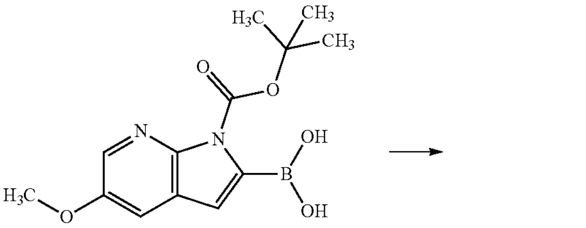

-continued

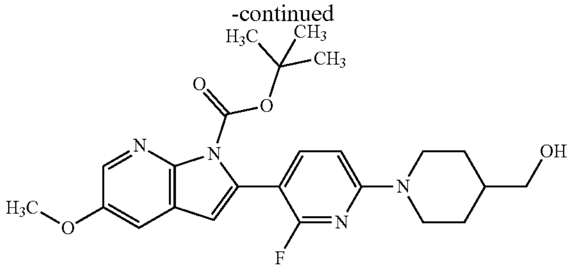

{1-[(tert-Butoxy)carbonyl]-5-methoxy-1H-pyrrolo[2,3-b]pyridin-2-yl}boronic acid (intermediate 34, 350 mg, 1.2 eq) and [1-(5-bromo-6-fluoropyridin-2-yl)piperidin-4-yl]methanol (intermediate 12-1, 289 mg, 1 mmol) were dissolved in dioxane (6 ml) in a 20 ml microwave vial. The solution was bubbled with $N_2$ for 3 min, then $Pd(dppf)Cl_2$ DCM 1:1 complex (41 mg, 5 mol %) was added followed by 2 M $K_2CO_3$ (1.5 ml, 3 eq). The solution was again bubbled with $N_2$ for 5 min. The reaction was run in a preheated oil bath at 90° C. for 1 h.

The cooled reaction mixture was diluted with ethyl acetate, the aqueous phase removed, dried with $MgSO_4$, filtered and the solvent was removed in vacuo to give the crude product.

The crude product was purified on the ISCO (24 g silica, applied with DCM, eluted with 40-50% ethyl acetate/hexane over 4 min then 50-70% ethyl acetate/hexane from 9-13 min) to give tert-butyl 2-{2-fluoro-6-[4-(hydroxymethyl)piperidin-1-yl]pyridin-3-yl}-5-methoxy-1H-pyrrolo[2,3-b]pyridine-1-carboxylate (150 mg oil, yield 33%, HPLC Rf 3.21 min, m/z (M+1) 457.3) TLC ethyl acetate Rf 0.31.

Intermediate 36: {7-[(tert-Butoxy)carbonyl]-2-methoxy-7H-pyrrolo[2,3-d]pyrimidin-6-yl}boronic acid

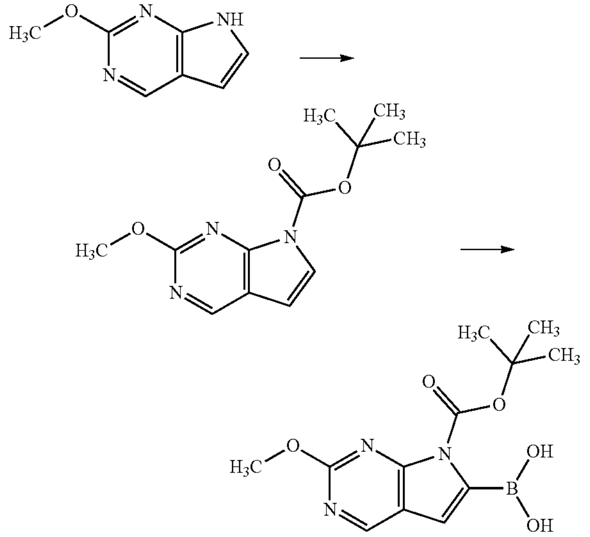

2-Methoxy-7H-pyrrolo(2,3-d)pyrimidine (0.54 mg, 3.62 mmol), di-tert-butyl dicarbonate (950 mg, 1.23 eq) and DMAP (89 mg, 0.2 eq) were suspended in THF (15 ml) and TEA (560 μl, 1.1 eq) was added. The reaction was stirred for 1 h.

The solution was diluted with ethyl acetate/water, extracted with ethyl acetate, treated with brine, dried with $MgSO_4$, filtered and the solvent was removed in vacuo to give the crude tert-butyl 2-methoxy-7H-pyrrolo[2,3-d]pyrimidine-7-carboxylate.

The crude tert-butyl 2-methoxy-7H-pyrrolo[2,3-d]pyrimidine-7-carboxylate was purified on the ISCO (12 g silica, applied with DCM, eluted with 10-30% ethyl acetate/hexane over 4 min) to give tert-butyl 2-methoxy-7H-pyrrolo[2,3-d]pyrimidine-7-carboxylate (0.71 g solid, 83% yield, m/z (M+1) 250.2). TLC: ethyl acetate Rf 0.57.

tert-Butyl 2-methoxy-7H-pyrrolo[2,3-d]pyrimidine-7-carboxylate (0.71 g, 2.85 mmol) and triisopropylborate (0.99 ml, 1.5 eq) were dissolved in dry THF (6 ml) and cooled to 0° C. 2 M lithium diisopropylamide (LDA) (2.85 ml, 1.5 eq) was added over 40 min, dropwise. The reaction was then allowed to stir at 0° C. for 1 h.

The reaction was then quenched (at 0° C.) with a saturated $NH_4Cl$ solution (10 ml and stirred for 5 min. It was then extracted with ethyl acetate, washed with a saturated $NH_4Cl$ solution, dried with $MgSO_4$, filtered and the solvent was removed in vacuo to give a crude {7-[(tert-butoxy)carbonyl]-2-methoxy-7H-pyrrolo[2,3-d]pyrimidin-6-yl}boronic acid used as is in the next reaction (0.77 g solid, 85% by HPLC Rf 2.01 min, m/z (M+1) 294.3, 292.3).

Intermediate 37: [1-(5-Bromopyridin-2-yl)piperidin-4-yl]methanol

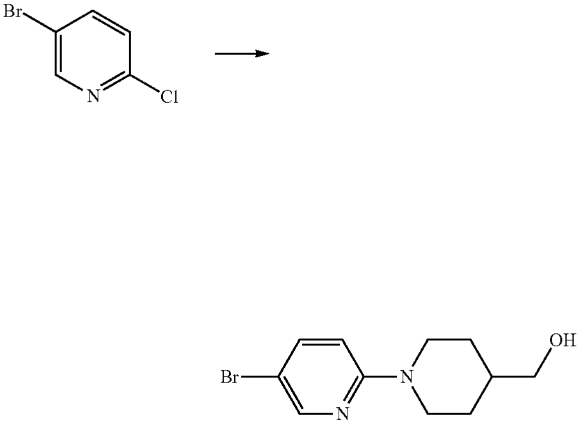 [SMILES: Clc1ccc(Br)cn1 ; OCC1CCN(c2ccc(Br)cn2)CC1]

5-Bromo-2-chloropyridine (770 mg, 4.0 mmol) and 4-piperidinemethanol (1.84 g, 4 eq) were dissolved in methanol (10 ml) in a 20 ml microwave vial. The reaction vial was capped and the reaction was subjected to the microwave for 90 min at 150° C.

The cooled reaction mixture was diluted with ethyl acetate, washed with water, treated with brine, dried with $MgSO_4$, filtered and the solvent was removed in vacuo to give the crude product.

The crude product was purified on the ISCO (24 g silica, applied with DCM, eluted with 35-60% ethyl acetate/hexane over 5 min) to give [1-(5-bromopyridin-2-yl)piperidin-4-yl]methanol (360 mg solid, 33% yield, MS m/z (M+1) 271.1, 273.1). TLC: 50% ethyl acetate/hexane Rf 0.17.

Intermediate 38: tert-Butyl 5-[(tert-butyldimethylsilyl)oxy]-2-{6-[4-(hydroxymethyl)piperidin-1-yl]pyridin-3-yl}-1H-indole-1-carboxylate

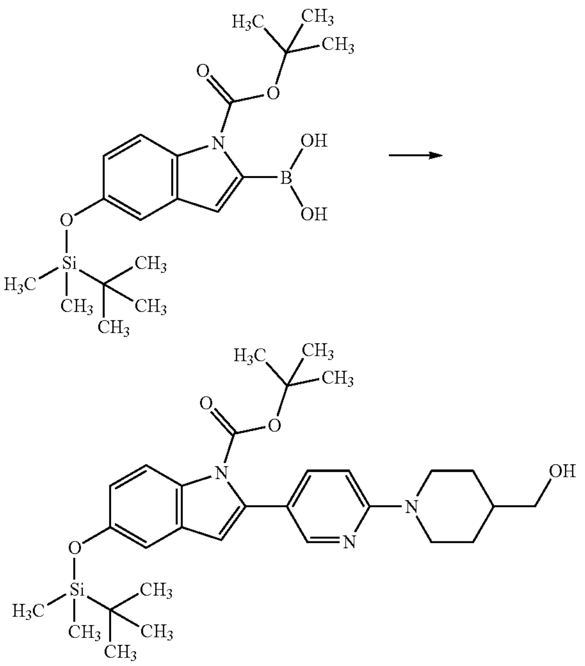

{1-[(tert-Butoxy)carbonyl]-5-[(tert-butyldimethylsilyl)oxy]-1H-indol-2-yl}boronic acid (410 mg, 1.05 eq) and [1-(5-bromopyridin-2-yl)piperidin-4-yl]methanol (intermediate 37, 272 mg, 1 mmol) were dissolved in dioxane (6 ml) in a 20 ml microwave vial. The solution was bubbled with $N_2$ for 3 min, then $Pd(dppf)Cl_2$ DCM 1:1 complex (41 mg, 5 mol %) was added followed by 2 M $K_2CO_3$ (1.5 ml, 3 eq). The solution was again bubbled with $N_2$ for 5 min then capped. The reaction was run in a preheated oil bath at 90° C. for 1 h.

The cooled reaction mixture was diluted ethyl acetate, the aqueous phase removed, the solution dried with $MgSO_4$, filtered and the solvent was removed in vacuo to give the crude product.

The crude product was purified on the ISCO (25 g silica, applied with DCM, eluted with 30-45% ethyl acetate/hexane over 6 min) to give tert-butyl 5-[(tert-butyldimethylsilyl)oxy]-2-{6-[4-(hydroxymethyl)piperidin-1-yl]pyridin-3-yl}-1H-indole-1-carboxylate (426 mg oil, 79% yield, m/z (M+1) 538.4). TLC 50% ethyl acetate/hexane 0.19.

Example Compounds

Example Compounds of Structure 1

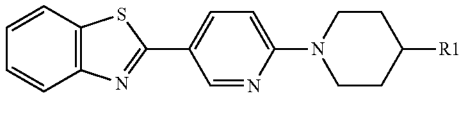

Example Compound 1: {1-[5-1,3-Benzothiazol-2-yl)pyridin-2-yl]piperidin-4-yl}methanol (R1 $=CH_2OH$)

Using the general method 'GP1', intermediate 1 (2-(6-chloro-3-pyridyl)-1,3-benzothiazole) and 4-methanolpiperidine were dissolved in NMP and the reaction mixture heated to 120° C. overnight in an oil bath.

The cooled reaction was diluted with ethyl acetate, washed with water, treated with brine, dried $MgSO_4$, filtered and the solvent was removed in vacuo to give the crude product.

The crude product was suspended in ether, the solid filtered to give {1-[5-(1,3-benzothiazol-2-yl)pyridin-2-yl]piperidin-4-yl}methanol (158 mg solid, 86% yield, HPLC Rf 3.12 min, MS m/z (M+1) 326.2).

Example Compound 2: 2-{6-[4-(Fluoromethyl)piperidin-1-yl]pyridin-3-yl}-1,3-benzothiazole ($R1=CH_2F$)

{1-[5-(1,3-Benzothiazol-2-yl)pyridin-2-yl]piperidin-4-yl}methanol (Example Compound 1, 30 mg, 92 μmol) was dissolved in DCM (3 ml), and cooled with an ice-bath. DAST (25 μl, 2 eq) was then added. The reaction mixture was allowed to stir for 3 h at rt then more DAST (2 eq.) was added at rt and the reaction was allowed to stir for 4 days at rt. Ethyl acetate was then added to the reaction mixture, the solid filtered off, the filtrate washed with a sodium carbonate solution, treated with brine, dried with $MgSO_4$ and the solvent was removed in vacuo to give a crude solid product.

The crude product was purified on the ISCO (4 g silica, applied with DCM, eluted with 10-15% ethyl acetate/hexane over 3 min) to give 2-{6-[4-(fluoromethyl)piperidin-1-yl]pyridin-3-yl}-1,3-benzothiazole (3 mg solid, 10% yield, HPLC Rf 3.73 min, MS m/z (M+1) 328.2). TLC 40% ethyl acetate/hexane Rf 0.47.

Example Compound 3: 2-(6-{4-[(4-Fluorobutoxy)methyl]piperidin-1-yl}pyridin-3-yl)-1,3-benzothiazole ($R1=CH_2O(CH_2)_4F$)

{1-[5-(1,3-Benzothiazol-2-yl)pyridin-2-yl]piperidin-4-yl}methanol (Example Compound 1) (23 mg, 71 μmol) was dissolved in DMF (500 μl) and NaH 60% in oil (>4 mg, >2 eq) was added. The reaction mixture was stirred for 30 min then 1-bromo-4-fluorobutane (14 μl, >1.5 eq) was added and the reaction was allowed to stir at 100° C. for 14 h.

The reaction mixture was cooled with an ice-bath, quenched with water, extracted with ethyl acetate, washed with water, treated with brine, dried with $MgSO_4$, filtered and the solvent was removed in vacuo to give the crude product.

The crude product was purified on the ISCO (4 g silica, applied with DCM eluted with 10-25% ethyl acetate/hexane over 3 min) to give 2-(6-{4-[(4-fluorobutoxy)methyl]piperidin-1-yl}pyridin-3-yl)-1,3-benzothiazole (10 mg, 29% yield, solid, HPLC Rf 4.03 min, MS m/z (M+1) 400.1). TLC: 20% hexane/ethyl Rf 0.13.

Example Compound 4: 1-[5-(1,3-Benzothiazol-2-yl)pyridin-2-yl]piperidin-4-ol ($R1=OH$)

Using the general method 'GP1', intermediate 1 (2-(6-chloro-3-pyridyl)-1,3-benzothiazole) and 4-hydroxypiperindine were dissolved in NMP and the reaction mixture heated to 120° C. overnight in an oil-bath.

The cooled reaction was diluted with ethyl acetate, washed with water, treated with brine, dried with $MgSO_4$, filtered and the solvent was removed in vacuo to give the crude product. The crude product was suspended in ether, the solid filtered to give 1-[5-(1,3-benzothiazol-2-yl)pyridin-2-yl]piperidin-4-ol (90 mg solid, 71% yield, HPLC Rf 2.96 min, MS m/z (M+1) 312.7).

Example Compound 5: 2-{6-[4-(4-Fluorobutoxy)piperidin-1-yl]pyridin-3-yl}-1,3-benzothiazole ($R1{=}O(CH_2)_4F$)

1-[5-(1,3-Benzothiazol-2-yl)pyridin-2-yl]piperidin-4-ol (Example Compound 4, 25 mg, 80 μmol) was dissolved in DMF (500 μl), and NaH 60% in oil (>4 mg, >2 eq) was added. The reaction was stirred for 30 min, and then 1-bromo-4-fluorobutane (14 μl, 1.5 eq) was added and the reaction mixture was allowed to stir at 100° C. for 14 h.

The reaction mixture was cooled with an ice-bath, quenched with water, extracted with ethyl acetate, washed with water, treated with brine, dried with MgSO4, filtered and the solvent was removed in vacuo to give the crude product.

The crude product was purified on the ISCO (4 g silica, applied with DCM, eluted with 10-25% ethyl acetate/hexane over 3 min) to give 2-{6-[4-(4-fluorobutoxy)piperidin-1-yl]pyridin-3-yl}-1,3-benzothiazole (4 mg solid, 71% yield, HPLC Rf 3.89 min, MS m/z (M+1) 386.1).

Example Compound 6: 2-[6-(4-{2-[2-(2-Fluoroethoxy)ethoxy]ethoxy}piperidin-1-yl)pyridin-3-yl]-1,3-benzothiazole ($R1{=}O(CH_2)_2O(CH_2)_2O(CH_2)_2F$)

1-[5-(1,3-Benzothiazol-2-yl)pyridin-2-yl]piperidin-4-ol (Example Compound 4, 25 mg, 80 μmol) was dissolved in DMF (500 μl), and NaH 60% in oil (>4 mg, >2 eq) was added. The reaction mixture was stirred for 15 min, then 2-[2-(2-fluoroethoxy)ethoxy]ethyl 4-methylbenzene-1-sulfonate (50 μl, 2 eq) was added, and the reaction was allowed to stir at 50° C. for 14 h.

The reaction mixture was quenched with water, extracted with ethyl acetate, washed with water, treated with brine, dried with $MgSO_4$, filtered and the solvent was removed in vacuo to give the crude product.

The crude product was purified on the ISCO (12 g silica, applied with DCM, eluted with 40-60% ethyl acetate/hexane over 6 min) to give 2-[6-(4-{2-[2-(2-fluoroethoxy)ethoxy]ethoxy}piperidin-1-yl)pyridin-3-yl]-1,3-benzothiazole (13 mg solid, 42% yield, HPLC Rf 3.51 min, MS m/z (M+1) 446.1). TLC: 75% ethyl acetate/hexane Rf 0.25.

Example Compound 7; 2-{1-[5-(1,3-Benzothiazol-2-yl)pyridin-2-yl]piperidin-4-yl}ethan-1-ol ($R1{=}CH_2CH_2OH$)

Using the general method 'GP1', intermediate 1 (2-(6-Chloro-3-pyridyl)-1,3-benzothiazole) and 4-ethanolpiperidine were dissolved in NMP and the reaction mixture heated to 120° C. overnight in an oil-bath.

The cooled reaction was diluted with ethyl acetate, washed with water, treated with brine, dried $MgSO_4$, filtered and the solvent was removed in vacuo to give the crude product. The crude product was suspended in ether, the solid filtered to give 2-{1-[5-(1,3-benzothiazol-2-yl)pyridin-2-yl]piperidin-4-yl}ethan-1-ol (130 mg solid, 77% yield, HPLC Rf 3.27 min, MS m/z (M+1) 340.1).

Example Compound 8: 2-{1-[5-(1,3-benzothiazol-2-yl)pyridin-2-yl]piperidin-4-yl}ethyl 4-Methylbenzene-1-sulfonate ($R1{=}CH_2CH_2OTS$)

2-{1-[5-(1,3-Benzothiazol-2-yl)pyridin-2-yl]piperidin-4-yl}ethan-1-ol (Example Compound 7) (40 mg, 0.12 mmol) was dissolved in DCM (2 ml), and TEA (25 μl, 1.5 eq) was then added, followed by tosyl chloride (25 mg, 1.1 eq). After stirring for 2 h at rt DMAP (15 mg, 1 eq) was added and the reaction was allowed to stir overnight.

The reaction was diluted with DCM, washed with water, dried with $MgSO_4$, and the solvent was removed in vacuo to give the crude product.

The crude product was purified on the ISCO (4 g silica, applied with DCM, eluted with 15-30% ethyl acetate/hexane over 6 min) to give 2-{1-[5-(1,3-benzothiazol-2-yl)pyridin-2-yl]piperidin-4-yl}ethyl 4-methylbenzene-1-sulfonate (43 mg solid, 74% yield, HPLC Rf 4.05 min, MS m/z (M+1) 494.6). TLC 40% ethyl acetate/hexane Rf 0.29

Example Compound 9: 2-{6-[4-(2-Fluoroethyl)piperidin-1-yl]pyridin-3-yl}-1,3-benzothiazole ($R1{=}CH_2CH_2F$)

2-{1-[5-(1,3-Benzothiazol-2-yl)pyridin-2-yl]piperidin-4-yl}ethyl 4-methylbenzene-1-sulfonate (Example Compound 8, 40 mg, 81 μmol) was dissolved in DMF and 1 M TBAF in THF (100 μl, 1.2 eq) was added. The reaction was subjected to the microwave for 20 min at 120° C.

The reaction mixture was diluted with ethyl acetate, washed with water three times, dried with $MgSO_4$, and the solvent was removed in vacuo to give the crude product.

The crude product was purified on the ISCO (4 g silica, applied with DCM, eluted with 10-15% ethyl acetate/hexane over 4 min) to give 2-{6-[4-(2-fluoroethyl)piperidin-1-yl]pyridin-3-yl}-1,3-benzothiazole (22 mg solid, 80% yield, HPLC Rf 3.81 min, MS m/z (M+1) 342.3). TLC 40% ethyl acetate/hex Rf 0.29.

Example Compound 10:2-({1-[5-(1,3-Benzothiazol-2-yl)pyridin-2-yl]piperidin-4-yl}oxy)acetamide ($R1{=}OCH_2CONH_2$)

Using the general method 'GP1', intermediate 1 (2-(6-chloro-3-pyridyl)-1,3-benzothiazole) and 2-(piperidin-4-yl)acetamide were dissolved in methanol and the reaction was subjected to the microwave at 150° C. for 90 min.

After cooling, the solid formed in the reaction mixture was filtered, and washed with cold methanol to give 2-({1-[5-(1,3-benzothiazol-2-yl)pyridin-2-yl]piperidin-4-yl}oxy)acetamide (18 mg solid, 60% yield, HPLC Rf 2.99 min, MS m/z (M+1) 369.1).

Example Compounds of Structure 2

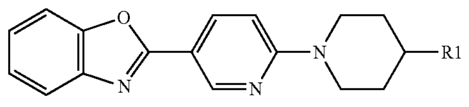

Example compound 11: 2-{1-[5-(1,3-Benzoxazol-2-yl)pyridin-2-yl]piperidin-4-yl}ethan-1-ol ($R1{=}CH_2CH_2OH$)

Using the general method 'GP1', intermediate 2 (2-(6-chloropyridin-3-yl)-1,3-benzoxazole) and 4-ethanolpiperidine were dissolved in methanol and the reaction was subjected to the microwave at 150° C. for 90 min.

After cooling, the solid formed in the reaction mixture was filtered, and washed with cold methanol to give 2-{1-[5-(1,3-benzoxazol-2-yl)pyridin-2-yl]piperidin-4-yl}ethan-1-ol (43 mg solid, 78% yield, HPLC Rf 3.14 min, MS m/z (M+1) 324.3).

Example compound 12: 2-{1-[5-(1,3-Benzoxazol-2-yl)pyridin-2-yl]piperidin-4-yl}ethyl Methanesulfonate (R1=$CH_2CH_2$OMS)

2-{1-[5-(1,3-Benzoxazol-2-yl)pyridin-2-yl]piperidin-4-yl}ethan-1-ol (Example compound 11, 20 mg, 61.8 μmol) was dissolved in THF (2 ml), and TEA (35 μl, 4 eq) was then added, followed by mesyl chloride (15 μl, 3 eq), and the reaction was allowed to stir at rt for 5 min.

The reaction mixture was diluted with ethyl acetate, washed with water, treated with brine, dried with $MgSO_4$, filtered, and the solvent was removed in vacuo.

The solid was slurried in ether and filtered to give 2-{1-[5-(1,3-benzoxazol-2-yl)pyridin-2-yl]piperidin-4-yl}ethyl (23 mg solid, 92% yield, HPLC Rf 3.41 min, MS m/z (M+1) 402.0).

Example compound 13:2-{6-[4-(2-Fluoroethyl)piperidin-1-yl]pyridin-3-yl}-1,3-benzoxazole (R1=$CH_2CH_2$F)

2-{1-[5-(1,3-Benzoxazol-2-yl)pyridin-2-yl]piperidin-4-yl}ethyl methanesulfonate (Example Compound 12, 52 μmol) was dissolved in THF (2 ml) and 1 M TBAF in THF (80 μl, 1.5 eq) was added, and the reaction was subjected to the microwave 120° C. for 15 min. The solvent was removed in vacuo to give the crude product.

The crude product was purified on the ISCO (4 g silica, applied with DCM, eluted with 10-20% ethyl acetate/hexane over 9 min) to give 2-{6-[4-(2-fluoroethyl)piperidin-1-yl]pyridin-3-yl}-1,3-benzoxazole (7 mg white solid, 41% yield, HPLC Rf 3.69 min, MS m/z (M+1) 326.0). TLC 30% ethyl acetate/hexane Rf 0.29.

Example compound 14: 2-[6-(Piperidin-1-yl)pyridin-3-yl]-1,3-benzoxazole (R1=H)

Using the general method 'GP1', intermediate 2 (2-(6-chloropyridin-3-yl)-1,3-benzoxazole) and piperidine were dissolved in methanol and the reaction was subjected to the microwave at 150° C. for 60 min.

After cooling, the solid that had formed in the reaction mixture was filtered, and washed with cold methanol to give 2-[6-(piperidin-1-yl)pyridin-3-yl]-1,3-benzoxazole (18 mg solid, 73% yield, HPLC Rf 3.72 min, MS m/z (M+1) 280.0).

Example Compound 15:2-[6-(4-Methoxypiperidin-1-yl)pyridin-3-yl]-1,3-benzoxazole (R1=OMe)

Using the general method 'GP1', intermediate 2 (2-(6-chloropyridin-3-yl)-1,3-benzoxazole) and 4-methoxypiperidine were dissolved in methanol and the reaction was subjected to the microwave at 150° C. for 90 min.

After cooling, the solid that had formed in the reaction mixture was filtered, and washed with cold methanol to give 2-[6-(4-methoxypiperidin-1-yl)pyridin-3-yl]-1,3-benzoxazole (7 mg solid, 26% yield, HPLC Rf 3.33 min, MS m/z (M+1) 310.0).

Example Compound 16:2-[6-(4-Methylpiperidin-1-yl)pyridin-3-yl]-1,3-benzoxazole (R1=Me)

Using the general method 'GP1', intermediate 2 (2-(6-chloropyridin-3-yl)-1,3-benzoxazole) and 4-methylpiperidine were dissolved in methanol and the reaction was subjected to the microwave at 150° C. for 60 min.

After cooling, the solid that had formed in the reaction mixture was filtered, washed with cold methanol to give 2-[6-(4-methylpiperidin-1-yl)pyridin-3-yl]-1,3-benzoxazole (14 mg solid, 63% yield, HPLC Rf 3.93 min, MS m/z (M+1) 294.0).

Example Compound 17: 1-[5-(1,3-Benzoxazol-2-yl)pyridin-2-yl]piperidine-4-carbonitrile (R1=CN)

Using the general method 'GP1', intermediate 2 (2-(6-chloropyridin-3-yl)-1,3-benzoxazole) and 4-cyanopiperidine were dissolved in methanol and the reaction was subjected to the microwave at 150° C. for 3 h.

The solvent was evaporated, and the crude product was dissolved in DCM, washed with water, dried with $MgSO_4$ and the solvent was t removed in vacuo, to give the crude product.

The crude product was purified on the ISCO (4 g silica, eluted with 10-50% ethyl acetate) to give 1-[5-(1,3-Benzoxazol-2-yl)pyridin-2-yl]piperidine-4-carbonitrile (21 mg solid, 76% yield, HPLC Rf 3.06 min, MS m/z (M+1) 305.0).

Example Compounds of Structure 3

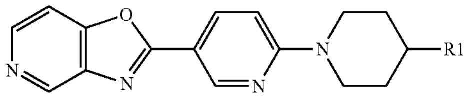

Example Compound 18:2-[1-(5-{[1,3]Oxazolo[4,5-c]pyridin-2-yl}pyridin-2-yl)piperidin-4-yl]ethan-1-ol (R1=$CH_2CH_2$OH)

Using the general method 'GP1', intermediate 3 (2-chloro-5-{[1,3]oxazolo[4,5-c]pyridin-2-yl}pyridine) and 4-ethanolpiperidine were dissolved in methanol and the reaction was subjected to the microwave at 150° C. for 90 min.

After cooling, the solid formed in the reaction mixture was filtered, and washed with cold methanol to give 2-[1-(5-{[1,3]oxazolo[4,5-c]pyridin-2-yl}pyridin-2-yl)piperidin-4-yl]ethan-1-ol (60 mg solid, 86% yield, HPLC Rf 2.51 min, MS m/z (M+1) 325.0).

Example Compound 19:2-[1-(5-{1,3]Oxazolo[4,5-c]pyridin-2-yl}pyridin-2-yl)piperidin-4-yl]ethyl methanesulfonate (R1=$CH_2CH_2$OMS)

2-[1-(5-{[1,3]Oxazolo[4,5-c]pyridin-2-yl}pyridin-2-yl)piperidin-4-yl]ethan-1-ol (Example Compound 18, 47 mg, 146 μmol) was dissolved in THF (4 ml), and TEA (81 μl, 4 eq) was then added, followed by mesyl chloride (34 μl, 3 eq), and the reaction was allowed to stir at rt for 10 min.

The reaction mixture was diluted with ethyl acetate, washed with water, treated with brine, dried with $MgSO_4$, filtered, the solvent was removed in vacuo.

The solid was slurried in ether and filtered to give 2-[1-(5-{[1,3]oxazolo[4,5-c]pyridin-2-yl}pyridin-2-yl)piperidin-4-yl]ethyl methanesulfonate (59 mg, white solid, 99% yield, HPLC Rf 2.85 min, MS m/z (M+1) 403.0).

Example Compound 20:2-[4-(2-Fluoroethyl)piperidin-1-yl]-5-{[1,3]oxazolo[4,5-c]pyridin-2-yl}pyridine (R1═$CH_2CH_2F$)

2-[1-(5-{[1,3]Oxazolo[4,5-c]pyridin-2-yl}pyridin-2-yl) piperidin-4-yl]ethyl methanesulfonate (Example Compound 19, 52 mg, 3 μmol) was dissolved in DMF (1.5 ml) and 1 M TBAF in THF (115 μl, 1.5 eq) was added, and the reaction was subjected to the microwave 110° C. for 10 min.

After standing for 3 weeks, the solid that had formed in the reaction mixture was filtered to give 7 mg solid. The solid was dissolved in DMSO and filtered through a 0.2 μm filter to remove undissolved particles. The solid was purified on the semiprep (methanol/50 mM ammonium acetate) to give 2-[4-(2-fluoroethyl)piperidin-1-yl]-5-{[1,3]oxazolo[4,5-c]pyridin-2-yl}pyridine (3 mg solid, 10% yield, HPLC Rf 3.20 min, MS m/z (M+1) 327.0).

Example Compounds of Structure 4

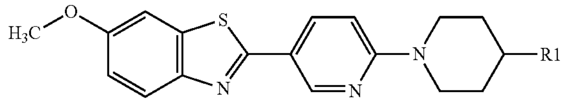

Example Compound 21:2-{1-[5-(6-Methoxy-1,3-benzothiazol-2-yl)pyridin-2-yl]piperidin-4-yl}ethan-1-ol (R1═$CH_2CH_2OH$)

Using the general method 'GP1', intermediate 4 (2-(6-chloropyridin-3-yl)-6-methoxy-1,3-benzothiazole) and 4-ethanolpiperidine were dissolved in methanol and the reaction was subjected to the microwave at 150° C. for 90 min.

After cooling, the solid that had formed in the reaction mixture was filtered and washed with cold methanol.

The crude solid product was purified on the ISCO (4 g silica, applied with DCM (heating), eluted with 50% ethyl acetate/hexane then quickly up to 100% ethyl acetate) to give 2-{1-[5-(6-methoxy-1,3-benzothiazol-2-yl)pyridin-2-yl]piperidin-4-yl}ethan-1-ol (23 mg solid, 64% yield, HPLC Rf 3.23 min, MS m/z (M+1) 370.0) TLC: ethyl acetate Rf 0.33

Example Compound 22:2-{6-[4-(2-{2-[2-(2-Fluoroethoxy)ethoxy]ethoxy}ethyl)piperidin-1-yl]pyridin-3-yl}-6-methoxy-1,3-benzothiazole (R1═$CH_2CH_2O(CH_2)_2O(CH_2)_2O(CH_2)_4F$)

2-{1-[5-(6-Methoxy-1,3-benzothiazol-2-yl)pyridin-2-yl] piperidin-4-yl}ethan-1-ol (Example Compound 21, 27 mg, 74 μmol) was dissolved in DMF (1 ml), and NaH 60% in oil (>4 mg, >2 eq) was added. The reaction was stirred for 30 min, and then 2-[2-(2-fluoroethoxy)ethoxy]ethyl 4-methylbenzene-1-sulfonate (45 μl, 2 eq) was added and the reaction was allowed to stir at 50° C. for 14 h.

The reaction mixture was quenched with ice, extracted with ethyl acetate, washed with water, treated with brine, dried with $MgSO_4$, filtered and the solvent was removed in vacuo to give the crude product.

The crude product was purified on the ISCO (12 g silica, applied with DCM, eluted with 20-40% ethyl acetate/hexane over 13 min) to give 2-{6-[4-(2-{2-[2-(2-fluoroethoxy) ethoxy]ethoxy}ethyl)piperidin-1-yl]pyridin-3-yl}-6-methoxy-1,3-benzothiazole (11 mg solid, 30% yield, HPLC Rf 3.68 min, MS m/z (M+1) 504.1).

Example Compound 23:2-({1-[5-(6-Methoxy-1,3-benzothiazol-2-yl)pyridin-2-yl]piperidin-4-yl}oxy) ethan-1-ol (R1═$O(CH_2)_2OH$)

Using the general method 'GP1', intermediate 4 (2-(6-chloropyridin-3-yl)-6-methoxy-1,3-benzothiazole) and 2-(piperidin-4-yloxy)ethan-1-ol HCl were dissolved, with an excess of trimethylamine (TEA), in methanol and the reaction mixture was subjected to the microwave at 150° C. for 90 min.

The solvent was evaporated from the reaction mixture, DCM was added, and the solution washed with water, dried with $MgSO_4$, filtered, and the solvent was removed in vacuo to give the crude product.

The crude product was purified on the ISCO (4 g silica, applied with DCM, eluted with 50-70% ethyl acetate/hexane over 7 min) to give 2-({1-[5-(6-methoxy-1,3-benzothiazol-2-yl)pyridin-2-yl]piperidin-4-yl}oxy)ethan-1-ol (13 mg solid, 44% yield, HPLC Rf 3.04 min, MS m/z (M+1) 386.1).

Example Compound 24:2-{6-[4-(2-Fluoroethyl) piperidin-1-yl]pyridin-3-yl}-6-methoxy-1,3-benzothiazole (R1═$CH_2CH_2F$)

Using the general method 'GP1', intermediate 4 (2-(6-chloropyridin-3-yl)-6-methoxy-1,3-benzothiazole) and 4-(2-fluoroethyl)piperidine HCl were dissolved, with an excess of trimethylamine (TEA) in methanol and the reaction mixture was subjected to the microwave at 150° C. for 3 h.

The solvent was removed in vacuo to give the crude product.

The crude product was purified on the ISCO (4 g silica, applied with DCM, eluted with 15-20% ethyl acetate/hexane over 3 min) to give 2-{6-[4-(2-fluoroethyl)piperidin-1-yl] pyridin-3-yl}-6-methoxy-1,3-benzothiazole (6 mg solid, 16% yield, HPLC Rf 3.81 min, MS m/z (M+1) 372.4). TLC: Rf 30% ethyl acetate/hexane Rf 0.25

Example Compound of Structure 5

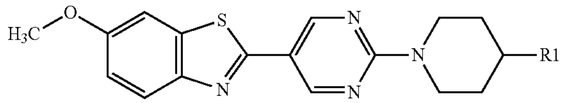

Example Compound 25:2-{1-[5-(6-Methoxy-1,3-benzothiazol-2-yl)pyrimidin-2-yl]piperidin-4-yl}ethan-1-ol (R1═$CH_2CH_2OH$)

A cooled solution of crude {2-[4-(2-hydroxyethyl)piperidin-1-yl]pyrimidin-5-yl}boronic acid (Intermediate 5, 370 μmol), formed as described above, was diluted with dioxane (1.5 ml), and 6-methoxy-2-bromobenzothiazole (91 mg, 1 eq) was added followed by bubbling of $N_2$ for 2 min. Then 2 M $K_2CO_3$ (561 μl, 3 eq) was added, followed by Pd(dppf) $Cl_2$ DCM complex 1:1 (16 mg, 5 mol %). The solution was again bubbled with $N_2$ for 3 min then the vial was capped. The reaction was run in a preheated oil bath at 90° C. overnight.

The reaction mixture was cooled, diluted with ethyl acetate/water, and filtered through celite. The organic portion was separated, washed with water, treated with brine, dried with $MgSO_4$, filtered, and the solvent was removed in vacuo to give the crude product.

The crude product was purified on the ISCO (12 g column, applied with hot DCM, eluted with 50-60% over 5 min) to give a solid, which was then refluxed with ether, cooled, filtered, and washed with ether to give 2-{1-[5-(6-methoxy-1,3-benzothiazol-2-yl)pyrimidin-2-yl]piperidin-4-yl}ethan-1-ol (65 mg solid, 47% yield, HPLC Rf 3.25 min, MS m/z (M+1) 371.1). TLC: 75% ethyl acetate/hexane Rf 0.33.

Example Compound 26:2-{2-[4-(2-{2-[2-(2-Fluoroethoxy)ethoxy]ethoxy}ethyl)piperidin-1-yl]pyrimidin-5-yl}-6-methoxy-1,3-benzothiazole ($R1{=}CH_2CH_2O(CH_2)_2O(CH_2)_2O(CH_2)_2F$)

2-{1-[5-(6-Methoxy-1,3-benzothiazol-2-yl)pyrimidin-2-yl]piperidin-4-yl}ethan-1-ol (Example compound 25, 21 mg, 57 μmol) was dissolved in DMF (500 μl), and NaH 60% in oil (>4 mg, >2 eq) was added. The reaction mixture was stirred for 30 min then 2-[2-(2-fluoroethoxy)ethoxy]ethyl 4-methylbenzene-1-sulfonate (35 μl, 2 eq) was added and the reaction mixture was allowed to stir at 50° C. for 14 h.

The reaction was quenched with ice, and the reaction mixture was taken into ethyl acetate, washed three times with water, dried with $MgSO_4$, filtered and the solvent was removed in vacuo to give the crude product.

The crude product was purified on the ISCO (4 g silica, applied with DCM, eluted with 45-49% ethyl acetate/hexane over 3 min) to give 2-{2-[4-(2-{2-[2-(2-fluoroethoxy)ethoxy]ethoxy}ethyl)piperidin-1-yl]pyrimidin-5-yl}-6-methoxy-1,3-benzothiazole (17 mg solid, 56% yield, HPLC Rf 3.74 min, MS m/z (M+1) 505.1).

Example Compound of Structure 6

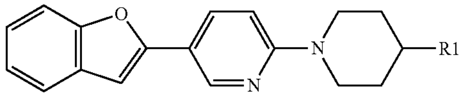

Example Compound 27:2-{1-[5-(1-Benzofuran-2-yl)pyridin-2-yl]piperidin-4-yl}ethan-1-ol ($R1{=}CH_2CH_2OH$)

Using the general method 'GP1', 5-(1-benzofuran-2-yl)-2-chloropyridine (Intermediate 6) and 4-ethanolpiperidine were dissolved in methanol, and the reaction mixture was subjected to the microwave at 160° C. for 3 h.

After cooling, the solid that had formed in the reaction mixture was filtered, and washed with cold methanol to give 2-{1-[5-(1-benzofuran-2-yl)pyridin-2-yl]piperidin-4-yl}ethan-1-ol (6 mg solid, 25% yield, HPLC Rf 3.48 min, MS m/z (M+1) 323.0).

Example Compounds of Structure 7

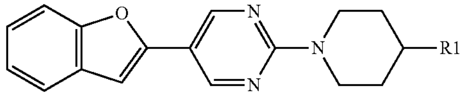

Example Compound 28:2-{1-[5-(1-Benzofuran-2-yl)pyrimidin-2-yl]piperidin-4-yl}ethan-1-ol ($R1{=}CH_2CH_2OH$)

Using the general method 'GP1', 5-(1-benzofuran-2-yl)-2-chloropyrimidine (Intermediate 7) and 4-ethanolpiperidine were dissolved in methanol, and the reaction was subjected to the microwave at 160° C. for 90 min.

After cooling the solid was filtered, and washed with cold methanol to give 2-{1-[5-(1-benzofuran-2-yl)pyrimidin-2-yl]piperidin-4-yl}ethan-1-ol (19 mg solid, 70% yield, HPLC Rf 3.47 min, MS m/z (M+1) 324.0).

Example Compound 29: Methyl 2-{1-[5-(1-Benzofuran-2-yl)pyrimidin-2-yl]piperidin-4-yl}ethane-1-sulfonate ($R1{=}CH_2CH_2OMS$)

2-{1-[5-(1-Benzofuran-2-yl)pyrimidin-2-yl]piperidin-4-yl}ethan-1-ol (Example Compound 28, 47 mg, 146 μmol) was dissolved in THF (4 ml), and TEA (81 μl, 4 eq) was added followed by mesyl chloride (34 μl, 3 eq). The reaction was allowed to stir at rt for 5 min.

The reaction mixture was diluted with ethyl acetate, washed with saturated sodium bicarbonate solution, treated with brine, dried with $MgSO_4$, filtered, and the solvent was removed in vacuo to give the crude solid product.

The crude solid product was slurried in hexane, filtered, and washed with hexane to give methyl 2-{1-[5-(1-benzofuran-2-yl)pyrimidin-2-yl]piperidin-4-yl}ethane-1-sulfonate (75 mg solid, 99% yield, HPLC Rf 2.90 min, MS m/z (M+1) 402.1).

Example Compound 30:5-(1-Benzofuran-2-yl)-2-[4-(2-fluoroethyl)piperidin-1-yl]pyrimidine ($R1{=}CH_2CH_2F$)

Methyl 2-{1-[5-(1-benzofuran-2-yl)pyrimidin-2-yl]piperidin-4-yl}ethane-1-sulfonate (Example Compound 29, 25 mg, 62 μmol) was suspended with tert-butanol (3 ml) and CsF (92 mg, hygroscopic). The reaction mixture was heated to 80° C. for 3 h.

The reaction mixture diluted with ethyl acetate, washed with water, treated with brine, dried with $MgSO_4$, filtered and the solvent was removed in vacuo to give the crude solid product.

The crude product was purified on the ISCO (4 g silica, applied with hexane/DCM) eluted with 5-10% ethyl acetate/hexane over 3 min) to give 5-(1-benzofuran-2-yl)-2-[4-(2-fluoroethyl)piperidin-1-yl]pyrimidine (12 mg solid, 57% yield, HPLC 4.05 min, MS m/z (M+1) 326.1). TLC 10% ethyl acetate/hexane Rf 0.16.

Example Compound 31:2-({1-[5-(1-Benzofuran-2-yl)pyrimidin-2-yl]piperidin-4-yl}oxy)ethan-1-ol ($R1{=}OCH_2CH_2OH$)

Using the general method 'GP1', 5-(1-benzofuran-2-yl)-2-chloropyrimidine (Intermediate 7) and 2-(piperidin-4- yloxy)ethan-1-ol HCl and an excess of triethylamine (TEA) were dissolved in methanol, and the reaction was subjected to the microwave at 150° C. for 90 min.

After cooling, the solvent was removed, then DCM was added and the solution was washed with water, dried with $MgSO_4$, filtered, and the solvent was removed in vacuo to give the crude product.

The crude product was purified on the ISCO (4 g silica, applied with DCM, eluted with 40-45% ethyl acetate/hexane) to give 2-({1-[5-(1-benzofuran-2-yl)pyrimidin-2-yl]piperidin-4-yl}oxy)ethan-1-ol (21 mg solid, 57% yield, HPLC Rf 3.26 min, MS m/z (M+1) 340.1).

Example Compound 32: 1-[5-(1-Benzofuran-2-yl) pyrimidin-2-yl]piperidin-4-ol (R1=OH)

Using the general method 'GP1', 5-(1-benzofuran-2-yl)-2-chloropyrimidine (Intermediate 7) and 4-hydroxypiperidine were dissolved in methanol, and the reaction was subjected to the microwave at 150° C. for 90 min.

After cooling the solid was filtered and washed with cold methanol to give 1-[5-(1-benzofuran-2-yl)pyrimidin-2-yl] piperidin-4-ol (33 mg solid, 87% yield, HPLC Rf 3.18 min, MS m/z (M+1) 296.1).

Example Compound 33:5-(1-Benzofuran-2-yl)-2-(4-{2-[2-(2-fluoroethoxy)ethoxy]ethoxy}piperidin-1-yl) pyrimidine (R1=$O(CH_2)_2O(CH_2)_2O(CH_2)_2F$)

1-[5-(1-Benzofuran-2-yl)pyrimidin-2-yl]piperidin-4-ol (Example Compound 32, 25 mg, 80 μmol) was dissolved in DMF (500 μl) and NaH 60% in oil (>4 mg, >2 eq) was added. The reaction was stirred for 15 min then 2-[2-(2-fluoroethoxy)ethoxy]ethyl 4-methylbenzene-1-sulfonate (50 μl, 2 eq) was added and the reaction mixture was allowed to stir at 50° C. for 2 h.

The reaction mixture was quenched with water, extracted with ethyl acetate, washed with water, treated with brine, dried with $MgSO_4$, filtered and the solvent was removed in vacuo to give the crude product.

The crude product was purified on the ISCO (4 g silica, applied with DCM) eluted with 15-30% ethyl acetate/hexane over 6 min) to give 5-(1-benzofuran-2-yl)-2-(4-{2-[2-(2-fluoroethoxy)ethoxy]ethoxy}piperidin-1-yl)pyrimidine (10 mg solid, 29% yield, HPLC Rf 3.68, MS m/z (M+1) 430.2).

Example Compound 34: 2-({1-[5-(1-benzofuran-2-yl)pyrimidin-2-yl]piperidin-4-yl}oxy)acetamide (R1=$OCH_2CONH_2$)

Using the general method 'GP1', 5-(1-benzofuran-2-yl)-2-chloropyrimidine (Intermediate 7) and 2-(piperidin-4-yl) acetamide were dissolved in methanol, and the reaction mixture was subjected to the microwave at 150° C. for 90 min.

The solid formed in the reaction mixture was filtered, washed with cold methanol, and dried to give 2-({1-[5-(1-benzofuran-2-yl)pyrimidin-2-yl]piperidin-4-yl}oxy)acetamide (23 mg solid, 73% yield, HPLC Rf 3.15, MS m/z (M+1) 353.1).

Example Compound of Structure 8

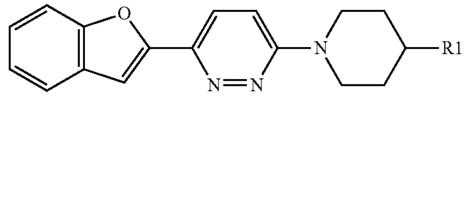

Example Compound 35:2-{1-[6-(1-Benzofuran-2-yl)pyridazin-3-yl]piperidin-4-yl}ethan-1-ol (R1=$CH_2CH_2OH$)

Using the general method 'GP1' 3-(1-benzofuran-2-yl)-6-chloropyridazine (Intermediate 8) and 4-ethanolpiperidine were dissolved in methanol, and the reaction was subjected to the microwave at 150° C. for 90 min.

After cooling, the solvent was removed from the reaction mixture, then DCM was added and the solution washed with water, dried with $MgSO_4$, filtered, and the solvent was removed in vacuo to give the crude product.

The crude product was purified on the ISCO (4 g silica, eluted with 40-90% ethyl acetate/hexane) to give 25 mg solid, which was recrystallized from methanol to give 2-{1-[6-(l-benzofuran-2-yl)pyridazin-3-yl]piperidin-4-yl}ethan-1-ol (8 mg solid, 21% yield, HPLC Rf 2.98 min, MS m/z (M+1) 324.0). TLC: ethyl acetate Rf 0.26.

Example Compounds of Structure 9

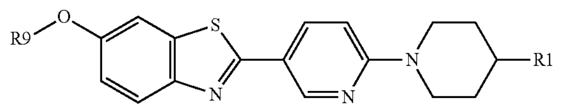

Example Compound 36:2-{6-[4-(2-Hydroxyethyl) piperidin-1-yl]pyridin-3-yl}-1,3-benzothiazol-6-ol (R1=$CH_2CH_2OH$, R9=H)

Using the general method 'GP1', 2-(6-chloropyridin-3-yl)-1,3-benzothiazol-6-ol (Intermediate 9) and 4-ethanolpiperidine were dissolved in methanol, and the reaction was subjected to the microwave at 150° C. for 90 min.

The cooled solvent was evaporated, ethyl acetate/water added, and the solution was extracted with ethyl acetate twice, dried with $MgSO_4$, filtered and a $N_2$ stream was used to remove most of the solvent. A solid formed and a small volume of hexane was added, and the solid was filtered, and then allowed to dry, to give 2-{6-[4-(2-hydroxyethyl)piperidin-1-yl]pyridin-3-yl}-1,3-benzothiazol-6-ol (11 mg solid, 61% yield, HPLC Rf 2.64 min, MS m/z (M+1) 356.0, (M−1) 354.0). TLC: ethyl acetate Rf 0.32.

Example Compound 37: 1-Fluoro-3-[(2-{6-[4-(2-hydroxyethyl)piperidin-1-yl]pyridin-3-yl}-1,3-benzothiazol-6-yl)oxy]propan-2-ol (R1=$CH_2CH_2OH$, R9=$CH_2CH(OH)CH_2F$)

2-{6-[4-(2-Hydroxyethyl)piperidin-1-yl]pyridin-3-yl}-1,3-benzothiazol-6-ol (Example Compound 36, 20 mg, 56 μmol) was dissolved in dry DMF (500 μl) and NaH 60% in oil (5-10 mg, about 2-4 eq) was added. After 15 min with stirring, 1-bromo-3-fluoropropan-2-ol (12 μl, 2 eq) was added and the reaction stirred at 60° C. for 4 days.

The reaction mixture was then extracted with ethyl acetate, washed with water, treated with brine, dried with $MgSO_4$, filtered and the solvent was removed in vacuo to give the crude product.

The crude product was purified by reversed phase chromatography (isocratic 55% AcCN in 50 mM NH4OAc, Kromasil 100 C18, 250×10 m, 7 μm, 254 nm, 2 ml/min) to give 1-fluoro-3-[(2-{6-[4-(2-hydroxyethyl)piperidin-1-yl]

pyridin-3-yl}-1,3-benzothiazol-6-yl)oxy]propan-2-ol (4 mg solid, 17% yield, HPLC Rf 2.79 min, MS m/z (M+1) 432.1).

Example Compound 55:2-{6-[4-(Hydroxymethyl) piperidin-1-yl]pyridin-3-yl}-1,3-benzothiazol-6-ol ($R1{=}CH_2OH$, $R9{=}H$)

In a microwave vial, 6-[(tert-butyldimethylsilyl)oxy]-2-(6-chloropyridin-3-yl)-1,3-benzothiazole (Intermediate 17,100 mg, 0.27 mmol) and 4-piperidinemethanol (122 mg, 4 eq) were suspended in methanol (3 ml) and subjected to a microwave for 1.5 h at 150° C. The solvent was removed and the remains were taken into ethyl acetate/water. The mixture was extracted twice with ethyl acetate, treated with brine, dried with $MgSO_4$, and the solvent was removed in vacuo to give the crude product.

The crude product was taken into a DCM/toluene mixture and the solid was filtered and washed with DCM to give 2-{2-[4-(2-hydroxyethyl)piperidin-1-yl]pyrimidin-5-yl}-1,3-benzothiazol-6-ol (52 mg solid, 57% yield, HPLC Rf 2.54 min, MS m/z (M+1) 342.2, (M−1) 340.2). TLC ethyl acetate Rf 0.26.

Example Compound 56: (1-{5-[6-(2-Fluoroethoxy)-1,3-benzothiazol-2-yl]pyridin-2-yl}piperidin-4-yl) methanol ($R1{=}CH_2OH$, $R9{=}CH_2CH_2F$)

2-{2-[4-(2-Hydroxyethyl)piperidin-1-yl]pyrimidin-5-yl}-1,3-benzothiazol-6-ol (Example Compound 38, 29 mg, 86 μmol) was dissolved in DMF (1 ml). Cesium carbonate (42 mg, 1.5 eq) was added, followed by 1-fluoro-2-iodoethane (11 μl, 1.5 eq) and the reaction was stirred at 50° C. for 40 min.

The reaction mixture was filtered through a 0.22 urn filter and the crude was purified by reversed phase chromatography (20-80% AcCN/ammonia, Kromasil 100 C18, 250×10 m, 7 μm, 254 nm, 2 ml/min) to give (1-{5-[6-(2-fluoroethoxy)-1,3-benzothiazol-2-yl]pyridin-2-yl}piperidin-4-yl) methanol (7 mg solid, 21% yield, HPLC Rf 3.06 min, MS m/z (M+1) 388.2).

Example Compounds of Structure 10

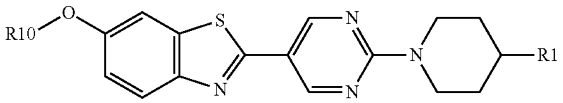

Example Compound 38:2-{2-[4-(2-Hydroxyethyl) piperidin-1-yl]pyrimidin-5-yl}-1,3-benzothiazol-6-ol ($R1{=}CH_2CH_2OH$, $R10{=}H$))

A cooled solution of crude {2-[4-(2-hydroxyethyl)piperidin-1-yl]pyrimidin-5-yl}boronic acid (intermediate 5), formed as described above, was diluted with dioxane (6 ml) and 2-bromo-6-[(tert-butyldimethylsilyl)oxy]-1,3-benzothiazole (689 mg, 1 eq) was added, followed by bubbling of $N_2$ through the solution for 5 min. Then 2 M $K_2CO_3$ (3 ml, 3 eq) was added, followed by Pd(dppf)$Cl_2$ DCM complex 1:1 (82 mg, 5 mol %). The solution was again bubbled with $N_2$ for 5 min, then the reaction vial was capped and was stirred at 90° C. in an oil-bath overnight.

LCMS showed that the silyl group was cleaved at this stage. The reaction mixture was cooled and diluted with ethyl acetate, then filtered. The filtrate was washed twice with water, treated with brine, dried with $MgSO_4$, filtered and the solvent was removed in vacuo. DCM was added to the filtered solid and the solution was refluxed with methanol, cooled, filtered, and washed with methanol to give 480 mg dark solid.

The dark solid (460 mg, 1.29 mmol) was purified by dissolving it in DMF (10 ml) with imidazole (100 mg, 1.1 eq), and then cooling the solution with an ice bath and adding t-butyldimethylsilyl chloride (214 mg, 1.1 eq). The solution was allowed to stir at rt for 1 h. More imidazole (40 mg) and t-butyldimethylsilyl chloride (90 mg) were added and the solution stirred for a further 15 min at rt.

The reaction was diluted with ethyl acetate, washed three times with water, treated with brine, dried with $MgSO_4$, filtered and the solvent was removed in vacuo to give the crude product.

The crude product was purified on silica (7 cm filter funnel packed in DCM, eluted with 20-25% ethyl acetate/hexane) to give a foam (455 mg, 75% yield). A portion of the foam (50 mg, 106 μmol) was dissolved in THF (2.5 ml) and tetrabutylammonium fluoride (TBAF 1 M in THF) (420 μl, 4 eq) was added. The solution was stirred at rt for 4 h. Water was added, and the solid that formed was filtered and dried ($P_2O_5$, vacuum) to give 2-{2-[4-(2-hydroxyethyl)piperidin-1-yl]pyrimidin-5-yl}-1,3-benzothiazol-6-ol (27 mg solid, 71% yield, HPLC Rf 2.64 min, MS m/z (M+1) 357.3, (M−1) 355.2). TLC: ethyl acetate Rf 0.30.

Example Compound 39:2-{2-[4-(2-Fluoroethyl) piperidin-1-yl]pyrimidin-5-yl}-1,3-benzothiazol-6-ol ($R1{=}CH_2CH_2F$, $R10{=}H$)

2-{2-[4-(2-Hydroxyethyl)piperidin-1-yl]pyrimidin-5-yl}-1,3-benzothiazol-6-ol (Example Compound 38, 22 mg, 62 μmol) was dissolved in THF (2 ml) with heating, and the reaction was cooled with an ice-bath and DAST (30 μl, 3.7 eq) was added and the reaction stirred at rt for 1 h.

The reaction was quenched with saturated sodium bicarbonate, extracted with ethyl acetate, treated with brine, dried with $MgSO_4$, filtered and the solvent was removed in vacuo to give the crude product.

The crude product was purified on the ISCO (4 g silica gold, applied with DCM, eluted with 25-28% ethyl acetate/hexane over 2 min) to give 2-{2-[4-(2-fluoroethyl)piperidin-1-yl]pyrimidin-5-yl}-1,3-benzothiazol-6-ol (10 mg solid, 45% yield, HPLC Rf 3.30, MS m/z (M+1) 359.3, (M−1) 357.2) TLC: 30% ethyl acetate/hexane Rf 0.17.

Example Compound 57:2-{2-[4-(Hydroxymethyl) piperidin-1-yl]pyrimidin-5-yl}-1,3-benzothiazol-6-ol ($R1{=}CH_2OH$, $R10{=}H$)

A cooled solution of crude {2-[4-(hydroxymethyl)piperidin-1-yl]pyrimidin-5-yl}boronic acid (Intermediate 18 formed as described above, 2.0 mmol), was diluted with dioxane (6 ml) and 2-bromo-6-[(tert-butyldimethylsilyl)oxy]-1,3-benzothiazole (689 mg, 1 eq) was added, followed by bubbling of $N_2$ through the solution for 3 min. Then 2 M $K_2CO_3$ (3 ml, 3 eq) was added, followed by Pd(dppf)$Cl_2$ DCM complex 1:1 (82 mg, 5 mol %). The solution was again bubbled with $N_2$ for 5 min, then the reaction vial was capped and the reaction was run in a preheated oil bath at 90° C. for 30 min.

The reaction mixture was cooled and diluted with ethyl acetate, treated with brine, dried with $MgSO_4$, filtered and the solvent was removed in vacuo to give the crude product.

The crude product was purified on the ISCO (40 g silica, applied with DCM, eluted with 20-100% ethyl acetate/hexane) to give 2-{2-[4-(hydroxymethyl)piperidin-1-yl]pyrimidin-5-yl}-1,3-benzothiazol-6-ol (92 mg solid, 14% yield, HPLC Rf 2.53 min, MS m/z (M+1) 343.2, (M−1) 341.1) TLC: ethyl acetate Rf 0.31.

Example Compound 58: (1-{5-[6-(2-Fluoroethoxy)-1,3-benzothiazol-2-yl]pyrimidin-2-yl}piperidin-4-yl) methanol (R1═$CH_2OH$, R10═$CH_2CH_2F$)

2-{2-[4-(Hydroxymethyl)piperidin-1-yl]pyrimidin-5-yl}-1,3-benzothiazol-6-ol (Example Compound 57, 30 mg, 88 μmol) was dissolved in DMF (1 ml). Cesium carbonate (42 mg, 1.5 eq) was added followed by the addition of 1-fluoro-2-iodoethane (11 μl, 1.5 eq) and the reaction was stirred at 50° C. for 40 min.

Ethyl acetate/water was added to the cooled mixture and the solid that formed was filtered and washed with water followed by heptane. The solid was dried (high vacuum over $P_2O_5$) to give (1-{5-[6-(2-fluoroethoxy)-1,3-benzothiazol-2-yl]pyrimidin-2-yl}piperidin-4-yl)methano (20 mg solid, 59% yield, HPLC Rf 3.09, MS m/z (M+1) 389.3).

Example Compounds of Structure 11

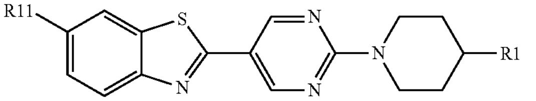

Example Compound 40:2-{2-[4-(2-Hydroxyethyl) piperidin-1-yl]pyrimidin-5-yl}-1,3-benzothiazole-6-carbonitrile (R1═$CH_2CH_2OH$, R11=CN)

A cooled solution of crude {2-[4-(2-hydroxyethyl)piperidin-1-yl]pyrimidin-5-yl}boronic acid (intermediate 5), formed as described above, was diluted with dioxane (3 ml), and 6-cyano-2-bromobenzothiazole (229 mg, 1 eq) was added followed by bubbling of $N_2$ for 1 min. Then 2 M $K_2CO_3$ (1.4 ml, 3 eq) was added followed by Pd(dppf)$Cl_2$ DCM complex 1:1 (40 mg, 5 mol %). The solution was again bubbled with $N_2$ for 5 min then the vial was capped. The reaction was run in a preheated oil bath at 90° C. overnight.

The reaction mixture was cooled, diluted with ethyl acetate and the solid filtered. The solid was refluxed with ethyl acetate, and then ethanol was added. The crude solid product was filtered hot. The solid that was filtered off (250 mg of crude product) was retained for use as the crude 2-{2-[4-(2-hydroxyethyl)piperidin-1-yl]pyrimidin-5-yl}-1,3-benzothiazole-6-carbonitrile starting material in the synthesis of Example Compound 41. The filtrate was allowed to cool and the solid was filtered to give the 2-{2-[4-(2-hydroxyethyl)piperidin-1-yl]pyrimidin-5-yl}-1,3-benzothiazole-6-carbonitrile (19 mg solid, HPLC Rf 3.11, MS m/z (M+1) 366.0). TLC: ethyl acetate Rf 0.33.

Example Compound 41:2-{2-[4-(2-Hydroxyethyl) piperidin-1-yl]pyrimidin-5-yl}-1,3-benzothiazole-6-carboxamide (R1═$CH_2CH_2OH$, R11=$CONH_2$)

The crude 2-{2-[4-(2-hydroxyethyl)piperidin-1-yl]pyrimidin-5-yl}-1,3-benzothiazole-6-carbonitrile (crude Example Compound 40 formed as described above, 168 mg, 660 μmol) was suspended in DMSO (7 ml) and EtOH (14 ml), and 1 M NaOH (7 ml) was added, followed by the dropwise addition of 30% $H_2O_2$. The exothermic reaction was allowed to stir for 20 min, then the solid was filtered, washed with water, and dried ($P_2O_5$, vacuum), to give 2-{2-[4-(2-hydroxyethyl)piperidin-1-yl]pyrimidin-5-yl}-1,3-benzothiazole-6-carboxamide (83 mg solid, 47% yield, HPLC Rf 2.39, MS m/z (M+1) 384.3, (M−1) 382.3).

Example Compound 42:2-{1-[5-(6-Carbamoyl-1,3-benzothiazol-2-yl)pyrimidin-2-yl]piperidin-4-yl}ethyl methanesulfonate (R1═$CH_2CH_2OMS$, R11═$CONH_2$)

2-{2-[4-(2-Hydroxyethyl)piperidin-1-yl]pyrimidin-5-yl}-1,3-benzothiazole-6-carboxamide (Example Compound 41, 31 mg, 82 μmol) was dissolved in DMF (2 ml), and TEA (35 μl, 3 eq) was added followed by mesyl chloride (15 μl, 2 eq). The reaction was stirred for 5 min at rt.

Water (2 to 4 ml) was added dropwise to give a gel-like semi-solid. The semi-solid was extracted with ethyl acetate five times, treated with brine, dried with $MgSO_4$, and the solvent was removed in vacuo give 2-{1-[5-(6-carbamoyl-1,3-benzothiazol-2-yl)pyrimidin-2-yl]piperidin-4-yl}ethyl methanesulfonate (28 mg solid, 76% yield, HPLC Rf 2.70, MS m/z (M+1) 462.4). TLC: ethyl acetate Rf 0.16.

Example Compound 43:2-{2-[4-(2-Fluoroethyl) piperidin-1-yl]pyrimidin-5-yl}-1,3-benzothiazole-6-carboxamide (R1═$CH_2CH_2F$, R11═$CONH_2$)

2-{1-[5-(6-Carbamoyl-1,3-benzothiazol-2-yl)pyrimidin-2-yl]piperidin-4-yl}ethyl methanesulfonate (Example Compound 42, (28 mg, 61 μmol) was suspended in tert-butanol (6 ml), and CsF (90 mg, 10 eq) was added. The reaction mixture was stirred at 80° C. for 6 h, then at 70° C. overnight.

The reaction mixture was diluted with ethyl acetate/water, extracted twice with ethyl acetate, treated with brine, dried with $MgSO_4$, filtered and the solvent was removed in vacuo to give the crude product.

The crude product was purified on the ISCO (4 g silica, dissolved in DCM+THF+EA and heating, eluted with 55-70% ethyl acetate/hexane over 4 min) to give 2-{2-[4-(2-Fluoroethyl)piperidin-1-yl]pyrimidin-5-yl}-1,3-benzothiazole-6-carboxamide (535 μg solid, 2% yield, HPLC Rf 3.03, MS m/z (M+1) 386.4). TLC: ethyl acetate Rf 0.29.

Alternative synthesis of Example Compound 43:2-{2-[4-(2-Fluoroethyl)piperidin-1-yl]pyrimidin-5-yl}-1,3-benzothiazole-6-carboxamide (R1═$CH_2CH_2F$, R11═$CONH_2$)

Ethyl 2-{2-[4-(2-fluoroethyl)piperidin-1-yl]pyrimidin-5-yl}-1,3-benzothiazole-6-carboxylate (Example Compound 44, 31 mg, 75 μmol) was slurried in THF (2 ml) and methanol (1.2 ml). LiOH (9 mg, 5 eq) was added followed by water (600 μl), and the slurry stirred overnight.

6 M HCl (75 μl, 6 eq) was then added to the cooled stirred solution. The solvent was removed in vacuo, dry toluene (2 ml) was added, and the solvent was removed in vacuo again. This was repeated four times. After the solvent was removed for the final time, the solid was suspended in thionyl chloride (2 ml) and DMF (6 μl) was added. The reaction mixture was allowed to stir at rt for 30 min. The excess thionyl chloride was removed under a stream of $N_2$, dry toluene was added, and the solvent was removed under a stream of $N_2$ to give a light yellow solid.

The yellow solid was suspended in dry DCM (1.5 ml), cooled with an ice bath, and concentrated ammonium hydroxide was added. The reaction was stirred for 5 min then the ice bath was removed. The reaction was allowed to stir at rt for 30 min, then the stopper was removed and the reaction mixture stirred overnight.

The solid was then filtered, washed with water, dried ($P_2O_5$, vacuum) to give the crude solid product. The crude product was then heated with ethyl acetate, cooled, filtered, and washed with ethyl acetate to give 2-{2-[4-(2-fluoroethyl)piperidin-1-yl]pyrimidin-5-yl}-1,3-benzothiazole-6-carboxamide (15 mg solid, 54% yield, HPLC Rf 3.03, MS m/z (M+1) 386.1). TLC: ethyl acetate Rf 0.29.

Example Compound 44: Ethyl 2-{2-[4-(2-Fluoroethyl)piperidin-1-yl]pyrimidin-5-yl}-1,3-benzothiazole-6-carboxylate (R1═$CH_2CH_2F$, R11═$CO_2Et$)

In a sealed vial, 2-chloropyrimidin-5-yl)boronic acid (1 eq) and 4-(2-fluoroethyl)piperidine HCl (1 eq) were dissolved, with an excess of trimethylamine (TEA), in absolute methanol (2.5 ml). The reaction was run on a preheated oil bath at 80° C. for 45 min. The solution was cooled and diluted with dioxane (3 ml) and ethyl 2-bromo-6-benzothiazolecarboxylate (286 mg, 1 eq) was added, followed by bubbling of $N_2$ through the solution for 3 min. Then 2 M $K_2CO_3$ (1.5 ml, 3 eq) was added followed by Pd(dppf)$Cl_2$ DCM complex 1:1 (41 mg, 5 mol %). The solution was again bubbled with $N_2$ for 5 min then the vial was capped. The reaction was run in a preheated oil bath at 90° C. for 1 h.

The solution was cooled, diluted with ethyl acetate, and the solid filtered. The solid was then refluxed with ethyl acetate, and the insoluble portion was filtered off. A small volume of hexane was added to the solution, the solid was filtered, and washed with hexane to give ethyl 2-{2-[4-(2-fluoroethyl)piperidin-1-yl]pyrimidin-5-yl}-1,3-benzothiazole-6-carboxylate (50 mg solid, 12% yield, HPLC Rf 4.10 min, MS m/z (M+1) 415.3). TLC: 30% ethyl acetate/hexane Rf 0.40.

Example Compound 59: Ethyl 2-{2-[4-(2-Hydroxyethyl)piperidin-1-yl]pyrimidin-5-yl}-1,3-benzothiazole-6-carboxylate (R1═$CH_2CH_2OH$, R11═$CO_2Et$)

A cooled solution of crude {2-[4-(2-hydroxyethyl)piperidin-1-yl]pyrimidin-5-yl}boronic acid (Intermediate 5 formed as described above and dissolved in 5 ml absolute ethanol, 2.0 mmol), was diluted with dioxane (6 ml) and ethyl 2-bromo-6-benzothiazolecarboxylate (572 mg, 1 eq) was added, followed by bubbling of $N_2$ through the solution for 3 min. Then 2 M $K_2CO_3$ (3 ml, 3 eq) was added, followed by Pd(dppf)$Cl_2$ DCM complex 1:1 (82 mg, 5 mol %). The solution was again bubbled with $N_2$ for 5 min, then the reaction vial was capped and the reaction was run in a preheated oil bath at 90° C. for 1 h.

The reaction mixture was cooled, the solid was filtered, washed with dioxane to give ethyl 2-{2-[4-(2-hydroxyethyl)piperidin-1-yl]pyrimidin-5-yl}-1,3-benzothiazole-6-carboxylate (415 mg solid, 50% yield, HPLC Rf 3.65 min, MS m/z (M+1) 413.3).

Example Compound 60:2-{2-[4-(2-Fluoroethyl)piperidin-1-yl]pyrimidin-5-yl}-N-(2-hydroxyethyl)-1,3-benzothiazole-6-carboxamide (R1═$CH_2CH_2F$, R11═$CONHCH_2CH_2OH$)

Ethyl 2-{2-[4-(2-fluoroethyl)piperidin-1-yl]pyrimidin-5-yl}-1,3-benzothiazole-6-carboxylate (Example Compound 44, 20 mg, 48 μmol) was slurried in methanol (0.5 ml) then 2-aminoethanol (0.5 ml) and potassium cyanide (0.3 mg, 10 mol %) was added. The reaction was stirred at 70° C. overnight.

Methanol was added to the cooled solution, the solid was filtered to give 2-{2-[4-(2-fluoroethyl)piperidin-1-yl]pyrimidin-5-yl}-N-(2-hydroxyethyl)-1,3-benzothiazole-6-carboxamide (19 mg solid, 90% yield, HPLC Rf 2.99 min, MS m/z (M+1) 430.4, (M−1) 428.5).

Example Compound 61: N-(2-Fluoroethyl)-2-{2-[4-(2-hydroxyethyl)piperidin-1-yl]pyrimidin-5-yl}-1,3-benzothiazole-6-carboxamide (R1═$CH_2CH_2OH$, R11═$CONHCH_2CH_2F$)

Ethyl 2-{2-[4-(2-hydroxyethyl)piperidin-1-yl]pyrimidin-5-yl}-1,3-benzothiazole-6-carboxylate (Example Compound 59, 50 mg, 121 μmol) was dissolved in THF (5 ml), and methanol (5 ml) and lithium hydroxide monohydrate (20 mg, 4 eq) were added followed by water (1 ml). The reaction was allowed to stir at 50° C. overnight.

Water was added to the cooled reaction mixture, the solution was made acidic (1 M HCl) and the solvent was removed in vacuo to give the crude intermediate acid used in the next reaction step (MS m/z (M+1) 385.3, (M−1) 383.2).

The crude intermediate acid was dissolved in DMF (5 ml), and HOBt (22 mg, 1.3 eq) and EDC HCl (24 mg, 1.3 eq) were added and the reaction stirred for 15 min. 2-Fluoroethylamine HCl (50 mg, 4 eq) was then added, followed by triethylamine (170 μl, 10 eq), and the reaction was allowed to stir for 2 h at rt.

The reaction was diluted with water, extracted with ethyl acetate, treated with brine, dried with $MgSO_4$, filtered and the solvent was removed in vacuo to give the crude product.

The crude product was purified on the ISCO (4 g silica, applied with DCM, eluted with 80-90% ethyl acetate/hexane) to give N-(2-fluoroethyl)-2-{2-[4-(2-hydroxyethyl)piperidin-1-yl]pyrimidin-5-yl}-1,3-benzothiazole-6-carboxamide (3 mg solid, 9% yield, HPLC Rf 2.70 min, MS m/z (M+1) 430.3, (M−1) 428.3). TLC: ethyl acetate Rf 0.20.

Example Compounds of Structure 12

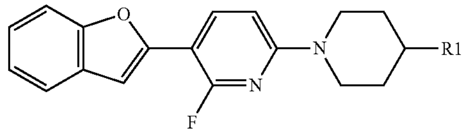

Example Compound 45: {1-[5-(1-Benzofuran-2-yl)-6-fluoropyridin-2-yl]piperidin-4-yl}methanol (R1═$CH_2OH$)

Benzofuran-2-boronic acid (178 mg, 1.1 eq) and [1-(5-bromo-6-fluoropyridin-2-yl)piperidin-4-yl]methanol (intermediate 12-1, 289 mg, 1.0 mmol) were dissolved in dioxane (6 ml) in a 20 ml microwave vial. The solution was bubbled with $N_2$ for 2 min, then Pd(dppf)$Cl_2$ DCM 1:1 complex (41 mg, 5 mol %) was added followed by 2 M $K_2CO_3$ (1.5 ml, 3 eq). The solution was again bubbled with $N_2$ for 5 min then the vial was capped. The reaction was run in a preheated oil bath at 90° C. overnight.

The cooled reaction mixture was diluted with ethyl acetate, washed with water, treated with brine, dried with $MgSO_4$, filtered through celite and the solvent was removed in vacuo to give the crude product.

The crude product was purified on the ISCO (24 g silica, applied with DCM, eluted with 20-50% ethyl acetate/hexane over 18 min). The fractions with product were collected, the solvent was removed in vacuo, hexane was added, and the solid was filtered to give {1-[5-(1-benzofuran-2-yl)-6-fluoropyridin-2-yl]piperidin-4-yl}methanol (46 mg solid, 14% yield, HPLC Rf 3.62, MS m/z (M+1) 327.3, (M−1) 325.2). TLC: 50% ethyl acetate Rf 0.18.

Example Compound 46:2-{1-[5-(1-Benzofuran-2-yl)-6-fluoropyridin-2-yl]piperidin-4-yl}ethan-1-ol (R1=$CH_2CH_2OH$)

Benzofuran-2-boronic acid (90 mg, 1.1 eq) and 2-[1-(5-bromo-6-fluoropyridin-2-yl)piperidin-4-yl]ethan-1-ol (intermediate 12-2,152 mg, 0.5 mmol) were dissolved in dioxane (3 ml) in a 5 ml microwave vial. The solution was bubbled with $N_2$ for 2 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then the vial was capped. The reaction was run in a preheated oil bath at 90° C. overnight.

The cooled reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 20-40% ethyl acetate/hexane over 12 min). The fractions with product were collected, and the solid was refluxed in hexane. The solid was then filtered and washed with hot hexane to give 2-{1-[5-(1-benzofuran-2-yl)-6-fluoropyridin-2-yl]piperidin-4-yl}ethan-1-ol (38 mg solid, 22% yield, HPLC Rf 3.74, MS m/z (M+1) 341.3).

Example Compounds of Structure 13

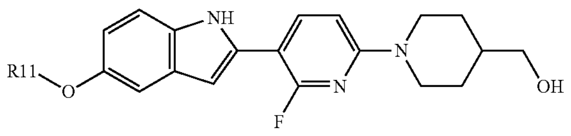

Example Compound 47: {1-[6-Fluoro-5-(5-methoxy-1H-indol-2-yl)pyridin-2-yl]piperidin-4-yl}methanol (R11=Me)

{1-[(tert-Butoxy)carbonyl]-5-methoxy-1H-indol-2-yl}boronic acid (160 mg, 1.1 eq) and intermediate 12-1 (145 mg, 0.5 mmol) were dissolved in dioxane (3 ml) in a 5 ml microwave vial. The solution was bubbled with $N_2$ for 2 min, then Pd(dppf)$Cl_2$ DCM 1:1 complex (20 mg, mol %) was added followed by 2 M $K_2CO_3$ (0.75 ml, 3 eq). The solution was again bubbled with $N_2$ for 5 min then the vial was capped. The reaction was run in a preheated oil bath at 90° C. overnight.

The cooled reaction mixture was diluted with ethyl acetate, washed with water, treated with brine, filtered through celite and the solvent was removed in vacuo to give the crude product.

The crude product was purified on the ISCO (12 g silica, applied with DCM, eluted with 20-40% ethyl acetate/hexane over 14 min) to give a light foam (167 mg, 73% yield, M+1 446). The foam (160 mg, 0.35 mmol) was then dissolved in DCM (10 ml) and 1 ml TFA was added. After 1 h product was seen, but the hydroxy group had formed an ester with the TFA.

The solvent was then removed in vacuo, and 3 M HCl (3 ml) was added. Methanol (15 ml) was added until a clear solution was seen. Concentrated HCl (12 M, 5 ml) was added and the reaction stirred overnight at rt. The solution was then heated and HCl in dioxane was added, and then HCl in iPrOH was added, and the reaction mixture heated to 110° C. for 1 hour. The reaction mixture was poured out on ice, made basic (4 M NaOH). The mixture was decanted and the remains were taken up in ethyl acetate that was treated with brine, dried with $MgSO_4$, filtered and the solvent was removed in vacuo to give the crude product.

The crude product was purified on the ISCO (12 g silica, applied with DCM, eluted with 25-45% ethyl acetate/hexane over 16 min) to give {1-[6-fluoro-5-(5-methoxy-1H-indol-2-yl)pyridin-2-yl]piperidin-4-yl}methanol (22 mg solid, 18% yield, HPLC Rf 3.11 min, MS m/z (M+1) 356.4, (M−1) 354.4). TLC: Rf 50% EA/hex 0.18.

Example Compound 48:2-{2-Fluoro-6-[4-(hydroxymethyl)piperidin-1-yl]pyridin-3-yl}-1H-indol-5-ol (R11=H)

Step (i)

{1-[(tert-Butoxy)carbonyl]-5-[(tert-butyldimethylsilyl)oxy]-1H-indol-2-yl}boronic acid (215 mg, 1.1 eq) and [1-(5-bromo-6-fluoropyridin-2-yl)piperidin-4-yl]methanol (intermediate 12-1,145 mg, 0.5 mmol) were dissolved in dioxane (3 ml) in a 5 ml microwave vial. The solution was bubbled with $N_2$ for 2 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then the vial was capped. The reaction was run in a preheated oil bath at 90° C. overnight.

The cooled reaction mixture was diluted with ethyl acetate, washed with water, treated with brine, filtered through celite, and the solvent was removed in vacuo to give the crude intermediate, tert-butyl 5-[(tert-butyldimethylsilyl)oxy]-2-{2-fluoro-6-[4-(hydroxymethyl)piperidin-1-yl]pyridin-3-yl}-1H-indole-1-carboxylate.

The crude intermediate was purified on the ISCO (24 g silica, applied with DCM, eluted with 10-35% ethyl acetate/hexane over 10 min) to give an oil of tert-butyl 5-[(tert-butyldimethylsilyl)oxy]-2-{2-fluoro-6-[4-(hydroxymethyl)piperidin-1-yl]pyridin-3-yl}-1H-indole-1-carboxylate (241 mg solid, MS m/z (M+1) 556.3).

tert-Butyl 5-[(tert-butyldimethylsilyl)oxy]-2-{2-fluoro-6-[4-(hydroxymethyl)piperidin-1-yl]pyridin-3-yl}-1H-indole-1-carboxylate (241 mg, 0.434 mmol, 80% pure) was dissolved in THF, cooled with an ice-bath and tetrabutylammonium fluoride (TBAF) (1 M in THF) (480 μl, 1.1 eq) was added. The reaction mixture was stirred for 30 min at 0° C. The reaction mixture was then diluted with ethyl acetate, washed with water, treated with brine, filtered through celite and the solvent was removed in vacuo to give the crude second intermediate, tert-butyl 2-{2-fluoro-6-[4-(hydroxymethyl)piperidin-1-yl]pyridin-3-yl}-5-hydroxy-1H-indole-1-carboxylate.

The crude intermediate was purified on the ISCO (12 g silica, applied with DCM, eluted with 25-60% ethyl acetate/hexane over 12 min) to give tert-butyl 2-{2-fluoro-6-[4-

(hydroxymethyl)piperidin-1-yl]pyridin-3-yl}-5-hydroxy-1H-indole-1-carboxylate (144 mg solid, 94% yield, MS m/z (M+1) 442.3, (M−1) 440.2).

Step (ii)

tert-Butyl 2-{2-fluoro-6-[4-(hydroxymethyl)piperidin-1-yl]pyridin-3-yl}-5-hydroxy-1H-indole-1-carboxylate (255 mg, 58 mmol) was dissolved in dry DCM (5 ml), cooled with an ice-bath and TFA (2 ml) was added. The reaction was stirred for 30 min at 0° C. then at rt for 1 h.

The solvent was removed ($N_2$), DCM added, and the solution was treated with saturated sodium bicarbonate, extracted three times with DCM, and the DCM discarded. The aqueous phase was re-extracted three times with hot ethyl acetate, and dried with $MgSO_4$ to give a crude solid product. DCM was added to the crude product and the solid was filtered.

The crude product was purified on a semiprep (methanol/50 mM ammonium acetate) to give 2-{2-fluoro-6-[4-(hydroxymethyl)piperidin-1-yl]pyridin-3-yl}-1H-indol-5-ol (2 mg solid, 5% yield, HPLC Rf 2.52 min, MS m/z (M+1) 342.3, (M−1) 340.2).

Alternative Step (ii)

tert-Butyl 2-{2-fluoro-6-[4-(hydroxymethyl)piperidin-1-yl]pyridin-3-yl}-5-hydroxy-1H-indole-1-carboxylate (255 mg, 58 mmol) was dissolved in dry DCM (5 ml), cooled with an ice-bath and TFA (5 ml) was added. The reaction was stirred at rt for 1 h.

The solvent was removed ($N_2$) then the remains were subjected to vacuum.

The remains were suspended in methanol (10 ml), lithium hydroxide (242 mg, 10 eq) was added followed by water (2 ml). The reaction was stirred for 1 h at rt.

Water (6-10 ml) was added to the suspension and the reaction was quenched with a saturated ammonium chloride solution (6 ml). The mixture stirred for 10 min then the solid was filtered, washed with water, dried (vacuum over $P_2O_5$) to give 2-{2-fluoro-6-[4-(hydroxymethyl)piperidin-1-yl]pyridin-3-yl}-1H-indol-5-ol (170 mg solid, 86% yield, HPLC Rf 2.52 min, MS m/z (M+1) 342.2, (M−1) 340.1).

Example Compounds of Structure 14

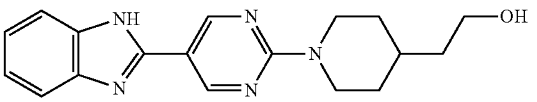

Example Compound 49:2-{1-[5-(1H-1,3-Benzodiazol-2-yl)pyrimidin-2-yl]piperidin-4-yl}ethan-1-ol A cooled solution of crude {2-[4-(2-hydroxyethyl)piperidin-1-yl]pyrimidin-5-yl}boronic acid (intermediate 5), formed as described above, was diluted with dioxane (3 ml), and 2-bromobenzimidazole (200 mg, 1 eq) was added followed by bubbling of $N_2$ for 5 min. Then 2 M $K_2CO_3$ (1.5 ml, 3 eq) was added, followed by Pd(dppf)$Cl_2$ DCM complex 1:1 (41 mg, 5 mol %). The solution was again bubbled with $N_2$ for 5 min then the vial was capped. The reaction mixture was stirred at 90° C. on an oil-bath for 3 h.

The reaction mixture was cooled and diluted with ethyl acetate, washed with water, filtered through celite, treated with brine, dried with $MgSO_4$ and the solvent was removed in vacuo to give the crude product. The crude product was refluxed in DCM, then the solid was filtered and washed with hot DCM. The solid was refluxed with ethyl acetate, cooled, and filtered to give 2-{1-[5-(1H-1,3-benzodiazol-2-yl)pyrimidin-2-yl]piperidin-4-yl}ethan-1-ol (66 mg solid, 20% yield, HPLC Rf 2.43 min, MS m/z (M+1) 324.4, (M−1) 322.2). TLC: ethyl acetate Rf 0.1.

Example Compounds of Structure 15

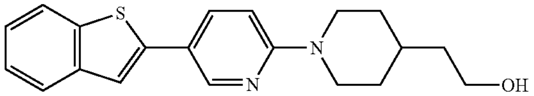 [SMILES: OCCC1CCN(c2ccc(-c3cc4ccccc4s3)cn2)CC1]

Example Compound 50: 2-{1-[5-(1-Benzothiophen-2-yl)pyridin-2-yl]piperidin-4-yl}ethan-1-ol Benzothiophene-2-boronic acid (75 mg, 1.2 eq) and {2-[1-(5-bromopyridin-2-yl)piperidin-4-yl]ethan-1-ol (intermediate 15,100 mg, 0.35 mmol) were dissolved in dioxane (2.1 ml) in a 5 ml microwave vial. The solution was bubbled with $N_2$ for 2.5 min, then Pd(dppf)$C_{1-2}$ DCM 1:1 complex (14 mg, 5 mol %) was added, followed by 2 M $K_2CO_3$ (0.53 ml, 3 eq). The solution was again bubbled with $N_2$ for 5 min then the vial was capped. The reaction was run in a preheated oil bath at 90° C. overnight.

The reaction mixture was cooled and then filtered through celite and the solvent was removed in vacuo to give the crude product.

The crude product was purified on the ISCO (12 g silica, applied with DCM, eluted with 30-50% ethyl acetate/hexane over 8 min) to give a solid, which was then refluxed in hexane, filtered, and washed with hexane to give 2-{1-[5-(1-benzothiophen-2-yl)pyridin-2-yl]piperidin-4-yl}ethan-1-ol (5 mg solid, 3% yield, HPLC Rf 3.59, MS m/z (M+1) 339.4). TLC: 60% ethyl acetate/hexane 0.23.

Example Compounds of Structure 16

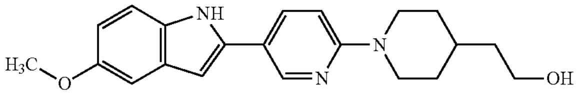 [SMILES: COc1ccc2[nH]c(-c3ccc(N4CCC(CCO)CC4)nc3)cc2c1]

Example Compound 51: 2-{1-[5-(5-Methoxy-1H-indol-2-yl)pyridin-2-yl]piperidin-4-yl}ethan-1-ol tert-Butyl 2-{6-[4-(2-hydroxyethyl)piperidin-1-yl]pyridin-3-yl}-5-methoxy-1H-indole-1-carboxylate (Intermediate 16,107 mg, 0.24 mmol) was dissolved in dioxane (1 ml), and 4 M HCl in dioxane (5 ml) was added. The reaction was allowed to stir at rt, then water (1 ml) and concentrated HCl (2 ml) were added, and the reaction mixture was heated for 2 h.

The reaction mixture was cooled and poured onto ice. The mixture was made basic with the addition of $Na_2CO_3$, then extracted with ethyl acetate, washed with water, treated with brine, dried with $MgSO_4$, filtered and the solvent was removed in vacuo to give the crude product.

The crude product was purified on the ISCO (4 g gold silica, applied with DCM, eluted with 40-55% ethyl acetate/hexane over 6 min) to give 2-{1-[5-(5-methoxy-1H-indol- 2-yl)pyridin-2-yl]piperidin-4-yl}ethan-1-ol (6 mg solid, 7% yield, HPLC Rf 2.98, MS m/z (M+1) 352.4, (M−1) 350.2). TLC: ethyl acetate Rf 0.30.

Example Compounds of Structure 17

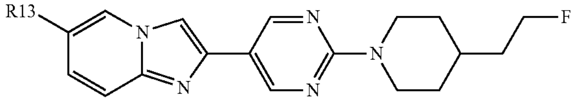

Example Compound 52:2-[4-(2-Fluoroethyl)piperidin-1-yl]-5-{imidazo[1,2-a]pyridin-2-yl}pyrimidine (R13=H)

In a sealed vial, 2-chloropyrimidin-5-yl)boronic acid (1 eq) and 4-(2-fluoroethyl)piperidine HCl (1 eq) were dissolved, with an excess of trimethylamine (TEA), in absolute methanol (2.5 ml). The reaction was run in a preheated oil bath at 80° C. for 45 min.

The solution was cooled, diluted with dioxane (3 ml), and 2-bromoimidazo[1,2-a]pyridine (197 mg, 1 eq) was added followed by bubbling of $N_2$ for 2 min. Then 2 M $K_2CO_3$ (1.5 ml, 3 eq) was added, followed by Pd(dppf)$Cl_2$ DCM complex 1:1 (41 mg, 5 mol %). The solution was again bubbled with $N_2$ for 5 min then the vial was capped. The reaction was run in a preheated oil bath at 90° C. for 1 h.

The reaction mixture was cooled then diluted with ethyl acetate, washed with water, dried with $MgSO_4$, filtered and the solvent removed in vacuo to give the crude product.

The crude product was purified on the ISCO (24 g silica, applied with DCM, eluted with 15-80% ethyl acetate/hexane) to give 2-[4-(2-fluoroethyl)piperidin-1-yl]-5-{imidazo[1,2-a]pyridin-2-yl}pyrimidine (25 mg solid, 8% yield, HPLC Rf 2.99, MS m/z (M+1) 326.3). TLC: ethyl acetate Rf 0.26.

Example Compound 53:2-[4-(2-Fluoroethyl)piperidin-1-yl]-5-{6-methoxyimidazo[1,2-a]pyridin-2-yl}pyrimidine (R13=OMe)

In a sealed vial, 2-chloropyrimidin-5-yl)boronic acid (1 eq) and 4-(2-fluoroethyl)piperidine HCl (1 eq) were dissolved, with an excess of trimethylamine (TEA), in absolute methanol (2.5 ml). The reaction was run in a preheated oil bath at 80° C. for 45 min.

The solution was cooled, diluted with dioxane (2.7 ml), and 2-bromo-6-methoxyimidazo[1,2-a]pyridine (203 mg, 1 eq) was added followed by bubbling of $N_2$ for 2 min. Then 2 M $K_2CO_3$ (1.34 ml, 3 eq) was added, followed by Pd(dppf)$Cl_2$ DCM complex 1:1 (37 mg, 5 mol %). The solution was again bubbled with $N_2$ for 5 min then the vial was capped. The reaction was run in a preheated oil bath at 90° C. for 1 h.

The reaction mixture was cooled, diluted with ethyl acetate, washed with water, dried with $MgSO_4$, filtered and the solvent removed in vacuo to give the crude product.

The crude product was purified on the ISCO (24 g silica, applied with DCM, eluted with 40-80% ethyl acetate/hexane) to give 2-[4-(2-fluoroethyl)piperidin-1-yl]-5-{6-methoxyimidazo[1,2-a]pyridin-2-yl}pyrimidine (32 mg solid, 11% yield, HPLC Rf 3.05, MS m/z (M+1) 356.3). TLC: ethyl acetate Rf 0.26.

Example Compounds of Structure 18

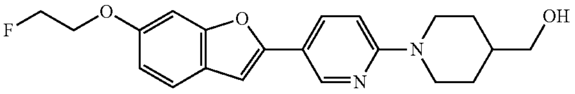

Example Compound 62: (1-{5-[6-(2-Fluoroethoxy)-1,3-benzoxazol-2-yl]pyridin-2-yl}piperidin-4-yl) methanol 2-(6-Chloropyridin-3-yl)-1,3-benzoxazol-6-ol (intermediate 19, 61 mg, 0.25 mmol) and 4-piperidinemethanol (114 mg, 4 eq) were suspended in methanol (3 ml) and subjected to the microwave for 1.5 h at 150° C.

The solvent was removed and the remains were refluxed with DCM and decanted 3 times to give crude 2-{6-[4-(hydroxymethyl)piperidin-1-yl]pyridin-3-yl}-1,3-benzoxazol-6-ol used in the next reaction step (MS m/z (M+1) 326.2, (M−1) 324.1).

The crude 2-{6-[4-(hydroxymethyl)piperidin-1-yl]pyridin-3-yl}-1,3-benzoxazol-6-ol (0.25 mmol) was dissolved in DMF (2 ml), and cesium carbonate (163 mg, 1.5 eq) was added followed by 1-fluoro-2-iodoethane (61 μl, 3 eq). The reaction was allowed to stir for 40 min at 50° C.

The cooled solution was dissolved in ethyl acetate, washed with water, treated with brine, dried with $MgSO_4$, filtered and the solvent was removed in vacuo to give the crude product.

The crude product was purified on the ISCO (4 g silica, applied with DCM, eluted with 60-75% ethyl acetate/hexane) to give (1-{5-[6-(2-Fluoroethoxy)-1,3-benzoxazol-2-yl]pyridin-2-yl}piperidin-4-yl)methanol (22 mg solid, 24% yield, HPLC Rf 2.94 min, MS m/z (M+1) 372.3, (M−1) 370.3). TLC: ethyl acetate Rf 0.24.

Example Compounds of Structure 19

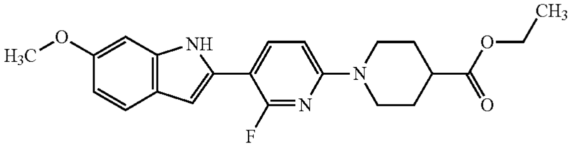 [SMILES: CCOC(=O)C1CCN(c2ccc(-c3cc4ccc(OC)cc4[nH]3)c(F)n2)CC1]

Example Compound 63: Ethyl 1-[6-Fluoro-5-(6-methoxy-1H-indol-2-yl)pyridin-2-yl]piperidine-4-carboxylate Ethyl 1-(5-bromo-6-fluoropyridin-2-yl)piperidine-4-carboxylate mg, (intermediate 20,165 mg, 0.5 mmol) and {1-[(tert-butoxy)carbonyl]-5-methoxy-1H-indol-2-yl}boronic acid (175 mg, 1.2 eq) were dissolved in dioxane (3 ml) in a 5 ml microwave vial. The solution was bubbled with $N_2$ for 3 min, then Pd(dppf)$Cl_2$ DCM complex 1:1 (20 mg, 5 mol %) was added followed by 2 M $K_2CO_3$ (0.75 ml, 3 eq). The solution was again bubbled with $N_2$ for 5 min then capped. The reaction was run in a preheated oil bath at 90° C. for 1 h.

The cooled reaction was diluted with ethyl acetate (the aqueous phase was removed with a pasteur pipette), filtered through celite, washed with ethyl acetate. The organic was washed with water, treated with brine, dried with $MgSO_4$, filtered and the solvent was removed in vacuo to give the crude tert-butyl 2-{6-[4-(ethoxycarbonyl)piperidin-1-yl]-2-fluoropyridin-3-yl}-5-methoxy-1H-indole-1-carboxylate.

The crude tert-butyl 2-{6-[4-(ethoxycarbonyl)piperidin-1-yl]-2-fluoropyridin-3-yl}-5-methoxy-1H-indole-1-carboxylate was purified on the ISCO (12 g silica, applied with hexane/DCM 1:1, eluted with 10-18% ethyl acetate/hexane over 5 min) to give tert-butyl 2-{6-[4-(ethoxycarbonyl)piperidin-1-yl]-2-fluoropyridin-3-yl}-5-methoxy-1H-indole-1-carboxylate (227 mg foam, 91% yield, MS m/z (M+1) 498.4).

tert-Butyl 2-{6-[4-(ethoxycarbonyl)piperidin-1-yl]-2-fluoropyridin-3-yl}-5-methoxy-1H-indole-1-carboxylate (215 mg, 0.43 mmol) was dissolved in anhydrous DCM (20 ml), and the mixture was cooled with an ice-bath then TFA (7 ml) was added. After 10 min the cooling bath was removed and the reaction stirred at rt overnight.

The solvent was removed with $N_2$, ethyl acetate was added followed by a saturated solution of $NaHCO_3$ and the mixture stirred until the solid went into solution. The organic portion was separated then treated with brine, dried with $MgSO_4$, and filtered. Most of the solvent was removed with $N_2$ then hexane was added and the solid filtered, washed with hexane, dried to give ethyl 1-[6-fluoro-5-(5-methoxy-1H-indol-2-yl)pyridin-2-yl]piperidine-4-carboxylate (133 mg solid, 77% yield, HPLC Rf 3.65 min, MS m/z (M+1) 398.3, (M−1) 396.2). TLC 50% ethyl acetate/hexane Rf 0.50.

Example Compounds of Structure 20

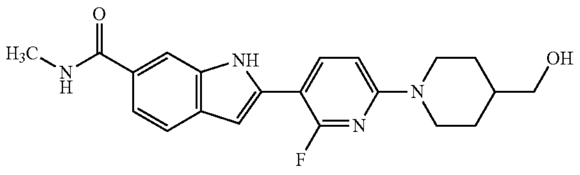 [SMILES: CNC(=O)c1ccc2cc(-c3ccc(N4CCC(CO)CC4)nc3F)[nH]c2c1]

Example Compound 64:2-{2-Fluoro-6-[4-(hydroxymethyl)piperidin-1-yl]pyridin-3-yl}-N-methyl-1H-indole-6-carboxamide {1-[(tert-Butoxy)carbonyl]-6-(methylcarbamoyl)-1H-indol-2-yl}boronic acid (intermediate 21, 277 mg, 1.2 eq) and [1-(5-bromo-6-fluoropyridin-2-yl)piperidin-4-yl]methanol (intermediate 12-1, 210 mg, 0.73 mmol) were dissolved in dioxane (5 ml) in a 20 ml microwave vial. The solution was bubbled with $N_2$ for 2 min, then Pd(dppf)Cl2 DCM 1:1 complex (30 mg, 5 mol %) was added followed by 2 M $K_2CO_3$ (1.1 ml, 3 eq). The solution was again bubbled with $N_2$ for 5 min then capped. The reaction was run in a preheated oil bath at 90° C. for 1 h.

The cooled reaction was diluted with ethyl acetate, treated with brine, dried with $MgSO_4$, filtered and the solvent was removed in vacuo to give crude tert-butyl 2-{2-fluoro-6-[4-(hydroxymethyl)piperidin-1-yl]pyridin-3-yl}-6-(methylcarbamoyl)-1H-indole-1-carboxylate.

The crude tert-butyl 2-{2-fluoro-6-[4-(hydroxymethyl)piperidin-1-yl]pyridin-3-yl}-6-(methylcarbamoyl)-1H-indole-1-carboxylate was purified on the ISCO (12 g silica, applied with DCM, eluted with 50-90% ethyl acetate/hexane over 10 min) to give tert-butyl 2-{2-fluoro-6-[4-(hydroxymethyl)piperidin-1-yl]pyridin-3-yl}-6-(methylcarbamoyl)-1H-indole-1-carboxylate (159 mg oil, 45% yield, MS m/z (M+1) 483.4, (M−1) 481.3).

tert-Butyl 2-{2-fluoro-6-[4-(hydroxymethyl)piperidin-1-yl]pyridin-3-yl}-6-(methylcarbamoyl)-1H-indole-1-carboxylate (163 mg, 0.33 mmol) was dissolved in anhydrous DCM (15 ml), cooled with an ice bath and TFA (5 ml) was added. The reaction was allowed reaction stir overnight at rt then was put in the refrigerator over the weekend.

The solvent was removed ($N_2$, then vacuum), the remains were suspended in methanol (15 ml), lithium hydroxide (138 mg, 10 eq) was added followed by water (3 ml). The reaction was stirred for 30 h at rt.

The reaction was quenched with saturated ammonium chloride, the solid was filtered, washed with water, dried ($P_2O_5$, vacuum) to give 2-{2-fluoro-6-[4-(hydroxymethyl)piperidin-1-yl]pyridin-3-yl}-N-methyl-1H-indole-6-carboxamide (80 mg solid, 62% yield, HPLC Rf 2.61 min, MS m/z (M+1) 383.3, (M−1) 381.3).

Example Compounds of Structure 21

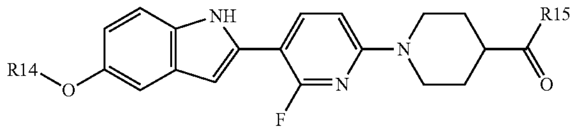

Example Compound 65: Ethyl 1-[6-Fluoro-5-(5-hydroxy-1H-indol-2-yl)pyridin-2-yl]piperidine-4-carboxylate (R14=H, R15=OEt)

tert-Butyl 5-[(tert-butyldimethylsilyl)oxy]-2-{6-[4-(ethoxycarbonyl)piperidin-1-yl]-2-fluoropyridin-3-yl}-1H-indole-1-carboxylate (intermediate 22, 269 mg, 0.45 mmol) was dissolved in THF (4.5 ml), cooled with an ice-bath and TBAF (500 μl, 1.1 eq) was added. The reaction was stirred 30 min at 0° C.

The reaction was diluted with ethyl acetate, washed with water, treated with brine, dried with $MgSO_4$, filtered, stripped to give tert-butyl 2-{6-[4-(ethoxycarbonyl)piperidin-1-yl]-2-fluoropyridin-3-yl}-5-hydroxy-1H-indole-1-carboxylate that was used as is in the next reaction (MS m/z (M+1) 484.3, (M−1) 482.2).

The crude, tert-butyl 2-{6-[4-(ethoxycarbonyl)piperidin-1-yl]-2-fluoropyridin-3-yl}-5-hydroxy-1H-indole-1-carboxylate (0.45 mmol) was dissolved in anhydrous DCM (20 ml), the mixture was cooled with an ice-bath then TFA (10 ml) was added. After 10 min the cooling bath was removed and the reaction stirred at rt overnight.

The solvent was removed with $N_2$ (a solid formed). The solution was extracted with ethyl acetate, twice, treated with brine, dried with $MgSO_4$, and filtered. When most of the solvent was removed (N2) hexane was added and the solid was filtered and washed with hexane. The solid was slurried in DCM and filtered to give ethyl 1-[6-fluoro-5-(5-hydroxy-1H-indol-2-yl)pyridin-2-yl]piperidine-4-carboxylate (103 mg solid (HPLC, 54% yield for 2 steps MS m/z (M+1) 384.3, (M−1) 382.3). TLC 50% ethyl acetate/hexane Rf 0.32.

Example Compound 66: 1-[6-Fluoro-5-(5-hydroxy-1H-indol-2-yl)pyridin-2-yl]piperidine-4-carboxamide (R14=H, R15=$NH_2$)

tert-Butyl 5-[(tert-butyldimethylsilyl)oxy]-2-[6-(4-carbamoylpiperidin-1-yl)-2-fluoropyridin-3-yl]-1H-indole-1-carboxylate (intermediate 24, 186 mg, 0.33 mmol) was dissolved in THF (4 ml), cooled with an ice-bath and TBAF (360 μl, 1.1 eq) was added. The reaction was stirred 30 min at 0° C.

The solvent was removed in vacuo and the crude was used as is in the next reaction to give tert-butyl 2-[6-(4-carbamoylpiperidin-1-yl)-2-fluoropyridin-3-yl]-5-hydroxy-1H-indole-1-carboxylate (MS m/z (M+1) 455.3, (M−1) 453.3).

The crude (tert-butyl 2-[6-(4-carbamoylpiperidin-1-yl)-2-fluoropyridin-3-yl]-5-hydroxy-1H-indole-1-carboxylate) was dissolved in TFA (5 ml) and the clear solution stirred for 10 min.

The excess TFA was removed by $N_2$, acetonitrile was added to the remains and this was allowed to stir for 10 min. The solid was filtered, washed with acetonitrile to give 1-[6-Fluoro-5-(5-hydroxy-1H-indol-2-yl)pyridin-2-yl]piperidine-4-carboxamide (75 mg solid, 65% yield, HPLC Rf 2.31 min, MS m/z (M+1) 355.2, (M−1) 353.3).

Example Compound 67: Methyl 1-[6-Fluoro-5-(5-hydroxy-1H-indol-2-yl)pyridin-2-yl]piperidine-4-carboxylate (R14=FI, R15=OMe)

Ethyl 1-[6-Fluoro-5-(5-hydroxy-1H-indol-2-yl)pyridin-2-yl]piperidine-4-carboxylate (Example Compound 65, 24 mg, 63 μmol) was slurried in methanol (3 ml) and potassium cyanide (0.4 mg, 10 mol %) was added and the reaction stirred at 70° C. overnight.

The solvent was removed in vacuo and the remains were dissolved in DMSO (1.5 ml) and purified on the semi-prep (Kromasil 100 C8, 250×20 mm, (50-85% AcCN/ammonia solution) with 2 injections.

The organic solvent was removed, the product was filtered, washed with water, dried (vacuum over $P_2O_5$) to give methyl 1-[6-fluoro-5-(5-hydroxy-1H-indol-2-yl)pyridin-2-yl]piperidine-4-carboxylate (9.4 mg solid, 41% yield, HPLC Rf 3.01 min, MS m/z (M+1) 370.2, (M−1) 368.1).

Example Compound 68: 1-[6-Fluoro-5-(5-methoxy-1H-indol-2-yl)pyridin-2-yl]piperidine-4-carboxamide (R14=Me, R15=$NH_2$)

tert-Butyl 2-[6-(4-carbamoylpiperidin-1-yl)-2-fluoropyridin-3-yl]-5-methoxy-1H-indole-1-carboxylate (intermediate 25, 184 mg, 0.39 mmol) were dissolved in TFA (6 ml) and the solution stirred for 10 min.

The excess TFA was removed by $N_2$ then subjected to vacuum. Acetonitrile was added to the remains and the solid was filtered, washed with acetonitrile to give 1-[6-fluoro-5-(5-methoxy-1H-indol-2-yl)pyridin-2-yl]piperidine-4-carboxamide (90 mg solid, 63% yield, HPLC Rf 2.91 min, MS m/z (M+1) 369.3, (M−1) 367.2).

Example Compounds of Structure 22

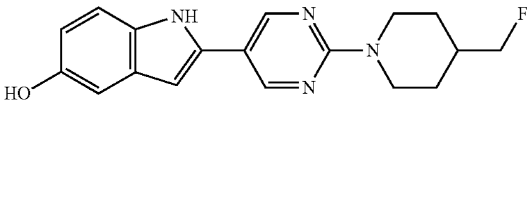 [SMILES: Oc1ccc2[nH]c(-c3cnc(N4CCC(CF)CC4)nc3)cc2c1]

Example Compound 69: 2-{2-[4-(Fluoromethyl)piperidin-1-yl]pyrimidin-5-yl}-1H-indol-5-ol tert-Butyl 5-[(tert-butyldimethylsilyl)oxy]-2-{2-[4-(fluoromethyl)piperidin-1-yl]pyrimidin-5-yl}-1H-indole-1-carboxylate (intermediate 27, 225 mg, 0.42 mmol) was dissolved in THF (4 ml). The solution was cooled with an ice-bath and TBAF (460 μl, 1.1 eq) was added. The reaction was stirred 30 min at 0° C.

The reaction mixture was diluted with ethyl acetate, washed with water, treated with brine, dried with $MgSO_4$, filtered and the solvent was removed in vacuo to give crude tert-butyl 2-{2-[4-(fluoromethyl)piperidin-1-yl]pyrimidin-5-yl}-5-hydroxy-1H-indole-1-carboxylate.

The crude tert-butyl 2-{2-[4-(fluoromethyl)piperidin-1-yl]pyrimidin-5-yl}-5-hydroxy-1H-indole-1-carboxylate was purified on the ISCO (12 g silica, applied with DCM, eluted with 10-30% ethyl acetate/hexane over 5 min) to give tert-butyl 2-{2-[4-(fluoromethyl)piperidin-1-yl]pyrimidin-5-yl}-5-hydroxy-1H-indole-1-carboxylate (177 solid, 99% yield, MS m/z (M+1) 427.4, (M−1) 425.3). TLC 40% ethyl acetate/hexane Rf 0.27.

tert-Butyl 2-{2-[4-(fluoromethyl)piperidin-1-yl]pyrimidin-5-yl}-5-hydroxy-1H-indole-1-carboxylate (177 mg, 0.415 mmol) was dissolved in anhydrous DCM (16 ml), and the mixture was cooled with an ice-bath then TFA (8 ml) was added. After 10 min the cooling bath was removed and the reaction stirred for 2 h.

The solvent was removed with $N_2$. The solution was slurried in water, made basic with a saturated solution of sodium bicarbonate, extracted twice with DCM, dried with $MgSO_4$, filtered and the solvent removed in vacuo to give the crude product.

The crude product was purified on the ISCO (4 g silica, dissolved in DCM with some EA, eluted with 25-30% ethyl acetate/hexane) to give 2-{2-[4-(fluoromethyl)piperidin-1-yl]pyrimidin-5-yl}-1H-indol-5-ol (17 mg solid, 13% yield, HPLC Rf 2.92 min, MS m/z (M+1) 327.3, (M−1) 325.3). TLC 40% ethyl acetate/hexane Rf 0.17.

Example Compounds of Structure 23

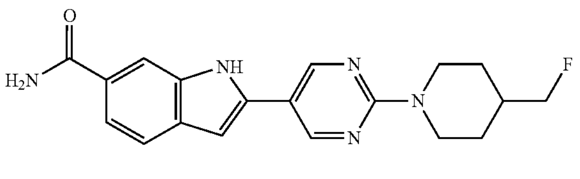 [SMILES: NC(=O)c1ccc2cc(-c3cnc(N4CCC(CF)CC4)nc3)[nH]c2c1]

Example Compound 70: 2-{2-[4-(Fluoromethyl)piperidin-1-yl]pyrimidin-5-yl}-1H-indole-6-carboxamide 1-tert-Butyl 6-methyl 2-{2-[4-(fluoromethyl)piperidin-1-yl]pyrimidin-5-yl}-1H-indole-1,6-dicarboxylate (intermediate 28,170 mg, 0.36 mol) was dissolved in THF (15 ml) and methanol (15 ml). LiOH monohydrate (183 mg, 12 eq) was added followed by water (6 ml). The reaction was allowed to stir at 60° C. for 5 h.

The reaction was quenched with a saturated solution of $NH_4Cl$ and the clear mixture was stirred overnight in an open flask. The formed solid was filtered and dried (vacuum over $P_2O_5$) to give crude 2-{2-[4-(fluoromethyl)piperidin-1-yl]pyrimidin-5-yl}-1H-indole-6-carboxylic acid.

The crude 2-{2-[4-(fluoromethyl)piperidin-1-yl]pyrimidin-5-yl}-1H-indole-6-carboxylic acid was dissolved in DMSO (2-3 ml with heating), the solution filtered through a 0.45 μm filter and separated on a Gilson semi-prep Kromasil C8 7 μm, 250×25 mm, eluted with 35-90% AcCN/50 mM NH4OAc, 5 runs) to give 2-{2-[4-(fluoromethyl)piperidin-1-yl]pyrimidin-5-yl}-1H-indole-6-carboxylic acid (56 mg solid, 44% yield, MS m/z (M+1) 355.2, (M−1) 353.2).

2-{2-[4-(Fluoromethyl)piperidin-1-yl]pyrimidin-5-yl}-1H-indole-6-carboxylic acid (54 mg, 152 μmol) was dissolved in DMF (8 ml, heating then cooled to rt) and HOBt (61 mg, 3 eq) was added followed by EDC HCl (87 mg, 3 eq). The reaction was stirred for 30 min at rt then 25% aqueous ammonia (120 μl) was added and the reaction was followed. More HOBt (61 mg mg, 3 eq) and EDC HCl (87 mg, 3 eq) were added and the reaction was stirred for 10 min at rt. 25% aqueous ammonia (120 μl) was added again. The reaction was stirred for 6 h in total.

Water was then added, dropwise, to the reaction mixture until the solution turned cloudy (slightly exothermic reaction, and a precipitate formed). After stirring for 15 min, the solid was filtered, washed with water and the solid was dried (vacuum over P2O5) to give 2-{2-[4-(fluoromethyl)piperidin-1-yl]pyrimidin-5-yl}-1H-indole-6-carboxamide (36 mg solid, 67% yield, HPLC 2.78 min, MS m/z (M+1) 354.3, (M−1) 352.2).

Example Compounds of Structure 24

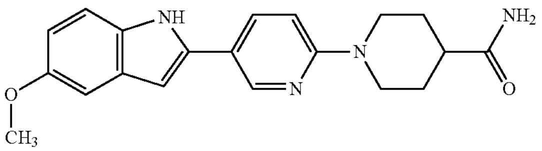 [SMILES: COc1ccc2[nH]c(-c3ccc(N4CCC(C(N)=O)CC4)nc3)cc2c1]

Example Compound 71: 1-[5-(5-Methoxy-1H-indol-2-yl)pyridin-2-yl]piperidine-4-carboxamide tert-Butyl 2-[6-(4-carbamoylpiperidin-1-yl)pyridin-3-yl]-5-methoxy-1H-indole-1-carboxylate (intermediate 30,110 mg, 0.24 mmol) was dissolved in TFA (4 ml) and the clear solution stirred for 10 min.

The excess TFA was removed by $N_2$ then vacuum. Water was added to the remains, the solution was made basic with a saturated solution of sodium bicarbonate and was extracted with ethyl acetate. The organic phase was filtered through $MgSO_4$, hexane was added, and the solvent was partially removed. More hexane was added and the solid was filtered to give 1-[5-(5-methoxy-1H-indol-2-yl)pyridin-2-yl]piperidine-4-carboxamide (64 mg, yield 76%, HPLC Rf 2.67 min, MS m/z (M+1) 351.3, (M−1) 49.3).

Example Compounds of Structure 25

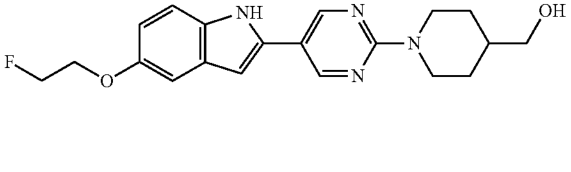 [SMILES: OCC1CCN(c2ncc(-c3cc4cc(OCCF)ccc4[nH]3)cn2)CC1]

Example Compound 72: (1-{5-[5-(2-Fluoroethoxy)-1H-indol-2-yl]pyrimidin-2-yl}piperidin-4-yl)methanol tert-Butyl 5-[(tert-butyldimethylsilyl)oxy]-2-{2-[4-(hydroxymethyl)piperidin-1-yl]pyrimidin-5-yl}-1H-indole-1-carboxylate (intermediate 32, 450 mg, 0.84 mmol) was dissolved in THF (10 ml), cooled with an ice-bath and TBAF 1 M in THF (920 μl, 1.1 eq) was added. The reaction was stirred 30 min at 0° C.

The reaction was diluted with ethyl acetate, washed with water, treated with brine, dried with $MgSO_4$, filtered and the solvent was removed in vacuo to give crude tert-butyl 5-hydroxy-2-{2-[4-(hydroxymethyl)piperidin-1-yl]pyrimidin-5-yl}-1H-indole-1-carboxylate.

The crude tert-butyl 5-hydroxy-2-{2-[4-(hydroxymethyl)piperidin-1-yl]pyrimidin-5-yl}-1H-indole-1-carboxylate was purified on the ISCO (12 g silica, applied with DCM, eluted with 40-60% ethyl acetate/hexane over 8 min) to give tert-butyl 5-hydroxy-2-{2-[4-(hydroxymethyl)piperidin-1-yl]pyrimidin-5-yl}-1H-indole-1-carboxylate (332 mg foam, yield 93%, HPLC Rf 3.05 min, MS m/z (M+1) 425.3, (M−1) 423.2). TLC 50% ethyl acetate/hexane. Rf 0.10.

tert-Butyl 5-hydroxy-2-{2-[4-(hydroxymethyl)piperidin-1-yl]pyrimidin-5-yl}-1H-indole-1-carboxylate (270 mg, 0.64 mmol) was dissolved in DMF (5 ml), cesium carbonate (310 mg, 1.5 eq) was added followed by the addition of 1-fluoro-2-iodoethane (80 μl, 1.5 eq). The reaction was stirred for at 50° C. for 2 h.

The cooled solution added to water, the solution was extracted with ethyl acetate, washed with water three times, treated with brine, dried with $MgSO_4$, filtered and the solvent was removed in vacuo to give crude tert-butyl 5-(2-fluoroethoxy)-2-{2-[4-(hydroxymethyl)piperidin-1-yl]pyrimidin-5-yl}-1H-indole-1-carboxylate.

The crude tert-butyl 5-(2-fluoroethoxy)-2-{2-[4-(hydroxymethyl)piperidin-1-yl]pyrimidin-5-yl}-1H-indole-1-carboxylate was purified on the ISCO (12 g silica, applied with DCM, eluted with 30-50% ethyl acetate/hexane over 8 min) to give tert-butyl 5-(2-fluoroethoxy)-2-{2-[4-(hydroxymethyl)piperidin-1-yl]pyrimidin-5-yl}-1H-indole-1-carboxylate (249 mg foam, 83% yield, HPLC Rf 3.55 min, MS m/z (M+1) 471.3). TLC 80% ethyl acetate/hexane Rf 0.32).

tert-Butyl 5-(2-fluoroethoxy)-2-{2-[4-(hydroxymethyl)piperidin-1-yl]pyrimidin-5-yl}-1H-indole-1-carboxylate (249 mg, 0.53 mmol) was dissolved in anhydrous DCM (5 ml), cooled with an ice bath and TFA (5 ml) was added. After 1 h, at rt, TFA (2 ml) was added and the reaction was stirred for 30 min.

The solvent was removed ($N_2$, then vacuum) and the remains were dissolved in methanol (10 ml). Lithium hydroxide monohydrate (222 mg, 10 eq) was added followed by water (2 ml). The reaction was still acidic so more lithium hydroxide monohydrate (222 mg, 10 eq) was added again. After stirring for 2 h a precipitate formed. The solid was filtered and the solid was washed with cold methanol/water 2:1. The solid was dried (high vacuum over $P2O_5$) to give (1-{5-[5-(2-fluoroethoxy)-1H-indol-2-yl]pyrimidin-2-yl}piperidin-4-yl)methanol (80 mg solid, 41% yield, HPLC, Rf 2.89 min, MS m/z (M+1) 371.3, (M−1) 369.2). TLC ethyl acetate Rf 0.30.

Example Compounds of Structure 26

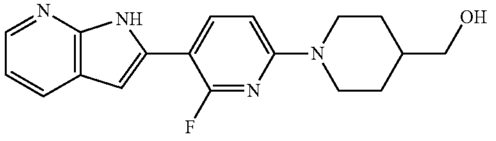 [SMILES: OCC1CCN(c2ccc(-c3cc4cccnc4[nH]3)c(F)n2)CC1]

Example Compound 73: [1-(6-Fluoro-5-{1H-pyrrolo[2,3-b]pyridin-2-yl}pyridin-2-yl)piperidin-4-yl] methanol tert-Butyl 2-{2-fluoro-6-[4-(hydroxymethyl)piperidin-1-yl]pyridin-3-yl}-1H-pyrrolo[2,3-b]pyridine-1-carboxylate (intermediate 33, 46 mg, 110 μmol) was dissolved in anhydrous DCM (2 ml), cooled with an ice bath and TFA (2 ml) was added. The reaction was allowed reaction stir for 1 h at rt.

The solvent was removed ($N_2$, then vacuum), the remains were dissolved in methanol (2 ml), and the solution cooled with an ice-bath. Lithium hydroxide monohydrate (46 mg, 10 eq) was then added followed by water (0.5 ml). The reaction was stirred for 30 min at rt.

The reaction was quenched with water, stirred, and then the solid was filtered, washed with water, and dried (vacuum, dried over $P_2O_5$) to give [1-(6-fluoro-5-{1H-pyrrolo[2,3-b]pyridin-2-yl}pyridin-2-yl)piperidin-4-yl] methanol (25 mg solid, yield 69%, HPLC Rf 2.83 min, MS m/z (M+1) 327.2, (M−1) 325.2).

Example Compounds of Structure 27

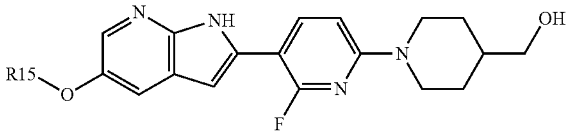

Example Compound 74: [1-(6-Fluoro-5-{5-methoxy-1H-pyrrolo[2,3-b]pyridin-2-yl}pyridin-2-yl)piperidin-4-yl]methanol (R15=Me)

tert-Butyl 2-{2-fluoro-6-[4-(hydroxymethyl)piperidin-1-yl]pyridin-3-yl}-5-methoxy-1H-pyrrolo[2,3-b]pyridine-1-carboxylate (intermediate 35, 38 mg, 83 μmol) was dissolved in anhydrous DCM (1.5 ml), cooled with an ice-bath and TFA (2 ml) was added. The reaction was allowed to stir for 1.5 h at rt.

The solvent was removed ($N_2$), the remains were dissolved in methanol (3 ml), and lithium hydroxide hydrate (35 mg, 10 eq) was added followed by water (1 ml). The reaction was stirred for 30 min at rt.

Water (1 ml) was added and the mixture stirred for 5 min, and then the solid was filtered, washed with water, dried (vacuum over $P_2O_5$) to give [1-(6-fluoro-5-{5-methoxy-1H-pyrrolo[2,3-b]pyridin-2-yl}pyridin-2-yl)piperidin-4-yl] methanol (13 mg solid, 43% yield, HPLC Rf 2.84 min, MS m/z (M+1) 357.2, (M−1) 355.2).

Example Compound 75:2-{2-Fluoro-6-[4-(hydroxymethyl)piperidin-1-yl]pyridin-3-yl}-1H-pyrrolo[2,3-b]pyridin-5-ol (R15=Fl)

tert-Butyl 2-{2-fluoro-6-[4-(hydroxymethyl)piperidin-1-yl]pyridin-3-yl}-5-methoxy-1H-pyrrolo[2,3-b]pyridine-1-carboxylate (intermediate 35,110 mg, 0.24 mmol) was dissolved in anhydrous DCM (5 ml), cooled with a dry-ice bath and 1 M $BBr_3$ in DCM (1.2 ml, 5 eq) was added dropwise. The reaction was allowed to stir at rt for 4 h.

The reaction was added to an ice/2 M $NH_3$ mixture. After the ice melted the aqueous phase was decanted and the solid was filtered. Water was added to the remaining DCM portion and the aqueous phase was decanted again and the solid was filtered. The solid was dried (vacuum over $P_2O_5$) dissolved in DMSO (2 ml) and purified on the semi-prep (Kromasil 100 C8, 250×20 mm, (40-85% AcCN/ammonia solution) with 3 injections to give 2-{2-fluoro-6-[4-(hydroxymethyl) piperidin-1-yl]pyridin-3-yl}-1H-pyrrolo[2,3-b]pyridin-5-ol (14 mg light solid, 18% yield, HPLC Rf 2.38 min, MS m/z (M+1) 343.2, (M−1) 341.1).

Example Compounds of Structure 28

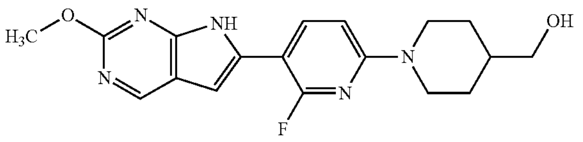 [SMILES: COc1ncc2cc(-c3ccc(N4CCC(CO)CC4)nc3F)[nH]c2n1]

Example Compound 76: [1-(6-Fluoro-5-{2-methoxy-7H-pyrrolo[2,3-d]pyrimidin-6-yl}pyridin-2-yl)piperidin-4-yl]methanol

[1-(5-Bromo-6-fluoropyridin-2-yl)piperidin-4-yl]methanol (intermediate 12-1, 434 mg, 1.5 mmol) and {7-[(tert-butoxy)carbonyl]-2-methoxy-7H-pyrrolo[2,3-d]pyrimidin-6-yl}boronic acid (intermediate 36, 0.66 g, 1.9 mmol) were dissolved in dioxane (9 ml) in a 20 ml microwave vial. The solution was bubbled with $N_2$ for 3 min, then $Pd(dppf)Cl_2$ DCM 1:1 complex (62 mg, 5 mol %) was added followed by 2 M $K_2CO_3$ (2.25 ml, 3 eq). The solution was again bubbled with $N_2$ for 5 min then capped. The reaction was run in a preheated oil bath at 90° C. for 1 h.

The cooled reaction mixture was diluted ethyl acetate, washed with saturated brine, dried with $MgSO_4$, filtered and the solvent was removed in vacuo to give the crude product.

The crude product was purified on the ISCO (25 g silica, applied with DCM (filtered first), eluted with 80% ethyl acetate/hexane for 6 min then 100% ethyl acetate to give [1-(6-fluoro-5-{2-methoxy-7H-pyrrolo[2,3-d]pyrimidin-6-yl}pyridin-2-yl)piperidin-4-yl]methanol (46 mg solid, 9% yield, HPLC 2.57 min, MS m/z (M+1) 358.2, (M−1) 356.1). TLC ethyl acetate Rf 0.15.

Example Compounds of Structure 29

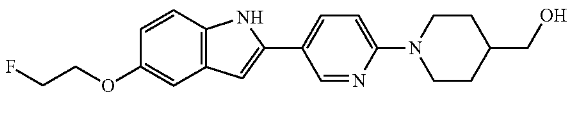 [SMILES: OCC1CCN(c2ccc(-c3cc4cc(OCCF)ccc4[nH]3)cn2)CC1]

Example Compound 77: (1-{5-[5-(2-Fluoroethoxy)-1H-indol-2-yl]pyridin-2-yl}piperidin-4-yl)methanol tert-Butyl 5-[(tert-butyldimethylsilyl)oxy]-2-{6-[4-(hydroxymethyl)piperidin-1-yl]pyridin-3-yl}-1H-indole-1-carboxylate (Intermediate 38, 426 mg, 0.79 mmol) was dissolved in THF (8 ml), cooled with an ice-bath and TBAF 1 M in THF (870 μl, 1.1 eq) was added. The reaction was stirred 30 min at 0° C.

The reaction was diluted with ethyl acetate, washed with water, treated with brine, dried with $MgSO_4$, filtered and the solvent was removed in vacuo to give crude tert-butyl 5-hydroxy-2-{6-[4-(hydroxymethyl)piperidin-1-yl]pyridin-3-yl}-1H-indole-1-carboxylate.

The crude tert-butyl 5-hydroxy-2-{6-[4-(hydroxymethyl)piperidin-1-yl]pyridin-3-yl}-1H-indole-1-carboxylate was purified on the ISCO (12 g silica, applied with DCM, eluted with 35-70% ethyl acetate/hexane over 2 min) to give tert-butyl 5-hydroxy-2-{2-[4-(hydroxymethyl)piperidin-1-yl]pyrimidin-5-yl}-1H-indole-1-carboxylate (245 mg oil, yield 65%, HPLC Rf 3.05 min, MS m/z (M+1) 424.3, (M−1) 422.2). TLC 50% ethyl acetate/hexane. Rf 0.10.

tert-Butyl 5-hydroxy-2-{6-[4-(hydroxymethyl)piperidin-1-yl]pyridin-3-yl}-1H-indole-1-carboxylate (114 mg, 270 μmol) was dissolved in DMF (1.5 ml), cesium carbonate (132 mg, 1.5 eq) was added followed by the addition of 1-fluoro-2-iodoethane (33 μl, 1.5 eq). The reaction was stirred for at 50° C. for 2 h.

The cooled solution was added to water, and the solution was extracted with ethyl acetate, washed with water three times, treated with brine, dried with $MgSO_4$, filtered and the solvent was removed in vacuo to give crude tert-butyl 5-(2-fluoroethoxy)-2-{6-[4-(hydroxymethyl)piperidin-1-yl]pyridin-3-yl}-1H-indole-1-carboxylate.

The crude was purified on the ISCO (4 g silica, applied with DCM, eluted with 40-60% ethyl acetate/hexane over 4 min) to give tert-butyl 5-(2-fluoroethoxy)-2-{6-[4-(hydroxymethyl)piperidin-1-yl]pyridin-3-yl}-1H-indole-1-carboxylate (104 mg oil, 83% yield, HPLC Rf 3.48 min, MS m/z (M+1) 470.3). TLC 70% ethyl acetate/hexane Rf 0.22).

tert-Butyl 5-(2-fluoroethoxy)-2-{6-[4-(hydroxymethyl)piperidin-1-yl]pyridin-3-yl}-1H-indole-1-carboxylate (103 mg, 0.22 mmol) was dissolved in anhydrous DCM (4 ml), cooled on an ice bath and TFA (4 ml) was added. The reaction was stirred for 1 h, at rt.

The solvent was removed ($N_2$, then vacuum) and the remains were dissolved in methanol (6 ml). After stirring for 30 min water was added to the reaction and the precipitate was filtered. The solid was washed with cold methanol/water 2:1. The solid was dried (high vacuum over $P_2O_5$) to give (1-{5-[5-(2-fluoroethoxy)-1H-indol-2-yl]pyridin-2-yl}piperidin-4-yl)methanol (62 mg solid, 11% yield, HPLC, Rf 2.88 min, MS m/z (M+1) 370.3, (M−1) 368.2).

A summary of the structure of example compounds 1 to 77, the CLogP of the compounds, is provided below in Table 1.

TABLE 1

| Example Compound No. | Mol. Weight | Structure | CLogP |
|---|---|---|---|
| 53 | 355 | 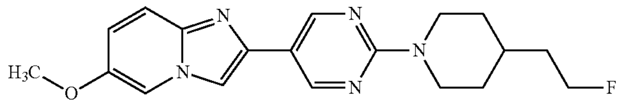 [SMILES: COc1ccc2nc(-c3cnc(N4CCC(CCF)CC4)nc3)cn2c1] | 2.5 |
| 52 | 325 | 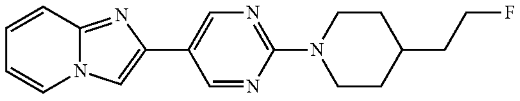 [SMILES: FCCC1CCN(c2ncc(-c3cn4ccccc4n3)cn2)CC1] | 2.7 |
| 48 | 341 | 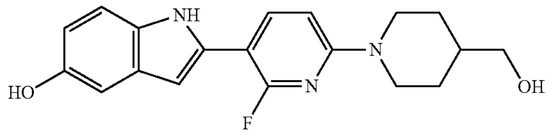 [SMILES: OCC1CCN(c2ccc(-c3cc4cc(O)ccc4[nH]3)c(F)n2)CC1] | 3.1 |
| 44 | 414 | 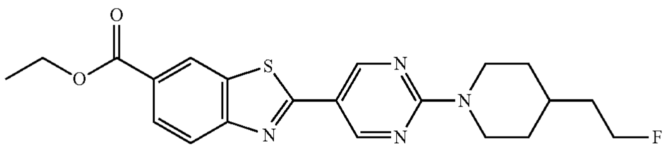 [SMILES: CCOC(=O)c1ccc2nc(-c3cnc(N4CCC(CCF)CC4)nc3)sc2c1] | 4.4 |
| 24 | 371 | 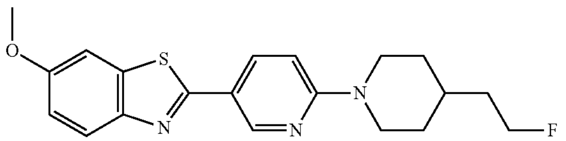 [SMILES: COc1ccc2nc(-c3ccc(N4CCC(CCF)CC4)nc3)sc2c1] | 4.5 |
| 50 | 338 | 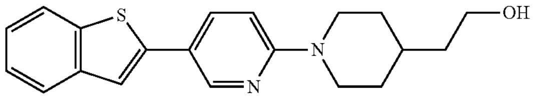 | 4.1 |

TABLE 1-continued
| Example Compound No. | Mol. Weight | Structure | CLogP |
|---|---|---|---|
| 51 | 351 | 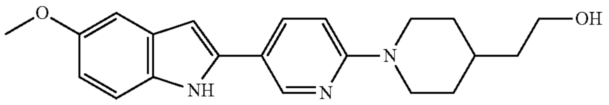 | 3.1 |
| 49 | 323 | 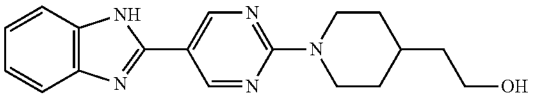 [SMILES: OCCC1CCN(c2ncc(-c3nc4ccccc4[nH]3)cn2)CC1] | 2.3 |
| 47 | 355 | 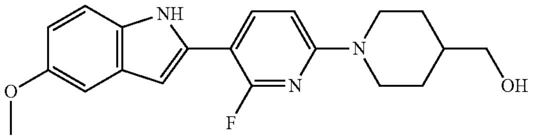 [SMILES: COc1ccc2[nH]c(-c3ccc(N4CCC(CO)CC4)nc3F)cc2c1] | 3.3 |
| 46 | 340 | 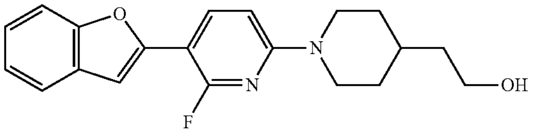 [SMILES: OCCC1CCN(c2ccc(-c3cc4ccccc4o3)c(F)n2)CC1] | 3.9 |
| 45 | 326 | 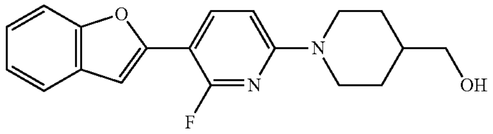 [SMILES: OCC1CCN(c2ccc(-c3cc4ccccc4o3)c(F)n2)CC1] | 3.5 |
| 42 | 462 | 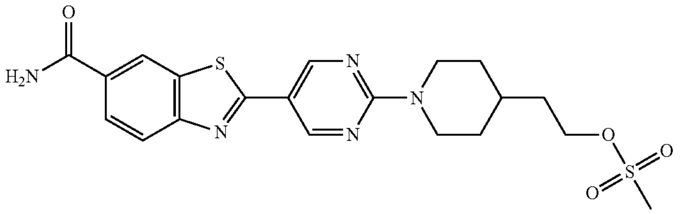 [SMILES: CS(=O)(=O)OCCC1CCN(c2ncc(-c3nc4ccc(C(N)=O)cc4s3)cn2)CC1] | 1.9 |
| 43 | 385 | 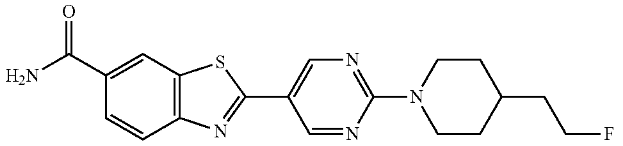 [SMILES: NC(=O)c1ccc2nc(-c3cnc(N4CCC(CCF)CC4)nc3)sc2c1] | 2.9 |
| 39 | 358 | 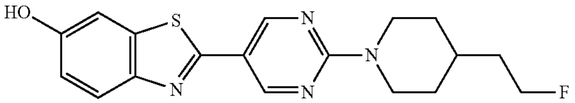 [SMILES: Oc1ccc2nc(-c3cnc(N4CCC(CCF)CC4)nc3)sc2c1] | 3.7 |
| 41 | 383 | 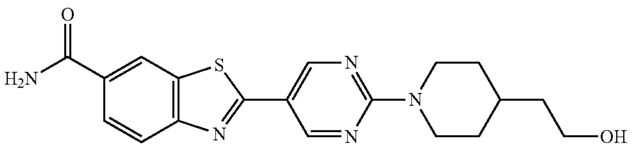 [SMILES: NC(=O)c1ccc2nc(-c3cnc(N4CCC(CCO)CC4)nc3)sc2c1] | 2.0 |
| 38 | 356 | 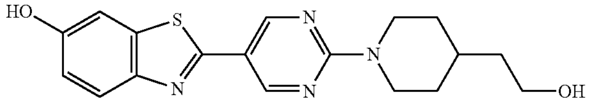 | 2.8 |
| 40 | 365 | 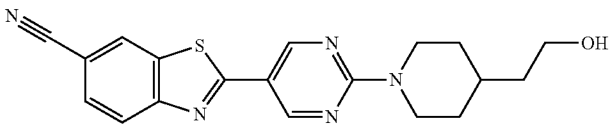 [SMILES: N#Cc1ccc2nc(-c3cnc(N4CCC(CCO)CC4)nc3)sc2c1] | 3.0 |

TABLE 1-continued
| Example Compound No. | Mol. Weight | Structure | CLogP |
|---|---|---|---|
| 26 | 505 | 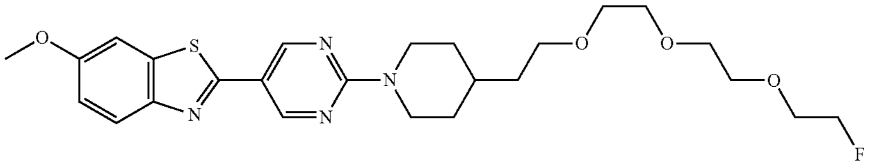 | 3.7 |
| 25 | 370 | 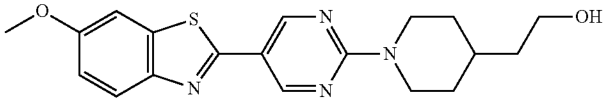 | 3.0 |
| 22 | 504 | 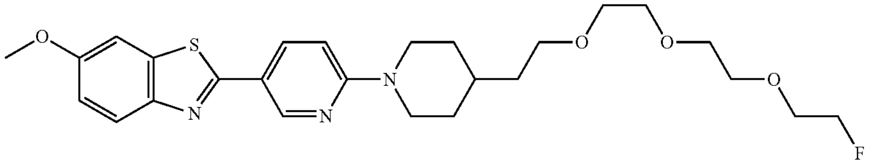 [SMILES: COc1ccc2nc(-c3ccc(N4CCC(CCOCCOCCOCCF)CC4)nc3)sc2c1] | 4.4 |
| 33 | 429 | 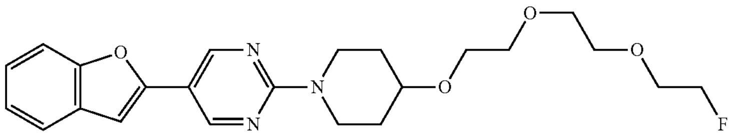 [SMILES: FCCOCCOCCOC1CCN(c2ncc(-c3cc4ccccc4o3)cn2)CC1] | 2.6 |
| 32 | 295 | 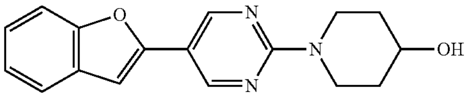 [SMILES: OC1CCN(c2ncc(-c3cc4ccccc4o3)cn2)CC1] | 1.9 |
| 6 | 446 | 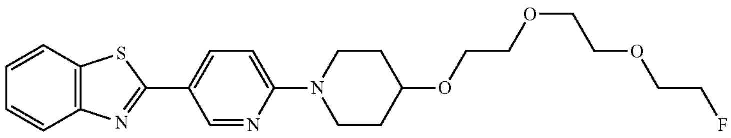 [SMILES: FCCOCCOCCOC1CCN(c2ccc(-c3nc4ccccc4s3)cn2)CC1] | 3.7 |
| 37 | 431 | 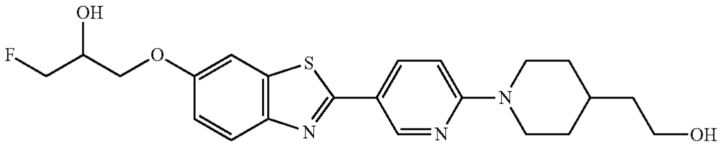 [SMILES: OCCC1CCN(c2ccc(-c3nc4ccc(OCC(O)CF)cc4s3)cn2)CC1] | 3.2 |
| 34 | 352 | 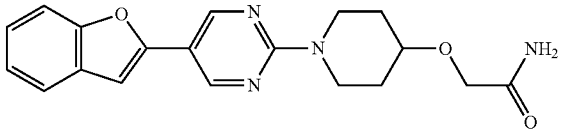 [SMILES: NC(=O)COC1CCN(c2ncc(-c3cc4ccccc4o3)cn2)CC1] | 1.2 |
| 10 | 368 | 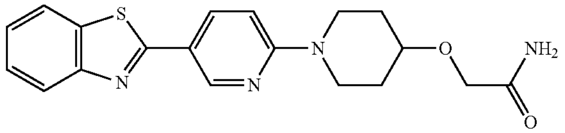 [SMILES: NC(=O)COC1CCN(c2ccc(-c3nc4ccccc4s3)cn2)CC1] | 2.3 |
| 3 | 400 | 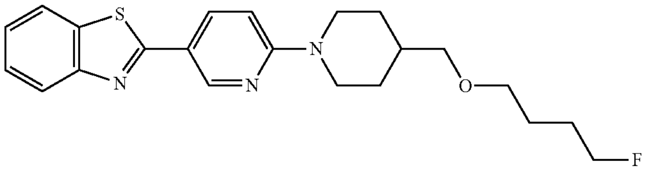 [SMILES: FCCCCOCC1CCN(c2ccc(-c3nc4ccccc4s3)cn2)CC1] | 4.8 |

TABLE 1-continued
| Example Compound No. | Mol. Weight | Structure | CLogP |
|---|---|---|---|
| 5 | 386 | 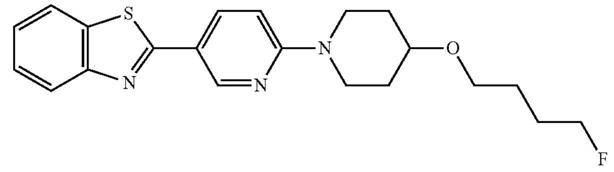 [SMILES: FCCCCOC1CCN(c2ccc(-c3nc4ccccc4s3)cn2)CC1] | 4.4 |
| 31 | 339 | 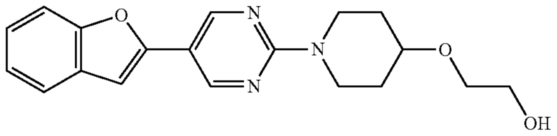 [SMILES: OCCOC1CCN(c2ncc(-c3cc4ccccc4o3)cn2)CC1] | 1.8 |
| 23 | 385 | 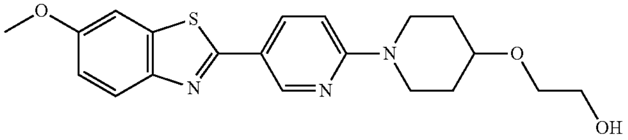 [SMILES: COc1ccc2nc(-c3ccc(N4CCC(OCCO)CC4)nc3)sc2c1] | 2.7 |
| 30 | 325 | 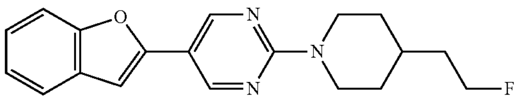 [SMILES: FCCC1CCN(c2ncc(-c3cc4ccccc4o3)cn2)CC1] | 3.6 |
| 29 | 401 | 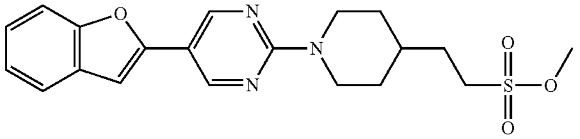 [SMILES: COS(=O)(=O)CCC1CCN(c2ncc(-c3cc4ccccc4o3)cn2)CC1] | 2.8 |
| 35 | 323 | 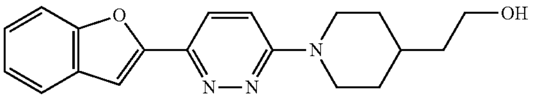 [SMILES: OCCC1CCN(c2ccc(-c3cc4ccccc4o3)nn2)CC1] | 2.7 |
| 17 | 304 | 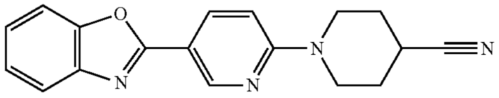 | 3.0 |
| 28 | 323 | 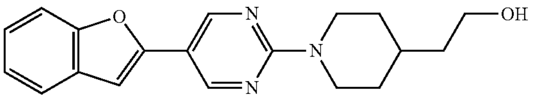 [SMILES: OCCC1CCN(c2ncc(-c3cc4ccccc4o3)cn2)CC1] | 2.7 |
| 36 | 355 | 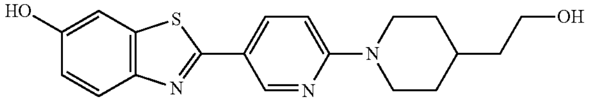 [SMILES: OCCC1CCN(c2ccc(-c3nc4ccc(O)cc4s3)cn2)CC1] | 3.5 |
| 27 | 322 | 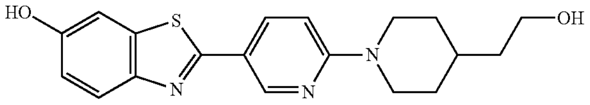 [SMILES: OCCC1CCN(c2ccc(-c3nc4ccc(O)cc4s3)cn2)CC1] | 3.3 |
| 20 | 326 | 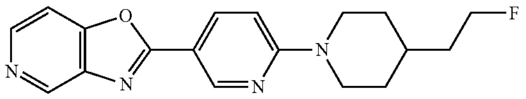 [SMILES: FCCC1CCN(c2ccc(-c3nc4cnccc4o3)cn2)CC1] | 2.6 |
| 16 | 293 | 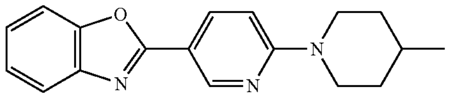 [SMILES: CC1CCN(c2ccc(-c3nc4ccccc4o3)cn2)CC1] | 4.0 |

TABLE 1-continued
| Example Compound No. | Mol. Weight | Structure | CLogP |
|---|---|---|---|
| 15 | 309 | 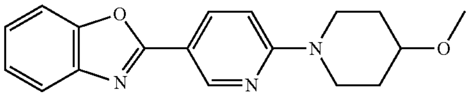 [SMILES: COC1CCN(c2ccc(-c3nc4ccccc4o3)cn2)CC1] | 2.8 |
| 21 | 369 | 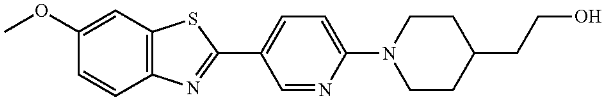 [SMILES: COc1ccc2nc(-c3ccc(N4CCC(CCO)CC4)nc3)sc2c1] | 3.6 |
| 19 | 402 | 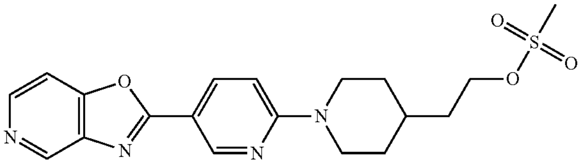 [SMILES: CS(=O)(=O)OCCC1CCN(c2ccc(-c3nc4cnccc4o3)cn2)CC1] | 1.7 |
| 14 | 279 | 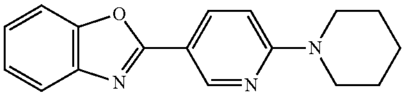 [SMILES: c1ccc2oc(-c3ccc(N4CCCCC4)nc3)nc2c1] | 3.7 |
| 13 | 325 | 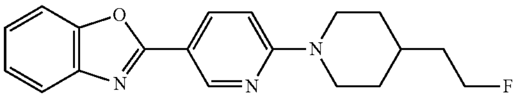 | 3.9 |
| 12 | 401 | 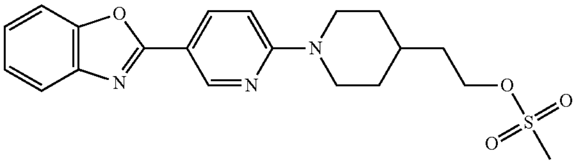 [SMILES: CS(=O)(=O)OCCC1CCN(c2ccc(-c3nc4ccccc4o3)cn2)CC1] | 2.9 |
| 18 | 324 | 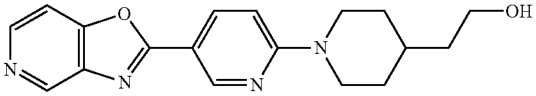 [SMILES: OCCC1CCN(c2ccc(-c3nc4cnccc4o3)cn2)CC1] | 1.8 |
| 9 | 341 | 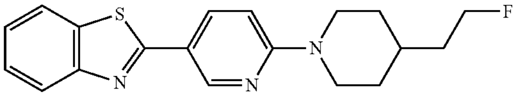 [SMILES: FCCC1CCN(c2ccc(-c3nc4ccccc4s3)cn2)CC1] | 4.7 |
| 8 | 494 | 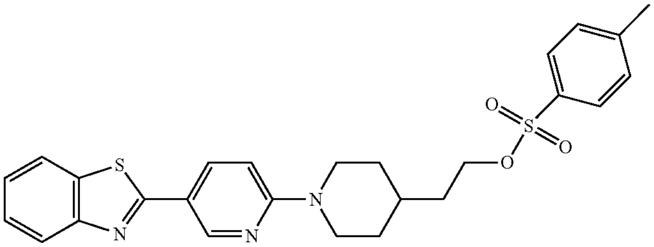 [SMILES: Cc1ccc(S(=O)(=O)OCCC2CCN(c3ccc(-c4nc5ccccc5s4)cn3)CC2)cc1] | 6.3 |
| 11 | 323 | 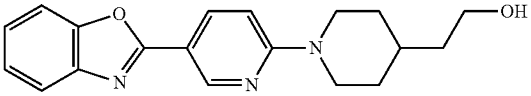 | 3.0 |
| 7 | 339 | 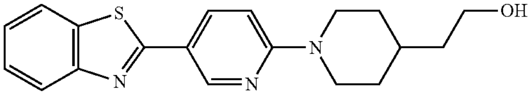 [SMILES: OCCC1CCN(c2ccc(-c3nc4ccccc4s3)cn2)CC1] | 3.8 |

TABLE 1-continued
| Example Compound No. | Mol. Weight | Structure | CLogP |
|---|---|---|---|
| 4 | 311 | 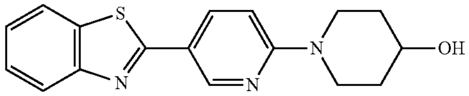 [SMILES: OC1CCN(c2ccc(-c3nc4ccccc4s3)cn2)CC1] | 2.9 |
| 2 | 327 | 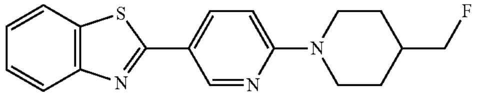 [SMILES: FCC1CCN(c2ccc(-c3nc4ccccc4s3)cn2)CC1] | 4.3 |
| 1 | 325 | 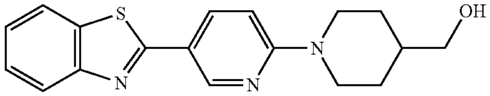 [SMILES: OCC1CCN(c2ccc(-c3nc4ccccc4s3)cn2)CC1] | 3.4 |
| 55 | 341 | 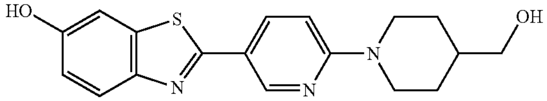 | 3.1 |
| 56 | 387 | 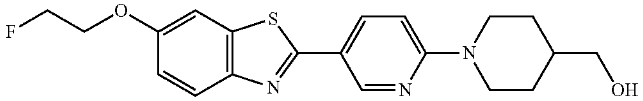 [SMILES: OCC1CCN(c2ccc(-c3nc4ccc(OCCF)cc4s3)cn2)CC1] | 3.4 |
| 57 | 342 | 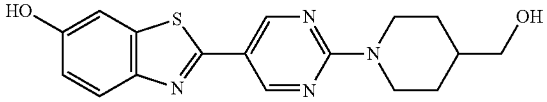 | 2.5 |
| 58 | 388 | 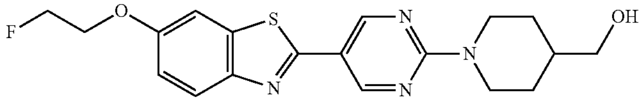 | 2.8 |
| 59 | 412 | 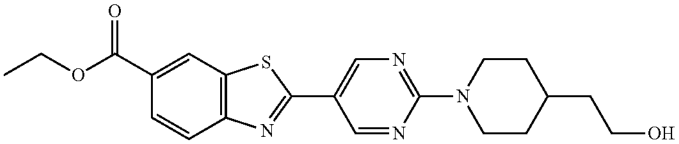 [SMILES: CCOC(=O)c1ccc2nc(-c3cnc(N4CCC(CCO)CC4)nc3)sc2c1] | 3.5 |
| 60 | 429 | 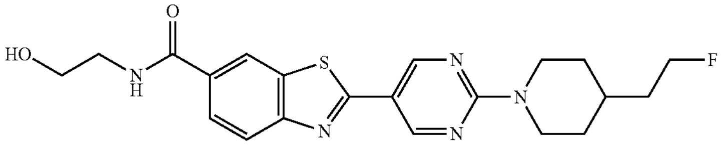 [SMILES: O=C(NCCO)c1ccc2nc(-c3cnc(N4CCC(CCF)CC4)nc3)sc2c1] | 2.4 |
| 61 | 429 | 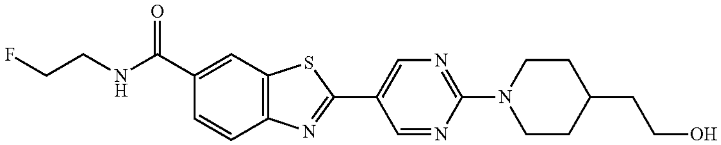 [SMILES: O=C(NCCF)c1ccc2nc(-c3cnc(N4CCC(CCO)CC4)nc3)sc2c1] | 2.4 |
| 62 | 371 | 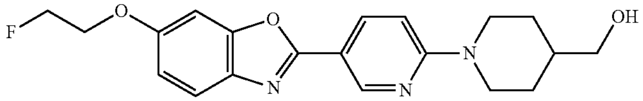 | 2.6 |
| 63 | 397 | 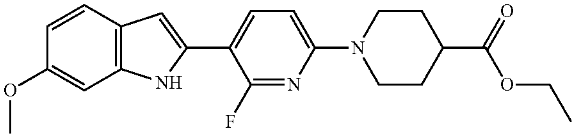 [SMILES: CCOC(=O)C1CCN(c2ccc(-c3cc4ccc(OC)cc4[nH]3)c(F)n2)CC1] | 4.1 |

TABLE 1-continued
| Example Compound No. | Mol. Weight | Structure | CLogP |
|---|---|---|---|
| 64 | 382 | 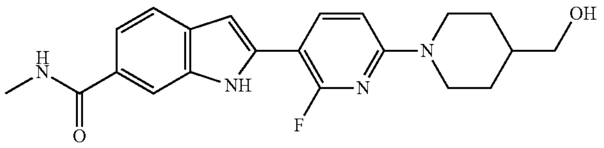 [SMILES: CNC(=O)c1ccc2cc(-c3ccc(N4CCC(CO)CC4)nc3F)[nH]c2c1] | 2.5 |
| 65 | 383 | 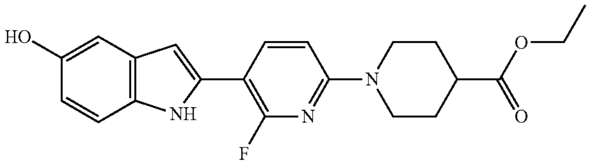 [SMILES: CCOC(=O)C1CCN(c2ccc(-c3cc4cc(O)ccc4[nH]3)c(F)n2)CC1] | 3.9 |
| 66 | 354 | 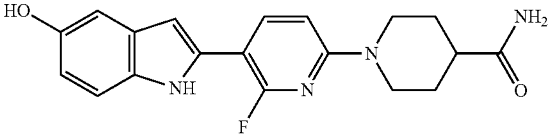 [SMILES: NC(=O)C1CCN(c2ccc(-c3cc4cc(O)ccc4[nH]3)c(F)n2)CC1] | 2.6 |
| 67 | 369 | 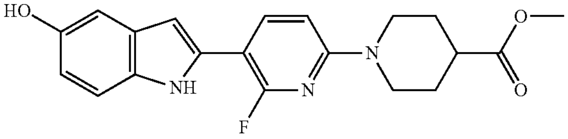 [SMILES: COC(=O)C1CCN(c2ccc(-c3cc4cc(O)ccc4[nH]3)c(F)n2)CC1] | 3.6 |
| 68 | 368 | 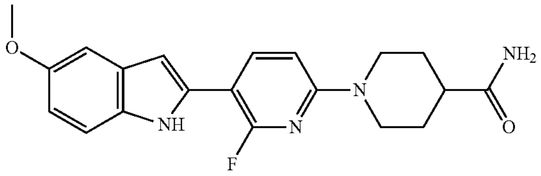 [SMILES: COc1ccc2[nH]c(-c3ccc(N4CCC(C(N)=O)CC4)nc3F)cc2c1] | 2.8 |
| 69 | 326 | 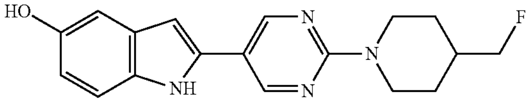 [SMILES: Oc1ccc2[nH]c(-c3cnc(N4CCC(CF)CC4)nc3)cc2c1] | 2.9 |
| 70 | 353 | 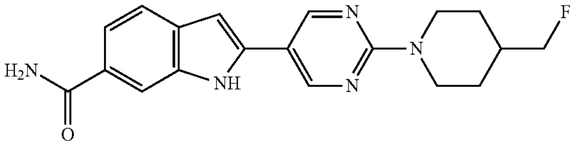 [SMILES: NC(=O)c1ccc2cc(-c3cnc(N4CCC(CF)CC4)nc3)[nH]c2c1] | 2.0 |
| 71 | 350 | 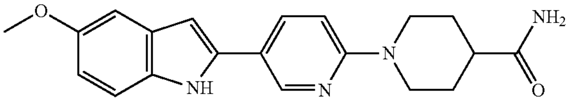 [SMILES: COc1ccc2[nH]c(-c3ccc(N4CCC(C(N)=O)CC4)nc3)cc2c1] | 2.2 |
| 72 | 370 | 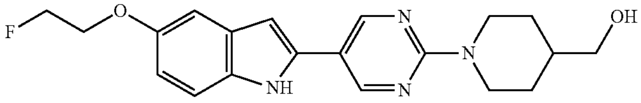 [SMILES: OCC1CCN(c2ncc(-c3cc4cc(OCCF)ccc4[nH]3)cn2)CC1] | 2.3 |
| 73 | 326 | 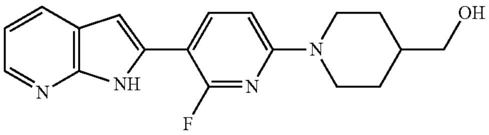 [SMILES: OCC1CCN(c2ccc(-c3cc4cccnc4[nH]3)c(F)n2)CC1] | 2.6 |

TABLE 1-continued

| Example Compound No. | Mol. Weight | Structure | CLogP |
|---|---|---|---|
| 74 | 356 | 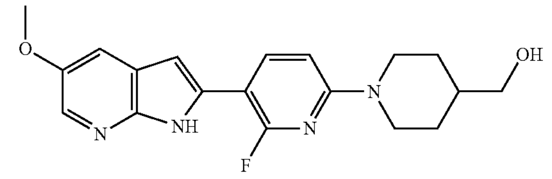 [SMILES: COc1cnc2[nH]c(-c3ccc(N4CCC(CO)CC4)nc3F)cc2c1] | 2.4 |
| 75 | 342 | 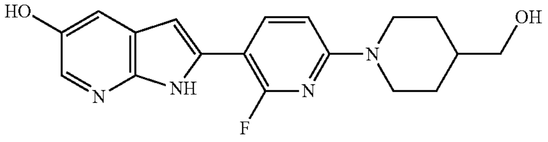 [SMILES: OCC1CCN(c2ccc(-c3cc4cc(O)cnc4[nH]3)c(F)n2)CC1] | 2.3 |
| 76 | 357 | 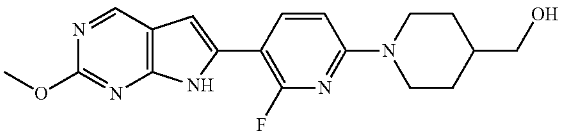 [SMILES: COc1ncc2cc(-c3ccc(N4CCC(CO)CC4)nc3F)[nH]c2n1] | 2.4 |
| 77 | 369 | 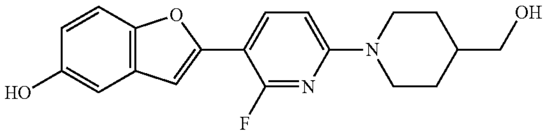 [SMILES: OCC1CCN(c2ccc(-c3cc4cc(O)ccc4o3)c(F)n2)CC1] | 2.9 |

Synthesis of Labeled Compounds of the Invention

(i) Synthesis of Tritium ($^3H$) Labeled Example Compounds

[$^3H$]-Example Compound 11 ([$^3H$] labeled 2-{1-[5-(1-Benzofuran-2-yl)pyridin-2-yl]piperidin-4-yl}ethan-1-ol)

Example Compound 11 (0.9 mg, 2.8 mol) and dimethylphenylphosphine-(1,5-cyclooctadiene[1,3-bis(2,4,6-trimethylphenyl)imidazol-2-ylidene]iridium(I) hexafluorophosphate (1.1 mg, 1.2 μmol) was dissolved in 2-methyl-THF (300 μL) and stirred at ambient temperature for 17 h under 700 mbar tritium gas.

Ethanol (1 mL) was added to the reaction mixture and the mixture was evaporated to near dryness. This step was then repeated once. The residue was subjected to silica flash chromatography using EtOAc:heptane (4:1) as eluant and after evaporation the residue was purified on reversed phase HPLC. The eluant was evaporated and the residue diluted in ethanol to afford 1080 MBq of [$^3H$] labeled 2-{1-[5-(1-benzofuran-2-yl)pyridin-2-yl]piperidin-4-yl}ethan-1-ol. MS m/z M+H (major peaks) 324 (3%), 326 (14%), 328 (46%), 330 (21.5%), 332 (11%), 334 (4%), 336 (0.5%).

[$^3H$]-Example Compound 28 ([$^3H$] labeled 2-{1-[5-(1-Benzofuran-2-yl)pyrimidin-2-yl]piperidin-4-yl}ethan-1-ol)

Example Compound 28 (1.1 mg, 3.5 mol) and Crabtree's catalyst (3.6 mg, 4.4 μmol) were dissolved in DCM (300 μL) and stirred at ambient temperature for 3 h under 570 mbar tritium gas.

Ethanol (1 mL) was added to the reaction mixture and the mixture was evaporated to near dryness. This step was then repeated twice. The residue was subjected to silica flash chromatograohy using DCM:MeOH (97.5:2.5) as eluant and after evaporation the residue was purified by reversed phase HPLC. The eluant was evaporated and the residue diluted in ethanol to afford 1295 MBq of [$^3H$] labeled 2-{1-[5-(1-benzofuran-2-yl)pyrimidin-2-yl]piperidin-4-yl}ethan-1-ol MS m/z M+H (major peaks) 324 (8%), 326 (22%), 328 (43%), 330 (22%), 332 (5%).

[$^3H$]-Example Compound 39 ([$^3H$] labeled 2-{2-[4-(2-Fluoroethyl)piperidin-1-yl]pyrimidin-5-yl}-1,3-benzothiazol-6-ol)

Example Compound 39 (1.9 mg, 5.3 μmol) was dissolved in dioxane (1 ml) and bromine (5 eq) was added. The reaction stirred at rt for 2 h then the solvent was removed in vacuo. The crude was purified by reversed phase HPLC to give bromo-2-{2-[4-(2-fluoroethyl)piperidin-1-yl]pyrimidin-5-yl}-1,3-benzothiazol-6-ol.

A portion of the brominated intermediate (0.2 mg, 0.5 μmol) and palladium on carbon (10%, 0.8 mg) in DMF (300 μL) was stirred for 12 h under 700 mbar tritium gas. The reaction mixture was filtered, ethanol (1 mL) was added, and the reaction mixture was evaporated to near dryness. This was repeated twice. The residue was purified on reversed phase HPLC and after evaporation of the eluant the residue was diluted in ethanol to afford 74 MBq of [$^3H$] labeled 2-{2-[4-(2-fluoroethyl)piperidin-1-yl]pyrimidin-5-yl}-1,3-benzothiazol-6-ol MS m/z M+H (major peaks) 359 (61%), 361 (39%).

[$^3H$]-Example Compound 48 ([$^3H$] labeled 2-(2-fluoro-6-{4-[hydroxymethyl]piperidin-1-yl}pyridin-3-yl)-1H-indol-5-ol)

Calcium carbonate (2.6 mg, 26 μmol) was added to an ice cooled slurry of $NaBT_4$ (1.7 mg, 45 μmol) in EtOH (300 μL)

and THF (300 μL). The mixture was stirred at 0° C. for 30 min. A solution of Example Compound 65 (1.7 mg, 4.4 μmol) in THF (300 μL) was added and the mixture was stirred for 2 h at 0° C. and then at ambient temperature for 2 h.

Water was then added (500 μL) and the mixture was purified on reversed phase HPLC. The eluant was evaporated and the residue diluted in ethanol to afford 55 MBq of [$^3$H] labeled 2-(2-fluoro-6-{4-[hydroxymethyl]piperidin-1-yl}pyridin-3-yl)-1H-indol-5-ol. MS m/z M+H (major peaks) 342 (32%), 344 (48%), 346 (20%).

[$^3$H]-Example Compound 68 ($^3$H] labeled 1-{6-Fluoro-5-[5-methoxy-1H-indol-2-yl]pyridin-2-yl}piperidine-4-carboxamide)

700 MBq [$^3$H]MeI in THF (300 μL) was added to a solution of tert-butyl 2-[6-(4-carbamoylpiperidin-1-yl)-2-fluoropyridin-3-yl]-5-hydroxy-1H-indole-1-carboxylate (the intermediate in Example Compound 66, 0.9 mg, 2.0 μmol) and NaOH (5 μL, 10M) in THF (400 μL). The reaction was stirred at 60° C. for 1 h after which the solvent was evaporated. TFA (500 μL) was added and the reaction was stirred at ambient temperature for 30 min.

The TFA was evaporated and the residue was subjected to reversed phase HPLC purification. The eluant was evaporated and the residue diluted in ethanol to afford 962 MBq of [$^3$H] labeled 1-{6-fluoro-5-[5-methoxy-1H-indol-2-yl]pyridin-2-yl}piperidine-4-carboxamide. MS m/z M+H (major peaks) 369 (8.5%), 371 (2.5%), 373 (22%), 375 (67%).

[$^3$H]-Example Compound 72 ([$^3$H] labeled (1-{5-[5-(2-Fluoroethoxy)-1H-indol-2-yl]pyrimidin-2-yl}piperidin-4-yl)methanol)

Example Compound 72 (0.3 mg, 0.8 μmol) and dimethylphenylphosphine-(1,5-cyclooctadiene[1,3-bis(2,4,6-trimethylphenyl)imidazol-2-ylidene]iridium(I) hexafluorophosphate (1.3 mg, 1.5 μmol) were dissolved in 2-methyl-THF (400 μL) and stirred at ambient temperature for 1.5 h under 681 mbar tritium gas.

The reaction mixture was evaporated and subjected to silica flash chromatography using EtOAc as eluant. After evaporation the residue was purified on reversed phase HPLC. The eluant was evaporated and the residue diluted in ethanol to afford 685 MBq of [$^3$H] labeled (1-{5-[5-(2-fluoroethoxy)-1H-indol-2-yl]pyrimidin-2-yl}piperidin-4-yl)methanol. MS m/z M+H (major peaks) 371 (2%), 373 (23%), 375 (42%), 377 (29%), 379 (4%).

[$^3$H]-Example Compound 76 ([$^3$H] labeled [1-(6-Fluoro-5-{2-methoxy-7H-pyrrolo[2,3-d]pyrimidin-6-yl}pyridin-2-yl)piperidin-4-yl]methanol)

Example Compound 76 (0.4 mg, 1.1 μmol) and dimethylphenylphosphine-(1,5-cyclooctadiene[1,3-bis(2,4,6-trimethylphenyl)imidazol-2-ylidene]iridium(I) hexafluorophosphate (1.1 mg, 1.2 μmol) were dissolved in 2-methyl-THF (300 μL) and stirred at ambient temperature for 19 h under 371 mbar tritium gas. Diethyl ether (1 mL) was added to the reaction mixture, and then the reaction mixture was evaporated and subjected to silica flash chromatography using EtOAc:MeOH (9:1) as eluant. After evaporation of the solvent the residue was purified on reversed phase HPLC. The eluant was evaporated and the residue diluted in ethanol to afford 750 MBq of [$^3$H] labeled [1-(6-fluoro-5-{2-methoxy-7H-pyrrolo[2,3-d]pyrimidin-6-yl}pyridin-2-yl)piperidin-4-yl]methanol. MS m/z M+H (major peaks) 358 (6%), 360 (5%), 362 (12%), 364 (27%), 366 (31%), 368 (16%), 370 (3%), 372 (1%).

(ii) Synthesis of [$^{18}$F]-Labeled Example Compounds

[$^{18}$F]-Example Compound 48 (2-[2-($^{18}$F)Fluoro-6-[4-(hydroxymethyl)piperidin-1-yl]pyridin-3-yl]-1H-indol-5-ol)

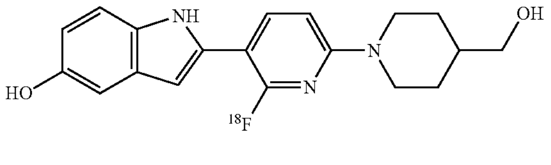 [SMILES: OCC1CCN(c2ccc(-c3cc4cc(O)ccc4[nH]3)c([18F])n2)CC1]

(a) Synthesis of starting material

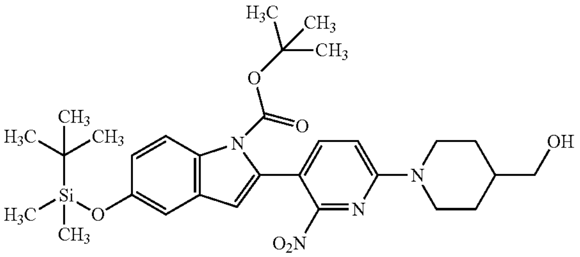 [SMILES: CC(C)(C)OC(=O)n1c(-c2ccc(N3CCC(CO)CC3)nc2[N+](=O)[O-])cc2cc(O[Si](C)(C)C(C)(C)C)ccc21]

Step (i)

2-Chloro-6-nitropyridine (1.0 g, 6.3 mmol) was dissolved in dioxane (10 ml) and 4-piperidinemethanol (1.09 g, 1.5 eq) was added followed by Hunig's base (1.6 ml, 1.5 eq). The reaction was heated to 100° C. for 90.

The reaction mixture was diluted with ethyl acetate, washed with water, treated with brine, dried with $MgSO_4$, filtered and the solvent was removed in vacuo to give the crude product.

The crude product was purified on the ISCO (40 g silica, applied with DCM, eluted with 40-50% ethyl acetate/hexane over 10 min) to give [1-(6-nitropyridin-2-yl)piperidin-4-yl]methanol (0.65 g oil, 43% yield, HPLC Rf 2.57 min, MS m/z (M+1) 238.3). TLC 50% ethyl acetate/hexane Rf 0.14.

Step (ii)

[1-(6-Nitropyridin-2-yl)piperidin-4-yl]methanol (0.65 g, 2.7 mmol) was dissolved in acetonitrile (15 ml), cooled with an ice-bath and NBS (1.8 g, 1.1 eq) was added. The reaction was allowed to stir overnight. The reaction mixture was poured onto ice and was allowed to stir overnight.

The reaction mixture was diluted with ethyl acetate, washed with water, treated with brine, dried with $MgSO_4$, filtered and the solvent was removed in vacuo to give the crude product.

The crude product was purified on the ISCO (24 g silica, applied with DCM, eluted with 30-60% ethyl acetate/hexane) to give [1-(5-bromo-6-nitropyridin-2-yl)piperidin-4-yl]methanol (0.71 g oil that solidified on standing, 83% yield, HPLC Rf 3.01 min, MS m/z (M+1) 318.3, 316.2). TLC: 50% ethyl acetate Rf 0.14.

Step (iii)

{1-[(tert-Butoxy)carbonyl]-5-[(tert-butyldimethylsilyl)oxy]-1H-indol-2-yl}boronic acid (215 mg, 1.1 eq) and [1-(5-bromo-6-nitropyridin-2-yl)piperidin-4-yl]methanol (158 mg, 0.5 mmol) were dissolved in dioxane (3 ml) in a 5 ml microwave vial. The solution was bubbled with $N_2$ for 2 min, then Pd(dppf)$Cl_2$ DCM 1:1 complex (20 mg, 5 mol %) was added followed by 2 M $K_2CO_3$ (0.75 ml, 3 eq). The solution was again bubbled with $N_2$ for 5 min then the vial was capped. The reaction was run in a preheated oil bath at 90° C. for 1 h.

The cooled reaction mixture was diluted with ethyl acetate, washed with water, treated with brine, filtered through celite, and the solvent was removed in vacuo to give the crude product.

The crude product was purified on the ISCO (24 g silica, applied with DCM, eluted with 30-48% ethyl acetate/hexane over 11 min) to give an oil of tert-butyl 5-[(tert-butyldimethylsilyl)oxy]-2-{6-[4-(hydroxymethyl)piperidin-1-yl]-2-nitropyridin-3-yl}-1H-indole-1-carboxylate (160 mg oil, yield 55%, HPLC Rf 4.50 min, MS m/z (M+1) 583.6).

(b) Synthesis of [$^{18}$F]-Example Compound 48

[$^{18}$F]-Example Compound 48 is synthesized from the aromatic nitro intermediate (tert-butyl 5-[(tert-butyldimethylsilyl)oxy]-2-{6-[4-(hydroxymethyl)piperidin-1-yl]-2-nitropyridin-3-yl}-1H-indole-1-carboxylate) following the method of WO 2015/110263 (AC Immune AS; Piramal Imaging SA). Silyl deprotection is then carried out following step (ii) of the experimental for Example Compound 48, above; and the BOC group deprotection is carried out by following the alternative step (iii) of the experimental for Example Compound 48, above, to give 2-[2-($^{18}$F)fluoro-6-[4-(hydroxymethyl)piperidin-1-yl]pyridin-3-yl]-1H-indol-5-ol.

Alternatively, silyl deprotection of tert-butyl 5-[(tert-butyldimethylsilyl)oxy]-2-{6-[4-(hydroxymethyl)piperidin-1-yl]-2-nitropyridin-3-yl}-1H-indole-1-carboxylate is carried out following step (ii) of the experimental for Example Compound 48, above. Incorporation of $^{18}$F into the compound is carried out following the method of WO 2015/110263 (AC Immune AS; Piramal Imaging SA). BOC group deprotection is then carried out by following the alternative step (iii) of the experimental for Example Compound 48, above, to give 2-[2-($^{18}$F)fluoro-6-[4-(hydroxymethyl)piperidin-1-yl]pyridin-3-yl]-1H-indol-5-ol.

[$^{18}$F]-Example Compound 66 (1-[6-($^{18}$F)Fluoro-5-(5-hydroxy-1H-indol-2-yl)pyridin-2-yl]piperidine-4-carboxamide)

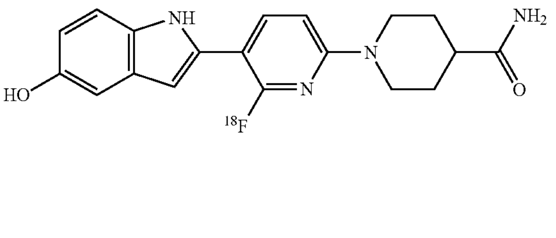 [SMILES: NC(=O)C1CCN(c2ccc(-c3cc4cc(O)ccc4[nH]3)c([18F])n2)CC1]

(a) Synthesis of starting material

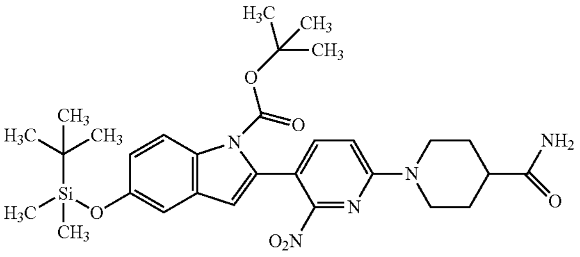 [SMILES: CC(C)(C)OC(=O)n1c(-c2ccc(N3CCC(C(N)=O)CC3)nc2[N+](=O)[O-])cc2cc(O[Si](C)(C)C(C)(C)C)ccc21]

Step (i)

In a 20 ml microwave vial, 2-chloro-6-nitropyridine (1.0 g, 6.3 mmol) was dissolved in dioxane (10 ml) and piperidine-4-carboxamide (1.05 g, 1.3 eq) was added followed by Hunig's base (3.3 ml, 3 eq). The reaction was subjected to in the microwave for 2.5 h at 180° C.

The reaction mixture was diluted with water, the mixture was extracted twice with hot ethyl acetate, treated with brine, dried with $MgSO_4$, filtered and the solvent was removed in vacuo to give the crude product.

The crude product was refluxed with DCM (10 ml), the solution was allowed to cool and washed with DCM to give the purified crude product as a solid. The solid was recrystallized from 2% hexane/ethyl acetate to give [1-(6-nitropyridin-2-yl)piperidine-4-carboxamide (0.53 g solid, 33% yield, HPLC Rf 2.18 min, MS m/z (M+1) 251.3, (M−1) 249.2). TLC ethyl acetate Rf 0.26.

Step (ii)

[1-(6-Nitropyridin-2-yl)piperidine-4-carboxamide (0.53 g, 2.1 mmol) was dissolved in acetonitrile (15 ml), cooled with an ice-bath and NBS (0.53 g, 1.4 eq) was added. The reaction was heated for 30 min at 60° C. to give a clear solution. Upon cooling a precipitate formed that was filtered and washed with cold acetonitrile to give 1-(5-bromo-6-nitropyridin-2-yl)piperidine-4-carboxamide (311 mg solid, 45% yield, HPLC Rf 2.70 min, MS m/z (M+1) 331.2, 329.2, (M−1) 329.1, 327.1).

Step (iii)

{1-[(tert-Butoxy)carbonyl]-5-[(tert-butyldimethylsilyl)oxy]-1H-indol-2-yl}boronic acid (118 mg, 1.2 eq) and 1-(5-bromo-6-nitropyridin-2-yl)piperidine-4-carboxamide (82 mg, 0.25 mmol) were dissolved in dioxane (1.5 ml) in a 5 ml microwave vial. The solution was bubbled with $N_2$ for 2 min, then Pd(dppf)$Cl_2$ DCM 1:1 complex (10 mg, 5 mol %) was added followed by 2 M $K_2CO_3$ (380 μl, 3 eq). The solution was again bubbled with $N_2$ for 5 min then the vial was capped. The reaction was run in a preheated oil bath at 90° C. for 1 h.

The cooled reaction mixture was diluted with ethyl acetate, washed with water, treated with brine, filtered through celite, and the solvent was removed in vacuo to give the crude product.

The crude product was purified on the ISCO (12 g silica, applied with DCM, eluted with 90-100% ethyl acetate/hexane over 5 min) to give tert-butyl 5-[(tert-butyldimethylsilyl)oxy]-2-[6-(4-carbamoylpiperidin-1-yl)-2-nitropyridin-3-yl]-1H-indole-1-carboxylate (86 mg solid, yield 58%, HPLC Rf 4.34 min, MS m/z (M+1) 596.5, (M−1) 594.4). TLC ethyl acetate Rf 0.16.

(b) Synthesis of [$^{18}$F]-Example Compound 66

[$^{18}$F]-Example Compound 66 is synthesized from the nitro intermediate (tert-butyl 5-[(tert-butyldimethylsilyl)

oxy]-2-[6-(4-carbamoylpiperidin-1-yl)-2-nitropyridin-3-yl]-1H-indole-1-carboxylate) following the method of WO 2015/110263 (AC Immune AS; Piramal Imaging SA). Then, following the experimental for Example Compound 66, above, silyl deprotection is performed followed by the deprotection of the BOC group using TFA, to give 1-[6-($^{18}$F)fluoro-5-(5-hydroxy-1H-indol-2-yl)pyridin-2-yl]piperidine-4-carboxamide.

Alternatively, silyl deprotection of tert-butyl 5-[(tert-butyldimethylsilyl)oxy]-2-[6-(4-carbamoylpiperidin-1-yl)-2-nitropyridin-3-yl]-1H-indole-1-carboxylate is carried out following the experimental for Example Compound 66, above. Incorporation of $^{18}$F into the compound is carried out following the method of WO 2015/110263 (AC Immune AS; Piramal Imaging SA). BOC group deprotection is then carried out by following the the experimental for Example Compound 48, above, to give 1-[6-($^{18}$F)fluoro-5-(5-hydroxy-1H-indol-2-yl)pyridin-2-yl]piperidine-4-carboxamide.

[$^{18}$F]-Example Compound 67 (Methyl 1-[6-($^{18}$F)fluoro-5-(5-hydroxy-1H-indol-2-yl)pyridin-2-yl]piperidine-4-carboxylate.)

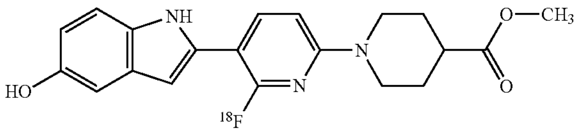 [SMILES: COC(=O)C1CCN(c2ccc(-c3cc4cc(O)ccc4[nH]3)c([18F])n2)CC1]

(a) Synthesis of Starting Material

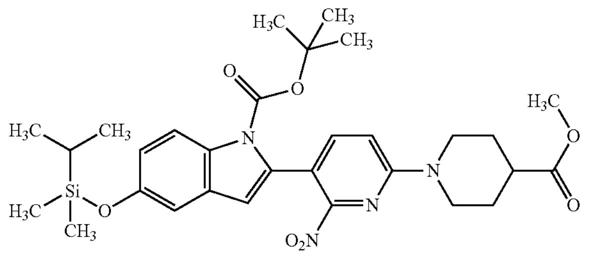 [SMILES: COC(=O)C1CCN(c2ccc(-c3cc4cc(O[Si](C)(C)C(C)C)ccc4n3C(=O)OC(C)(C)C)c([N+](=O)[O-])n2)CC1]

Step (i)

In a 20 ml microwave vial, 2-chloro-6-nitropyridine (0.79 g, 5 mmol) was dissolved in dioxane (10 ml) and methyl piperidine-4-carboxylate (0.72 g, 1 eq) was added followed by Hunig's base (0.96 ml, 1.1 eq). The reaction was subjected to in the microwave for 1 h at 150° C.

The reaction mixture was diluted with water, the mixture was extracted ethyl acetate, treated with brine, dried with $MgSO_4$, filtered and the solvent was removed in vacuo to give the crude product.

The crude product was purified by flash chromatography eluting with 15% ethyl acetate/hexane to give methyl 1-(6-nitropyridin-2-yl)piperidine-4-carboxylate (554 mg solid, 42% yield, MS m/z $(M+1)_{266}$). TLC 40% ethyl acetate/hexane Rf 0.35.

Step (ii)

Methyl 1-(6-nitropyridin-2-yl)piperidine-4-carboxylate (550 mg, 2.1 mmol) was dissolved in acetonitrile (10 ml), cooled with an ice-bath and NBS (0.37 g, 1 eq) was added. The reaction was allowed to stir at rt overnight.

The reaction mixture was diluted with water, the mixture was extracted ethyl acetate, treated with brine, dried with $MgSO_4$, filtered and the solvent was removed in vacuo to give the crude product.

The crude product was purified by flash chromatography eluting with 15-30% ethyl acetate/hexane to give methyl 1-(5-bromo-6-nitropyridin-2-yl)piperidine-4-carboxylate (520 mg solid, 43% yield, MS m/z (M+1) 346, 344). TLC 30% ethyl acetate/hexane Rf 0.15.

Step (iii)

{1-[(tert-Butoxy)carbonyl]-5-[(tert-butyldimethylsilyl)oxy]-1H-indol-2-yl}boronic acid (633 mg, 1.1 eq) and methyl 1-(5-bromo-6-nitropyridin-2-yl)piperidine-4-carboxylate (507 mg, 1.5 mmol) were dissolved in dioxane (9 ml) in a 20 ml microwave vial. The solution was bubbled with $N_2$ for 2 min, then $Pd(dppf)Cl_2$ (62 mg, 6 mol %) was added followed by 2 M $K_2CO_3$ (2.2 ml, 3 eq). The solution was again bubbled with $N_2$ for 5 min then the vial was capped. The reaction was run in a preheated oil bath at 90° C. for 1 h then 80° C. over the weekend.

The cooled reaction mixture was diluted with ethyl acetate, washed with water, treated with brine, filtered through celite, and the solvent was removed in vacuo to give the crude product.

The crude product was purified by flash chromatography eluting with 20% ethyl acetate/hexane to give tert-butyl 5-[(tert-butyldimethylsilyl)oxy]-2-{6-[4-(methoxycarbonyl)piperidin-1-yl]-2-nitropyridin-3-yl}-1H-indole-1-carboxylate (247 mg foam, 27% yield, HPLC Rf 4.60 min, MS m/z (M+1) 611.4). TLC 40% ethyl acetate/hexane Rf 0.50.

(b) Synthesis of [$^{18}$F]-Example Compound 67

[$^{18}$F]-Example Compound 67 is synthesized from the aromatic nitro intermediate (tert-butyl 5-[(tert-butyldimethylsilyl)oxy]-2-{6-[4-(methoxycarbonyl)piperidin-1-yl]-2-nitropyridin-3-yl}-1H-indole-1-carboxylate) following the method of WO 2015/110263 (AC Immune AS; Piramal Imaging SA). Then, following the experimental for Example Compound 67, above, the silyl deprotection is performed followed by the deprotection of the BOC group with TFA to give methyl 1-[6-($^{18}$F)fluoro-5-(5-hydroxy-1H-indol-2-yl)pyridin-2-yl]piperidine-4-carboxylate.

Alternatively, silyl deprotection of tert-butyl 5-[(tert-butyldimethylsilyl)oxy]-2-[6-(4-carbamoylpiperidin-1-yl)-2-nitropyridin-3-yl]-1H-indole-1-carboxylate is carried out following the experimental for Example Compound 66, above. Incorporation of $^{18}$F into the compound is carried out following the method of WO 2015/110263 (AC Immune AS; Piramal Imaging SA). BOC group deprotection is then carried out by following the experimental for Example Compound 48, above, to give methyl 1-[6-($^{18}$F)fluoro-5-(5-hydroxy-1H-indol-2-yl)pyridin-2-yl]piperidine-4-carboxylate.

[$^{18}$F]-Example Compound 72

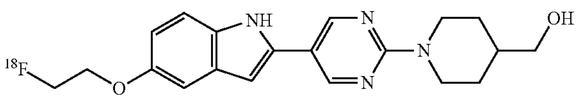 [SMILES: OCC1CCN(c2ncc(-c3cc4cc(OCC[18F])ccc4[nH]3)cn2)CC1]

Synthesis of [18F]-Example Compound 72 ([1-(5-{5-[2-(18F)Fluoroethoxy]-1H-indol-2-yl}pyrimidin-2-yl)piperidin-4-yl]methanol)

[18F]-Example Compound 72 is synthesized by reacting the phenol intermediate, tert-butyl 5-hydroxy-2-{2-[4-(hydroxymethyl)piperidin-1-yl]pyrimidin-5-yl}-1H-indole-1-carboxylate (synthesized in Example Compound 72, above), with [18F]fluoroethyl bromide following the method described in *Chem. Soc. Rev.,* 2017, 46, 4709-4773. Then, following the experimental for Example Compound 72, above, the BOC group is deprotected using TFA to give [1-(5-{5-[2-(18F)fluoroethoxy]-1H-indol-2-yl}pyrimidin-2-yl)piperidin-4-yl]methanol.

Alternatively, [18F]-Example Compound 72 is synthesized by reacting the phenol intermediate, tert-butyl 5-hydroxy-2-{2-[4-(hydroxymethyl)piperidin-1-yl]pyrimidin-5-yl}-1H-indole-1-carboxylate (synthesized in Example Compound 72, above), with [18F]fluoroethyl tosylate following the method described in *Chem. Soc. Rev.,* 2017, 46, 4709-4773. Then, following the experimental for Example Compound 72, above, the BOC group is deprotected using TFA to give [1-(5-{5-[2-(18F)fluoroethoxy]-1H-indol-2-yl}pyrimidin-2-yl)piperidin-4-yl]methanol.

[18F]-Example Compound 76 ({1-[6-(18F)Fluoro-5-{2-methoxy-7H-pyrrolo[2,3-d]pyrimidin-6-yl}pyridin-2-yl]piperidin-4-yl}methanol)

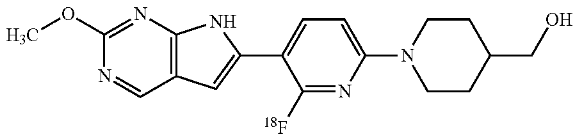 [SMILES: COc1ncc2cc(-c3ccc(N4CCC(CO)CC4)nc3[18F])[nH]c2n1]

(a) Synthesis of Starting Material

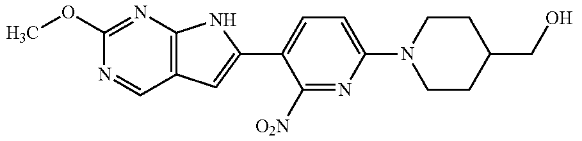 [SMILES: COc1ncc2cc(-c3ccc(N4CCC(CO)CC4)nc3[N+](=O)[O-])[nH]c2n1]

[1-(5-Bromo-6-nitropyridin-2-yl)piperidin-4-yl]methanol (product of step (ii) of the synthesis of the starting material used for [18F]-Example Compound 48,115 mg, 1.5 mmol) and {7-[(tert-butoxy)carbonyl]-2-methoxy-7H-pyrrolo[2,3-d]pyrimidin-6-yl}boronic acid (intermediate 36,107 mg, 1 eq) were dissolved in dioxane (2.2 ml) in a 5 ml microwave vial. The solution was bubbled with $N_2$ for 3 min, then Pd(dppf)$Cl_2$ DCM 1:1 complex (15 mg, 5 mol %) was added followed by 2 M $K_2CO_3$ (540 µl, 3 eq). The solution was again bubbled with $N_2$ for 5 min then capped. The reaction was run in a preheated oil bath at 90° C. for 1 h.

The cooled reaction mixture was diluted ethyl acetate, washed with saturated brine, dried with $MgSO_4$, filtered and the solvent was removed in vacuo to give the crude product.

The crude product was purified on the ISCO (4 g silica, applied with DCM, eluted with 80%-100% ethyl acetate/hexane for 4 min to give [1-(5-{2-methoxy-7H-pyrrolo[2,3-d]pyrimidin-6-yl}-6-nitropyridin-2-yl)piperidin-4-yl]methanol (38 mg solid, 27% yield, HPLC 2.63 min, MS m/z (M+1) 385.2, (M−1) 383.1). TLC ethyl acetate Rf 0.10.

(b) Synthesis of [18F]-Example Compound 76

[18F]-Example Compound 76 is synthesized from the aromatic nitro intermediate ([1-(5-{2-methoxy-7H-pyrrolo[2,3-d]pyrimidin-6-yl}-6-nitropyridin-2-yl)piperidin-4-yl]methanol) following the method of WO 2015/110263 (AC Immune AS; Piramal Imaging SA), to give {1-[6-(18F)fluoro-5-{2-methoxy-7H-pyrrolo[2,3-d]pyrimidin-6-yl}pyridin-2-yl]piperidin-4-yl}methanol.

Biological Testing

Example (a): Biological Assay Methods and Results

3H-THK5117 competition binding to tau fibrils in vitro

Preparation of recombinant 0N4R Tau fibrils was performed as previously described in Morozova, O. A., Biochemistry (2013), Vol., 52(40), pages 6960-6967. Competition binding experiments to 0N4R Tau fibrils were performed by incubating increasing concentrations [$10^{-10}$-$10^{-6}$ M] of the Example compounds of the invention, or the known tau specific ligand PBB3 (PBB3 was synthesized as previously described in M. Maruyama, et al, Neuron 2013, 79, 1094-1108) or MK6240 (Novandi Chemistry AB), in the presence of 3 nM of the known tau ligand [3H]-THK5117 (Novandi Chemistry) and 0.2 mM 0N4R tau fibrils in binding buffer (50 mM Tris-HCl, pH 7.4, 0.1% BSA) for 1 h in the dark, and at 22° C. The incubation was terminated by filtration through a Whatman GF/B glass filter (Whatman International, Kent, UK) using a Brandel cell harvester. The filter was then washed rapidly four times with 3 mL of ice-cold wash buffer (5 mM Tris-HCl, 0.25 mM NaCl, 5% EtOH), and equilibrated for 1 h in scintillation vials containing 5 mL of Ultima Gold scintillation fluid before being analysed using a Liquid Scintillation Analyzer.

The results are shown in Table 2 in the column labeled "Tau $IC_{50}$". For compounds that were run in the competition binding experiment more than once, the Tau $IC_{50}$ value in Table 2 is the average of the results of each experiment.

3H-AZD2184 Competition Binding to Aβ(1-42) Fibrils In Vitro

Competition binding experiments to Aβ(1-42) amyloid fibrils were performed as previously described in Jureus, A., et al, Journal of Neurochemistry (2010), Vol. 114, pages 784-794 for the Example compounds of the invention indicated in Table 2, or the known tau specific ligand PBB3 (PBB3 was synthesized as previously described in M. Maruyama, et al, Neuron 2013, 79, 1094-1108).

The results are shown in Table 2 in the column labeled "Aβ $IC_{50}$". For compounds that were run in the competition binding experiment more than once, the Aβ $IC_{50}$ value in Table 2 is the average of the results of each experiment.

Relative Selectivity for Tau Vs. A6

Relative selectivity for tau compared to Aβ for the exemplified compounds was calculated using the results for the [3H]-THK5117 tau and [3H]-AZD2184 Aβ assays described above. The calculated results are shown in Table 2 in the column labeled "Selectivity for tau relative to Aβ".

Biological Assay Results

TABLE 2

| Example Compound No. | Tau $IC_{50}$ (nM) | Aβ $IC_{50}$ (nM) | Selectivity for tau relative to Aβ |
|---|---|---|---|
| 53 | 14 | 37 | 2.6 |
| 52 | 49 | 84 | 1.7 |
| 48 | 5 | 187 | 37 |
| 44 | 4 | | |
| 24 | 2 | 1 | 0.5 |
| 50 | 4 | | 0 |
| 51 | 13 | | |
| 49 | 49 | | |
| 47 | 2 | 33 | 17 |
| 46 | 6 | 53 | 8.8 |
| 45 | 9 | 42 | 4.7 |
| 42 | 15 | | 0 |
| 43 | 4 | 72 | 18 |
| 39 | 1.5 | 50 | 33 |
| 41 | 10 | | |
| 38 | 6 | 250 | 42 |
| 40 | 6 | 70 | 12 |
| 26 | 5 | 8 | 1.6 |
| 25 | 3 | 65 | 22 |
| 22 | 4 | 4 | 1 |
| 33 | 28 | 6 | 0.2 |
| 32 | 43 | 66 | 1.5 |
| 6 | 16 | 3 | 0.2 |
| 37 | 14 | | |
| 34 | 32 | | |
| 10 | 31 | | |
| 3 | 11 | 43 | 3.9 |
| 5 | 5 | 24 | 4.8 |
| 31 | 15 | | |
| 23 | 4 | 4 | 1 |
| 30 | 12 | 25 | 2.1 |
| 29 | 32 | | |
| 35 | 100 | | |
| 17 | 73 | | |
| 28 | 10 | 15 | 1.5 |
| 36 | 3 | 91 | 30 |
| 27 | 7 | 34 | 4.9 |
| 20 | 60 | | |
| 16 | 59 | | |
| 15 | 39 | | |
| 21 | 5 | 70 | 14 |
| 19 | 76 | | |
| 14 | 22 | | |
| 13 | 13 | | |
| 12 | 17 | | |
| 18 | 39 | | |
| 9 | 6 | | |
| 8 | 8 | | |
| 11 | 64 | | |
| 7 | 7 | 15 | 2.1 |
| 4 | 43 | | |
| 2 | 7 | | |
| 1 | 19 | | |
| 55 | 7 | | |
| 56 | 2 | 3 | 1.5 |
| 57 | 12 | 302 | 25 |
| 58 | 6 | 37 | 6.2 |
| 59 | 5 | | |
| 60 | 11 | 28 | 2.5 |
| 61 | 19 | | |
| 62 | 22 | 9 | 0.4 |
| 63 | 2.3 | | |
| 64 | 24 | | |
| 65 | 2 | 44 | 22 |
| 66 | 21 | 272 | 13 |
| 67 | 4 | 32 | 8 |
| 68 | 7 | 72 | 10 |
| 69 | 10 | 169 | 17 |
| 70 | 20 | | |
| 71 | 16 | 114 | 7.1 |
| 72 | 7 | 42 | 6 |
| 73 | 41 | | |
| 74 | 14 | | |
| 75 | 14 | | |

TABLE 2-continued

| Example Compound No. | Tau $IC_{50}$ (nM) | Aβ $IC_{50}$ (nM) | Selectivity for tau relative to Aβ |
|---|---|---|---|
| 76 | 9 | 322 | 36 |
| 77 | 14 | | |
| PBB3 | 7 | 28 | 4 |
| MK-6420 | >1000 (inactive) | | |

The results in Table 2 show that the Example compounds of the invention have high affinity binding to recombinant 4R tau fibrils. The results in Table 2 also show that of the compounds of the invention tested in the Aβ(1-42) amyloid fibrils competition binding assay, the majority of the compounds of the invention showed higher binding affinity to recombinant 4R tau fibrils compared to Aβ(1-42) amyloid fibrils. The results in Table 2 further show that several examples compounds of the invention have a higher affinity binding to recombinant 4R tau fibrils than the known tau ligand PBB3; and/or have better selectively to recombinant 4R tau fibrils compared to Aβ(1-42) amyloid fibrils than PBB3. The results in Table 2 also show that the example compounds of the invention do not share the same tau binding site as MK-6240, which was inactive in the recombinant 4R tau fibrils assay.

The results in FIG. 1 further show that Example Compound 48, Example Compound 68 and PBB3 all share the same binding site, and that MK-6240 does not share the same binding site.

Example (b): In Vitro Binding to Beta-Amyloid Fibrils in Cortical Tissue Samples To examine binding of the example compounds of the present invention to tau plaques in vitro, autoradiography was carried out on brain sections from corticobasal degeneration (CBD) and progressive supranuclear palsy (PSP) patients incubated with $[^3H]$-Example Compound 72 or $[^3H]$-Example Compound 48 in the presence or absence of unlabeled Example Compound 78 (1 μM) or unlabeled Example Compound 48 (1 μM), respectively. The experiment was performed as previously described in Johnson, A. E., et al, Journal of Neurochemistry (2009), Vol. 108, pages 1177-1186, but using post mortem cortical samples from corticobasal degeneration (CBD) and progressive supranuclear palsy (PSP) patients instead of from Alzheimer's disease patients.

Briefly, brain sections from the cortical samples were incubated for 30 min at 22° C. in 50 mN Tris buffer (pH 7.4) together with 3 nM $[^3H]$-Example Compound 72 or 3 nM $[^3H]$-Example Compound 48 in the presence of absence of on unlabeled Example Compound 72 (1 μM) or unlabeled Example Compound 48 (1 μM), respectively. The sections were then washed (3×10 min) in Tris buffer (1° C.) followed by a rinse in deionized water (1° C.) and air-dried at 22° C. in front of a fan. Binding was then measured and analysed as described in Johnson, A. E., et al.

The tau pathology was confirmed on adjacent brain sections by immunohisto-chemistry (IHC) using Phospho-Tau (Ser202, Thr205) Monoclonal Antibody (AT8) as previously as described in Biernat, J., et al, EMBO J. (1992) Vol. 4, pages 1593-1597. AT8 was obtained from Thermo Fisher Scientific (Phospho-PHF-Tau, Thermo Ficher Scientific, Catalog No. MN1020, Stock cone: 0.2 mg/ml, Working solution: 1/100).

Results

Figure 2A:
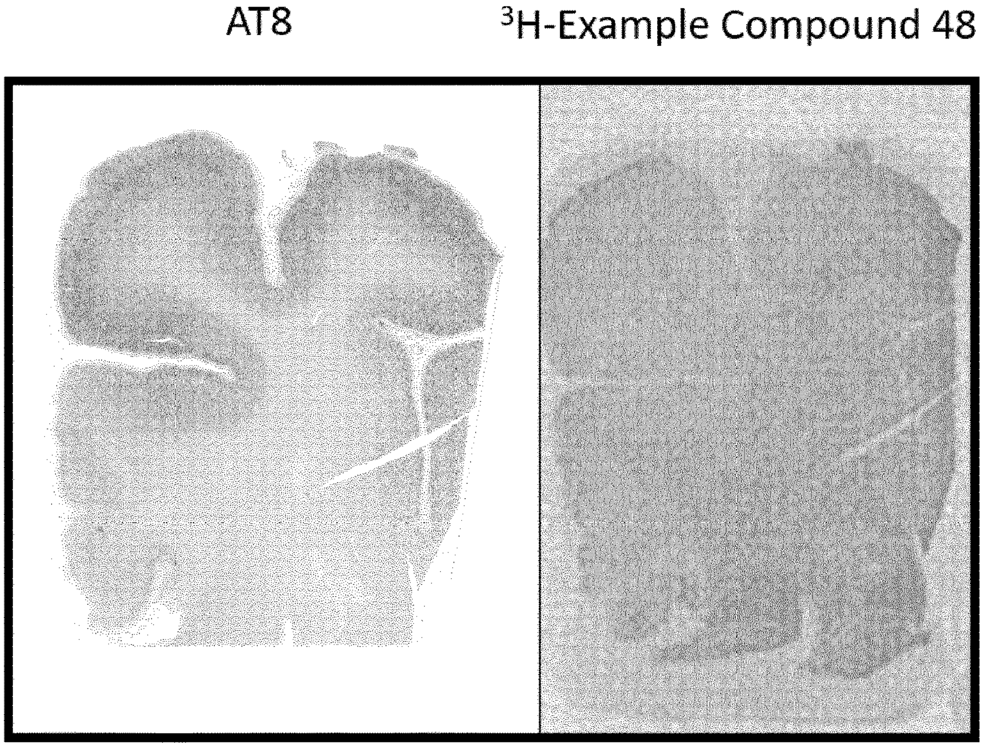
FIG. 2*a* shows autoradiograms of CBD brain sections incubated with the tau-specific antibody AT-8 or with [$^3$H]-Example Compound 48.
Figure 2B:
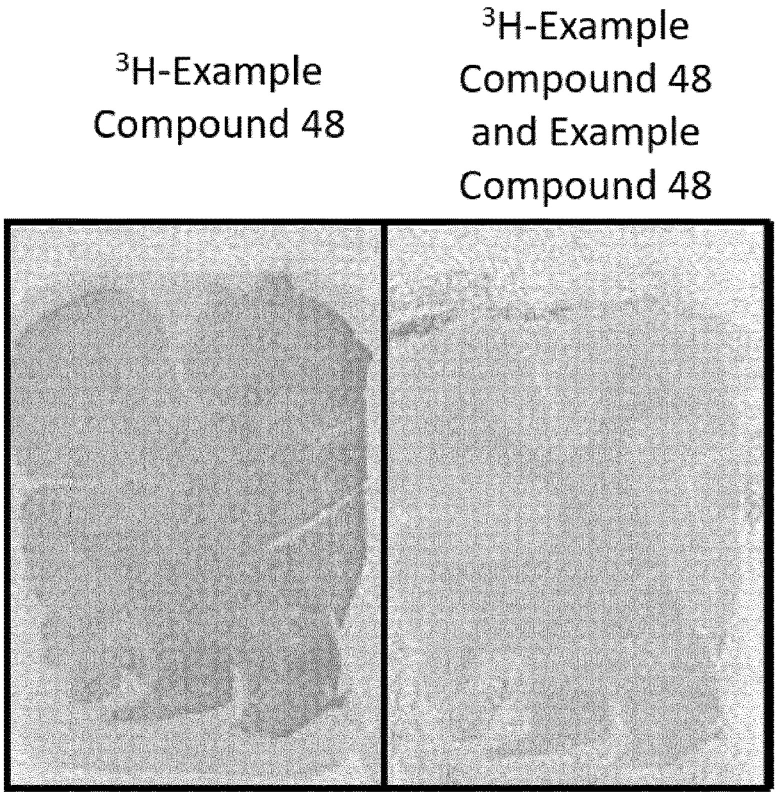
FIG. 2*b* shows autoradiograms of CBD brain sections incubated with [$^3$H]-Example Compound 48, or with [$^3$H]-Example Compound 48 and unlabeled Example Compound 48.
Figure 2C:
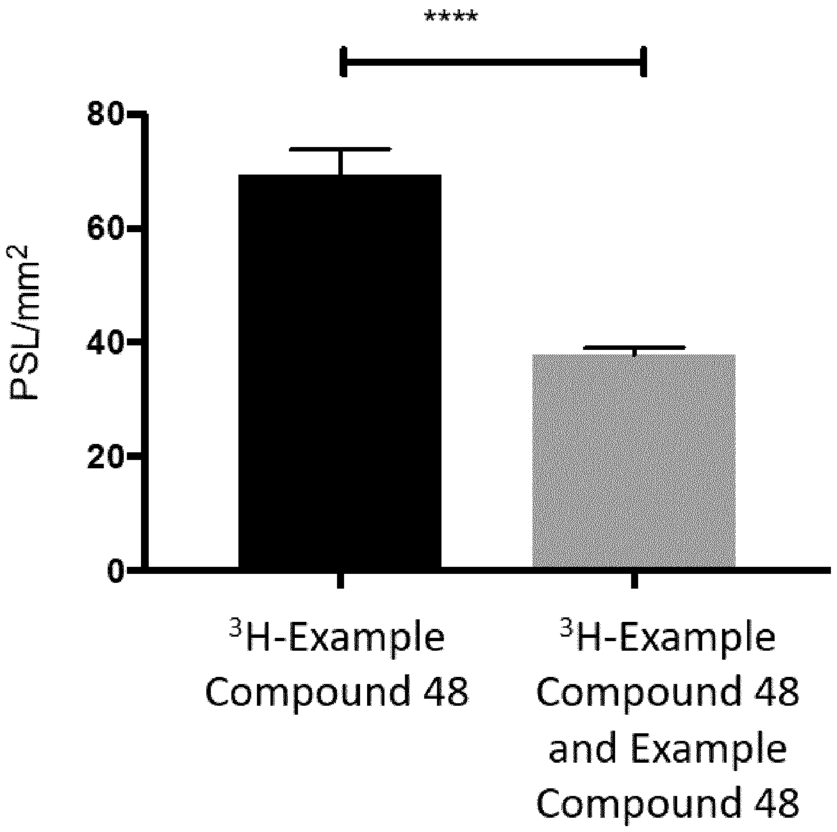
FIG. 2*c* shows the radiotracer binding determined in photostimulated luminescence per $mm^2$ (psl/$mm^2$) of the autoradiograms of FIG. 2*b*.

FIG. 2*a* shows autoradiograms of CBD brain sections incubated with the tau-specific antibody AT-8 or with [$^3$H]-Example Compound 48. FIG. 2*b* shows the autoradiograms of CBD brain sections incubated with [$^3$H]-Example Compound 48, or with [$^3$H]-Example Compound 48 and unlabeled Example Compound 48. FIG. 2*c* shows the radiotracer binding determined in photostimulated luminescence per mm$^2$ (psl/mm$^2$) of the autoradiograms of FIG. 2*b*.

Figure 3A:
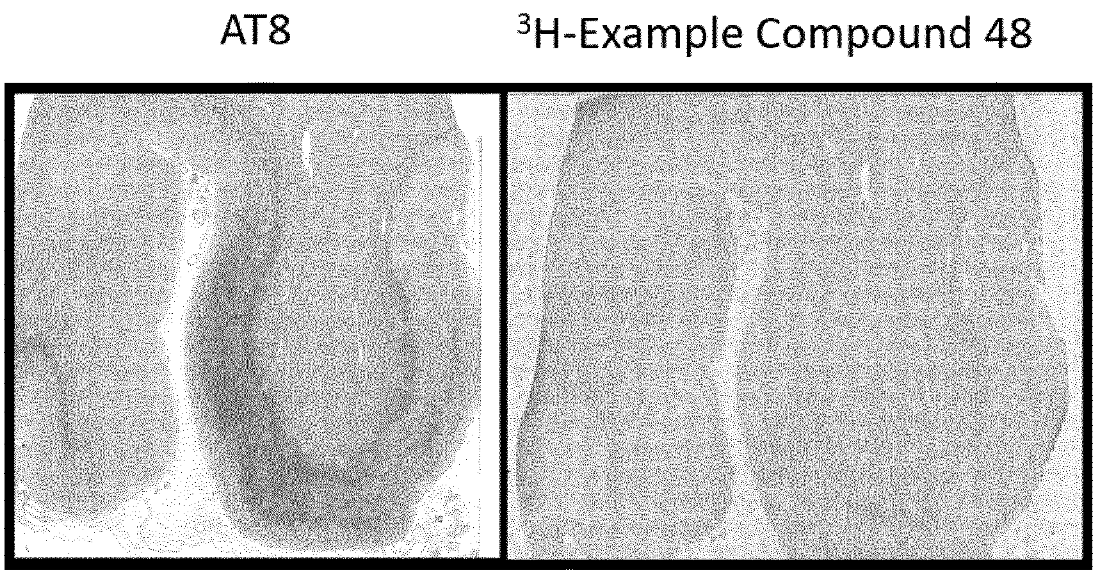
FIG. 3*a* shows autoradiograms of PSP brain sections incubated with the tau-specific antibody AT-8 or with [$^3$H]-Example Compound 48.
Figure 3B:
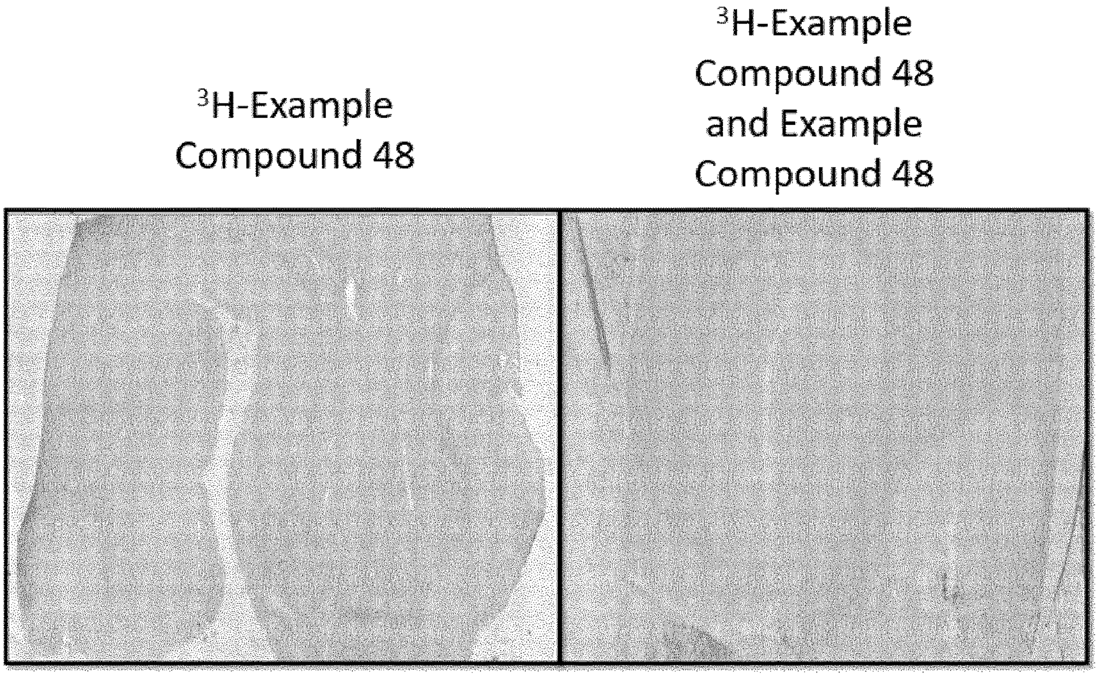
FIG. 3*b* shows autoradiograms of PSP brain sections incubated with [$^3$H]-Example Compound 48, or with [$^3$H]-Example Compound 48 and unlabeled Example Compound 48.
Figure 3C:
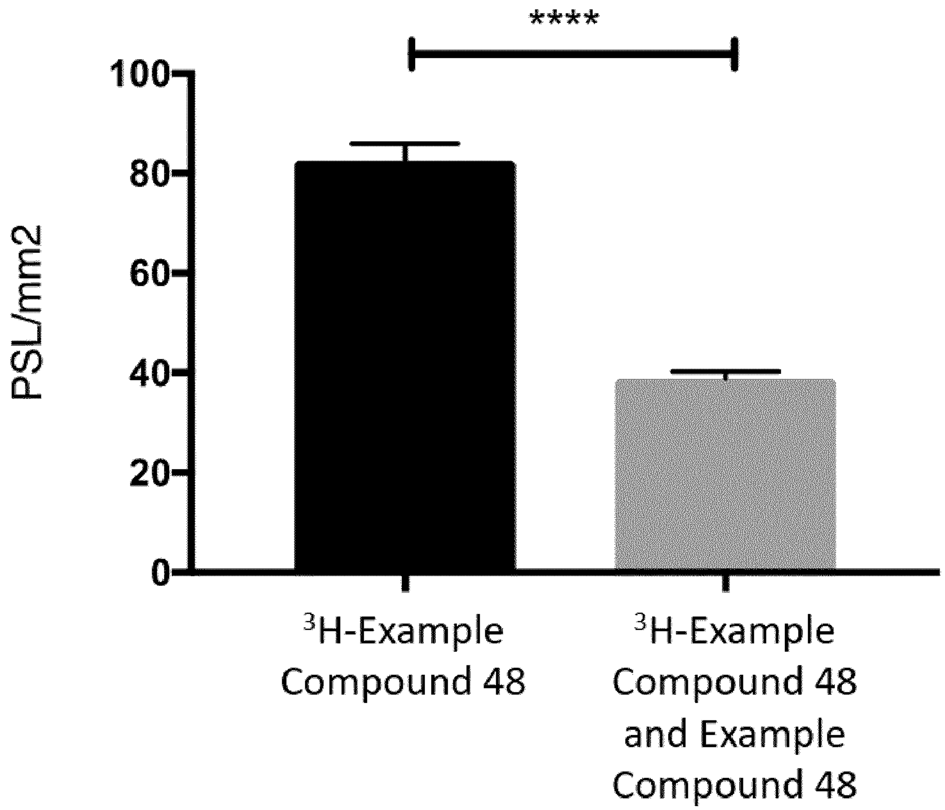
FIG. 3*c* shows the radiotracer binding determined in photostimulated luminescence per $mm^2$ (psl/$mm^2$) of the autoradiograms of FIG. 3*b*.

FIG. 3*a* shows autoradiograms of PSP brain sections incubated with the tau-specific antibody AT-8 or with [$^3$H]-Example Compound 48. FIG. 3*b* shows the autoradiograms of PSP brain sections incubated with [$^3$H]-Example Compound 48, or with [$^3$H]-Example Compound 48 and unlabeled Example Compound 48. FIG. 3*c* shows the radiotracer binding determined in photostimulated luminescence per mm$^2$ (psl/mm$^2$) of the autoradiograms of FIG. 3*b*.

The results in FIG. 2*a* to 2*c* show that [$^3$H]-Example Compound 48 shows displaceable binding in CBD brain tissue that correlates with the tau-specific antibody AT8; and the results in FIG. 3*a* to 3*c* show [$^3$H]-Example Compound 48 shows displaceable binding in PSP brain tissue that correlates with the tau-specific antibody AT8.

Figure 4A:
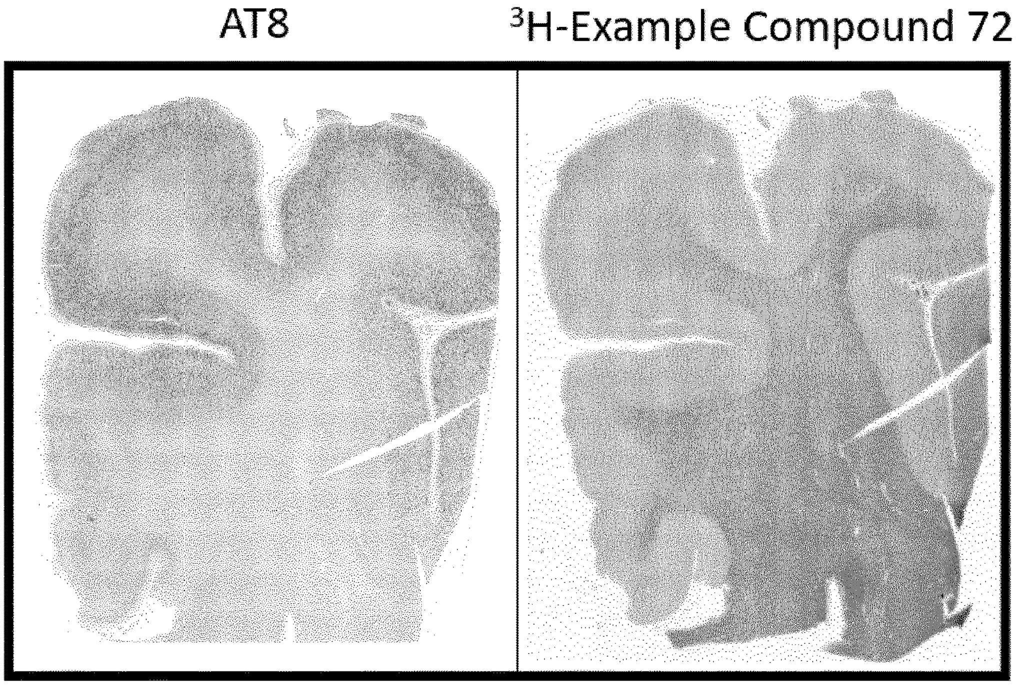
FIG. 4*a* shows autoradiograms of CBD brain sections incubated with the tau-specific antibody AT-8 or with [$^3$H]-Example Compound 72.
Figure 4B:
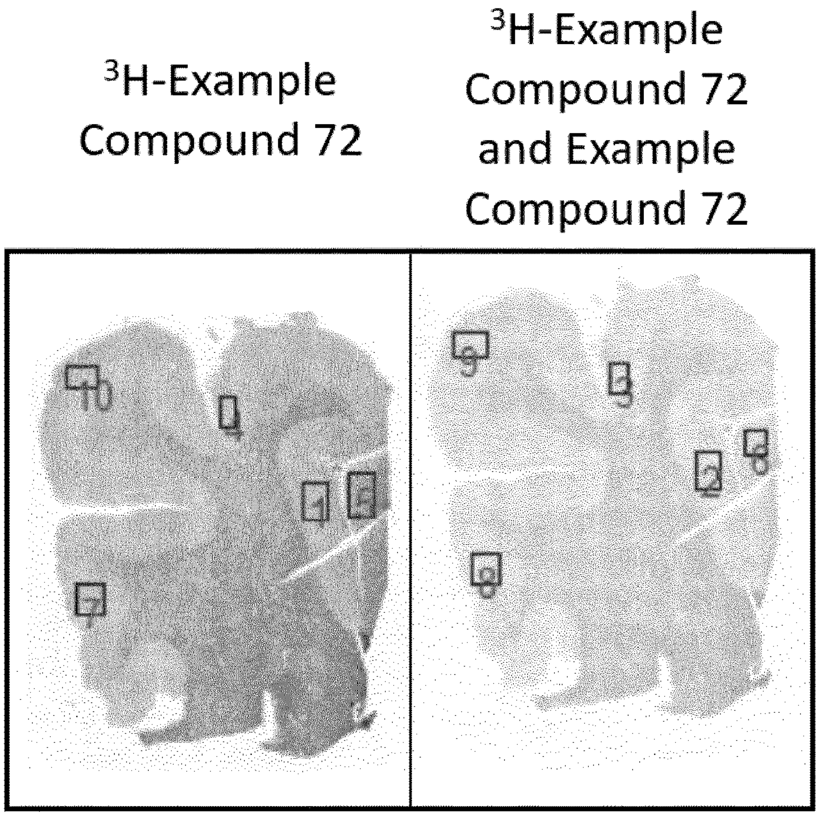
FIG. 4*b* shows autoradiograms of CBD brain sections incubated with [$^3$H]-Example Compound 72, or with [$^3$H]-Example Compound 72 and unlabeled Example Compound 72.
Figure 4C:
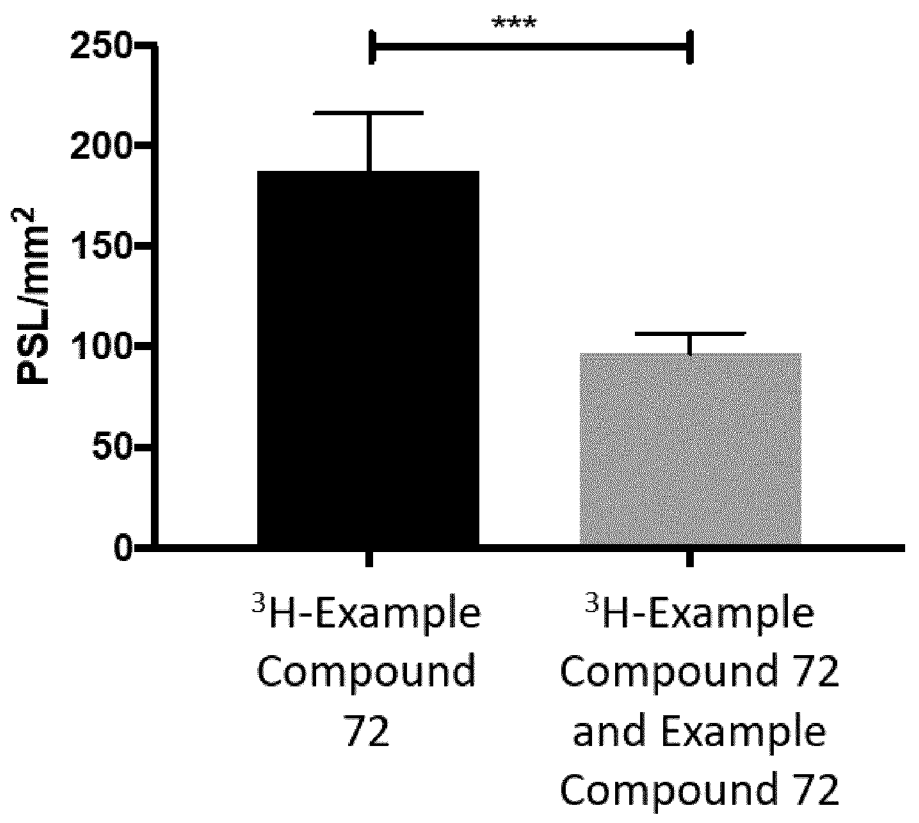
FIG. 4*c* shows the radiotracer binding determined in photostimulated luminescence per $mm^2$ (psl/$mm^2$) of the autoradiograms of FIG. 4*b*.

FIG. 4*a* shows autoradiograms of CBD brain sections incubated with the tau-specific antibody AT-8 or with [$^3$H]-Example Compound 72. FIG. 4*b* shows the autoradiograms of CBD brain sections incubated with [$^3$H]-Example Compound 72, or with [$^3$H]-Example Compound 72 and unlabeled Example Compound 72. FIG. 4*c* shows the radiotracer binding determined in photostimulated luminescence per mm$^2$ (psl/mm$^2$) of the autoradiograms of FIG. 4*b*.

Figure 5A:
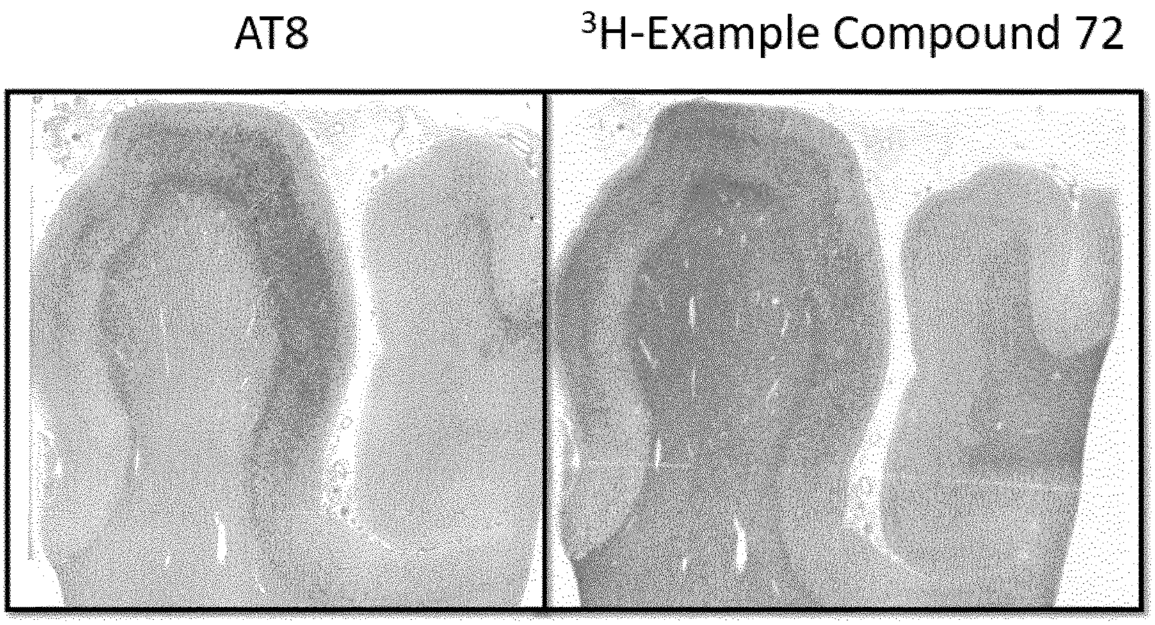
FIG. 5*a* shows autoradiograms of PSP brain sections incubated with the tau-specific antibody AT-8 or with [$^3$H]-Example Compound 72.
Figure 5B:
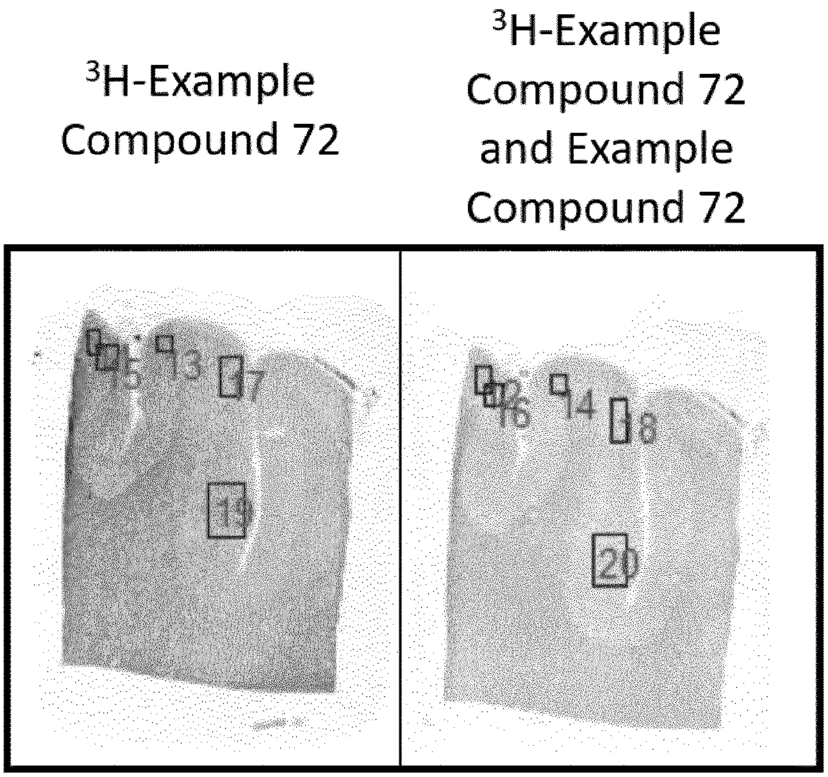
FIG. 5*b* shows autoradiograms of PSP brain sections incubated with [$^3$H]-Example Compound 12, or with [$^3$H]-Example Compound 72 and unlabeled Example Compound 72.
Figure 5C:
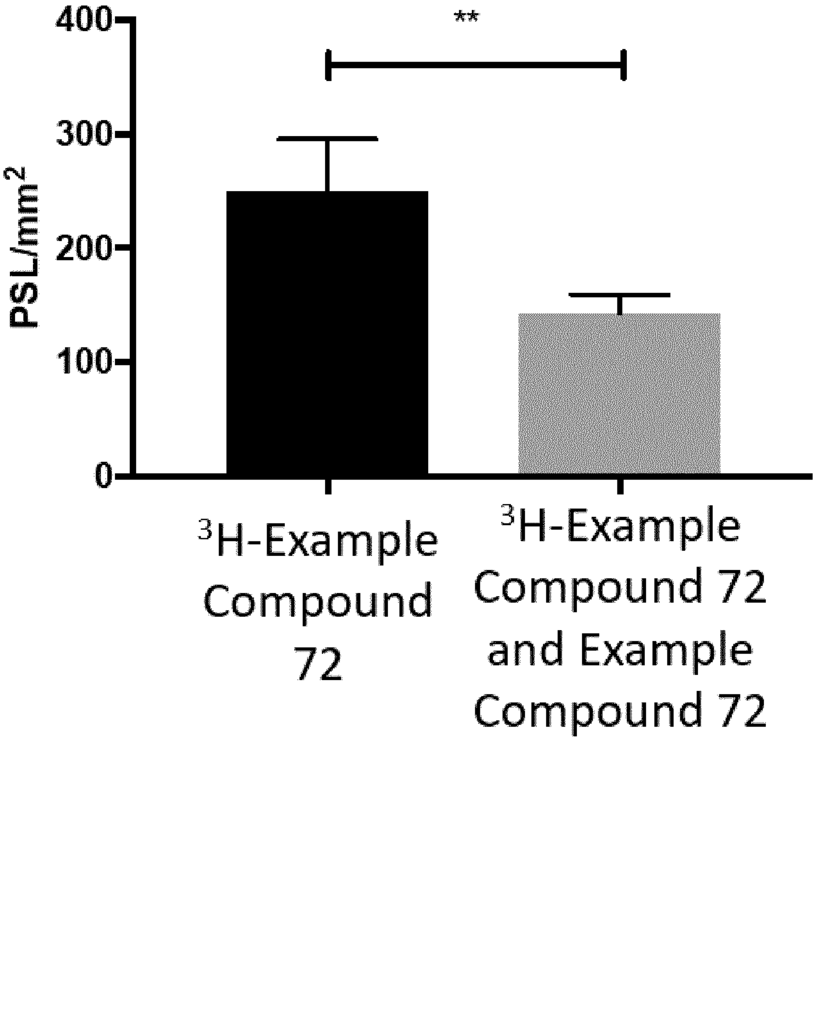
FIG. 5*c* shows the radiotracer binding determined in photostimulated luminescence per $mm^2$ (psl/$mm^2$) of the autoradiograms of FIG. 5*b*.

FIG. 5*a* shows autoradiograms of PSP brain sections incubated with the tau-specific antibody AT-8 or with [$^3$H]-Example Compound 72. FIG. 5*b* shows the autoradiograms of PSP brain sections incubated with [$^3$H]-Example Compound 72, or with [$^3$H]-Example Compound 72 and unlabeled Example Compound 72. FIG. 5*c* shows the radiotracer binding determined in photostimulated luminescence per mm$^2$ (psl/mm$^2$) of the autoradiograms of FIG. 5*b*.

The results in FIG. 2*a* to 2*c* show that [$^3$H]-Example Compound 48 shows displaceable binding in CBD brain tissue that correlates with the tau-specific antibody AT8; and the results in FIG. 3*a* to 3*c* show [$^3$H]-Example Compound 48 shows displaceable binding in PSP brain tissue that correlates with the tau-specific antibody AT8.

The results in FIG. 4*a* to 4c show that [$^3$H]-Example Compound 72 shows displaceable binding in CBD brain tissue that correlate with tau-specific antibody AT8; and the results in FIG. 5*a* to 5*c* show [$^3$H]-Example Compound 72 shows displaceable binding in PSP brain tissue that correlate with tau-specific antibody AT8.

The autoradiograms of FIGS. 2*a*, 3*a*, 4*a* and 5*a* also show that [$^3$H]-Example Compound 72 and [$^3$H]-Example Compound 48 display similar binding distribution patterns in CDB and PSP brain sections. The autoradiograms of FIGS. 2*b*, 3*b*, 4*b* and 5*b*, and the binding results shown in FIGS. 2*c*, 3*c*, 4*c* and 5*c*, show that binding of [$^3$H]-Example Compound 72 and [$^3$H]-Example Compound 48 can be inhibited with unlabeled [$^3$H]-Example Compound 48 (1 μL) in CDB and PSP brain sections.

Example (c): Rat Brain Cassette Exposure Study

The in vivo pharmacokinetic characteristics of the example compounds of the invention were compared directly with the known beta-amyloid specific ligand AZD2184 (Johnson, A. E., et al, Journal of Neurochemistry (2009), Vol. 108, pages 1177-1186). Rat brain exposure to three compounds of the invention and AZD2184 was measured by intravenous cassette dosing three test compound: Example Compound 43, Example Compound 47 and Example Compound 48; and AZD2184 (Novandi Chemistry) (concentration of 0.25 μmol/mL each) using the procedure previously described in Johnson, A. E., et al, Journal of Neurochemistry (2009), Vol. 108, pages 1177-1186. 6 male Sprague Dawley rat were used in the experiments, three rats per time point (2 min and 30 min).

Results

Figure 6A:
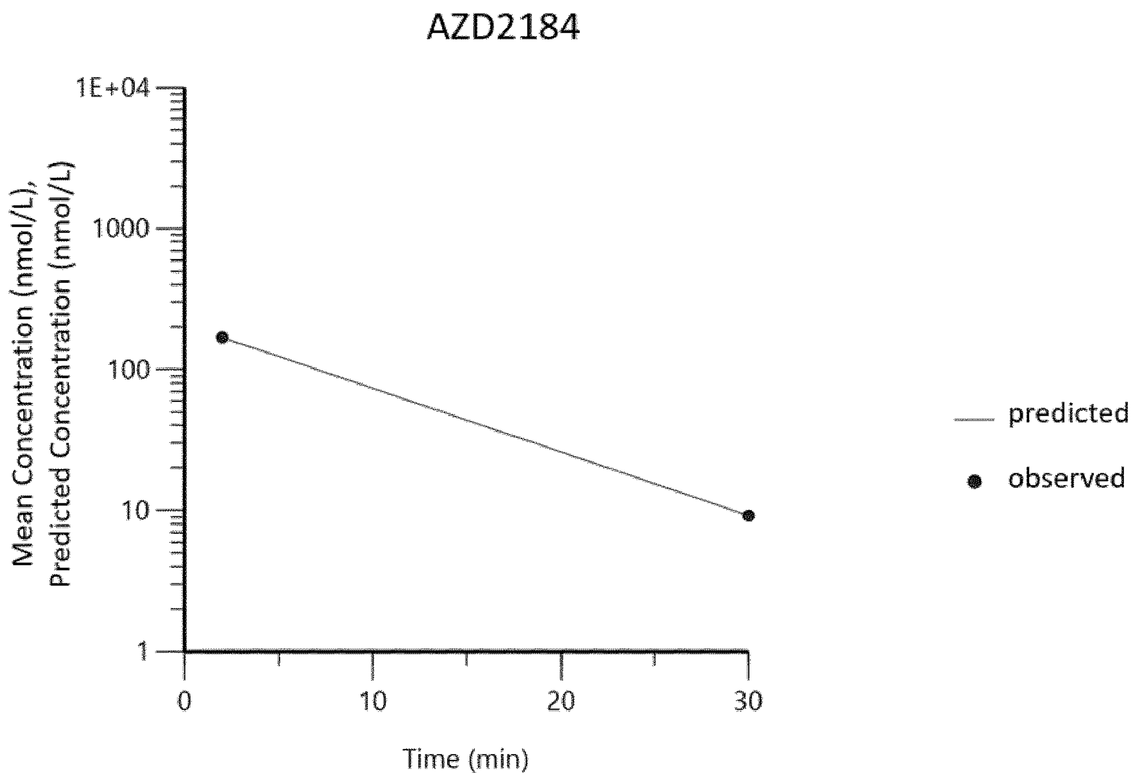
FIG. 6*a* shows the mean observed concentration (nmol/L, t=3) of AZD2184 in rat brain tissue samples at 2 minutes and 30 minutes after bolus administration of AZD2184 as part of a cassette dodge (circles), and the predicted concentration (nmol/L) between 2 minutes and 30 minutes (line).
Figure 6B:
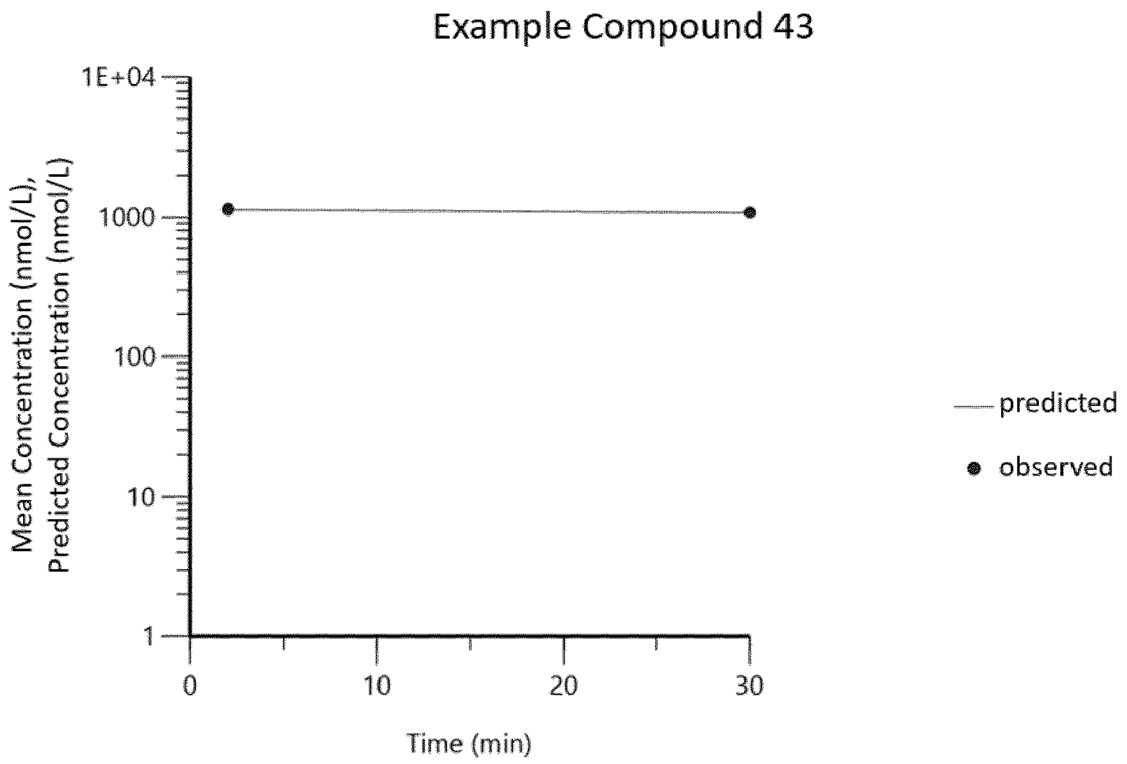
FIG. 6*b* shows the mean observed concentration (nmol/L, t=3) of Example Compound 43 in rat brain tissue samples at 2 minutes and 30 minutes after bolus administration of Example Compound 43 as part of a cassette dodge (circles), and the predicted concentration (nmol/L) between 2 minutes and 30 minutes (line).
Figure 6C:
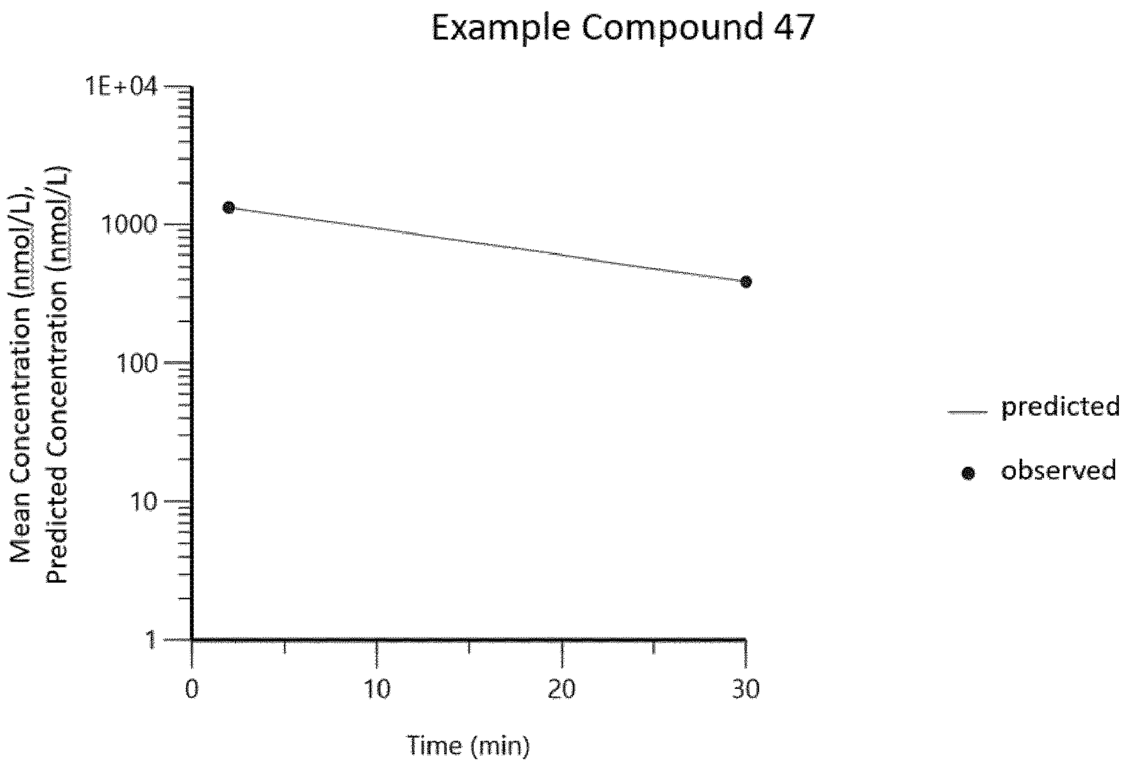
FIG. 6*c* shows the mean observed concentration (nmol/L, t=3) of Example Compound 47 in rat brain tissue samples at 2 minutes and 30 minutes after bolus administration of Example Compound 47 as part of a cassette dodge (circles), and the predicted concentration (nmol/L) between 2 minutes and 30 minutes (line).
Figure 6D:
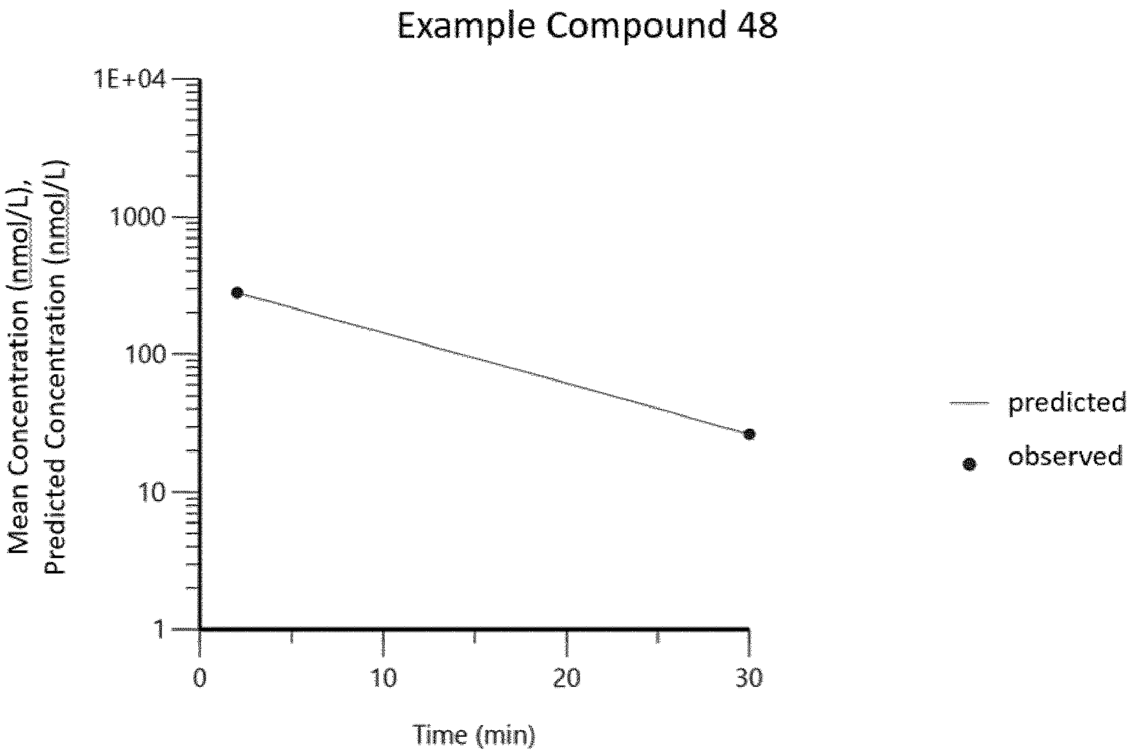
FIG. 6*d* shows the mean observed concentration (nmol/L, t=3) of Example Compound 48 in rat brain tissue samples at 2 minutes and 30 minutes after bolus administration of Example Compound 48 as part of a cassette dodge (circles), and the predicted concentration (nmol/L) between 2 minutes and 30 minutes (line).

The results of the rat brain cassette exposure study are shown in FIGS. 6*a* to 6*d* and FIG. 7. FIG. 6*a* shows the mean observed concentration (nmol/L, t=3) of AZD2184 in rat brain tissue samples at 2 minutes and 30 minutes after bolus administration of that compound as part of the cassette dodge (circles), and the predicted concentration (nmol/L) between 2 minutes and 30 minutes (line). FIG. 6*b* shows the mean observed concentration (nmol/L, t=3) of Example Compound 43 in rat brain tissue samples at 2 minutes and 30 minutes after bolus administration of that compound as part of the cassette dodge (circles), and the predicted concentration (nmol/L) between 2 minutes and 30 minutes (line). FIG. 6*c* shows the mean observed concentration (nmol/L, t=3) of Example Compound 47 in rat brain tissue samples at 2 minutes and 30 minutes after bolus administration of that compound as part of the cassette dodge (circles), and the predicted concentration (nmol/L) between 2 minutes and 30 minutes (line). FIG. 6*d* shows the mean observed concentration (nmol/L, t=3) of Example Compound 48 in rat brain tissue samples at 2 minutes and 30 minutes after bolus administration of that compound as part of the cassette dodge (circles), and the predicted concentration (nmol/L) between 2 minutes and 30 minutes (line).

FIG. 7 shows the calculated half-life ($t_{1/2}$) in minutes of Example Compound 43, Example Compound 47 and Example Compound 48, and AZD2184 in rat brain tissue. As can be seen from FIG. 7, Example Compound 48 has a similar half-life in rat brain tissue (8.21 min) as AZD2184 (6.65 min); and Example Compounds 43 and 47 have longer half-lives (379 min and 15.8 min, respectively) than AZD2184. It is noted that the $t_{1/2}$ for AZD2184 is consistent with the $t_{1/2}$ for AZD2184 reported in Table 3 of Johnson, A. E., et al (6.8 min).

The results in FIGS. 5*a* to 5*d* show that the Example Compounds tested quickly entered the brain; and that Example Compounds 47 and 48 were rapidly cleared from normal rat brain tissue.

Example (d): MAO Binding Assay and Enzyme and Uptake Assays

A monoamine oxidase inhibitor (MAO) binding assay for MAO-A was performed (EuroFins Pharma Discovery Service) for Example Compound 43, Example Compound 48 and the known tau ligand THK-5117. The three compounds were tested at 1 μM. Compound binding was calculated as a % inhibition of the binding of the selective MAO-A inhibitor [$^3$H]-Ro41-1049 for MAO-A binding.

The MAO-A binding assay was carried our as described in Cesura, A. M., et al, Mol. Phamacol. (1990), Vol 37, pages 358-366, using the materials and conditions described in Table 3.

TABLE 3

| Assay | Source | Ligand | Conc. | Kd | Non-specific | Incubation | Detection method |
|---|---|---|---|---|---|---|---|
| MAO-A (antagonist radioligand) | Rat cerebral cortex | $^{3}$H-Ro41-1049 | 10 nM | 14 nM | Clorgyline (1 μM) | 30 min 37° C. | Scintillation counting |

MAO enzyme and uptake assays were also performed (EuroFins Pharma Discovery Service) as described in Weyler, W., et al., J. Biol. Chem. (1985), Vol. 260, pages 13199-13207, using the materials and conditions described in Table 4; and as described in Tsugeno, U., et al., J Biochem. (1995), Vol. 118, pages 974-980, using the materials and conditions described in Table 5, for Example Compound 43, Example Compound 48 and the known tau ligand THK-5117. The three compounds were tested at 1 μM. Compound enzyme/uptake inhibition effect was calculated as a % inhibition of control enzyme activity.

TABLE 4

| Assay | Source | Ligand | Incubation | Measured Component | Detection method |
|---|---|---|---|---|---|
| MAO-A (antagonist radioligand) | Human placenta | kynuramine (0.5 mM) | 20 min Room temperature | 4-OHquinoline | Photometry |

TABLE 5

| Assay | Source | Ligand | Incubation | Measured Component | Detection method |
|---|---|---|---|---|---|
| MAO-B recombinant enzyme | Human recombinant | D-Luciferin derivative (4 μM) | 60 min 37° C. | Methyl ester luciferin | Luminenscence |

Analysis and Expression of Results

The results of the MAO-A binding assay are expressed as a percent inhibition of control specific binding obtained in the presence of the test compounds:

$$100-\left(\frac{\text{measured specific binding}}{\text{control specific binding}}*100\right)$$

The results of the enzyme and uptake assays are expressed as a percent inhibition of control specific activity obtained in the presence of the test compounds:

$$100-\left(\frac{\text{measured specific activity}}{\text{control specific activity}}*100\right)$$

Results

The results of the MAO-A binding assay are shown in FIG. 8; and the result of the MAO enzyme and uptake assays are shown in FIG. 9. Results showing an inhibition or stimulation higher than 50% are considered to represent significant effect of the test compound. No such effects were observed for Example Compound 43 or Example Compound 48, or for THK-5117, in the binding assay, or in the enzyme and uptake assays. Results showing an inhibition or stimulation between 25% and 50% are indicative of weak to moderate effects. No such effects were observed for Example Compound 43 or Example Compound 48 in the binding assay, or in the enzyme and uptake assays. Results showing an inhibition or stimulation lower than 25% are not considered significant and are mostly attributable to variability of the signal around the control level. The results for Example Compound 43 and Example Compound 48 are within this region for the MAO binding assay carried out and for the enzyme and uptake assays carried out. As such, the results of this experiment show that Example Compound 43 and Example Compound 48 exhibit no binding activity towards MAO-A and did not inhibit activity of MAO-A or MAO-B. Thus these results suggest that the compounds of the invention will have low binding affinity for MAO enzymes in the human brain.

As reported in Murugan, N. A., et al, Eur J Nucl Med Mol Imaging. (2019) doi: 10.1007/s00259-019-04305-8, areas of the brain with the highest concentrations of MAO-B overlap with areas of tau pathology in tauopathies such as CBD and PSP. Therefore, it is undesirable for a tau deposit ligand to have off-target binding to MAO, as such off-target effects severely limit the use of the tau deposit ligand for in vivo tau imaging. As Example Compound 43 and Example Compound 48 have been shown to have no MAO binding or inhibitory activity, the compounds of the invention are expected to be specific to tau accumulation in the brain, and thus have good specificity and sensitivity when used as tau imaging agent in vivo in all tauopathies, including CBD and PSP.

The invention claimed is:

1. A compound of formula (I), or a pharmaceutically acceptable salt thereof,

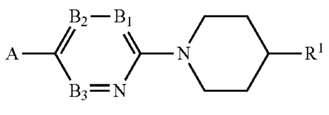

(I)

wherein

A is

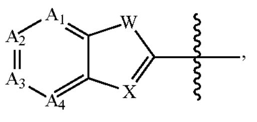

and $A_1$ and $A_4$ are independently selected from the group consisting of N and CH;

$A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

provided at least one of $A_2$ and $A_3$ is $CR^2$;

W is selected from the group consisting of O, S and NH;

X is selected from the group consisting of N and CH, with a proviso that if W is NH then X is CH; and with a proviso that if W is S, X is N;

or A is

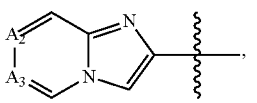

and $A_2$ is selected from the group consisting of N, $CR^2$ and CH and $A_3$ is selected from the group consisting of N and CH, or $A_2$ is selected from the group consisting of N and CH and $A_3$ is selected from the group consisting of N, $CR^2$ and CH;

provided at least one of $A_2$ and $A_3$ is $CR^2$;

$B_1$, $B_2$, and $B_3$, are each independently selected from the group consisting of N, CH and $CR^3$, wherein at least one of $B_1$, $B_2$, and $B_3$ is CH or $CR^3$;

$R^1$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$-$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkyl N($R^c$)$_2$; —C(O)—N($R^4$)$_2$; N($R^4$)C(O)H; N($R^4$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^4$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; $C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2$—$R^f$; and —$(OCH_2CH_2)_p$—$R^f$;

each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS; $C_{1-6}$alkylS═O; $C_{1-6}$alkyl$SO_2$; $NO_2$; —N($R^a$)$_2$; $C_{1-6}$alkylN($R^a$)$_2$; —N($R^a$)C(O)H; —N($R^a$)C(O)$C_{1-6}$alkyl optionally substituted with 1, 2 or 3 halogen; C(O)N($R^g$)$_2$; and —$C_{1-6}$alkylC(O)N($R^g$)$_2$;

$R^3$ is selected from the group consisting of halogen; OH; $C_{1-6}$alkyl optionally substituted with 1, 2 or 3 halogen; and —O$C_{1-6}$alkyl optionally substituted with 1, 2 or 3 halogen;

$R^a$, $R^b$, $R^c$ and $R^d$ are each independently selected from the group consisting of H and $C_{1-6}$alkyl optionally substituted with 1, 2 or 3 halogen;

$R^e$ is selected from the group consisting of H and $C_{1-6}$alkyl optionally substituted with 1, 2 or 3 halogens;

$R^f$ is selected from the group consisting of H; halogen; —$CH_2$(halogen), —CH(halogen)$_2$, C(halogen)$_3$, and OH;

each $R^g$ is independently selected from the group consisting of H; $C_{1-6}$alkyl; $C_{1-6}$alkyl substituted with 1, 2 or 3 halogen; $C_{1-6}$alkyl substituted with 1, 2 or 3 OH group; $C_{1-6}$alkyl substituted with 1, 2 or 3 —O$C_{1-3}$alkyl groups; $C_{1-6}$alkyl substituted with a —OS(O)$_2$$CH_3$ group; and $C_{1-6}$alkyl substituted with a —S(O)$_2$O$CH_3$ group; and p is 2, 3, 4, 5, 6, 7 or 8.

2. The compound of claim 1, wherein $R^1$ is —$C_{1-3}$alkyl optionally substituted with 1, 2 or 3 halogen or OH groups; C(O)—N(H)$_2$ or C(O)—O—$C_{1-3}$alkyl.

3. The compound of claim 1, wherein $R^3$ is selected from the group consisting of halogen and —O$C_{1-6}$alkyl optionally substituted with 1 halogen.

4. The compound of claim 1, wherein W is NH and X is CH.

5. The compound of claim 1, wherein $A_1$ and $A_4$ are CH, or wherein $A_1$ is N and $A_4$ is CH.

6. The compound of claim 1, wherein $A_3$ is selected from the group consisting of N and CH, and at least three of $A_1$, $A_2$, $A_3$ and $A_4$ are CH.

7. The compound of claim 1, wherein the compound is a compound of formula (Ia)

(Ia)

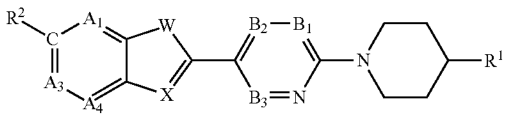

wherein $A_1$, $A_3$, and $A_4$ are independently selected from the group consisting of N and CH, and at least one of $A_1$, $A_3$, and $A_4$ is CH.

8. The compound of claim 1, wherein the compound is a compound of formula (Ib)

(Ib)

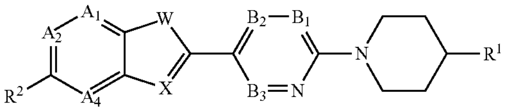

wherein $A_1$, $A_2$, and $A_4$ are independently selected from the group consisting of N and CH, and at least one of $A_1$, $A_2$, and $A_4$ is CH.

9. The compound of claim 1, wherein at least two of $B_1$, $B_2$, and $B_3$ are selected from the group consisting of CH and $CR^3$.

10. The compound of claim 1, wherein at least one of $B_1$, $B_2$, and $B_3$ is CH, and at least one of $B_1$, $B_2$, and $B_3$ is $CR^3$.

11. The compound of claim 1, wherein $B_2$ and $B_3$ are independently selected from the group consisting of $CR^3$ and CH, and $B_1$ is selected from the group consisting of N, $CR^3$ and CH.

12. The compound of claim 1, wherein $B_1$ and $B_2$ are independently selected from the group consisting of N and CH, and $B_3$ is selected from the group consisting of N, CH and $CR^3$.

13. The compound of claim 1, wherein $B_1$ or $B_3$ is $CR^3$.

14. The compound of claim 1, wherein each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; —N($R^a$)C(O)H; —N($R^a$)C(O)$C_{1-6}$alkyl optionally substituted with 1, 2 or 3 halogen; C(O)N($R^g$)$_2$; and —$C_{1-6}$alkylC(O)N($R^g$)$_2$.

15. The compound of claim 1, wherein the compound comprises one or more radioisotopes.

16. The compound of claim 1, wherein the compound comprises one or more radioisotopes, wherein the one or more radioisotopes is independently selected from the group consisting of $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

17. The compound of claim 1, wherein the compound is selected from the group consisting of:

2-{1-[5-(6-methoxy-1,3-benzothiazol-2-yl)pyridin-2-yl]piperidin-4-yl}ethan-1-ol;

2-{6-[4-(2-{2-[2-(2-fluoroethoxy)ethoxy]ethoxy}ethyl)piperidin-1-yl]pyridine-3-yl}-6-methoxy-1,3-benzothiazole;

2-({1-[5-(6-methoxy-1,3-benzothiazol-2-yl)pyridin-2-yl]piperidin-4-yl}oxy)ethan-1-ol;

2-{6-[4-(2-fluoroethyl)piperidin-1-yl]pyridin-3-yl}-6-methoxy-1,3-benzothiazole;

2-{1-[5-(6-methoxy-1,3-benzothiazol-2-yl)pyrimidin-2-yl]piperidin-4-yl}ethan-1-ol;

2-{2-[4-(2-{2-[2-(2-fluoroethoxy)ethoxy]ethoxy}ethyl)piperidin-1-yl]pyrimidin-5-yl}-6-methoxy-1,3-benzothiazole;

2-{1-[5-(1-benzofuran-2-yl)pyridin-2-yl]piperidin-4-yl}ethan-1-ol;

2-{6-[4-(2-hydroxyethyl)piperidin-1-yl]pyridin-3-yl}-1,3-benzothiazol-6-ol;

1-fluoro-3-[(2-{6-[4-(2-hydroxyethyl)piperidin-1-yl]pyridin-3-yl}-1,3-benzothiazol-6-yl)oxy]propan-2-ol;

2-{2-[4-(2-hydroxyethyl)piperidin-1-yl]pyrimidin-5-yl}-1,3-benzothiazol-6-ol;

2-{2-[4-(2-fluoroethyl)piperidin-1-yl]pyrimidin-5-yl}-1,3-benzothiazol-6-ol;

2-{2-[4-(2-hydroxyethyl)piperidin-1-yl]pyrimidin-5-yl}-1,3-benzothiazole-6-carbonitrile;

2-{2-[4-(2-hydroxyethyl)piperidin-1-yl]pyrimidin-5-yl}-1,3-benzothiazole-6-carboxamide;

2-{1-[5-(6-carbamoyl-1,3-benzothiazol-2-yl)pyrimidin-2-yl]piperidin-4-yl}ethyl methanesulfonate;

2-{2-[4-(2-fluoroethyl)piperidin-1-yl]pyrimidin-5-yl}-1,3-benzothiazole-6-carboxamide;

ethyl 2-{2-[4-(2-fluoroethyl)piperidin-1-yl]pyrimidin-5-yl}-1,3-benzothiazole-6-carboxylate;

{1-[6-fluoro-5-(5-methoxy-1H-indol-2-yl)pyridin-2-yl]piperidin-4-yl}methanol;

2-{2-fluoro-6-[4-(hydroxymethyl)piperidin-1-yl]pyridin-3-yl}-1H-indol-5-ol;

2-{1-[5-(5-methoxy-1H-indol-2-yl)pyridin-2-yl]piperidin-4-yl}ethan-1-ol;

2-[4-(2-fluoroethyl)piperidin-1-yl]-5-{6-methoxyimidazo[1,2-a]pyridine-2-yl}pyrimidine;

2-{6-[4-(Hydroxymethyl)piperidin-1-yl]pyridin-3-yl}-1,3-benzothiazol-6-ol;

(1-{5-[6-(2-Fluoroethoxy)-1,3-benzothiazol-2-yl]pyridin-2-yl}piperidin-4-yl)methanol;

2-{2-[4-(Hydroxymethyl)piperidin-1-yl]pyrimidin-5-yl}-1,3-benzothiazol-6-ol;

(1-{5-[6-(2-Fluoroethoxy)-1,3-benzothiazol-2-yl]pyrimidin-2-yl}piperidin-4-yl)methanol;

Ethyl 2-{2-[4-(2-Hydroxyethyl)piperidin-1-yl]pyrimidin-5-yl}-1,3-benzothiazole-6-carboxylate;

2-{2-[4-(2-Fluoroethyl)piperidin-1-yl]pyrimidin-5-yl}-N-(2-hydroxyethyl)-1,3-benzothiazole-6-carboxamide;

N-(2-Fluoroethyl)-2-{2-[4-(2-hydroxyethyl)piperidin-1-yl]pyrimidin-5-yl}-1,3-benzothiazole-6-carboxamide;

(1-{5-[6-(2-Fluoroethoxy)-1,3-benzoxazol-2-yl]pyridin-2-yl}piperidin-4-yl)methanol;

Ethyl 1-[6-Fluoro-5-(6-methoxy-1H-indol-2-yl)pyridine-2-yl]piperidine-4-carboxylate;

2-{2-Fluoro-6-[4-(hydroxymethyl)piperidin-1-yl]pyridin-3-yl}-N-methyl-1H-indole-6-carboxamide;

Ethyl 1-[6-Fluoro-5-(5-hydroxy-1H-indol-2-yl)pyridin-2-yl]piperidine-4-carboxylate;

1-[6-Fluoro-5-(5-hydroxy-1H-indol-2-yl)pyridin-2-yl]piperidine-4-carboxamide;

Methyl 1-[6-Fluoro-5-(5-hydroxy-1H-indol-2-yl)pyridin-2-yl]piperidine-4-carboxylate;

1-[6-Fluoro-5-(5-methoxy-1H-indol-2-yl)pyridin-2-yl]piperidine-4-carboxamide;

2-{2-[4-(Fluoromethyl)piperidin-1-yl]pyrimidin-5-yl}-1H-indol-5-ol;

2-{2-[4-(Fluoromethyl)piperidin-1-yl]pyrimidin-5-yl}-1H-indole-6-carboxamide;

1-[5-(5-Methoxy-1H-indol-2-yl)pyridin-2-yl]piperidine-4-carboxamide;

(1-{5-[5-(2-Fluoroethoxy)-1H-indol-2-yl]pyrimidin-2-yl}piperidin-4-yl)methanol;

[1-(6-Fluoro-5-{5-methoxy-1H-pyrrolo[2,3-b]pyridin-2-yl}pyridin-2-yl)piperidin-4-yl]methanol;

2-{2-Fluoro-6-[4-(hydroxymethyl)piperidin-1-yl]pyridin-3-yl}-1H-pyrrolo[2,3-b]pyridin-5-ol[1-(6-Fluoro- 5-{2-methoxy-7H-pyrrolo[2,3-d]pyrimidin-6-yl}pyridine-2-yl)piperidin-4-yl]methanol); and (1-{5-[5-(2-Fluoroethoxy)-1H-indol-2-yl]pyridin-2-yl}piperidin-4-yl)methanol;

or a pharmaceutically acceptable salt thereof; and wherein the compound optionally comprises one or more radioisotopes selected from the group consisting of $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

18. A pharmaceutical composition comprising a compound of formula (I), or a pharmaceutically acceptable salt thereof, (I)

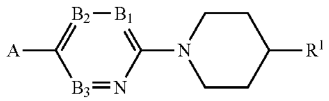

wherein

A is

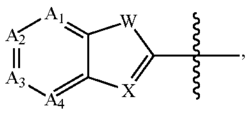

and $A_1$ and $A_4$ are independently selected from the group consisting of N and CH;

$A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

provided at least one of $A_2$ and $A_3$ is $CR^2$;

W is selected from the group consisting of O, S and NH;

X is selected from the group consisting of N and CH, with a proviso that if W is NH then X is CH; and with a proviso that if W is S, X is N;

or A is

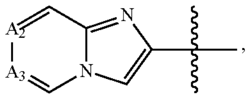

and $A_2$ is selected from the group consisting of N, $CR^2$ and CH and $A_3$ is selected from the group consisting of N and CH, or $A_2$ is selected from the group consisting of N and CH and $A_3$ is selected from the group consisting of N, $CR^2$ and CH; provided at least one of $A_2$ and $A_3$ is $CR^2$;

$B_1$, $B_2$, and $B_3$, are each independently selected from the group consisting of N, CH and $CR^3$, wherein at least one of $B_1$, $B_2$, and $B_3$ is CH or $CR^3$;

$R^1$ is selected from the group consisting of halogen; OH; —CN; —$C_{1-6}$alkyl optionally substituted with 1, 2 or 3 halogen or OH groups; —O—$C_{1-6}$alkyl optionally substituted with 1, 2 or 3 halogen or OH groups; $C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkyl N($R^c$)$_2$; —C(O)—N($R^4$)$_2$; N($R^4$)C(O)H; N($R^4$)C(O) $C_{1-6}$alkyl optionally substituted with 1, 2 or 3 halogen; —$C_{1-6}$alkyl-C(O)—N($R^4$)$_2$; —O—$C_{1-6}$alkyl-C (O)—N($R^4$)$_2$; —C(O)—O—$C_{1-6}$alkyl optionally substituted with 1, 2 or 3 halogen; —O—C(O) $C_{1-6}$alkyl optionally substituted with 1, 2 or 3 halogen; —$C_{1-6}$alkyl-C(O)—O—$C_{1-6}$alkyl optionally substituted with 1, 2 or 3 halogen; $C_{1-6}$alkyl-O—C (O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS; $C_{1-6}$alkylS═O; $C_{1-6}$alkyl$SO_2$; $NO_2$; —N($R^a$)$_2$; —$C_{1-6}$alkylN($R^a$)$_2$; —N($R^a$)C(O)H; —N($R^a$)C(O) $C_{1-6}$alkyl optionally substituted with 1, 2 or 3 halogen; C(O)N($R^g$)$_2$; and —$C_{1-6}$alkylC(O)N($R^g$)$_2$;

$R^3$ is selected from the group consisting of halogen; OH; $C_{1-6}$alkyl optionally substituted with 1, 2 or 3 halogen; and —O$C_{1-6}$alkyl optionally substituted with 1, 2 or 3 halogen;

$R^a$, $R^b$, $R^c$ and $R^d$ are each independently selected from the group consisting of H and $C_{1-6}$alkyl optionally substituted with 1, 2 or 3 halogen;

$R^e$ is selected from the group consisting of H or $C_{1-6}$alkyl optionally substituted with 1, 2 or 3 halogens;

$R^f$ is selected from the group consisting of H; halogen; —$CH_2$(halogen), —CH(halogen)$_2$, —C(halogen)$_3$, and OH;

each $R^g$ is independently selected from the group consisting of H; $C_{1-6}$alkyl; $C_{1-6}$alkyl substituted with 1, 2 or 3 halogen; $C_{1-6}$alkyl substituted with 1, 2 or 3 OH group; $C_{1-6}$alkyl substituted with 1, 2 or 3-O$C_{1-3}$alkyl groups; $C_{1-6}$alkyl substituted with a —$OS(O)_2CH_3$ group; and $C_{1-6}$alkyl substituted with a —$S(O)_2OCH_3$ group; and p is 2, 3, 4, 5, 6, 7 or 8;

together with a pharmaceutically suitable carrier.

19. The compound of claim 1, which is: 2-{2-[4-(2-fluoroethyl)piperidin-1-yl]pyrimidin-5-yl}-1,3-benzothiazole-6-carboxamide; or a pharmaceutically acceptable salt thereof.

* * * * *